United States Patent
Connor

(10) Patent No.: US 10,716,573 B2
(45) Date of Patent: Jul. 21, 2020

(54) JANJUA ANEURYSM NET WITH A RESILIENT NECK-BRIDGING PORTION FOR OCCLUDING A CEREBRAL ANEURYSM

(71) Applicant: Robert A. Connor, St. Paul, MN (US)

(72) Inventor: Robert A. Connor, St. Paul, MN (US)

(73) Assignee: Aneuclose, St. Paul, MN (US)

( * ) Notice: Subject to any disclaimer, the term of this patent is extended or adjusted under 35 U.S.C. 154(b) by 193 days.

(21) Appl. No.: 15/865,822

(22) Filed: Jan. 9, 2018

(65) Prior Publication Data

US 2018/0140305 A1    May 24, 2018

Related U.S. Application Data

(63) Continuation-in-part of application No. 14/526,600, filed on Oct. 29, 2014, now abandoned, which is a
(Continued)

(51) Int. Cl.
*A61B 17/12* (2006.01)
*A61F 2/90* (2013.01)
(Continued)

(52) U.S. Cl.
CPC .. *A61B 17/12118* (2013.01); *A61B 17/12113* (2013.01); *A61B 17/12163* (2013.01); *A61B 17/12172* (2013.01); *A61F 2/90* (2013.01); *A61F 2/95* (2013.01); *A61B 17/1214* (2013.01); *A61B 17/12181* (2013.01); *A61B 17/12186* (2013.01); *A61B 2017/00862* (2013.01); *A61B 2017/00946* (2013.01); *A61F 2002/823* (2013.01); *A61F 2230/0004* (2013.01); *A61F 2230/008* (2013.01);
(Continued)

(58) Field of Classification Search
CPC ........ A61B 17/12168; A61B 17/12151; A61B 17/12118; A61B 17/12177; A61B 17/12113
See application file for complete search history.

(56) References Cited

U.S. PATENT DOCUMENTS

| | | | |
|---|---|---|---|
| 4,364,392 A | 12/1982 | Strother et al. | |
| 4,994,069 A | 2/1991 | Ritchart et al. | |

(Continued)

FOREIGN PATENT DOCUMENTS

WO PCT/US/2009/002537    4/2009

OTHER PUBLICATIONS

U.S. Appl. No. 12/387,637, 2009, Connor et al.
U.S. Appl. No. 13/889,451, 2013, Connor et al.

*Primary Examiner* — Shaun L David
*Assistant Examiner* — Christina C Lauer

(57) ABSTRACT

This invention is an intrasacular aneurysm occlusion device with a proximal resilient stent which becomes wider than the aneurysm neck and a distal flexible net which is expanded by being filled with embolic members. The stent and the net work together. The stent occludes the aneurysm neck and prevents the device from slipping out. The net conforms to the walls of even an irregularly-shaped aneurysm sac and keeps the stent pressed against the inside of the aneurysm neck. This has advantages over the prior art, especially for aneurysms with irregularly-shaped sacs.

5 Claims, 22 Drawing Sheets

Related U.S. Application Data continuation-in-part of application No. 12/989,048, filed on Oct. 21, 2010, now Pat. No. 8,974,487, application No. 15/865,822, which is a continuation-in-part of application No. 15/081,909, filed on Mar. 27, 2016, now abandoned, which is a continuation-in-part of application No. 14/526,600, filed on Oct. 29, 2014, now abandoned, which is a continuation-in-part of application No. 12/989,048, filed on Oct. 21, 2010, now Pat. No. 8,974,487.

(60) Provisional application No. 61/126,047, filed on May 1, 2008, provisional application No. 61/897,245, filed on Oct. 30, 2013, provisional application No. 61/126,027, filed on May 1, 2008, provisional application No. 62/472,519, filed on Mar. 16, 2017, provisional application No. 62/589,754, filed on Nov. 22, 2017.

(51) Int. Cl.
*A61F 2/95* (2013.01)
*A61B 17/00* (2006.01)
*A61F 2/82* (2013.01)

(52) U.S. Cl.
CPC ............... *A61F 2230/0065* (2013.01); *A61F 2230/0071* (2013.01); *A61F 2230/0076* (2013.01); *A61F 2230/0078* (2013.01)

(56) References Cited

U.S. PATENT DOCUMENTS

| | | |
|---|---|---|
| 5,226,889 A | 7/1993 | Sheiban |
| 5,304,132 A | 4/1994 | Jang |
| 5,334,210 A | 8/1994 | Gianturco |
| 5,350,397 A | 9/1994 | Palermo et al. |
| 5,370,691 A | 12/1994 | Samson |
| 5,382,259 A | 1/1995 | Phelps et al. |
| 5,405,379 A | 4/1995 | Lane |
| 5,411,549 A | 5/1995 | Peters |
| 5,423,829 A | 6/1995 | Pham et al. |
| 5,443,478 A | 8/1995 | Purdy |
| 5,522,822 A | 6/1996 | Phelps et al. |
| 5,536,252 A | 7/1996 | Imran et al. |
| 5,582,619 A | 12/1996 | Ken |
| 5,603,722 A | 2/1997 | Phan et al. |
| 5,624,449 A | 4/1997 | Pham et al. |
| 5,624,461 A | 4/1997 | Mariant |
| 5,624,685 A | 4/1997 | Takahashi et al. |
| 5,639,277 A | 6/1997 | Mariant et al. |
| 5,645,559 A | 7/1997 | Hachtman et al. |
| 5,649,949 A | 7/1997 | Wallace et al. |
| 5,690,666 A | 11/1997 | Berenstein et al. |
| 5,690,667 A | 11/1997 | Gia |
| 5,693,088 A | 12/1997 | Lazarus |
| 5,702,361 A | 12/1997 | Evans et al. |
| 5,718,711 A | 2/1998 | Berenstein et al. |
| 5,723,004 A | 3/1998 | Dereume et al. |
| 5,733,294 A | 3/1998 | Forber et al. |
| 5,733,329 A | 3/1998 | Wallace et al. |
| 5,743,905 A | 4/1998 | Eder et al. |
| 5,749,891 A | 5/1998 | Ken et al. |
| 5,749,894 A | 5/1998 | Engelson |
| 5,766,160 A | 6/1998 | Samson et al. |
| 5,766,219 A | 6/1998 | Horton |
| 5,769,882 A | 6/1998 | Fogarty et al. |
| 5,769,884 A | 6/1998 | Solovay |
| 5,776,097 A | 7/1998 | Massoud |
| 5,785,679 A | 7/1998 | Abolfathi et al. |
| 5,795,331 A | 8/1998 | Cragg et al. |
| 5,800,453 A | 9/1998 | Gia |
| 5,800,455 A | 9/1998 | Palermo et al. |
| 5,826,587 A | 10/1998 | Berenstein et al. |
| 5,833,657 A | 11/1998 | Reinhardt et al. |
| 5,833,705 A | 11/1998 | Ken et al. |
| 5,836,966 A | 11/1998 | St. Germain |
| 5,853,418 A | 12/1998 | Ken et al. |
| 5,868,780 A | 2/1999 | Lashinski et al. |
| 5,873,907 A | 2/1999 | Frantzen |
| 5,888,546 A | 3/1999 | Ji et al. |
| 5,891,130 A | 4/1999 | Palermo et al. |
| 5,894,022 A | 4/1999 | Ji et al. |
| 5,911,731 A | 6/1999 | Pham et al. |
| 5,916,235 A | 6/1999 | Guglielmi |
| 5,922,019 A | 7/1999 | Hankh et al. |
| 5,925,059 A | 7/1999 | Palermo et al. |
| 5,928,260 A | 7/1999 | Chin et al. |
| 5,935,145 A | 8/1999 | Villar et al. |
| 5,935,148 A | 8/1999 | Villar et al. |
| 5,938,697 A | 8/1999 | Killion et al. |
| 5,941,249 A | 8/1999 | Maynard |
| 5,941,888 A | 8/1999 | Wallace et al. |
| 5,948,018 A | 9/1999 | Dereume et al. |
| 5,951,599 A | 9/1999 | McCrory |
| 5,957,948 A | 9/1999 | Mariant |
| 5,957,975 A | 9/1999 | Lafont et al. |
| 5,964,797 A | 10/1999 | Ho |
| 5,980,514 A | 11/1999 | Kupiecki et al. |
| 6,004,338 A | 12/1999 | Ken et al. |
| 6,007,573 A | 12/1999 | Wallace et al. |
| 6,013,084 A | 1/2000 | Ken et al. |
| 6,015,424 A | 1/2000 | Rosenbluth et al. |
| 6,015,433 A | 1/2000 | Roth |
| 6,017,977 A | 1/2000 | Evans et al. |
| 6,024,754 A | 2/2000 | Engelson |
| 6,024,765 A | 2/2000 | Wallace et al. |
| 6,027,526 A | 2/2000 | Limon et al. |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Villar et al. |
| 6,063,111 A | 5/2000 | Hieshima et al. |
| 6,071,298 A | 6/2000 | Lashinski et al. |
| 6,074,407 A | 6/2000 | Levine et al. |
| 6,086,610 A | 7/2000 | Duerig et al. |
| 6,093,199 A | 7/2000 | Brown et al. |
| 6,096,021 A | 8/2000 | Helm et al. |
| 6,096,034 A | 8/2000 | Kupiecki et al. |
| 6,096,175 A | 8/2000 | Roth |
| 6,099,546 A | 8/2000 | Gia |
| 6,099,559 A | 8/2000 | Nolting |
| 6,123,712 A | 9/2000 | Di Caprio et al. |
| 6,123,714 A | 9/2000 | Gia et al. |
| 6,136,011 A | 10/2000 | Stambaugh |
| 6,139,564 A | 10/2000 | Teoh |
| 6,140,452 A | 10/2000 | Felt et al. |
| 6,143,007 A | 11/2000 | Mariant et al. |
| 6,149,681 A | 11/2000 | Houser et al. |
| 6,159,165 A | 12/2000 | Ferrera et al. |
| 6,159,238 A | 12/2000 | Killion et al. |
| 6,165,193 A | 12/2000 | Greene et al. |
| 6,165,212 A | 12/2000 | Dereume et al. |
| 6,168,592 B1 | 1/2001 | Kupiecki et al. |
| 6,168,615 B1 | 1/2001 | Ken et al. |
| 6,168,622 B1 | 1/2001 | Mazzocchi |
| 6,187,027 B1 | 2/2001 | Mariant et al. |
| 6,190,406 B1 | 2/2001 | Duerig et al. |
| 6,193,728 B1 | 2/2001 | Ken et al. |
| 6,210,429 B1 | 4/2001 | Vardi et al. |
| 6,221,066 B1 | 4/2001 | Ferrera et al. |
| 6,231,586 B1 | 5/2001 | Mariant |
| 6,231,597 B1 | 5/2001 | Deem et al. |
| 6,238,403 B1 | 5/2001 | Greene et al. |
| 6,254,592 B1 | 7/2001 | Samson et al. |
| 6,258,115 B1 | 7/2001 | Dubrul |
| 6,258,117 B1 | 7/2001 | Camrud et al. |
| 6,270,523 B1 | 8/2001 | Herweck et al. |
| 6,273,910 B1 | 8/2001 | Limon |
| 6,273,911 B1 | 8/2001 | Cox et al. |
| 6,280,457 B1 | 8/2001 | Wallace et al. |
| 6,281,263 B1 | 8/2001 | Evans et al. |
| 6,287,318 B1 | 9/2001 | Villar et al. |

(56) References Cited

U.S. PATENT DOCUMENTS

| | | |
|---|---|---|
| 6,299,619 B1 | 10/2001 | Greene et al. |
| 6,306,177 B1 | 10/2001 | Felt et al. |
| 6,309,367 B1 | 10/2001 | Boock |
| 6,309,413 B1 | 10/2001 | Dereume et al. |
| 6,312,421 B1 | 11/2001 | Boock |
| 6,312,463 B1 | 11/2001 | Rourke et al. |
| 6,331,191 B1 | 12/2001 | Chobotov |
| 6,335,384 B1 | 1/2002 | Evans et al. |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,371,972 B1 | 4/2002 | Wallace et al. |
| 6,375,668 B1 | 4/2002 | Gifford et al. |
| 6,375,669 B1 | 4/2002 | Rosenbluth et al. |
| 6,379,373 B1 | 4/2002 | Sawhney et al. |
| 6,383,174 B1 | 5/2002 | Eder |
| 6,391,037 B1 | 5/2002 | Greenhalgh |
| 6,395,018 B1 | 5/2002 | Castaneda |
| 6,398,803 B1 | 6/2002 | Layne et al. |
| 6,406,490 B1 | 6/2002 | Roth |
| 6,409,721 B1 | 6/2002 | Wheelock et al. |
| 6,409,749 B1 | 6/2002 | Maynard |
| 6,416,543 B1 | 7/2002 | Hilaire et al. |
| 6,419,685 B2 | 7/2002 | Di Caprio et al. |
| 6,423,085 B1 | 7/2002 | Murayama et al. |
| 6,428,558 B1 | 8/2002 | Jones et al. |
| 6,432,128 B1 | 8/2002 | Wallace et al. |
| 6,454,738 B1 | 9/2002 | Tran et al. |
| 6,454,780 B1 * | 9/2002 | Wallace ........... A61B 17/12022 606/151 |
| 6,458,119 B1 | 10/2002 | Berenstein et al. |
| 6,463,317 B1 | 10/2002 | Kucharczyk et al. |
| 6,468,302 B2 | 10/2002 | Cox et al. |
| 6,471,672 B1 | 10/2002 | Brown et al. |
| 6,475,233 B2 | 11/2002 | Trozera |
| 6,475,236 B1 | 11/2002 | Roubin et al. |
| 6,485,509 B2 | 11/2002 | Killion et al. |
| 6,485,510 B1 | 11/2002 | Camrud et al. |
| 6,497,722 B1 | 12/2002 | Von Oepen et al. |
| 6,500,190 B2 | 12/2002 | Greene et al. |
| 6,506,201 B2 | 1/2003 | Di Caprio et al. |
| 6,506,204 B2 | 1/2003 | Mazzocchi |
| 6,511,468 B1 | 1/2003 | Cragg et al. |
| 6,511,505 B2 | 1/2003 | Cox et al. |
| 6,520,985 B1 | 2/2003 | Burpee et al. |
| 6,520,987 B1 | 2/2003 | Plante |
| 6,527,919 B1 | 3/2003 | Roth |
| 6,533,801 B2 | 3/2003 | Wallace et al. |
| 6,547,804 B2 | 4/2003 | Porter et al. |
| 6,551,305 B2 | 4/2003 | Ferrera et al. |
| 6,558,414 B2 | 5/2003 | Layne |
| 6,569,190 B2 | 5/2003 | Whalen et al. |
| 6,569,193 B1 | 5/2003 | Cox et al. |
| 6,579,305 B1 | 6/2003 | Lashinski |
| 6,579,314 B1 | 6/2003 | Lombardi et al. |
| 6,585,748 B1 | 7/2003 | Jeffree |
| 6,585,753 B2 | 7/2003 | Eder et al. |
| 6,585,758 B1 | 7/2003 | Chouinard et al. |
| 6,589,230 B2 | 7/2003 | Gia et al. |
| 6,599,316 B2 | 7/2003 | Vardi et al. |
| 6,602,261 B2 | 8/2003 | Greene et al. |
| 6,602,269 B2 | 8/2003 | Wallace et al. |
| 6,602,284 B2 | 8/2003 | Cox et al. |
| 6,603,994 B2 | 8/2003 | Wallace et al. |
| 6,605,056 B2 | 8/2003 | Eidenschink et al. |
| 6,605,101 B1 | 8/2003 | Schaefer et al. |
| 6,605,111 B2 | 8/2003 | Bose et al. |
| 6,613,074 B1 | 9/2003 | Mitelberg et al. |
| 6,616,617 B1 | 9/2003 | Ferrera et al. |
| 6,623,493 B2 | 9/2003 | Wallace et al. |
| 6,629,947 B1 | 10/2003 | Sahatjian et al. |
| 6,645,237 B2 | 11/2003 | Klumb et al. |
| 6,652,576 B1 | 11/2003 | Stalker |
| 6,656,214 B1 | 12/2003 | Fogarty et al. |
| 6,660,020 B2 | 12/2003 | Wallace et al. |
| 6,660,032 B2 | 12/2003 | Klumb et al. |
| 6,669,719 B2 | 12/2003 | Wallace et al. |
| 6,669,723 B2 | 12/2003 | Killion et al. |
| 6,673,103 B1 | 1/2004 | Golds et al. |
| 6,676,701 B2 | 1/2004 | Rourke et al. |
| 6,689,148 B2 | 2/2004 | Sawhney et al. |
| 6,699,277 B1 | 3/2004 | Freidberg et al. |
| 6,719,783 B2 | 4/2004 | Lentz et al. |
| 6,723,108 B1 | 4/2004 | Jones et al. |
| 6,746,468 B1 | 6/2004 | Sepetka et al. |
| 6,746,475 B1 | 6/2004 | Rivelli |
| 6,770,087 B2 | 8/2004 | Layne et al. |
| 6,780,196 B2 | 8/2004 | Chin et al. |
| 6,786,920 B2 | 9/2004 | Shannon et al. |
| 6,790,225 B1 | 9/2004 | Shannon et al. |
| 6,796,997 B1 | 9/2004 | Penn et al. |
| 6,802,851 B2 | 10/2004 | Jones et al. |
| 6,811,560 B2 | 11/2004 | Jones et al. |
| 6,814,754 B2 | 11/2004 | Greenhalgh |
| 6,818,018 B1 | 11/2004 | Sawhney |
| 6,833,003 B2 | 12/2004 | Jones et al. |
| 6,835,203 B1 | 12/2004 | Vardi et al. |
| 6,855,153 B2 | 2/2005 | Saadat |
| 6,855,154 B2 | 2/2005 | Abdel-Gawwad |
| 6,860,899 B1 | 3/2005 | Rivelli |
| 6,899,730 B1 | 5/2005 | Rivelli |
| 6,913,618 B2 | 7/2005 | Denardo et al. |
| 6,916,337 B2 | 7/2005 | Roth |
| 6,929,658 B1 | 8/2005 | Freidberg et al. |
| 6,958,061 B2 | 10/2005 | Truckai et al. |
| 6,962,602 B2 | 11/2005 | Vardi et al. |
| 6,964,657 B2 | 11/2005 | Cragg et al. |
| 6,969,401 B1 | 11/2005 | Marotta et al. |
| 6,979,344 B2 | 12/2005 | Jones et al. |
| 6,984,240 B1 | 1/2006 | Ken et al. |
| 6,994,721 B2 | 2/2006 | Israel |
| 7,001,422 B2 | 2/2006 | Escamilla et al. |
| 7,014,645 B2 | 3/2006 | Greene et al. |
| 7,029,486 B2 | 4/2006 | Schaefer et al. |
| 7,029,487 B2 | 4/2006 | Greene et al. |
| 7,033,374 B2 | 4/2006 | Schaefer et al. |
| 7,033,385 B2 | 4/2006 | Eder et al. |
| 7,037,327 B2 | 5/2006 | Salmon et al. |
| 7,037,330 B1 | 5/2006 | Rivelli et al. |
| 7,041,129 B2 | 5/2006 | Rourke et al. |
| 7,052,510 B1 | 5/2006 | Richter |
| 7,052,513 B2 | 5/2006 | Thompson |
| 7,060,091 B2 | 6/2006 | Killion et al. |
| 7,070,609 B2 | 7/2006 | West |
| 7,081,129 B2 | 7/2006 | Chobotov |
| 7,083,632 B2 | 8/2006 | Avellanet et al. |
| 7,083,640 B2 | 8/2006 | Lombardi et al. |
| 7,083,643 B2 | 8/2006 | Whalen et al. |
| 7,112,216 B2 | 9/2006 | Gregorich |
| 7,118,656 B2 | 10/2006 | Roth |
| 7,128,736 B1 | 10/2006 | Abrams et al. |
| 7,137,993 B2 | 11/2006 | Acosta et al. |
| 7,141,063 B2 | 11/2006 | White et al. |
| 7,147,655 B2 | 12/2006 | Chermoni |
| 7,147,659 B2 | 12/2006 | Jones |
| 7,147,660 B2 | 12/2006 | Chobotov et al. |
| 7,147,661 B2 | 12/2006 | Chobotov et al. |
| 7,153,323 B1 * | 12/2006 | Teoh ................ A61B 17/12022 623/1.23 |
| 7,156,871 B2 | 1/2007 | Jones et al. |
| 7,182,744 B2 | 2/2007 | Yamasaki et al. |
| 7,186,263 B2 | 3/2007 | Golds et al. |
| 7,195,636 B2 | 3/2007 | Avellanet et al. |
| 7,195,648 B2 | 3/2007 | Jones et al. |
| 7,201,762 B2 | 4/2007 | Greene et al. |
| 7,211,109 B2 | 5/2007 | Thompson |
| 7,220,270 B2 | 5/2007 | Sawhney et al. |
| 7,226,475 B2 | 6/2007 | Lenz et al. |
| 7,229,461 B2 | 6/2007 | Chin et al. |
| 7,231,260 B2 | 6/2007 | Wallace et al. |
| 7,232,461 B2 | 6/2007 | Ramer |
| 7,235,098 B2 | 6/2007 | Palmaz |

(56) References Cited

U.S. PATENT DOCUMENTS

| | | |
|---|---|---|
| 7,238,194 B2 | 7/2007 | Monstadt et al. |
| 7,241,301 B2 | 7/2007 | Thramann et al. |
| 7,241,308 B2 | 7/2007 | Andreas et al. |
| 7,244,261 B2 | 7/2007 | Lorenzo et al. |
| 7,247,159 B2 | 7/2007 | Lorenzo et al. |
| 7,288,112 B2 | 10/2007 | Denardo et al. |
| 7,294,123 B2 | 11/2007 | Jones et al. |
| 7,294,137 B2 | 11/2007 | Rivelli et al. |
| 7,294,146 B2 | 11/2007 | Chew et al. |
| 7,300,459 B2 | 11/2007 | Heuser |
| 7,300,661 B2 | 11/2007 | Henson et al. |
| 7,306,598 B2 | 12/2007 | Truckai et al. |
| 7,306,622 B2 | 12/2007 | Jones et al. |
| 7,306,624 B2 | 12/2007 | Yodfat et al. |
| 7,309,351 B2 | 12/2007 | Escamilla et al. |
| 7,309,352 B2 | 12/2007 | Eder et al. |
| 7,311,861 B2 | 12/2007 | Lanphere et al. |
| 7,323,005 B2 | 1/2008 | Wallace et al. |
| 7,326,225 B2 | 2/2008 | Ferrera et al. |
| 7,326,236 B2 | 2/2008 | Andreas et al. |
| 7,331,974 B2 | 2/2008 | Schaefer et al. |
| 7,338,511 B2 | 3/2008 | Mirigian et al. |
| 7,361,367 B2 | 4/2008 | Henson et al. |
| 7,374,568 B2 | 5/2008 | Whalen et al. |
| 7,384,426 B2 | 6/2008 | Wallace et al. |
| 7,402,169 B2 | 7/2008 | Killion et al. |
| 7,410,482 B2 | 8/2008 | Murphy et al. |
| 7,413,573 B2 | 8/2008 | Hartley et al. |
| 7,414,038 B2 | 8/2008 | Kinugasa et al. |
| 7,442,382 B2 | 10/2008 | Henson et al. |
| 7,449,236 B2 | 11/2008 | Lanphere et al. |
| 7,455,753 B2 | 11/2008 | Roth |
| 7,481,821 B2 | 1/2009 | Fogarty et al. |
| 7,483,558 B2 | 1/2009 | Greene et al. |
| 7,485,123 B2 | 2/2009 | Porter |
| 7,491,214 B2 | 2/2009 | Greene et al. |
| 7,491,226 B2 | 2/2009 | Palmaz et al. |
| 7,491,229 B2 | 2/2009 | Eder et al. |
| 7,520,893 B2 | 4/2009 | Rivelli |
| 7,537,609 B2 | 5/2009 | Davidson et al. |
| 7,547,321 B2 | 6/2009 | Silvestri et al. |
| 7,563,270 B2 | 7/2009 | Gumm |
| 7,569,066 B2 | 8/2009 | Gerberding et al. |
| 7,572,288 B2 | 8/2009 | Cox |
| 7,572,290 B2 | 8/2009 | Yodfat et al. |
| 7,588,597 B2 | 9/2009 | Frid |
| 7,588,780 B2 | 9/2009 | Buiser et al. |
| 7,588,825 B2 | 9/2009 | Bell et al. |
| 7,608,088 B2 | 10/2009 | Jones et al. |
| 7,611,530 B2 | 11/2009 | Pomeranz et al. |
| 7,615,071 B2 | 11/2009 | Chobotov |
| 7,621,928 B2 | 11/2009 | Thramann et al. |
| 7,641,680 B2 | 1/2010 | Palmaz et al. |
| 7,645,298 B2 | 1/2010 | Hartley et al. |
| 7,651,525 B2 | 1/2010 | Dolan |
| 7,666,220 B2 | 2/2010 | Evans et al. |
| 7,666,333 B2 | 2/2010 | Lanphere et al. |
| 7,691,124 B2 | 4/2010 | Balgobin |
| 7,695,484 B2 | 4/2010 | Wallace et al. |
| 7,695,488 B2 * | 4/2010 | Berenstein ....... A61B 17/12022 606/191 |
| 7,695,507 B2 | 4/2010 | Rivelli et al. |
| 7,695,509 B2 | 4/2010 | Rourke et al. |
| 7,704,274 B2 | 4/2010 | Boyle et al. |
| 7,708,754 B2 | 5/2010 | Balgobin et al. |
| 7,708,755 B2 | 5/2010 | Davis et al. |
| 7,713,264 B2 | 5/2010 | Murphy et al. |
| 7,736,671 B2 | 6/2010 | DiCarlo et al. |
| 7,744,610 B2 | 6/2010 | Hausen |
| 7,744,652 B2 | 6/2010 | Morsi |
| 7,749,242 B2 | 7/2010 | Tran et al. |
| 7,758,892 B1 | 7/2010 | Chen et al. |
| 7,763,011 B2 | 7/2010 | Ortiz et al. |
| 7,766,933 B2 | 8/2010 | Davis et al. |
| 7,766,955 B2 | 8/2010 | Vardi et al. |
| 7,769,603 B2 | 8/2010 | Jung et al. |
| 7,776,079 B2 | 8/2010 | Gumm |
| 7,780,645 B2 | 8/2010 | Jones |
| 7,780,719 B2 | 8/2010 | Killion et al. |
| 7,799,047 B2 | 9/2010 | Greene et al. |
| 7,799,052 B2 | 9/2010 | Balgobin et al. |
| 7,803,179 B2 | 9/2010 | Denison |
| 7,803,180 B2 | 9/2010 | Burpee et al. |
| 7,811,300 B2 | 10/2010 | Feller et al. |
| 7,811,305 B2 | 10/2010 | Balgobin et al. |
| 7,818,084 B2 | 10/2010 | Boyden et al. |
| 7,819,891 B2 | 10/2010 | Balgobin et al. |
| 7,819,892 B2 | 10/2010 | Balgobin et al. |
| 7,842,054 B2 | 11/2010 | Greene et al. |
| 7,842,377 B2 | 11/2010 | Lanphere et al. |
| 7,850,725 B2 | 12/2010 | Vardi et al. |
| 7,857,843 B2 | 12/2010 | Henderson |
| 7,862,608 B2 | 1/2011 | Hogendijk et al. |
| 7,875,044 B2 | 1/2011 | Feller et al. |
| 7,883,526 B2 | 2/2011 | Jones et al. |
| 7,892,273 B2 | 2/2011 | George et al. |
| 7,892,279 B2 | 2/2011 | Davidson et al. |
| 7,896,899 B2 | 3/2011 | Patterson et al. |
| 7,901,445 B2 | 3/2011 | Wallace et al. |
| 7,905,913 B2 | 3/2011 | Chew et al. |
| 7,914,574 B2 | 3/2011 | Schmid et al. |
| 7,914,639 B2 | 3/2011 | Layne et al. |
| 7,918,881 B2 | 4/2011 | Andreas et al. |
| 7,922,755 B2 | 4/2011 | Acosta et al. |
| 7,935,142 B2 | 5/2011 | Gregorich |
| 7,938,845 B2 | 5/2011 | Aganon et al. |
| 7,942,925 B2 | 5/2011 | Yodfat et al. |
| 7,947,071 B2 | 5/2011 | Schmid et al. |
| 7,955,382 B2 | 6/2011 | Flanagan et al. |
| 7,959,662 B2 | 6/2011 | Erbel et al. |
| 7,963,987 B2 | 6/2011 | Melsheimer et al. |
| 7,976,527 B2 | 7/2011 | Cragg et al. |
| 7,976,823 B2 | 7/2011 | Lanphere et al. |
| 7,985,238 B2 | 7/2011 | Balgobin et al. |
| 7,988,721 B2 | 8/2011 | Morris et al. |
| 7,993,364 B2 | 8/2011 | Morsi |
| 8,002,789 B2 | 8/2011 | Ramzipoor et al. |
| 8,003,180 B2 | 8/2011 | Goffena et al. |
| 8,007,529 B2 | 8/2011 | Yan |
| 8,012,192 B2 | 9/2011 | Eidenschink et al. |
| 8,012,197 B2 | 9/2011 | Bashiri et al. |
| 8,016,853 B2 | 9/2011 | Griffen et al. |
| 8,016,870 B2 | 9/2011 | Chew et al. |
| 8,016,871 B2 | 9/2011 | Chew et al. |
| 8,016,876 B2 | 9/2011 | Gregorich et al. |
| 8,016,878 B2 | 9/2011 | Meyer et al. |
| 8,019,413 B2 | 9/2011 | Ferren et al. |
| 8,021,416 B2 | 9/2011 | Abrams |
| 8,024,036 B2 | 9/2011 | Ferren et al. |
| 8,034,073 B2 | 10/2011 | Davis et al. |
| 8,038,706 B2 | 10/2011 | Eidenschink et al. |
| 8,038,708 B2 | 10/2011 | Case et al. |
| 8,048,140 B2 | 11/2011 | Purdy |
| 8,052,736 B2 | 11/2011 | Doig et al. |
| 8,057,495 B2 | 11/2011 | Pal et al. |
| 8,062,379 B2 | 11/2011 | Morsi |
| 8,066,036 B2 | 11/2011 | Monetti et al. |
| 8,067,071 B2 | 11/2011 | Farnsworth et al. |
| 8,070,792 B2 | 12/2011 | Gregorich et al. |
| 8,075,585 B2 | 12/2011 | Lee et al. |
| 8,095,382 B2 | 1/2012 | Boyden et al. |
| 8,100,960 B2 | 1/2012 | Bruszewski |
| 8,133,256 B2 | 3/2012 | Wilson et al. |
| 8,142,456 B2 | 3/2012 | Rosqueta et al. |
| 8,147,534 B2 | 4/2012 | Berez et al. |
| 8,147,537 B2 | 4/2012 | Boyden et al. |
| 8,163,003 B2 | 4/2012 | Boyden et al. |
| 8,172,862 B2 | 5/2012 | Wallace et al. |
| 8,172,895 B2 | 5/2012 | Anderson et al. |
| 8,187,315 B1 | 5/2012 | Clauson et al. |
| 8,202,292 B2 | 6/2012 | Kellett |
| 8,211,141 B2 | 7/2012 | Davis et al. |
| 8,211,160 B2 | 7/2012 | Garrison et al. |
| 8,221,447 B2 | 7/2012 | Solar et al. |

(56) References Cited

U.S. PATENT DOCUMENTS

| | | |
|---|---|---|
| 8,226,660 B2 | 7/2012 | Teoh et al. |
| 8,226,706 B2 | 7/2012 | Hartley et al. |
| 8,236,042 B2 | 8/2012 | Berez et al. |
| 8,246,672 B2 | 8/2012 | Osborne |
| 8,252,040 B2 | 8/2012 | Cox |
| 8,257,421 B2 | 9/2012 | Berez et al. |
| 8,257,430 B2 | 9/2012 | Covalin et al. |
| 8,257,431 B2 | 9/2012 | Henderson et al. |
| 8,262,607 B2 | 9/2012 | Porter |
| 8,262,686 B2 | 9/2012 | Fogarty et al. |
| 8,267,923 B2 | 9/2012 | Murphy et al. |
| 8,267,955 B2 | 9/2012 | Patterson et al. |
| 8,267,985 B2 | 9/2012 | Garcia et al. |
| 8,267,986 B2 | 9/2012 | Berez et al. |
| 8,273,100 B2 | 9/2012 | Martinez |
| 8,273,101 B2 | 9/2012 | Garcia et al. |
| 8,277,500 B2 | 10/2012 | Schmid et al. |
| 8,282,679 B2 | 10/2012 | Denison |
| 8,292,914 B2 | 10/2012 | Morsi |
| 8,292,944 B2 | 10/2012 | Schmid et al. |
| 8,308,751 B2 | 11/2012 | Gerberding |
| 8,313,504 B2 | 11/2012 | Do et al. |
| 8,323,306 B2 | 12/2012 | Schaefer et al. |
| 8,328,860 B2 | 12/2012 | Strauss et al. |
| 8,353,943 B2 | 1/2013 | Kuppurathanam et al. |
| 8,357,178 B2 | 1/2013 | Grandfield et al. |
| 8,357,179 B2 | 1/2013 | Grandfield et al. |
| 8,357,180 B2 | 1/2013 | Feller et al. |
| 8,361,104 B2 | 1/2013 | Jones et al. |
| 8,361,106 B2 | 1/2013 | Solar et al. |
| 8,372,062 B2 | 2/2013 | Murphy et al. |
| 8,372,114 B2 | 2/2013 | Hines |
| 8,377,091 B2 | 2/2013 | Cruise et al. |
| 8,377,112 B2 | 2/2013 | Griffin et al. |
| 8,377,241 B2 | 2/2013 | Farnsworth et al. |
| 8,382,825 B2 | 2/2013 | Garcia et al. |
| 8,388,650 B2 | 3/2013 | Gerberding et al. |
| 8,388,677 B2 | 3/2013 | Herrmann |
| 8,394,136 B2 | 3/2013 | Hartley et al. |
| 8,398,670 B2 | 3/2013 | Amplatz et al. |
| 8,398,701 B2 | 3/2013 | Berez et al. |
| 8,409,267 B2 | 4/2013 | Berez et al. |
| 8,409,269 B2 | 4/2013 | Berez et al. |
| 8,414,637 B2 | 4/2013 | Chouinard |
| 8,419,787 B2 | 4/2013 | Yodfat et al. |
| 8,425,541 B2 | 4/2013 | Masters et al. |
| 8,425,542 B2 | 4/2013 | Moftakhar et al. |
| 8,425,548 B2 | 4/2013 | Connor |
| 8,430,922 B2 | 4/2013 | Jung et al. |
| 8,439,942 B2 | 5/2013 | Moran et al. |
| 8,444,667 B2 | 5/2013 | Porter |
| 8,444,668 B2 | 5/2013 | Jones et al. |
| 8,444,686 B2 | 5/2013 | Holman et al. |
| 8,449,532 B2 | 5/2013 | Murphy et al. |
| 8,449,592 B2 | 5/2013 | Wilson et al. |
| 8,454,649 B2 | 6/2013 | Cragg et al. |
| 8,460,240 B2 | 6/2013 | Towler |
| 8,470,013 B2 | 6/2013 | Duggal et al. |
| 8,470,035 B2 | 6/2013 | Cruise et al. |
| 8,473,030 B2 | 6/2013 | Greenan et al. |
| 8,475,517 B2 | 7/2013 | Jung et al. |
| 8,478,437 B2 | 7/2013 | Boyden et al. |
| 8,480,727 B2 | 7/2013 | Clarke |
| 8,486,101 B2 | 7/2013 | Tran et al. |
| 8,491,459 B2 | 7/2013 | Yun |
| 8,491,646 B2 | 7/2013 | Schreck |
| 8,500,788 B2 | 8/2013 | Berez et al. |
| 8,506,618 B2 | 8/2013 | Chouinard et al. |
| 8,506,619 B2 | 8/2013 | Ortiz et al. |
| 8,512,219 B2 | 8/2013 | Ferren et al. |
| 8,512,395 B2 | 8/2013 | Meyer et al. |
| 8,523,934 B2 | 9/2013 | Purdy |
| 8,529,556 B2 | 9/2013 | Murphy et al. |
| 8,529,596 B2 | 9/2013 | Grandfield et al. |
| 8,529,614 B2 | 9/2013 | Berez et al. |
| 8,529,616 B2 | 9/2013 | Boyle et al. |
| 8,529,619 B2 | 9/2013 | Abrams |
| 8,535,367 B2 | 9/2013 | Kim et al. |
| 8,535,590 B2 | 9/2013 | Milner et al. |
| 8,550,344 B2 | 10/2013 | Jung et al. |
| 8,551,155 B2 | 10/2013 | Jung et al. |
| 8,556,953 B2 | 10/2013 | Berez et al. |
| 8,562,636 B2 | 10/2013 | Fogarty et al. |
| 8,562,667 B2 | 10/2013 | Cox |
| 8,577,693 B2 | 11/2013 | Jung et al. |
| 8,597,320 B2 | 12/2013 | Sepetka et al. |
| 8,597,321 B2 | 12/2013 | Monstadt et al. |
| 8,597,323 B1 | 12/2013 | Plaza et al. |
| 8,597,342 B2 | 12/2013 | McKinsey et al. |
| 8,597,745 B2 | 12/2013 | Farnsworth et al. |
| 8,617,132 B2 | 12/2013 | Golzarian et al. |
| 8,623,071 B2 | 1/2014 | Lundkvist et al. |
| 8,636,760 B2 | 1/2014 | Garcia et al. |
| 8,647,377 B2 | 2/2014 | Kim et al. |
| 8,657,865 B2 | 2/2014 | Gumm |
| 8,663,309 B2 | 3/2014 | Chobotov |
| 8,668,716 B2 | 3/2014 | Hines |
| 8,668,717 B2 | 3/2014 | Hines |
| 8,671,815 B2 | 3/2014 | Hancock et al. |
| 8,696,701 B2 | 4/2014 | Becking et al. |
| 8,709,062 B2 | 4/2014 | Dusbabek et al. |
| 8,709,065 B2 | 4/2014 | Chobotov |
| 8,715,312 B2 | 5/2014 | Burke et al. |
| 8,715,317 B1 | 5/2014 | Janardhan et al. |
| 8,715,336 B2 | 5/2014 | Chu et al. |
| 8,721,706 B2 | 5/2014 | Jung et al. |
| 8,728,094 B2 | 5/2014 | Roorda et al. |
| 8,728,145 B2 | 5/2014 | Chuter et al. |
| 8,728,146 B2 | 5/2014 | Gregorich et al. |
| 8,734,502 B2 | 5/2014 | Orr |
| 8,740,966 B2 | 6/2014 | Brocker et al. |
| 8,747,430 B2 | 6/2014 | Porter |
| 8,747,432 B1 | 6/2014 | Janardhan et al. |
| 8,747,455 B2 | 6/2014 | Greenberg |
| 8,747,597 B2 | 6/2014 | Rosqueta et al. |
| 8,753,371 B1 | 6/2014 | Janardhan et al. |
| 8,764,788 B2 | 7/2014 | Martinez |
| 8,769,796 B2 | 7/2014 | Bourang et al. |
| 8,771,294 B2 | 7/2014 | Sepetka et al. |
| 8,771,341 B2 | 7/2014 | Strauss et al. |
| 8,771,342 B2 | 7/2014 | Vardi |
| 8,784,446 B1 | 7/2014 | Janardhan et al. |
| 8,784,475 B2 | 7/2014 | Martinson et al. |
| 8,784,477 B2 | 7/2014 | Bregulla et al. |
| 8,795,345 B2 | 8/2014 | Grandfield et al. |
| 8,795,346 B2 | 8/2014 | Alkhatib |
| 8,795,347 B2 | 8/2014 | Bourang et al. |
| 8,801,772 B2 | 8/2014 | Shobayashi et al. |
| 8,808,347 B2 | 8/2014 | Bourang et al. |
| 8,808,361 B2 | 8/2014 | Strauss et al. |
| 8,813,625 B1 | 8/2014 | Janardhan et al. |
| 8,821,564 B2 | 9/2014 | Schreck et al. |
| 8,828,071 B2 | 9/2014 | Bourang et al. |
| 8,840,867 B2 | 9/2014 | Sophie et al. |
| 8,845,679 B1 | 9/2014 | Janardhan et al. |
| 8,974,512 B2 | 3/2015 | Aboytes et al. |
| 8,998,947 B2 | 4/2015 | Aboytes et al. |
| 9,393,022 B2 | 7/2016 | Becking et al. |
| 9,492,174 B2 | 11/2016 | Hewitt et al. |
| 9,629,635 B2 | 4/2017 | Hewitt et al. |
| 9,713,475 B2 | 7/2017 | Divino et al. |
| 9,763,815 B2 | 9/2017 | Strauss et al. |
| 9,801,744 B2 | 10/2017 | Berez et al. |
| 9,844,382 B2 | 12/2017 | Aboytes et al. |
| 9,918,720 B2 | 3/2018 | Marchand et al. |
| 2001/0000797 A1 | 5/2001 | Mazzocchi |
| 2001/0001835 A1 | 5/2001 | Greene et al. |
| 2001/0009996 A1 | 7/2001 | Ferrera et al. |
| 2001/0016766 A1 | 8/2001 | Vardi et al. |
| 2001/0037137 A1 | 11/2001 | Vardi et al. |
| 2001/0056281 A1 | 12/2001 | Wallace et al. |
| 2002/0002382 A1 | 1/2002 | Wallace et al. |
| 2002/0018752 A1 | 2/2002 | Krall et al. |
| 2002/0042628 A1 | 4/2002 | Chin et al. |

(56) References Cited

U.S. PATENT DOCUMENTS

| | | |
|---|---|---|
| 2002/0058962 A1 | 5/2002 | Wallace et al. |
| 2002/0082620 A1 | 6/2002 | Lee |
| 2002/0082636 A1 | 6/2002 | Sawhney et al. |
| 2002/0087077 A1 | 7/2002 | Wallace et al. |
| 2002/0107534 A1 | 8/2002 | Schaefer et al. |
| 2002/0116047 A1 | 8/2002 | Vardi et al. |
| 2002/0120276 A1 | 8/2002 | Greene et al. |
| 2002/0128671 A1 | 9/2002 | Wallace et al. |
| 2002/0133190 A1 | 9/2002 | Horton et al. |
| 2002/0143348 A1 | 10/2002 | Wallace et al. |
| 2002/0151926 A1 | 10/2002 | Wallace et al. |
| 2002/0151965 A1 | 10/2002 | Roth |
| 2002/0156516 A1 | 10/2002 | Vardi et al. |
| 2002/0169473 A1 | 11/2002 | Sepetka et al. |
| 2002/0177855 A1 | 11/2002 | Greene et al. |
| 2003/0014007 A1 | 1/2003 | Eidenschink et al. |
| 2003/0014075 A1 | 1/2003 | Rosenbluth et al. |
| 2003/0018294 A1 | 1/2003 | Cox |
| 2003/0018356 A1 | 1/2003 | Schaefer et al. |
| 2003/0065375 A1 | 4/2003 | Eskuri |
| 2003/0074049 A1 | 4/2003 | Hoganson et al. |
| 2003/0074056 A1 | 4/2003 | Killion et al. |
| 2003/0083676 A1 | 5/2003 | Wallace |
| 2003/0083737 A1 | 5/2003 | Greene et al. |
| 2003/0088311 A1 | 5/2003 | Greene et al. |
| 2003/0093097 A1 | 5/2003 | Avellanet et al. |
| 2003/0093108 A1 | 5/2003 | Avellanet et al. |
| 2003/0093111 A1 | 5/2003 | Ken et al. |
| 2003/0100945 A1 | 5/2003 | Yodfat et al. |
| 2003/0109917 A1 | 6/2003 | Rudin et al. |
| 2003/0130689 A1 | 7/2003 | Wallace et al. |
| 2003/0135264 A1 | 7/2003 | Whalen et al. |
| 2003/0139802 A1 | 7/2003 | Wulfman et al. |
| 2003/0159920 A1 | 8/2003 | Roth |
| 2003/0181927 A1 | 9/2003 | Wallace |
| 2003/0187473 A1 | 10/2003 | Berenstein et al. |
| 2003/0195553 A1 | 10/2003 | Wallace et al. |
| 2003/0195606 A1 | 10/2003 | Davidson et al. |
| 2003/0223955 A1 | 12/2003 | Whalen et al. |
| 2004/0002752 A1 | 1/2004 | Griffin et al. |
| 2004/0015227 A1 | 1/2004 | Vardi et al. |
| 2004/0045554 A1 | 3/2004 | Schaefer et al. |
| 2004/0059370 A1 | 3/2004 | Greene et al. |
| 2004/0091543 A1 | 5/2004 | Bell et al. |
| 2004/0093014 A1 | 5/2004 | Ho et al. |
| 2004/0098027 A1 | 5/2004 | Teoh et al. |
| 2004/0098028 A1 | 5/2004 | Martinez |
| 2004/0111112 A1 | 6/2004 | Hoffmann |
| 2004/0111142 A1 | 6/2004 | Rourke et al. |
| 2004/0115164 A1 | 6/2004 | Pierce et al. |
| 2004/0158282 A1 | 8/2004 | Jones et al. |
| 2004/0161451 A1 | 8/2004 | Pierce et al. |
| 2004/0181253 A1 | 9/2004 | Sepetka et al. |
| 2004/0186551 A1 | 9/2004 | Kao et al. |
| 2004/0193246 A1 | 9/2004 | Ferrera |
| 2004/0210249 A1 | 10/2004 | Fogarty et al. |
| 2004/0215331 A1 | 10/2004 | Chew et al. |
| 2004/0220663 A1 | 11/2004 | Rivelli, Jr. |
| 2004/0243168 A1 | 12/2004 | Ferrera et al. |
| 2004/0243216 A1 | 12/2004 | Gregorich |
| 2004/0249435 A1 | 12/2004 | Andreas et al. |
| 2004/0249439 A1 | 12/2004 | Richter et al. |
| 2004/0260384 A1 | 12/2004 | Allen |
| 2005/0004660 A1 | 1/2005 | Rosenbluth et al. |
| 2005/0010281 A1 | 1/2005 | Yodfat et al. |
| 2005/0015110 A1 | 1/2005 | Fogarty et al. |
| 2005/0021077 A1 | 1/2005 | Chin et al. |
| 2005/0033349 A1 | 2/2005 | Jones et al. |
| 2005/0033350 A1 | 2/2005 | Ken et al. |
| 2005/0065592 A1 | 3/2005 | Holzer |
| 2005/0075405 A1 | 4/2005 | Wilson et al. |
| 2005/0080445 A1 | 4/2005 | Sawhney et al. |
| 2005/0090888 A1 | 4/2005 | Hines et al. |
| 2005/0095428 A1 | 5/2005 | Dicarlo et al. |
| 2005/0096728 A1 | 5/2005 | Ramer |
| 2005/0107863 A1 | 5/2005 | Brown |
| 2005/0119687 A1 | 6/2005 | Dacey et al. |
| 2005/0131516 A1 | 6/2005 | Greenhalgh |
| 2005/0131518 A1 | 6/2005 | Hartley et al. |
| 2005/0133046 A1 | 6/2005 | Becker et al. |
| 2005/0149159 A1 | 7/2005 | Andreas et al. |
| 2005/0149164 A1 | 7/2005 | Rivelli |
| 2005/0171572 A1 | 8/2005 | Martinez |
| 2005/0171597 A1 | 8/2005 | Boatman et al. |
| 2005/0192618 A1 | 9/2005 | Porter |
| 2005/0192621 A1 | 9/2005 | Wallace et al. |
| 2005/0192661 A1 | 9/2005 | Griffen et al. |
| 2005/0209674 A1 | 9/2005 | Kutscher et al. |
| 2005/0228434 A1 | 10/2005 | Amplatz et al. |
| 2005/0251247 A1 | 11/2005 | Roth |
| 2005/0267510 A1 | 12/2005 | Razack |
| 2005/0267568 A1 | 12/2005 | Berez et al. |
| 2005/0277978 A1 | 12/2005 | Greenhalgh |
| 2005/0283220 A1 | 12/2005 | Gobran et al. |
| 2006/0036045 A1 | 2/2006 | Wilson et al. |
| 2006/0036281 A1 | 2/2006 | Patterson et al. |
| 2006/0052816 A1* | 3/2006 | Bates .............. A61B 17/12013 606/200 |
| 2006/0058834 A1 | 3/2006 | Do et al. |
| 2006/0079923 A1 | 4/2006 | Chhabra et al. |
| 2006/0085061 A1 | 4/2006 | Vardi et al. |
| 2006/0116709 A1* | 6/2006 | Sepetka ............ A61B 17/12022 606/200 |
| 2006/0116712 A1 | 6/2006 | Sepetka et al. |
| 2006/0116713 A1 | 6/2006 | Sepetka et al. |
| 2006/0136033 A1 | 6/2006 | Hermann et al. |
| 2006/0149299 A1 | 7/2006 | Greene et al. |
| 2006/0155323 A1* | 7/2006 | Porter .............. A61B 17/12022 606/200 |
| 2006/0167494 A1* | 7/2006 | Suddaby ............ A61B 17/0057 606/213 |
| 2006/0184195 A1 | 8/2006 | Schaefer et al. |
| 2006/0184196 A1 | 8/2006 | Schaefer et al. |
| 2006/0206196 A1 | 9/2006 | Porter |
| 2006/0206200 A1 | 9/2006 | Garcia et al. |
| 2006/0206201 A1 | 9/2006 | Garcia et al. |
| 2006/0224230 A1 | 10/2006 | Rivelli et al. |
| 2006/0229714 A1 | 10/2006 | Lombardi et al. |
| 2006/0235464 A1 | 10/2006 | Avellanet et al. |
| 2006/0241690 A1 | 10/2006 | Amplatz et al. |
| 2006/0241740 A1 | 10/2006 | Vardi et al. |
| 2006/0251695 A1 | 11/2006 | Henson et al. |
| 2006/0251700 A1 | 11/2006 | Henson et al. |
| 2006/0271149 A1 | 11/2006 | Berez et al. |
| 2006/0271153 A1 | 11/2006 | Garcia et al. |
| 2006/0276831 A1 | 12/2006 | Porter et al. |
| 2006/0292206 A1 | 12/2006 | Kim et al. |
| 2007/0016233 A1 | 1/2007 | Ferrera et al. |
| 2007/0021816 A1 | 1/2007 | Rudin |
| 2007/0031584 A1 | 2/2007 | Roth |
| 2007/0032855 A1 | 2/2007 | Davidson et al. |
| 2007/0050008 A1 | 3/2007 | Kim et al. |
| 2007/0055355 A1 | 3/2007 | Kim et al. |
| 2007/0060994 A1 | 3/2007 | Gobran et al. |
| 2007/0061005 A1 | 3/2007 | Kim et al. |
| 2007/0067015 A1 | 3/2007 | Jones et al. |
| 2007/0083257 A1 | 4/2007 | Pal et al. |
| 2007/0088368 A1 | 4/2007 | Acosta et al. |
| 2007/0088387 A1 | 4/2007 | Eskridge et al. |
| 2007/0100301 A1 | 5/2007 | Gumm |
| 2007/0106311 A1 | 5/2007 | Wallace et al. |
| 2007/0129786 A1 | 6/2007 | Beach et al. |
| 2007/0135907 A1 | 6/2007 | Wilson et al. |
| 2007/0150041 A1 | 6/2007 | Evans et al. |
| 2007/0150045 A1 | 6/2007 | Ferrera |
| 2007/0167747 A1 | 7/2007 | Borgert et al. |
| 2007/0175536 A1 | 8/2007 | Monetti et al. |
| 2007/0176333 A1 | 8/2007 | Greene et al. |
| 2007/0207186 A1 | 9/2007 | Scanlon et al. |
| 2007/0219578 A1 | 9/2007 | Solar et al. |
| 2007/0219610 A1 | 9/2007 | Israel |
| 2007/0219619 A1 | 9/2007 | Dieck et al. |
| 2007/0225794 A1 | 9/2007 | Thramann et al. |
| 2007/0239261 A1 | 10/2007 | Bose et al. |

(56) References Cited

U.S. PATENT DOCUMENTS

| | | |
|---|---|---|
| 2007/0265656 A1 | 11/2007 | Amplatz et al. |
| 2007/0299464 A1 | 12/2007 | Cruise et al. |
| 2007/0299498 A1 | 12/2007 | Perez et al. |
| 2008/0004653 A1 | 1/2008 | Sherman et al. |
| 2008/0004692 A1 | 1/2008 | Henson et al. |
| 2008/0031919 A1 | 2/2008 | Henson et al. |
| 2008/0033341 A1 | 2/2008 | Grad |
| 2008/0033366 A1 | 2/2008 | Matson et al. |
| 2008/0039933 A1 | 2/2008 | Yodfat et al. |
| 2008/0097495 A1 | 4/2008 | Feller Lll et al. |
| 2008/0103585 A1 | 5/2008 | Monstadt et al. |
| 2008/0114391 A1 | 5/2008 | Dieck et al. |
| 2008/0114436 A1 | 5/2008 | Dieck et al. |
| 2008/0125852 A1 | 5/2008 | Garrison et al. |
| 2008/0147100 A1 | 6/2008 | Wallace |
| 2008/0152686 A1 | 6/2008 | Henson et al. |
| 2008/0161936 A1 | 7/2008 | Feller et al. |
| 2008/0195137 A1 | 8/2008 | Alleyne et al. |
| 2008/0200945 A1 | 8/2008 | Amplatz et al. |
| 2008/0221600 A1 | 9/2008 | Dieck et al. |
| 2008/0249608 A1 | 10/2008 | Dave |
| 2008/0281350 A1 | 11/2008 | Sepetka et al. |
| 2008/0312732 A1 | 12/2008 | Hartley et al. |
| 2008/0319521 A1 | 12/2008 | Norris et al. |
| 2008/0319525 A1 | 12/2008 | Tieu et al. |
| 2008/0319533 A1 | 12/2008 | Lehe |
| 2009/0062834 A1 | 3/2009 | Moftakhar et al. |
| 2009/0062841 A1 | 3/2009 | Amplatz et al. |
| 2009/0069880 A1 | 3/2009 | Vonderwalde et al. |
| 2009/0082846 A1 | 3/2009 | Chobotov |
| 2009/0088832 A1 | 4/2009 | Chew et al. |
| 2009/0105748 A1 | 4/2009 | Fogarty et al. |
| 2009/0112249 A1 | 4/2009 | Miles et al. |
| 2009/0112250 A1 | 4/2009 | Greene, Jr. et al. |
| 2009/0118761 A1 | 5/2009 | Masters et al. |
| 2009/0125053 A1 | 5/2009 | Ferrera et al. |
| 2009/0132028 A1 | 5/2009 | Vardi et al. |
| 2009/0149864 A1 | 6/2009 | Porter |
| 2009/0164013 A1 | 6/2009 | Cruise et al. |
| 2009/0171437 A1 | 7/2009 | Brocker et al. |
| 2009/0177268 A1 | 7/2009 | Lundkvist et al. |
| 2009/0192536 A1 | 7/2009 | Berez et al. |
| 2009/0198318 A1 | 8/2009 | Berez et al. |
| 2009/0227976 A1 | 9/2009 | Calabria et al. |
| 2009/0228029 A1 | 9/2009 | Lee |
| 2009/0232869 A1 | 9/2009 | Greene et al. |
| 2009/0248135 A1 | 10/2009 | Bruszewski et al. |
| 2009/0254111 A1 | 10/2009 | Monstadt et al. |
| 2009/0270970 A1 | 10/2009 | Yodfat et al. |
| 2009/0270974 A1 | 10/2009 | Berez et al. |
| 2009/0275974 A1 | 11/2009 | Marchand et al. |
| 2009/0287241 A1 | 11/2009 | Berez et al. |
| 2009/0287288 A1 | 11/2009 | Berez et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0292348 A1 | 11/2009 | Berez et al. |
| 2009/0297582 A1 | 12/2009 | Meyer et al. |
| 2009/0299326 A1 | 12/2009 | Morsi |
| 2009/0299390 A1 | 12/2009 | Dehnad |
| 2009/0299448 A1 | 12/2009 | Timko et al. |
| 2009/0318941 A1 | 12/2009 | Sepetka et al. |
| 2009/0318947 A1 | 12/2009 | Garcia et al. |
| 2009/0318948 A1 | 12/2009 | Linder et al. |
| 2009/0318949 A1 | 12/2009 | Ganpath et al. |
| 2009/0319017 A1 | 12/2009 | Berez et al. |
| 2009/0319023 A1 | 12/2009 | Hildebrand et al. |
| 2010/0004671 A1 | 1/2010 | Gerberding et al. |
| 2010/0004726 A1 | 1/2010 | Hancock et al. |
| 2010/0010624 A1 | 1/2010 | Berez et al. |
| 2010/0016833 A1 | 1/2010 | Ogle et al. |
| 2010/0023105 A1 | 1/2010 | Levy et al. |
| 2010/0036412 A1 | 2/2010 | Porter et al. |
| 2010/0042200 A1 | 2/2010 | Richter et al. |
| 2010/0063472 A1 | 3/2010 | Becker et al. |
| 2010/0063531 A1 | 3/2010 | Rudakov et al. |
| 2010/0069948 A1 | 3/2010 | Veznedaroglu et al. |
| 2010/0082091 A1 | 4/2010 | Berez et al. |
| 2010/0094335 A1 | 4/2010 | Gerberding et al. |
| 2010/0106240 A1 | 4/2010 | Duggal et al. |
| 2010/0114302 A1 | 5/2010 | Tzafriri et al. |
| 2010/0131002 A1 | 5/2010 | Connor et al. |
| 2010/0152828 A1 | 6/2010 | Pakbaz et al. |
| 2010/0152834 A1 | 6/2010 | Hannes et al. |
| 2010/0152837 A1 | 6/2010 | Lundkvist et al. |
| 2010/0168781 A1 | 7/2010 | Berenstein et al. |
| 2010/0174301 A1 | 7/2010 | Wallace et al. |
| 2010/0179640 A1 | 7/2010 | Reith |
| 2010/0179645 A1 | 7/2010 | Chen et al. |
| 2010/0198250 A1 | 8/2010 | Ricci et al. |
| 2010/0198334 A1 | 8/2010 | Yodfat et al. |
| 2010/0222804 A1 | 9/2010 | Murphy et al. |
| 2010/0222864 A1 | 9/2010 | Rivelli et al. |
| 2010/0274276 A1 | 10/2010 | Chow et al. |
| 2010/0274346 A1 | 10/2010 | Chouinard et al. |
| 2010/0280452 A1 | 11/2010 | Chen et al. |
| 2010/0305681 A1 | 12/2010 | Gumm |
| 2010/0312326 A1 | 12/2010 | Chuter et al. |
| 2010/0318173 A1 | 12/2010 | Kolandaivelu et al. |
| 2010/0324660 A1 | 12/2010 | Denison |
| 2011/0004294 A1 | 1/2011 | Bialas |
| 2011/0005062 A1 | 1/2011 | Greene et al. |
| 2011/0009940 A1 | 1/2011 | Grandfield et al. |
| 2011/0009941 A1 | 1/2011 | Grandfield et al. |
| 2011/0009950 A1 | 1/2011 | Grandfield et al. |
| 2011/0022149 A1 | 1/2011 | Cox et al. |
| 2011/0039967 A1 | 2/2011 | Wilson et al. |
| 2011/0046658 A1 | 2/2011 | Connor et al. |
| 2011/0046716 A1 | 2/2011 | Parkinson et al. |
| 2011/0054511 A1 | 3/2011 | Henson et al. |
| 2011/0054589 A1 | 3/2011 | Bashiri et al. |
| 2011/0066221 A1 | 3/2011 | White et al. |
| 2011/0082427 A1 | 4/2011 | Golzarian et al. |
| 2011/0082491 A1 | 4/2011 | Sepetka et al. |
| 2011/0082533 A1 | 4/2011 | Vardi et al. |
| 2011/0089592 A1 | 4/2011 | Farnsworth et al. |
| 2011/0092997 A1 | 4/2011 | Kang |
| 2011/0098814 A1 | 4/2011 | Monstadt et al. |
| 2011/0118777 A1 | 5/2011 | Patterson et al. |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0144686 A1 | 6/2011 | Wilson et al. |
| 2011/0144740 A1 | 6/2011 | Molaei et al. |
| 2011/0152993 A1 | 6/2011 | Marchand et al. |
| 2011/0152996 A1 | 6/2011 | Acosta et al. |
| 2011/0152998 A1 | 6/2011 | Berez et al. |
| 2011/0166588 A1 | 7/2011 | Connor et al. |
| 2011/0166592 A1 | 7/2011 | Garcia et al. |
| 2011/0166641 A1 | 7/2011 | Bales et al. |
| 2011/0182998 A1 | 7/2011 | Reb et al. |
| 2011/0184451 A1 | 7/2011 | Sahl |
| 2011/0184452 A1 | 7/2011 | Huynh et al. |
| 2011/0184453 A1 | 7/2011 | Levy et al. |
| 2011/0184454 A1 | 7/2011 | Barry et al. |
| 2011/0184455 A1 | 7/2011 | Keeley et al. |
| 2011/0184456 A1 | 7/2011 | Grandfield et al. |
| 2011/0196413 A1 | 8/2011 | Wallace et al. |
| 2011/0202085 A1 | 8/2011 | Loganathan et al. |
| 2011/0208227 A1 | 8/2011 | Becking |
| 2011/0213406 A1 | 9/2011 | Aganon et al. |
| 2011/0224776 A1 | 9/2011 | Sepetka et al. |
| 2011/0230957 A1 | 9/2011 | Bonsignore et al. |
| 2011/0238105 A1 | 9/2011 | Gelbart et al. |
| 2011/0245862 A1 | 10/2011 | Dieck et al. |
| 2011/0245863 A1 | 10/2011 | Martinez |
| 2011/0264192 A1 | 10/2011 | Hartley et al. |
| 2011/0265943 A1 | 11/2011 | Rosqueta et al. |
| 2011/0276071 A1 | 11/2011 | Connor et al. |
| 2011/0282378 A1 | 11/2011 | Murphy et al. |
| 2011/0286925 A1 | 11/2011 | Lerouge et al. |
| 2011/0288627 A1 | 11/2011 | Hartley et al. |
| 2011/0307044 A1 | 12/2011 | Bourang et al. |
| 2011/0307045 A1 | 12/2011 | Bourang et al. |

(56) References Cited

U.S. PATENT DOCUMENTS

| | | |
|---|---|---|
| 2011/0307046 A1 | 12/2011 | Bourang et al. |
| 2011/0307052 A1 | 12/2011 | Bourang et al. |
| 2011/0313443 A1 | 12/2011 | Lorenzo et al. |
| 2011/0313512 A1 | 12/2011 | Hartley et al. |
| 2011/0319926 A1 | 12/2011 | Becking et al. |
| 2011/0319928 A1 | 12/2011 | Griffin et al. |
| 2012/0004682 A1 | 1/2012 | Connor |
| 2012/0004719 A1 | 1/2012 | Gregorich et al. |
| 2012/0016462 A1 | 1/2012 | Gregorich et al. |
| 2012/0041540 A1 | 2/2012 | Shobayashi et al. |
| 2012/0046676 A1 | 2/2012 | Morsi |
| 2012/0053670 A1 | 3/2012 | Purdy |
| 2012/0055614 A1 | 3/2012 | Hancock et al. |
| 2012/0071911 A1 | 3/2012 | Sadasivan et al. |
| 2012/0078285 A1 | 3/2012 | Griffin |
| 2012/0089174 A1 | 4/2012 | Chen et al. |
| 2012/0116352 A1 | 5/2012 | Rangi |
| 2012/0116441 A1 | 5/2012 | Yamanaka et al. |
| 2012/0116442 A1 | 5/2012 | Monstadt et al. |
| 2012/0130479 A1 | 5/2012 | Chuter et al. |
| 2012/0143237 A1 | 6/2012 | Cam et al. |
| 2012/0143317 A1 | 6/2012 | Cam et al. |
| 2012/0165919 A1 | 6/2012 | Cox et al. |
| 2012/0165920 A1 | 6/2012 | Meyer et al. |
| 2012/0172921 A1 | 7/2012 | Yamanaka et al. |
| 2012/0172972 A1 | 7/2012 | Meyer et al. |
| 2012/0172977 A1 | 7/2012 | Bregulla et al. |
| 2012/0179192 A1 | 7/2012 | Fogarty et al. |
| 2012/0197283 A1 | 8/2012 | Marchand et al. |
| 2012/0209309 A1 | 8/2012 | Chen et al. |
| 2012/0209311 A1 | 8/2012 | Grandfield et al. |
| 2012/0215250 A1 | 8/2012 | Grandfield et al. |
| 2012/0221095 A1 | 8/2012 | Berez et al. |
| 2012/0238644 A1 | 9/2012 | Gong et al. |
| 2012/0239074 A1 | 9/2012 | Aboytes et al. |
| 2012/0245674 A1 | 9/2012 | Molaei et al. |
| 2012/0245675 A1 | 9/2012 | Molaei et al. |
| 2012/0253369 A1 | 10/2012 | Morsi |
| 2012/0253377 A1 | 10/2012 | Slazas et al. |
| 2012/0253448 A1 | 10/2012 | Hartley et al. |
| 2012/0259354 A1 | 10/2012 | Kellett |
| 2012/0259404 A1 | 10/2012 | Tieu et al. |
| 2012/0265287 A1 | 10/2012 | Sharma et al. |
| 2012/0271200 A1 | 10/2012 | Martinson et al. |
| 2012/0271399 A1 | 10/2012 | Perkins et al. |
| 2012/0277784 A1 | 11/2012 | Berez et al. |
| 2012/0283764 A1 | 11/2012 | Solar et al. |
| 2012/0283765 A1 | 11/2012 | Berez et al. |
| 2012/0283768 A1 | 11/2012 | Cox et al. |
| 2012/0283769 A1 | 11/2012 | Cruise et al. |
| 2012/0283815 A1 | 11/2012 | Berez et al. |
| 2012/0289995 A1 | 11/2012 | Constant et al. |
| 2012/0296361 A1 | 11/2012 | Cam et al. |
| 2012/0296362 A1 | 11/2012 | Cam et al. |
| 2012/0303052 A1 | 11/2012 | Connor |
| 2012/0303108 A1 | 11/2012 | Fogarty et al. |
| 2012/0303112 A1 | 11/2012 | Armstrong et al. |
| 2012/0310270 A1 | 12/2012 | Murphy et al. |
| 2012/0310271 A1 | 12/2012 | Kwon |
| 2012/0310611 A1 | 12/2012 | Sadasivan et al. |
| 2012/0316598 A1 | 12/2012 | Becking et al. |
| 2012/0316632 A1 | 12/2012 | Gao |
| 2012/0316638 A1 | 12/2012 | Grad et al. |
| 2012/0323268 A1 | 12/2012 | Martinez |
| 2012/0323309 A1 | 12/2012 | Cattaneo |
| 2012/0323547 A1 | 12/2012 | Baloch et al. |
| 2012/0330341 A1 | 12/2012 | Becking et al. |
| 2012/0330343 A1 | 12/2012 | Kim et al. |
| 2012/0330347 A1 | 12/2012 | Becking et al. |
| 2012/0330402 A1 | 12/2012 | Vad et al. |
| 2013/0012979 A1 | 1/2013 | Amplatz et al. |
| 2013/0018220 A1 | 1/2013 | Vad et al. |
| 2013/0018409 A1 | 1/2013 | Le et al. |
| 2013/0023903 A1 | 1/2013 | Roorda et al. |
| 2013/0035712 A1 | 2/2013 | Theobald et al. |
| 2013/0041454 A1 | 2/2013 | Dobson et al. |
| 2013/0045182 A1 | 2/2013 | Gong et al. |
| 2013/0046371 A1 | 2/2013 | Greenberg et al. |
| 2013/0053872 A1 | 2/2013 | Hansen |
| 2013/0053944 A1 | 3/2013 | Fogarty et al. |
| 2013/0060317 A1 | 3/2013 | Dusbabek et al. |
| 2013/0060322 A1 | 3/2013 | Leynov et al. |
| 2013/0066357 A1 | 3/2013 | Aboytes et al. |
| 2013/0066359 A1 | 3/2013 | Murphy et al. |
| 2013/0066360 A1 | 3/2013 | Becking et al. |
| 2013/0066413 A1 | 3/2013 | Jin et al. |
| 2013/0066415 A1 | 3/2013 | Hocking |
| 2013/0072959 A1 | 3/2013 | Wu et al. |
| 2013/0085518 A1 | 4/2013 | Trommeter et al. |
| 2013/0085522 A1 | 4/2013 | Becking et al. |
| 2013/0089576 A1 | 4/2013 | Maitland et al. |
| 2013/0090682 A1 | 4/2013 | Bachman et al. |
| 2013/0090719 A1 | 4/2013 | Bales et al. |
| 2013/0090721 A1 | 4/2013 | Bales et al. |
| 2013/0095087 A1 | 4/2013 | Shalaby et al. |
| 2013/0103074 A1 | 4/2013 | Riina et al. |
| 2013/0103135 A1 | 4/2013 | Vinluan |
| 2013/0108574 A1 | 5/2013 | Chevalier et al. |
| 2013/0116659 A1 | 5/2013 | Porter |
| 2013/0116722 A1 | 5/2013 | Aboytes et al. |
| 2013/0116774 A1 | 5/2013 | Strauss et al. |
| 2013/0123830 A1 | 5/2013 | Becking et al. |
| 2013/0123899 A1 | 5/2013 | Leopold et al. |
| 2013/0123901 A1 | 5/2013 | Connor et al. |
| 2013/0131711 A1 | 5/2013 | Bowman |
| 2013/0131716 A1 | 5/2013 | Cruise et al. |
| 2013/0131780 A1 | 5/2013 | Armstrong et al. |
| 2013/0131786 A1 | 5/2013 | Chobotov |
| 2013/0146173 A1 | 6/2013 | Krivoruchko et al. |
| 2013/0150946 A1 | 6/2013 | Hartley et al. |
| 2013/0166010 A1 | 6/2013 | Vad |
| 2013/0166017 A1 | 6/2013 | Cartledge et al. |
| 2013/0172925 A1 | 7/2013 | Garcia et al. |
| 2013/0172975 A1 | 7/2013 | Berez et al. |
| 2013/0172976 A1 | 7/2013 | Garcia et al. |
| 2013/0190795 A1 | 7/2013 | Matson et al. |
| 2013/0190800 A1 | 7/2013 | Murphy et al. |
| 2013/0190805 A1 | 7/2013 | Slazas et al. |
| 2013/0197547 A1 | 8/2013 | Fukuoka et al. |
| 2013/0197570 A1 | 8/2013 | Ebata et al. |
| 2013/0197617 A1 | 8/2013 | Armstrong et al. |
| 2013/0197624 A1 | 8/2013 | Armstrong et al. |
| 2013/0204288 A1 | 8/2013 | Johnson et al. |
| 2013/0204289 A1 | 8/2013 | Dasnurkar et al. |
| 2013/0204290 A1 | 8/2013 | Clarke et al. |
| 2013/0204347 A1 | 8/2013 | Armstrong et al. |
| 2013/0204351 A1 | 8/2013 | Cox et al. |
| 2013/0204354 A1 | 8/2013 | Adams |
| 2013/0211443 A1 | 8/2013 | Cragg et al. |
| 2013/0211492 A1 | 8/2013 | Schneider et al. |
| 2013/0211497 A1 | 8/2013 | Charlebois et al. |
| 2013/0211498 A1 | 8/2013 | Buckley et al. |
| 2013/0211505 A1 | 8/2013 | Robison |
| 2013/0211507 A1 | 8/2013 | LaDuca et al. |
| 2013/0218191 A1 | 8/2013 | Heltai |
| 2013/0226276 A1 | 8/2013 | Newell et al. |
| 2013/0226278 A1 | 8/2013 | Newell et al. |
| 2013/0231695 A1 | 9/2013 | Malek |
| 2013/0231732 A1 | 9/2013 | Vonderwalde et al. |
| 2013/0238083 A1 | 9/2013 | Duggal et al. |
| 2013/0245606 A1 | 9/2013 | Stam et al. |
| 2013/0245667 A1 | 9/2013 | Marchand et al. |
| 2013/0245745 A1 | 9/2013 | Vong et al. |
| 2013/0252900 A1 | 9/2013 | Reb et al. |
| 2013/0253086 A1 | 9/2013 | Wilson et al. |
| 2013/0253572 A1 | 9/2013 | Molaei et al. |
| 2013/0253631 A1 | 9/2013 | Schmid et al. |
| 2013/0253634 A1 | 9/2013 | Wilson et al. |
| 2013/0261728 A1 | 10/2013 | Perkins et al. |
| 2013/0261730 A1 | 10/2013 | Bose et al. |
| 2013/0261732 A1 | 10/2013 | Perkins et al. |
| 2013/0267986 A1 | 10/2013 | Hines |
| 2013/0268046 A1 | 10/2013 | Gerberding et al. |
| 2013/0268053 A1 | 10/2013 | Molaei et al. |

(56) References Cited

U.S. PATENT DOCUMENTS

| | | |
|---|---|---|
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0282096 A1 | 10/2013 | Berez et al. |
| 2013/0289690 A1 | 10/2013 | Thapliyal |
| 2013/0289713 A1 | 10/2013 | Pearson et al. |
| 2013/0289714 A1 | 10/2013 | Strauss et al. |
| 2013/0302251 A1 | 11/2013 | Constant et al. |
| 2013/0304109 A1 | 11/2013 | Abrams et al. |
| 2013/0310687 A1 | 11/2013 | Takizawa et al. |
| 2013/0325053 A1 | 12/2013 | Porter et al. |
| 2013/0331883 A1 | 12/2013 | Strauss et al. |
| 2013/0338688 A1 | 12/2013 | Rehman et al. |
| 2013/0344159 A1 | 12/2013 | Moine et al. |
| 2013/0345738 A1 | 12/2013 | Eskridge |
| 2013/0345785 A1 | 12/2013 | Hartley et al. |
| 2014/0005698 A1 | 1/2014 | Eskridge |
| 2014/0012303 A1 | 1/2014 | Heipl |
| 2014/0012307 A1 | 1/2014 | Franano et al. |
| 2014/0012363 A1 | 1/2014 | Franano et al. |
| 2014/0018843 A1 | 1/2014 | Berez et al. |
| 2014/0018902 A1 | 1/2014 | Myr |
| 2014/0025151 A1 | 1/2014 | Gao |
| 2014/0025154 A1 | 1/2014 | Liang et al. |
| 2014/0031858 A1 | 1/2014 | Bhagchandani et al. |
| 2014/0031918 A1 | 1/2014 | Newell et al. |
| 2014/0031920 A1 | 1/2014 | Malek |
| 2014/0039536 A1 | 2/2014 | Cully et al. |
| 2014/0039606 A1 | 2/2014 | Rudakov et al. |
| 2014/0046338 A1 | 2/2014 | Grandfield et al. |
| 2014/0047694 A1 | 2/2014 | Monstadt et al. |
| 2014/0052168 A1 | 2/2014 | Sawhney |
| 2014/0052233 A1 | 2/2014 | Cox et al. |
| 2014/0058420 A1 | 2/2014 | Hannes et al. |
| 2014/0058436 A1 | 2/2014 | Rosenbluth et al. |
| 2014/0058498 A1 | 2/2014 | Hannes et al. |
| 2014/0058500 A1 | 2/2014 | Lundkvist et al. |
| 2014/0074149 A1 | 3/2014 | Garcia et al. |
| 2014/0081313 A1 | 3/2014 | Elliott |
| 2014/0081374 A1 | 3/2014 | Kim et al. |
| 2014/0082924 A1 | 3/2014 | Lundkvist et al. |
| 2014/0083969 A1 | 3/2014 | Porter |
| 2014/0088690 A1 | 3/2014 | Fogarty et al. |
| 2014/0094896 A1 | 4/2014 | Berez et al. |
| 2014/0099374 A1 | 4/2014 | Golzarian et al. |
| 2014/0100647 A1 | 4/2014 | Bourang |
| 2014/0114342 A1 | 4/2014 | Berez et al. |
| 2014/0114343 A1 | 4/2014 | Lee et al. |
| 2014/0121744 A1 | 5/2014 | Kusleika |
| 2014/0121745 A1 | 5/2014 | Kusleika et al. |
| 2014/0121746 A1 | 5/2014 | Kusleika et al. |
| 2014/0121752 A1 | 5/2014 | Losordo et al. |
| 2014/0128901 A1 | 5/2014 | Kang et al. |
| 2014/0128907 A1 | 5/2014 | Hui et al. |
| 2014/0128957 A1 | 5/2014 | Losordo et al. |
| 2014/0130965 A1 | 5/2014 | Banks et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0142611 A1 | 5/2014 | Plaza et al. |
| 2014/0163604 A1 | 6/2014 | Monstadt |
| 2014/0172001 A1 | 6/2014 | Becking et al. |
| 2014/0172067 A1 | 6/2014 | Brown et al. |
| 2014/0172071 A1 | 6/2014 | Berez et al. |
| 2014/0180377 A1 | 6/2014 | Bose et al. |
| 2014/0180387 A1 | 6/2014 | Khenansho et al. |
| 2014/0180397 A1 | 6/2014 | Gerberding et al. |
| 2014/0188208 A1 | 7/2014 | Hancock et al. |
| 2014/0194973 A1 | 7/2014 | Chobotov |
| 2014/0200607 A1 | 7/2014 | Sepetka et al. |
| 2014/0200648 A1 | 7/2014 | Newell et al. |
| 2014/0207162 A1 | 7/2014 | Tran et al. |
| 2014/0207180 A1 | 7/2014 | Ferrera |
| 2014/0214071 A1 | 7/2014 | Thomas |
| 2014/0222128 A1 | 8/2014 | Dusbabek et al. |
| 2014/0222130 A1 | 8/2014 | Kusleika |
| 2014/0236216 A1 | 8/2014 | Gerberding |
| 2014/0243951 A1 | 8/2014 | Orr |
| 2014/0249614 A1 | 9/2014 | Levi et al. |
| 2014/0249616 A1 | 9/2014 | Strauss et al. |
| 2014/0249620 A1 | 9/2014 | Carman et al. |
| 2014/0257360 A1 | 9/2014 | Keillor |
| 2014/0260928 A1 | 9/2014 | Janardhan et al. |
| 2014/0265096 A1 | 9/2014 | Janardhan et al. |
| 2014/0277100 A1 | 9/2014 | Kang |
| 2014/0277361 A1 | 9/2014 | Farhat et al. |
| 2014/0277370 A1 | 9/2014 | Brocker et al. |
| 2014/0277391 A1 | 9/2014 | Layman et al. |
| 2014/0288633 A1 | 9/2014 | Burke et al. |
| 2014/0296358 A1 | 10/2014 | Maitland et al. |
| 2015/0209050 A1 | 7/2015 | Aboytes et al. |
| 2015/0272590 A1 | 10/2015 | Aboytes et al. |
| 2015/0297240 A1 | 10/2015 | Divino et al. |
| 2015/0313605 A1 | 11/2015 | Griffin |
| 2015/0342613 A1 | 12/2015 | Aboytes et al. |
| 2016/0030050 A1 | 2/2016 | Franano et al. |
| 2016/0249935 A1 | 9/2016 | Hewitt et al. |
| 2016/0262766 A1 | 9/2016 | Aboytes et al. |
| 2016/0367260 A9 | 12/2016 | Hewitt et al. |
| 2017/0000631 A1 | 1/2017 | Kusleika |
| 2017/0079661 A1 | 3/2017 | Bardsley et al. |
| 2017/0079662 A1 | 3/2017 | Rhee et al. |
| 2017/0086851 A1 | 3/2017 | Wallace et al. |
| 2017/0095254 A1 | 4/2017 | Hewitt et al. |
| 2017/0112502 A1 | 4/2017 | Le et al. |
| 2017/0128077 A1 | 5/2017 | Hewitt et al. |
| 2017/0156733 A1 | 6/2017 | Becking et al. |
| 2017/0156734 A1 | 6/2017 | Griffin |
| 2017/0164951 A1 | 6/2017 | Divino et al. |
| 2017/0189035 A1 | 7/2017 | Porter |
| 2017/0231789 A1 | 8/2017 | Cam et al. |
| 2017/0245862 A1 | 8/2017 | Cox et al. |
| 2017/0245864 A1 | 8/2017 | Franano et al. |
| 2017/0252045 A1 | 9/2017 | Ortega et al. |
| 2017/0252190 A1 | 9/2017 | Becking et al. |
| 2017/0258473 A1 | 9/2017 | Plaza et al. |
| 2017/0258613 A1 | 9/2017 | Franano et al. |
| 2017/0265869 A1 | 9/2017 | Cibulski et al. |
| 2017/0273691 A1 | 9/2017 | Riina et al. |
| 2017/0273692 A1 | 9/2017 | Choubey |
| 2017/0273810 A1 | 9/2017 | Choubey et al. |
| 2017/0281194 A1 | 10/2017 | Divino et al. |
| 2017/0290593 A1 | 10/2017 | Cruise et al. |
| 2017/0290654 A1 | 10/2017 | Sethna |
| 2017/0303944 A1 | 10/2017 | Grandfield et al. |
| 2017/0354402 A1 | 12/2017 | Lee et al. |
| 2018/0000489 A1 | 1/2018 | Marchand et al. |
| 2018/0036012 A1 | 2/2018 | Aboytes et al. |

\* cited by examiner

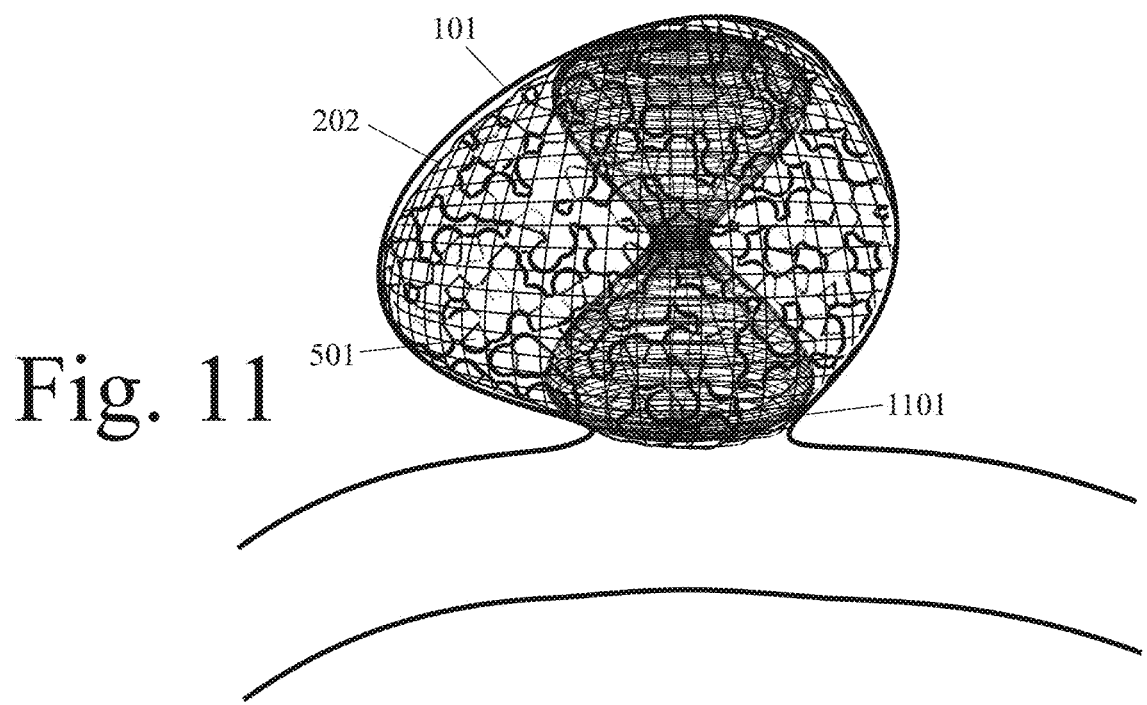
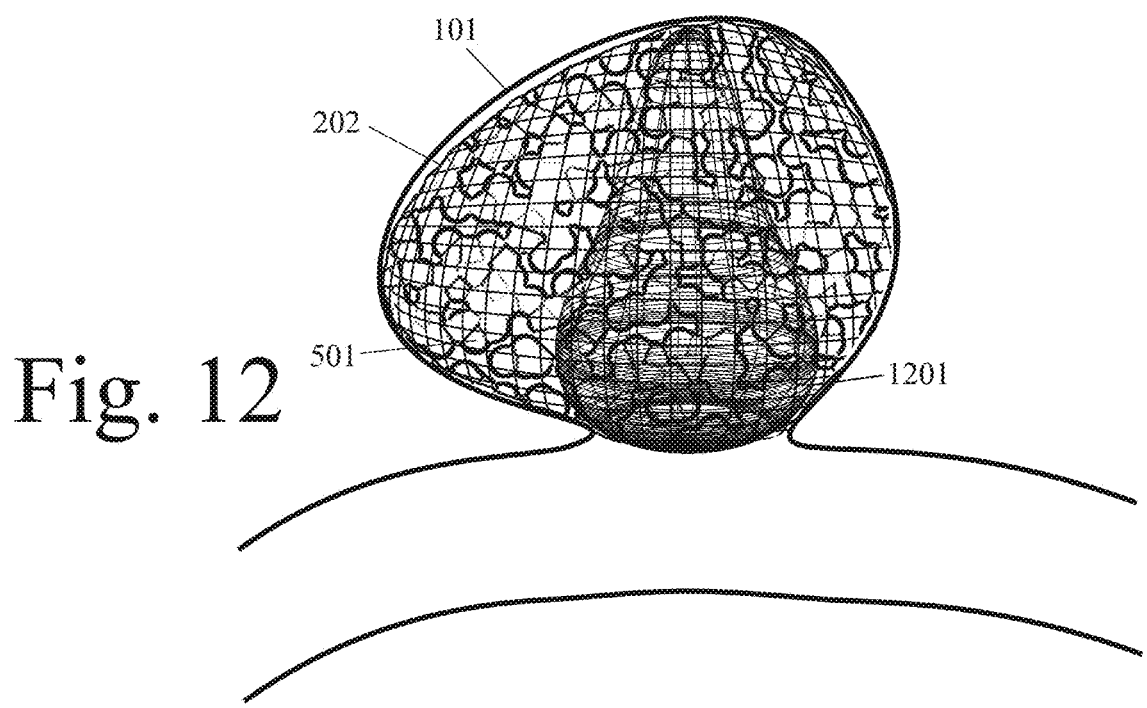

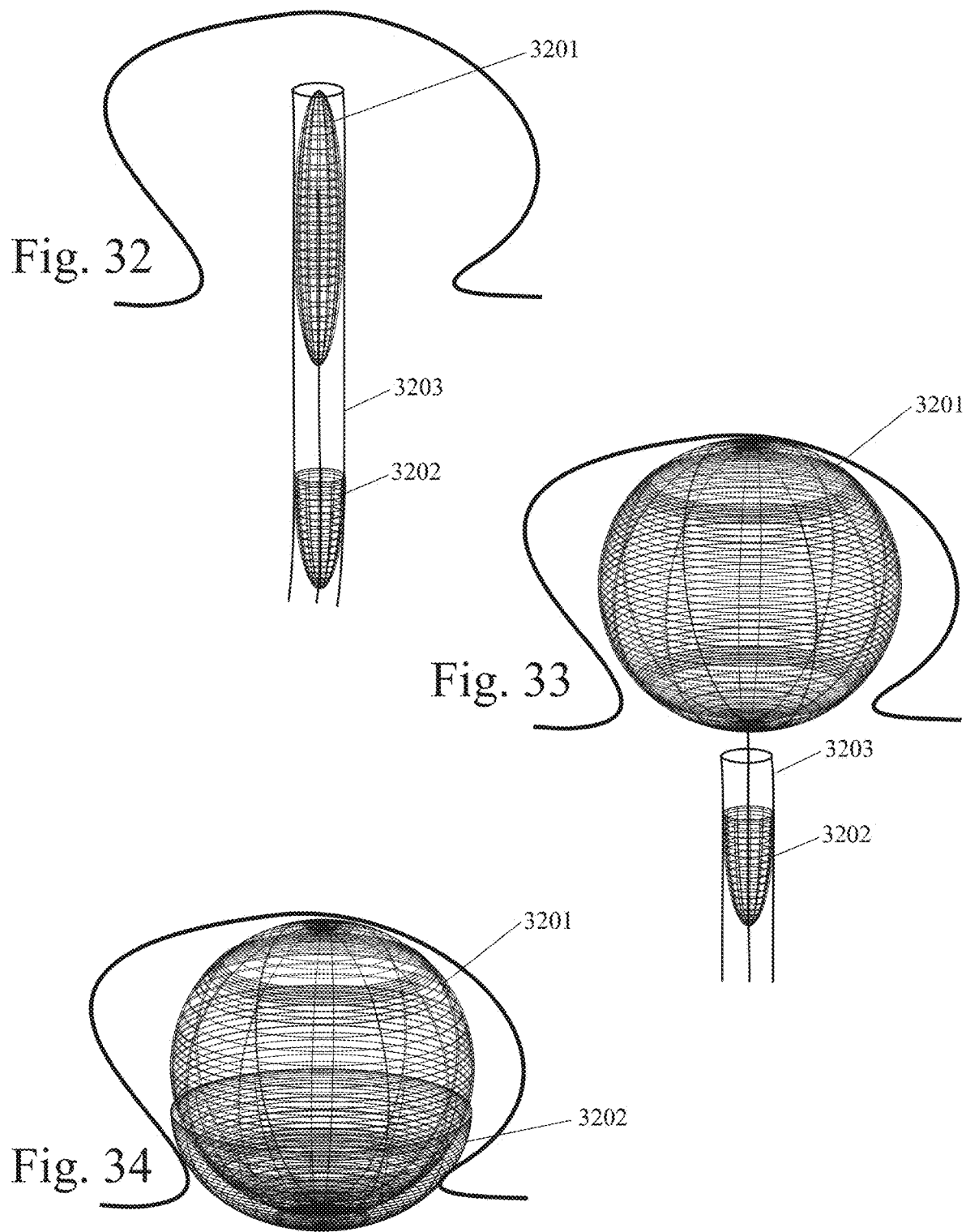

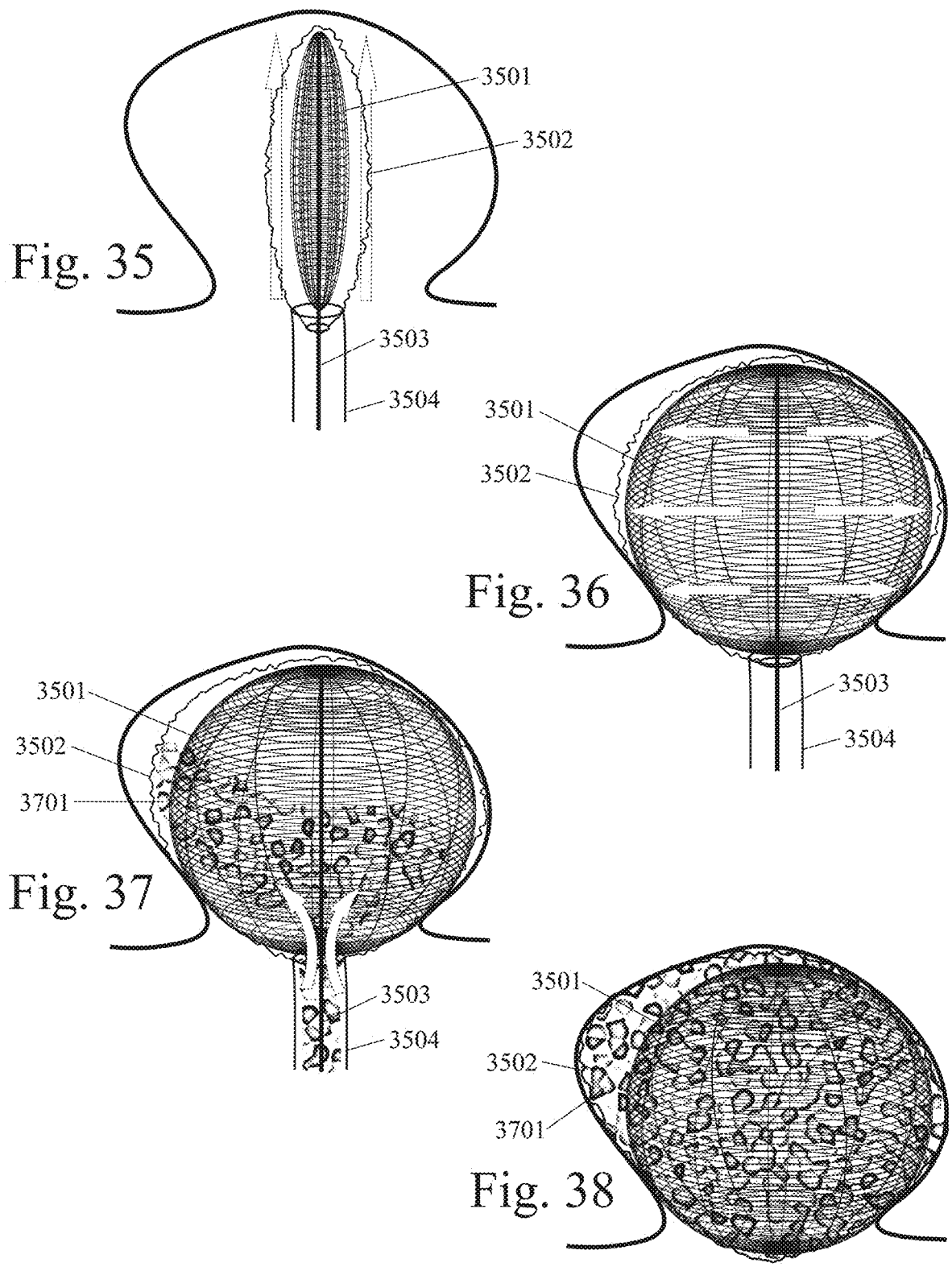

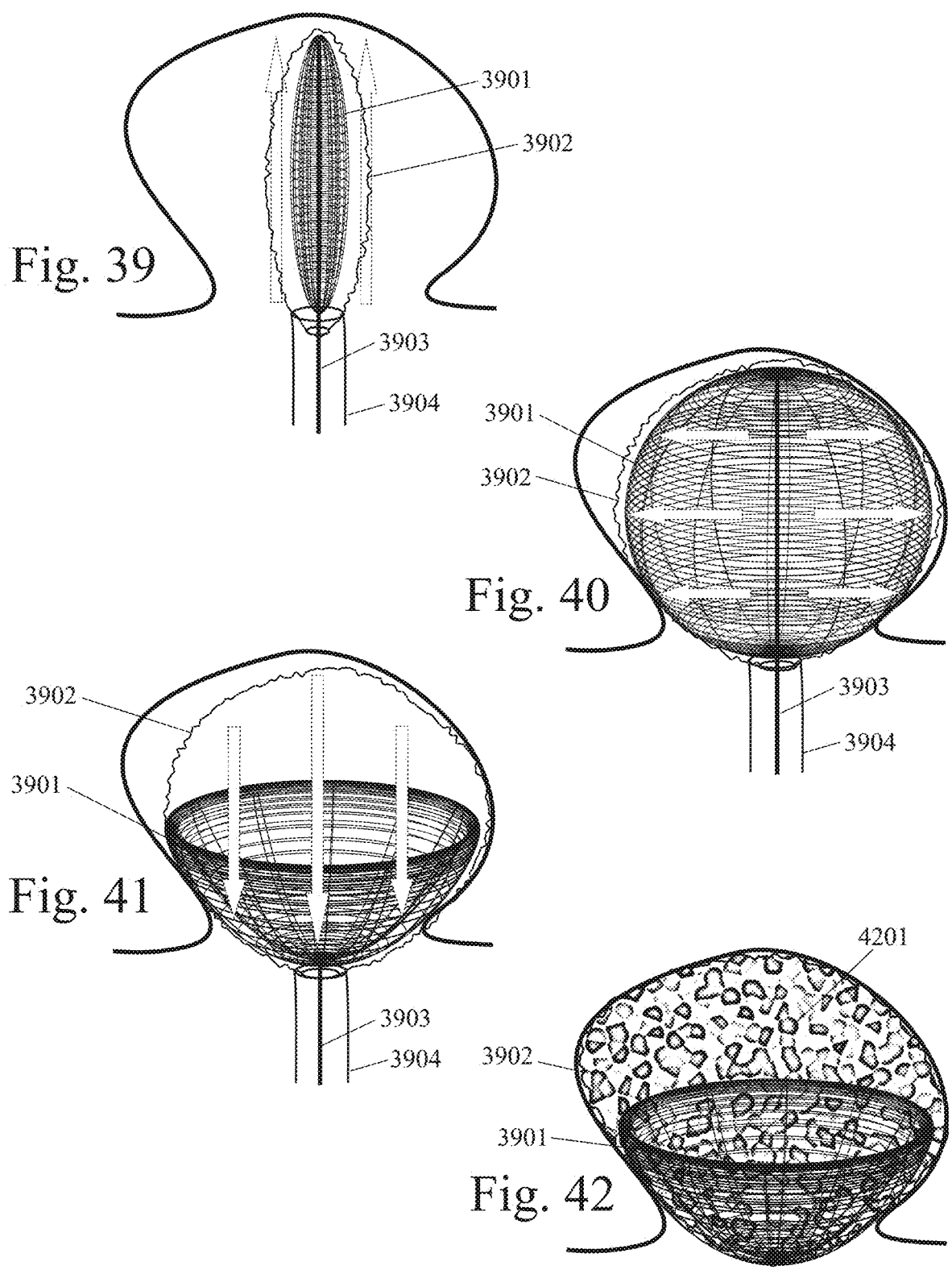

JANJUA ANEURYSM NET WITH A RESILIENT NECK-BRIDGING PORTION FOR OCCLUDING A CEREBRAL ANEURYSM

CROSS-REFERENCE TO RELATED APPLICATIONS

This patent application:

(1) is a continuation in part of U.S. patent application Ser. No. 14/526,600 entitled "Devices and Methods for Occluding a Cerebral Aneurysm" by Robert A. Connor which was filed on Oct. 29, 2014—which in turn was a continuation in part of U.S. patent application Ser. No. 12/989,048 entitled "Aneurysm Occlusion Device" (i.e. the Janjua Aneurysm Net) by Robert A. Connor and Muhammad Tariq Janjua which has a 371 date of Oct. 21, 2010, a filing date of Apr. 24, 2009, and a priority date of May 1, 2008 which is the U.S. national phase filing of PCT/US 2009/002537 entitled "Aneurysm Occlusion Device" by Robert A. Connor and Muhammad Tariq Janjua filed on Apr. 24, 2009 which claimed the priority benefit of U.S. Provisional Patent Application 61/126,047 entitled "Flow of Soft Members into a Net to Embolize an Aneurysm" by Robert A. Connor which received a filing date of May 1, 2008 and claimed the priority benefit of U.S. Provisional Patent Application 61/126,027 entitled "Net Filled with Soft Members to Embolize an Aneurysm" by Robert A. Connor which received a filing date of May 1, 2008; and also claimed the priority benefit of U.S. Provisional Patent Application 61/897,245 entitled "Devices and Methods for Occluding a Cerebral Aneurysm" by Robert A. Connor filed on Oct. 30, 2013;

(2) is a continuation in part of U.S. patent application Ser. No. 15/081,909 entitled "Aneurysm Occlusion Device with Sequence of Shape-Changing Embolic Members" by Robert A. Connor which was filed on Mar. 27, 2016—which in turn was a continuation in part of U.S. patent application Ser. No. 14/526,600 entitled "Devices and Methods for Occluding a Cerebral Aneurysm" by Robert A. Connor which was filed on Oct. 29, 2014 and was a continuation in part of U.S. patent application Ser. No. 12/989,048 entitled "Aneurysm Occlusion Device" (i.e. the Janjua Aneurysm Net) by Robert A. Connor and Muhammad Tariq Janjua which has a 371 date of Oct. 21, 2010, a filing date of Apr. 24, 2009, and a priority date of May 1, 2008 which is the U.S. national phase filing of PCT/US 2009/002537 entitled "Aneurysm Occlusion Device" by Robert A. Connor and Muhammad Tariq Janjua filed on Apr. 24, 2009 which claimed the priority benefit of U.S. Provisional Patent Application No. 61/126,047 entitled "Flow of Soft Members into a Net to Embolize an Aneurysm" by Robert A. Connor which received a filing date of May 1, 2008 and claimed the priority benefit of U.S. Provisional Patent Application No. 61/126,027 entitled "Net Filled with Soft Members to Embolize an Aneurysm" by Robert A. Connor which received a filing date of May 1, 2008; and also claimed the priority benefit of U.S. Provisional Patent Application 61/897,245 entitled "Devices and Methods for Occluding a Cerebral Aneurysm" by Robert A. Connor filed on Oct. 30, 2013;

(3) claims the priority benefit of U.S. Provisional Patent Application 62/472,519 entitled "Devices for Occluding a Cerebral Aneurysm" by Robert A. Connor filed on Mar. 16, 2017; and (4) claims the priority benefit of U.S. Provisional Patent Application 62/589,754 entitled "Intrasacular Aneurysm Occlusion Device with a Resilient Wider-Than-Neck Portion and a Flexible Sac-Filling Portion" by Robert A. Connor filed on Nov. 22, 2017.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for occluding a cerebral aneurysm.

Introduction to Cerebral Aneurysms

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain.

Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function.

Review of the Most Relevant Art

U.S. Patent Application Publications 20160249935 (Hewitt et al., Sep. 1, 2016, "Devices for Therapeutic Vascular Procedures") and 20160367260 (Hewitt et al., Dec. 22, 2016, "Devices for Therapeutic Vascular Procedures") disclose an intrasacular aneurysm occlusion device comprising a distal self-expanding resilient permeable shell, a proximal self-expanding resilient permeable shell, and an elongate support member between the distal and proximal permeable shells. U.S. Patent Application Publication 20170095254 (Hewitt et al., May 6, 2017, "Filamentary Devices for Treatment of Vascular Defects") discloses an aneurysm occlusion device comprising a self-expanding permeable shell having a radially constrained elongated state configured for delivery within a catheter lumen, an expanded state with a globular and longitudinally shortened configuration relative to the radially constrained state, and a plurality of elongate filaments that are woven together, which define a cavity of the permeable shell. U.S. Patent Application Publication 20170128077 (Hewitt et al., May 11, 2017, "Devices for Therapeutic Vascular Procedures") discloses an aneurysm occlusion device comprising a self-expanding resilient permeable shell and a metallic coil secured to the distal end of a shell.

U.S. Patent Application Publication 20170079662 (Rhee et al., Mar. 23, 2017, "Occlusive Devices") discloses an aneurysm occlusion device comprising frame and mesh components, wherein the frame and mesh components have different porosity levels. U.S. Patent Application Publication 20170086851 (Wallace et al., Mar. 30, 2017, "Vaso-Occlusive Devices and Methods of Use") discloses expandable vaso-occlusive implants that include one or more soft and expandable braided members coupled to a pushable member such as a coil that maybe inserted and retrieved from within an aneurism using a delivery catheter. U.S. Patent Application Publication 20170156733 (Becking et al., Jun. 8, 2017, "Multiple Layer Filamentary Devices for Treatment of Vascular Defects") discloses braid balls for aneurysm occlusion and/or parent vessel occlusion/sacrifice.

U.S. Patent Application Publications 20120239074 (Aboytes et al., Sep. 20, 2012, "Devices and Methods for the Treatment of Vascular Defects"), 20150209050 (Aboytes et al., Jul. 30, 2015, "Devices and Methods for the Treatment of Vascular Defects"), and 20160262766 (Aboytes et al., Sep. 15, 2016, "Devices and Methods for the Treatment of Vascular Defects") disclose an intrasacular aneurysm occlusion device comprising an expandable implant with a first configuration in which the first portion and the second portion are substantially linearly aligned and a second configuration in which the second portion at least partially overlaps the first portion.

U.S. Patent Application Publications 20150297240 (Divino et al., Oct. 22, 2015, "Embolic Medical Devices") and 20170281194 (Divino et al., Oct. 5, 2017, "Embolic Medical Devices") disclose an intrasacular aneurysm occlusion device with a collapsed configuration in which its first and second side edges are curled toward each other around a longitudinal axis and an expanded configuration forming a series of loops wherein the first and second side edges uncurl.

U.S. Patent Application Publication 20170189035 (Porter, Jul. 6, 2017, "Embolic Devices and Methods of Manufacturing Same") discloses an intrasacular aneurysm occlusion device comprising a flat embolic braid having a first side comprising a first side surface and a second side comprising a second side surface facing in an opposite direction than the first side surface, the braid having an elongated constrained configuration for being deployed through a delivery catheter, and a three-dimensional unconstrained configuration, wherein in the three-dimensional unconstrained configuration, the braid assumes a plurality of successive loops in which the braid is at least partially twisted between successive loops of the plurality, so that the first side surface faces externally of each loop, and the second side surface faces an interior of each loop, respectively, regardless of a change in direction and/or orientation of the braid.

SUMMARY OF THE INVENTION

This invention can be embodied in an intrasacular aneurysm occlusion device comprising: a proximal stent (or neck bridge) with a first configuration as it is transported to an aneurysm sac and a second configuration after it has been expanded within the aneurysm sac; wherein the stent (or neck bridge) in its second configuration has a width which is larger than the diameter of the neck of the aneurysm sac; and wherein the stent (or neck bridge) in its second configuration has a first level of flexibility, elasticity, and/or malleability; and a distal net (or mesh) with a first configuration as it is being transported to an aneurysm sac and a second configuration after it has been expanded within the aneurysm sac; wherein the net (or mesh) is expanded from its first configuration to its second configuration by the insertion of embolic members into the net (or mesh); and wherein the net (or mesh) in its second configuration has a second level of flexibility, elasticity, and/or malleability which is greater than the first level of flexibility, elasticity, and/or malleability.

The resilient wider-than-neck portion and flexible sac-filling portion of this device work together in a synergistic manner. The resilient wider-than-neck portion of this device in its second configuration bridges, spans, covers and/or occludes the aneurysm neck and prevents the device from protruding out of the aneurysm sac. The flexible sac-filling portion of this device in its second configuration expands and conforms to the walls of even an irregularly-shaped aneurysm sac, reducing the risk of recanalization.

This device can have advantages over aneurysm occlusion devices in the prior art, especially for aneurysms with irregularly-shaped sacs. A device with both a resilient wider-than-neck portion and a flexible sac-filling portion can fill a greater percentage of the volume of an irregularly-shaped aneurysm sac than is possible with a solitary ball stent because it can better conform to the walls of an irregularly-shaped aneurysm sac and decrease the probability of post-deployment blood flow through the aneurysm neck into the aneurysm sac. A device with both a resilient wider-than-neck portion and a flexible sac-filling portion can occlude blood flow into an irregularly-shaped aneurysm sac more completely than is possible with a single spherical (or ellipsoidal, apple, or toroidal) embolic structure.

A device with both a resilient wider-than-neck portion and a flexible sac-filling portion can also fill a greater percentage of the volume of an aneurysm sac than is possible with traditional aneurysm coils or undulating longitudinal ribbons. One reason that a device with a resilient wider-than-neck portion and a flexible sac-filling portion can be superior to an undulating ribbon is because it does not require careful placement of a wide portion of the undulating ribbon along the aneurysm neck in order to fully cover the neck. A device with both a proximal resilient wider-than-neck portion and a distal flexible sac-filling portion can also be superior to a neck bridge alone because it can better hold the proximal surface of the device snugly against the inner side of the aneurysm neck.

The synergistic design of this device can help to: completely occlude the aneurysm neck by pressing the wider-than-neck portion against the aneurysm neck; prevent blood from circulating around the periphery of the aneurysm sac by conforming to the contours of even an irregularly-shaped aneurysm sac; and frictionally engage the walls of the aneurysm sac so as to hold the entire device within the aneurysm sac. Ideally, this design can completely occlude even an irregularly-shaped aneurysm sac with a single deployment sequence of a single device—which can be called "one and done." This can potentially achieve better and quicker occlusion results than designs which require multiple deployment sequences and multiple devices for irregularly-shaped aneurysm sacs.

INTRODUCTION TO THE FIGURES

FIG. 11 shows a device with an hourglass-shaped resilient wider-than-neck portion and a flexible sac-filling portion.

FIG. 12 shows a device with a pear-shaped resilient wider-than-neck portion and a flexible sac-filling portion.

FIGS. 32 through 34 show three sequential views of a device with ball and bowl shaped portions being deployed in an aneurysm sac.

FIGS. 35 through 38 show four sequential views of a device with a ball-shaped resilient wider-than-neck portion and a flexible sac-filling portion being deployed in an aneurysm sac.

FIGS. 39 through 42 show four sequential views of a device with a bowl-shaped resilient wider-than-neck portion and a flexible sac-filling portion being deployed in an aneurysm sac.

DETAILED DESCRIPTION OF THE FIGURES

Figure 1:
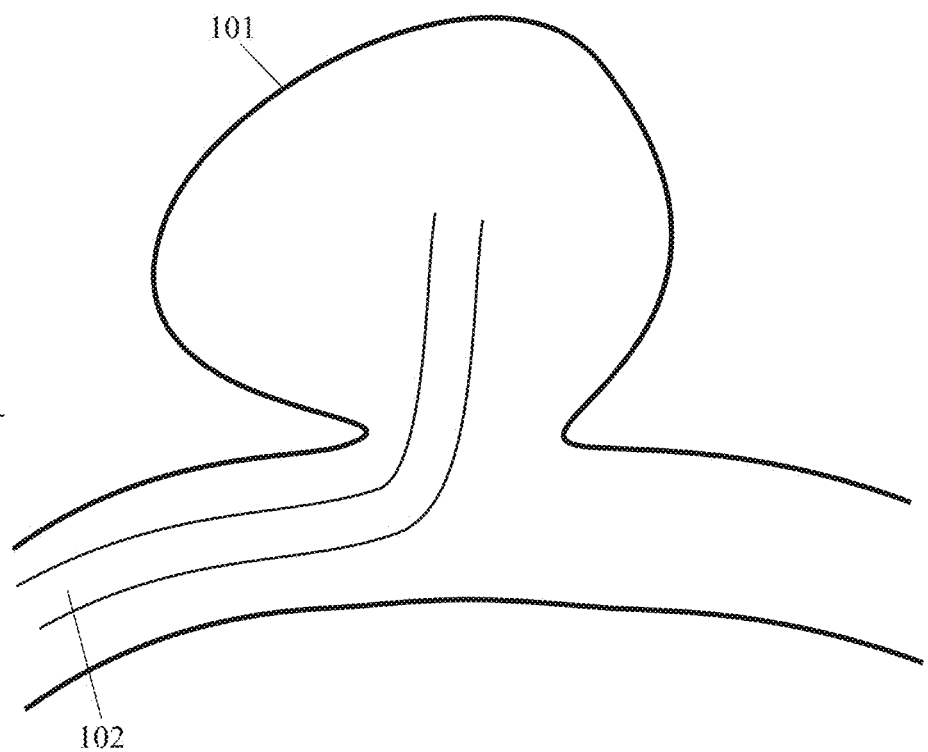
FIGS. 1 through 6 show six sequential views of an intrasacular aneurysm occlusion device with a proximal resilient wider-than-neck portion and a distal flexible sac-filling portion as it is being deployed within an aneurysm sac.

This invention can be embodied in an intrasacular aneurysm occlusion device comprising: (1) a resilient wider-than-neck portion with a first configuration as it is transported to an aneurysm sac and a second configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and (2) a flexible sac-filling portion with a first configuration as it is being transported to an aneurysm sac and a second configuration after it has been expanded within the aneurysm sac; wherein the flexible sac-filling portion is expanded from its first configuration to its second configuration by the insertion of embolic members into the flexible sac-filling portion; and wherein the flexible sac-filling portion in its second configuration has a second level of flexibility, elasticity, and/or malleability which is greater than the first level of flexibility, elasticity, and/or malleability.

In an example, a resilient wider-than-neck portion of this device can be a stent (or neck bridge) and a flexible sac-filling portion of this device can be a flexible net (or mesh). This invention can be embodied in an intrasacular aneurysm occlusion device comprising: (1) a stent (or neck bridge) with a first configuration as it is transported to an aneurysm sac and a second configuration after it has been expanded within the aneurysm sac; wherein the stent (or neck bridge) in its second configuration has a width which is larger than the diameter of the neck of the aneurysm sac; and wherein the stent (or neck bridge) in its second configuration has a first level of flexibility, elasticity, and/or malleability; and (2) a net (or mesh) with a first configuration as it is being transported to an aneurysm sac and a second configuration after it has been expanded within the aneurysm sac; wherein the net (or mesh) is expanded from its first configuration to its second configuration by the insertion of embolic members into the net (or mesh); and wherein the net (or mesh) in its second configuration has a second level of flexibility, elasticity, and/or malleability which is greater than the first level of flexibility, elasticity, and/or malleability.

This device has advantages over aneurysm occlusion devices in the prior art, especially for aneurysms with irregularly-shaped sacs. A device with both a resilient wider-than-neck portion and a flexible sac-filling portion can fill a greater percentage of the volume of an irregularly-shaped aneurysm sac than is possible with a single spherical, ellipsoidal, apple, or toroidal structure. This can better occlude the aneurysm. A device with both a resilient wider-than-neck portion and a flexible sac-filling portion can be superior to a solitary ball stent because it can better conform to the walls of an irregularly-shaped aneurysm sac and decrease the probability of post-deployment blood flow through the aneurysm neck into the aneurysm sac. A device with both a resilient wider-than-neck portion and a flexible sac-filling portion can occlude blood flow into an irregularly-shaped aneurysm sac more completely than a spherical, ellipsoidal, apple, or toroidal structure alone.

A device with both a resilient wider-than-neck portion and a flexible sac-filling portion can also fill a greater percentage of the volume of an aneurysm sac than is possible with traditional aneurysm coils or undulating longitudinal ribbons. One reason that a device with a resilient wider-than-neck portion and a flexible sac-filling portion can be superior to an undulating ribbon is because it does not require careful placement of a wide portion of the undulating ribbon along the aneurysm neck in order to fully cover the neck. A device with both a resilient wider-than-neck portion and a flexible sac-filling portion can occlude blood flow into an aneurysm sac more completely than traditional coils or undulating longitudinal ribbons.

The resilient wider-than-neck and flexible sac-filling portions of this device work together in a synergistic manner. The resilient wider-than-neck portion of this device in its second configuration bridges, spans, covers and/or occludes the aneurysm neck and prevents the device from protruding out of the aneurysm sac. The flexible sac-filling portion of this device in its second configuration expands and conforms to the walls of even an irregularly-shaped aneurysm sac. A device with both a proximal resilient wider-than-neck portion and a distal flexible sac-filling portion can be superior to a neck bridge alone because it can better hold the proximal surface of the device snugly against the inner side of the aneurysm neck.

The synergistic design of this device can help to: prevent blood from circulating through the periphery of the aneurysm sac; hold the device within the aneurysm sac; and press the resilient wider-than-neck portion of the device snuggly against the inside of the aneurysm neck. Ideally, this design can completely occlude even an irregularly-shaped aneurysm sac with a single deployment sequence of a single device—as may be called "one and done." This can potentially achieve better and quicker occlusion results than designs which require multiple deployment sequences and multiple devices for irregularly-shaped aneurysm sacs.

This invention can also be described with example variations on the above wording and with further itemization of components such as a delivery lumen to transport the device to the aneurysm sac and embolic members which are inserted into the flexible sac-filling portion of the device as follows. In an example, this invention can be embodied in an intrasacular aneurysm occlusion device comprising: (1) a resilient wider-than-neck portion of the device; wherein the resilient wider-than-neck portion has a first configuration while it is being transported to an aneurysm sac; wherein the resilient wider-than-neck portion has a second configuration after it has been delivered into and expanded within the aneurysm sac; wherein the resilient wider-than-neck portion in its second configuration has a width in a plane which is substantially parallel to the circumference of the neck of the aneurysm sac and this width is greater than the diameter of the neck of the aneurysm sac; and wherein the resilient wider-than-neck in its second configuration has a first level of resiliency, rigidity, and/or stiffness; and (2) a flexible sac-filling portion of the device; wherein the flexible sac-filling portion has a first configuration while it is being transported to an aneurysm sac; wherein the flexible sac-filling portion has a second configuration after it has been delivered into and expanded within the aneurysm sac; wherein the flexible sac-filling portion is expanded from its first configuration to its second configuration by the insertion of embolic members into the flexible sac-filling portion; and wherein the flexible sac-filling portion in its second configuration has a second level of resiliency, rigidity, and/or stiffness which is less than the first level of resiliency, rigidity, and/or stiffness.

In an example, this invention can be embodied in an intrasacular aneurysm occlusion device comprising: (1) a stent (or neck bridge); wherein the stent (or neck bridge) has a first configuration while it is being transported to an aneurysm sac; wherein the stent (or neck bridge) has a second configuration after it has been delivered into and expanded within the aneurysm sac; wherein the stent (or neck bridge) in its second configuration has a width in a plane which is substantially parallel to the circumference of the neck of the aneurysm sac and this width is greater than the diameter of the neck of the aneurysm sac; and wherein the stent (or neck bridge) in its second configuration has a first level of resiliency, rigidity, and/or stiffness; and (2) a flexible net (or mesh); wherein the flexible net (or mesh) has a first configuration while it is being transported to an aneurysm sac; wherein the flexible net (or mesh) has a second configuration after it has been delivered into and expanded within the aneurysm sac; wherein the flexible net (or mesh) is expanded from its first configuration to its second configuration by the insertion of embolic members into the flexible net (or mesh); and wherein the flexible net (or mesh) in its second configuration has a second level of resiliency, rigidity, and/or stiffness which is less than the first level of resiliency, rigidity, and/or stiffness.

In an example, this invention can be embodied in an intrasacular aneurysm occlusion device comprising: (1) an intravascular delivery lumen; (2) a plurality of embolic members; (3) a resilient wider-than-neck portion of the device; wherein the resilient wider-than-neck portion has a first configuration while it is being transported through the delivery lumen to an aneurysm sac; wherein the resilient wider-than-neck portion has a second configuration after it has left the delivery lumen and expanded within the aneurysm sac; wherein the resilient wider-than-neck portion in its second configuration has a width in a plane which is substantially parallel to the circumference of the neck of the aneurysm sac and this width is greater than the diameter of the neck of the aneurysm sac; and wherein the resilient wider-than-neck in its second configuration has a first level of flexibility, elasticity, and/or malleability; and (4) a flexible sac-filling portion of the device; wherein the flexible sac-filling portion has a first configuration while it is being transported through the delivery lumen to an aneurysm sac; wherein the flexible sac-filling portion has a second configuration after it has left the delivery lumen and been expanded within the aneurysm sac; wherein the flexible sac-filling portion is expanded from its first configuration to its second configuration by the insertion of the embolic members into the flexible sac-filling portion; and wherein the flexible sac-filling portion in its second configuration has a second level of flexibility, elasticity, and/or malleability which is greater than the first level of flexibility, elasticity, and/or malleability.

In an example, this invention can be embodied in an intrasacular aneurysm occlusion device comprising: (1) an intravascular delivery lumen; (2) a plurality of embolic members; (3) a neck bridging stent, wherein the neck bridging stent is configured to occlude the neck of an aneurysm sac; wherein the neck bridging stent has a first configuration while it is being transported through the delivery lumen to an aneurysm sac; wherein the neck bridging stent has a second configuration after it has left the delivery lumen and expanded within the aneurysm sac; wherein the neck bridging stent in its second configuration has a width in a plane which is substantially parallel to the circumference of the neck of the aneurysm sac and this width is greater than the diameter of the neck of the aneurysm sac; and wherein the neck bridging stent in its second configuration has a first level of flexibility, elasticity, and/or malleability; and (4) a net or mesh, wherein the net or mesh has a first configuration while it is being transported through the delivery lumen to an aneurysm sac; wherein the net or mesh has a second configuration after it has left the delivery lumen and been expanded within the aneurysm sac; wherein the net or mesh is configured to conform to the walls of an aneurysm sac in its second configuration; wherein the net or mesh is expanded from its first configuration to its second configuration by the insertion of the embolic members into the net or mesh; wherein the net or mesh in its second configuration has a second level of flexibility, elasticity, and/or malleability which is greater than the first level of flexibility, elasticity, and/or malleability.

In an example, this invention can be embodied in an intrasacular aneurysm occlusion device comprising: (1) an intravascular delivery lumen; (2) a plurality of embolic members; (3) a proximal neck bridge; wherein proximal is defined as closer to the aneurysm neck and distal is defined as closer to the aneurysm dome; wherein the neck bridge is configured to occlude the neck of an aneurysm sac; wherein the neck bridge has a first configuration while it is being transported through the delivery lumen to an aneurysm sac and a second configuration after it has been expanded within the aneurysm sac; wherein the neck bridge in its second configuration has a width which is greater than the diameter of the neck of the aneurysm sac; and wherein the neck bridge in its second configuration has a first level of flexibility, elasticity, and/or malleability; and (4) a distal net or mesh; wherein distal is defined as being closer to an aneurysm dome and proximal is defined as closer to the aneurysm neck; wherein the net or mesh has a first configuration while it is being transported through the delivery lumen to an aneurysm sac; wherein the net or mesh has a second configuration after it has been expanded within the aneurysm sac; wherein the net or mesh is configured to conform to the walls of an aneurysm sac in its second configuration; wherein the net or mesh is expanded from its first configuration to its second configuration by the insertion of the embolic members into the net or mesh; wherein the net or mesh in its second configuration has a second level of flexibility, elasticity, and/or malleability which is greater than the first level of flexibility, elasticity, and/or malleability.

In an example, this invention can be embodied in an intrasacular aneurysm occlusion device comprising: (1) an intravascular delivery lumen; (2) a plurality of embolic members; (3) a inner stent; wherein the inner stent is configured to occlude the neck of an aneurysm sac; wherein the inner stent has a first configuration while it is being transported through the delivery lumen to an aneurysm sac and a second configuration after it has been expanded within the aneurysm sac; wherein the inner stent in its second configuration has a width which is greater than the diameter of the neck of the aneurysm sac; and wherein the inner stent in its second configuration has a first level of flexibility, elasticity, and/or malleability; and (4) a outer net or mesh; wherein the net or mesh has a first configuration while it is being transported through the delivery lumen to an aneurysm sac; wherein the net or mesh has a second configuration after it has been expanded within the aneurysm sac; wherein the net or mesh is configured to conform to the walls of an aneurysm sac in its second configuration; wherein the net or mesh is expanded from its first configuration to its second configuration by the insertion of the embolic members into the net or mesh; wherein the net or mesh in its second configuration has a second level of flexibility, elasticity, and/or malleability which is greater than the first level of flexibility, elasticity, and/or malleability.

In different embodiments of this device, the resilient wider-than-neck and flexible sac-filling portions of this device can have different locations relative to each other and to an aneurysm sac. In an example, one portion can be more proximal (e.g. closer to the aneurysm neck) than the other portion. In an example, one portion can be inside the other portion. In an example, a resilient wider-than-neck portion of this device in its second configuration can be proximal relative to a flexible sac-filling portion of this device in its second configuration, wherein proximal is defined as closer to the aneurysm neck and distal is defined as closer to the top of the aneurysm dome. In an example, a resilient wider-than-neck portion of this device can be inside (e.g. nested within) a flexible sac-filling portion of this device. Alternatively, a flexible sac-filling portion of this device can be inside (e.g. nested within) a resilient wider-than-neck portion of this device. In an example, a resilient wider-than-neck portion of this device in its second configuration can be central relative to a flexible sac-filling portion of this device in its second configuration, wherein central is defined as closer to the centroid of the aneurysm sac and peripheral is defined as closer to the walls of the aneurysm sac. In an example, a resilient wider-than-neck portion of this device in its second configuration can be peripheral relative to a flexible sac-filling portion of this device in its second configuration.

There can also be differences among example embodiments of this device in whether the resilient wider-than-neck and flexible sac-filling portions of this device are separate structures or are portions of the same structure. In an example, resilient wider-than-neck and flexible sac-filling portions of this device can be separate structures. In an example, resilient wider-than-neck and flexible sac-filling portions of this device can be formed as separate structures, but can then be attached to each other at one or more points. In an example, resilient wider-than-neck and flexible sac-filling portions of this device can be different portions of the same structure. In an example, resilient wider-than-neck and flexible sac-filling portions of this device can be proximal and distal portions, respectively, of the same structure. In an example, resilient wider-than-neck and flexible sac-filling portions of this device can be proximal and distal portions, respectively, of a single continuous structure. In an example, resilient wider-than-neck and flexible sac-filling portions of this device can be inner and outer portions or layers, respectively, of the same structure. In an example, resilient wider-than-neck and flexible sac-filling portions of this device can be inner and outer portions or layers, respectively, of the same continuous structure.

In an example, a resilient wider-than-neck portion of this device can be an intrasacular stent or neck bridge. In an example, a resilient wider-than-neck portion of this device can be made from metal, a polymer, or both. In an example, a resilient wider-than-neck portion of this device can be an expandable intrasacular mesh, braid, lattice, or framework. In an example, a resilient wider-than-neck portion of this device can be an intrasacular stent which, in its second configuration, is shaped like a ball, ellipsoid, apple, pumpkin, pear, torus, hemisphere, bowl, or inverted-umbrella.

In an example, a resilient wider-than-neck portion of this device can be mesh, braid, lattice, or framework which covers an aneurysm neck from the inside of an aneurysm sac when the resilient wider-than-neck portion is in its second configuration. In an example, a resilient wider-than-neck portion of this device in its second configuration can be configured to bridge, span, cover and/or occlude an aneurysm neck from the inside of the aneurysm sac. In an example, a resilient wider-than-neck portion of this device in its second configuration can be held against the inside surface of the aneurysm neck by pressure from an expanded flexible sac-filling portion of the device in its second configuration. In this manner, the resilient wider-than-neck portion of this device is held against the aneurysm neck more consistently than is the case with a solitary neck bridge without such an accompanying flexible sac-filling portion.

In an example, a resilient wider-than-neck portion of this device can self-expand within an aneurysm sac after it is released from a delivery lumen. In an example, a resilient wider-than-neck portion of this device can self-expand from a first (radially-constrained) configuration within a delivery lumen to a second (radially-expanded) configuration within an aneurysm sac, covering an aneurysm neck from the inside of the sac in its second (radially-expanded) configuration. In an example, a resilient wider-than-neck portion of this device can be made from shape memory material which self-expands within an aneurysm sac after it is released from the constraints of a delivery lumen. In an example, a resilient wider-than-neck portion of this device can be a self-expanding stent and/or neck bridge. In an example, a resilient wider-than-neck portion of this device can be a self-expanding spherical, ellipsoidal, or toroidal wire mesh, braid, lattice, or framework. In an example, a resilient wider-than-neck portion of this device can be made from material which changes shape (e.g. expands) in response to the temperature within the aneurysm sac.

In an example, a resilient wider-than-neck portion of this device can be expanded by a balloon (or other inflatable member). In an example, a resilient wider-than-neck portion of this device can be expanded with an aneurysm by filling a balloon (or other inflatable member) with a fluid, gel, or gas. In an example, a resilient wider-than-neck portion of this device can be expanded by filling a balloon (or other inflatable member) inside the resilient wider-than-neck portion with a fluid, gel, or gas. After expansion of the resilient wider-than-neck portion, the balloon can be deflated and withdrawn. In an example, a resilient wider-than-neck portion of this device can be radially expanded by the inflation of one or more balloons (or other inflatable members) inside it. In an example, a resilient wider-than-neck portion of this device can be an arcuate stent and/or neck bridge which is radially expanded with an aneurysm sac by inflation of a balloon (or other inflatable member).

In an example, a resilient wider-than-neck portion of this device can be expanded by a small-scale actuator such as a Micro Electro Mechanical System (MEMS) unit. In an example, a resilient wider-than-neck portion of this device can be changed from its first configuration to its second configuration by activation of a microscale actuator such as a MEMS unit. In an example, the degree of radial expansion of a resilient wider-than-neck portion of this device can be adjusted by a device operator using a MEMS unit. In an example, the MEMS unit can be withdrawn from the aneurysm sac and the person's body after a resilient wider-than-neck portion of this device has been satisfactorily expanded in an aneurysm sac. In an example, a MEMS unit can also enable contraction of the resilient wider-than-neck portion if its initial expansion location is not optimal. In an example, a MEMS unit can reversibly change a resilient wider-than-neck portion of this device from its first (radially-constrained) configuration to its second (radially-expanded) configuration, and back, in multiple iterations, until the optimal expanded configuration in the aneurysm sac is achieved.

In an example, a resilient wider-than-neck portion of this device can be changed from a first (radially-constrained) configuration to a second (radially-expanded) configuration by the operator of the device by movement of a wire, cord, string, cable, or fiber attached to the resilient wider-than-neck portion of the device. In an example, a resilient wider-than-neck portion of this device can be changed from a first (radially-constrained) configuration to a second (radially-expanded) configuration when the operator pulls, pushes, or rotates a wire, cord, string, cable, and/or fiber which is attached to the resilient wider-than-neck portion of the device. In an example, a wire, cord, string, cable and/or fiber can be attached to a first part of the resilient wider-than-neck portion of the device but not to a second part, wherein pulling, pushing, or rotating the wire, cord, and/or fiber by the device operator causes the first part to move relative to the second part. In an example, this movement can be reversed when the device operator pulls, pushes, or rotates the wire, cord, string, cable, and/or fiber in an opposite direction. In an example, the shape and/or location of the wider-than-neck portion of this device can be reversibly adjusted by a user by reversibly pulling, pushing, or rotating such a wire, cable, and/or fiber until the optimal configuration for occluding the aneurysm neck is achieved.

In an example, the radial width of a resilient wider-than-neck portion of this device can increase from its first configuration to its second configuration. In an example, the radial width of a resilient wider-than-neck portion is smaller than the radial width of an aneurysm neck in the portion's first configuration and becomes larger than the radial width of the aneurysm neck in the portion's second configuration. In an example, a resilient wider-than-neck portion of this device in its first configuration (while being transported through a delivery lumen to an aneurysm sac) can have a longitudinal axis, a length dimension along the longitudinal axis, and a width which is perpendicular to the longitudinal axis. In an example, the longitudinal axis of the resilient wider-than-neck portion of this device can be parallel to the longitudinal axis of the delivery lumen as the portion is being transported through the lumen. In an example, a resilient wider-than-neck portion of this device can have a first length and a first width in its first configuration (while being transported through a delivery lumen to an aneurysm sac) and a second length and second width in its second configuration (after expansion within the aneurysm sac). In an example, the second width can be at least 50% greater than the first width. In an example, the second width can be at least twice the first width. In an example, the second width can be at least 50% greater than the first width and the second length can be less than half of the first length.

In an example, a resilient wider-than-neck portion of this device can have a shape in its first configuration wherein the longest axis of this shape is substantially parallel to the longitudinal axis of the delivery lumen through which it travels. In an example, a resilient wider-than-neck portion of this device can have a shape in its second configuration wherein the longest axis of this shape is configured to be substantially parallel to the circumference of the neck of an aneurysm into which it is inserted. In an example, a resilient wider-than-neck portion of this device can have a first configuration as is travels through a delivery lumen to an aneurysm sac and a second configuration after it is released from the delivery lumen and expanded within the aneurysm sac. In an example, a resilient wider-than-neck portion of this device can have a longitudinal axis in its first configuration and a cross-sectional plane which is parallel to its longitudinal axis in its first configuration. In an example, this cross-sectional plane can be substantially parallel to the plane defined by the circumference of the neck of the aneurysm sac when the resilient wider-than-neck portion of this device is in its second configuration.

In an example, a resilient wider-than-neck portion of this device in its first configuration (being transported through a delivery lumen) can have a longitudinal axis which is parallel to the longitudinal axis of the delivery lumen and a cross-sectional axis which is perpendicular to the longitudinal axis. In an example, the resilient wider-than-neck portion of this device can have a second configuration (after release from the delivery lumen into an aneurysm sac) wherein its longitudinal axis becomes shorter and its cross-sectional axis becomes longer. In an example, the resilient wider-than-neck portion of this device can have a second configuration (after release from the delivery lumen into an aneurysm sac) wherein the length of its longitudinal axis is less than half of its length in the first configuration and the width of its cross-sectional axis is more than twice its width in the first configuration.

In an example, a resilient wider-than-neck portion of this device can have a first length and a first width when it is in a first configuration (as it is delivered through a lumen to an aneurysm sac) and can have a second length and a second width when it is in a second configuration (after having been expanded within the aneurysm sac). In an example, the second width can be at least 400% greater than the first width. In an example, the second width can be at least twice the first width. In an example, the second width can be at least 50% greater than the first width. In an example, the second width can be greater than the first width. In an example, the second length can be less than 25% of the first length. In an example, the second length can be less than half of the first length. In an example, the second length can be less than the first length. In an example, the second width can be at least 400% greater than the first width and the second length can be less than 25% of the first length. In an example, the second width can be at least twice the first width and the second length can be less than half of the first length. In an example, the second width can be greater than the first width and the second length can be less than the first length.

In an example, a resilient wider-than-neck portion of this device can have a first configuration as it travels through a delivery lumen to an aneurysm sac and a second configuration after it exits the lumen into the aneurysm sac, wherein the resilient wider-than-neck portion has a Z axis which is substantially parallel to the longitudinal axis of the delivery lumen in the first configuration and an X axis which is perpendicular to the Z axis, and wherein the length of the Z axis is greater than the length of the X axis in the first configuration and the length of the Z axis is less than the length of the X axis in the second configuration. In an example, a resilient wider-than-neck portion of this device can have a Z axis (parallel to its delivery path) which expands less than its X axis (perpendicular to its Z axis) when the portion is expanded within an aneurysm sac.

In an example, a resilient wider-than-neck portion of this device can have a first size in a first configuration as it is being delivered through a person's vasculature to an aneurysm sac and a second size in a second configuration after it has been expanded within the aneurysm sac, wherein the second size is greater than the first size. In an example, a resilient wider-than-neck portion of this device can be compressed in a first configuration in a delivery lumen as it is transported through a person's body to an aneurysm sac and can be expanded in a second configuration after it has been inserted into the aneurysm sac. In an example, a resilient wider-than-neck portion of this device can have a first (compressed) configuration as it travels through a delivery lumen and a second (expanded) configuration after it exits the lumen within an aneurysm sac. In an example, a resilient wider-than-neck portion of this device can have a first density in a first configuration as it is being delivered to an aneurysm sac and a second density in a second configuration after expansion within the aneurysm sac, wherein the second density is less than the first density.

In an example, a resilient wider-than-neck portion of this device can have a first configuration in which it is compressed, folded, pleated, rolled, curved, and/or coiled for transportation in a delivery lumen through a person's vasculature to an aneurysm sac. In an example, a resilient wider-than-neck portion can have a second configuration after it has expanded, unfolded, unrolled, and/or uncoiled within an aneurysm sac. In an example, a resilient wider-than-neck portion of this device can have a first volume (or size) in its first (delivery) configuration and a second volume (or size) in its second (expanded) configuration, wherein the second volume (or size) is greater than the first volume (or size). In an example, a resilient wider-than-neck portion of this device can have a first volume (or size) in its first (delivery) configuration and a second volume (or size) in its second (expanded) configuration, wherein the second volume (or size) is at least twice the first volume (or size). In an example, a resilient wider-than-neck portion of this device can have a first volume (or size) in its first (delivery) configuration and a second volume (or size) in its second (expanded) configuration, wherein the second volume (or size) is at least 50% greater than the first volume (or size).

In an example, a resilient wider-than-neck portion of this device can be expanded into a second configuration within an aneurysm sac, wherein the maximum diameter of the resilient wider-than-neck portion in its second configuration is configured to be (at least 25%) larger than the maximum diameter of the aneurysm neck. In an example, a resilient wider-than-neck portion of this device can have a circumference in its second configuration that is (at least 25%) larger than the circumference of an aneurysm neck in order to keep the device within the aneurysm sac. In an example, a resilient wider-than-neck portion of this device can have a second (expanded) configuration with a maximum width (in a plane parallel to the plane of an aneurysm neck) which is (at least 25%) greater than the width of the aneurysm neck.

In an example, a resilient wider-than-neck portion of this device can be radially-expanded in the proximal portion of an aneurysm sac to a width which is (at least 25%) larger than the aneurysm neck. In an example, after expansion, a resilient wider-than-neck portion of this device in its second configuration occludes the aneurysm neck and blocks blood flow into the aneurysm. In an example, a resilient wider-than-neck portion of this device can have a diameter in its second configuration which is (at least 25%) wider than the diameter of an aneurysm neck diameter, wherein these diameters are in parallel planes. In an example, a resilient wider-than-neck portion of this device can have a circumference in its second configuration which is (at least 25%) wider than the circumference of an aneurysm neck diameter, wherein these diameters are in parallel planes. In an example, a resilient wider-than-neck portion of this device can have a cross-sectional plane in its second configuration which is configured to be substantially parallel (plus or minus 10 degrees) to the plane of the aneurysm neck circumference. In an example, a resilient wider-than-neck portion of this device can have a cross-sectional area plane in its second configuration which is (at least 25%) larger than a parallel cross-sectional area of the aneurysm neck circumference.

In an example, a resilient wider-than-neck portion of this device can be rolled or curled around its longitudinal axis in a first configuration as it is being transported through a delivery lumen to an aneurysm sac. In an example, a resilient wider-than-neck portion of this device can be rolled and/or curled around a lateral axis (which is perpendicular to its longitudinal axis) in a first configuration as it is delivered to an aneurysm sac through a delivery lumen. In an example, a resilient wider-than-neck portion of this device can have a helical shape in its first configuration as it is being delivered to an aneurysm sac. In an example, a resilient wider-than-neck portion of this device can be folded or pleated along its longitudinal axis in a first configuration as it is delivered to an aneurysm sac through a delivery lumen such as a catheter. In an example, a resilient wider-than-neck portion of this device can be folded or pleated along a lateral axis (which is perpendicular to its longitudinal axis) in a first configuration as it is delivered to an aneurysm sac through a delivery lumen such as a catheter.

In an example, a resilient wider-than-neck portion of this device can have a first porosity level in its first (delivery) configuration and a second porosity level in its second (expanded) configuration, wherein the second porosity level is less than the first porosity level. In an example, a resilient wider-than-neck portion of this device can have a first porosity level in its first (delivery) configuration and a second porosity level in its second (expanded) configuration, wherein the second porosity level is greater than the first porosity level. In an example, a resilient wider-than-neck portion of this device can have a single layer in its first configuration and be folded within an aneurysm sac that its proximal surface has multiple layers in its second configuration.

In an example, a resilient wider-than-neck portion of this device can have a first elasticity level in its first (delivery) configuration and a second elasticity level in its second (expanded) configuration, wherein the second elasticity level is less than the first elasticity level. In an example, a resilient wider-than-neck portion of this device can have a first rigidity or stiffness level in its first (delivery) configuration and a second rigidity or stiffness level in its second (expanded) configuration, wherein the second rigidity or stiffness level is greater than the first rigidity or stiffness level. In an example, a resilient wider-than-neck portion can be sufficiently rigid or stiff in its second configuration so as to resist compression once expanded within an aneurysm sac.

In an example, a resilient wider-than-neck portion of this device can have a convex shape in its second configuration. In an example, a resilient wider-than-neck portion of this device can comprise an ellipsoid, wherein this ellipsoid has a first orientation as it travels through a delivery lumen to an aneurysm sac and a second orientation after it has exited the delivery lumen and expanded within the aneurysm sac, wherein in the first orientation the longest axis of the ellipsoid is substantively parallel to the longitudinal axis of the delivery lumen, and wherein in the second orientation the longest axis of the ellipsoid is substantially perpendicular to the prior orientation of the longest axis traveling through the delivery lumen. In an example, a resilient wider-than-neck portion of this device can have a shape memory and a prior shape to which it returns after its release from a delivery lumen in an aneurysm sac. In an example, a resilient wider-than-neck portion of this device can have a concave shape in its second configuration.

In an example, the orientation and/or location of a resilient wider-than-neck portion of this device within an aneurysm sac can be changed, steered, directed, rotated, and/or adjusted by a device operator using a mechanism selected from the group consisting of: rotating a catheter, wire, or coil; pulling on string or cord; fusing or crimping members in the portion; cutting or melting members in the portion; adjusting the tension or elasticity of members in the portion; application of electromagnetic energy; activation of a microscale actuator; and selective inflation of multiple balloons.

In an example, a resilient wider-than-neck portion of this device can have a structure and/or framework which resists radial compression after it has been expanded into its second configuration in an aneurysm sac. In an example, this structure or framework can be locked into place after it has been expanded in an aneurysm sac. In an example, a resilient wider-than-neck portion of this device can have radial struts which resist radial compression after they have been expanded into their second configuration in an aneurysm sac. In an example, a resilient wider-than-neck portion of this device can have radial struts which lock and/or snap into a radially-expanded configuration in an aneurysm sac. In an example, a resilient wider-than-neck portion of this device can have radial struts which are melted (e.g. by application of electromagnetic energy) into place in a radially-expanded configuration in an aneurysm sac. In an example, a resilient wider-than-neck portion of this device can have radial struts which are locked into a radially-expanded configuration by a congealing substance.

In an example, a resilient wider-than-neck portion of this device can be expanded within an aneurysm sac in proximity to an aneurysm neck so as to bridge, cover, span, block, and/or occlude the aneurysm neck. In an example, a resilient wider-than-neck portion in its second configuration can be located entirely within the proximal 25% of the volume of an aneurysm sac. In an example, a resilient wider-than-neck portion in its second configuration can be located entirely within the proximal half of an aneurysm sac. In an example, a resilient wider-than-neck portion in its second configuration can be located entirely within the proximal 75% of the volume of an aneurysm sac.

In an example, at least 75% of the volume of a resilient wider-than-neck portion in its second configuration can be located within the proximal 25% of the volume of an aneurysm sac. In an example, at least 75% of the volume of a resilient wider-than-neck portion in its second configuration can be located within the proximal half of an aneurysm sac. In an example, at least 75% of the volume of a resilient wider-than-neck portion in its second configuration can be located within the proximal 75% of the volume of an aneurysm sac. In an example, less than 10% of a resilient wider-than-neck portion in its second configuration is located within the proximal 25% or the distal 25% of the volume of an aneurysm sac. In an example, none of a resilient wider-than-neck portion in its second configuration is located within the proximal 25% or the distal 25% of the volume of an aneurysm sac.

In an example, a resilient wider-than-neck portion of this device can have a bowl, hemispherical, inverted dome, paraboloid, and/or inverted umbrella shape in its second configuration. In an example, a resilient wider-than-neck portion can have a spherical, ball, globular, apple, or pumpkin shape in its second configuration. In an example, a resilient wider-than-neck portion can have a cross-sectional shape in its second configuration which is selected from the group consisting of: ellipse, reflected parabola, circle, oval, convex lens, and torus. In an example, a resilient wider-than-neck portion can have a cylindrical shape in its second configuration. In an example, a resilient wider-than-neck portion can have a disk shape in its second configuration. In an example, a resilient wider-than-neck portion can have a doughnut shape in its second configuration.

In an example, a resilient wider-than-neck portion of this device can have a ring shape in its second configuration. In an example, a resilient wider-than-neck portion of this device can be an annular, toroidal, doughnut-shape, and/or ring-shape stent with a (central) opening which can is closed after insertion of embolic members into a flexible sac-filling portion of this device which is distal to the resilient wider-than-neck portion of this device. In an example, a resilient wider-than-neck portion of this device can have a spherical shape in its second configuration. In an example, a resilient wider-than-neck portion of this device can have a wheel shape in its second configuration. In an example, a resilient wider-than-neck portion of this device can have a water lily shape in its second configuration.

In an example, a resilient wider-than-neck portion of this device can have a shape in its second (expanded) configuration selected from the group consisting of: arcuate section of the surface of a sphere (such as longitudinal sections of a globe), flower petal, full ellipsoid, bowl, convex lens, hourglass, hyperbola, keystone, lemon shape, apple shape, ovaloid shape, pear shape, pumpkin shape, lemon shape, spherical section, helical or spiral shape, tear drop shape, egg shape, pancake shape, frustum, tire, and torus. In an example, a resilient wider-than-neck portion of this device can be an ellipsoidal, ovaloidal, and/or disk-shaped stent with a (central) opening which can is closed after insertion of embolic members into a flexible sac-filling portion of this device. In an example, a resilient wider-than-neck portion of this device can have a flared, tapered, egg, tear drop, or wedge shape whose proximal half is wider than its distal half. In an example, a resilient wider-than-neck of this device can have a shape whose distal half is wider than its proximal half.

In an example, a resilient wider-than-neck portion of this device can be made from chromium or a nickel-aluminum alloy. In an example, a resilient wider-than-neck portion of this device can be made from bars of gold-pressed latinum. In an example, a resilient wider-than-neck portion of this device can be a polymer structure. In an example, a resilient wider-than-neck portion of this device can be made from polybutester, siloxane (e.g. siloxane-polyurethane), polyolefin, or ethylene vinyl alcohol. In an example, a resilient wider-than-neck portion of this device can be made from vinyltriethoxysilane, methylcellulose, or polylactide. In an example, a resilient wider-than-neck portion of this device can be made from diphenylmethane diisocyanate.

In an example, a resilient wider-than-neck portion of this device can have a flower petal shape in its second configuration. In an example, a resilient wider-than-neck portion of this device can have a generally spherical shape which is collapsed into a generally hemispherical and/or bowl shape in an aneurysm sac in order to create a double-layer barrier across an aneurysm neck. This can be done when the device operator pulls on a wire, cable, or cord connected to the distal surface of the resilient wider-than-neck portion. In an example, a resilient wider-than-neck portion of this device can have a keystone, bowl, hemisphere, sphere, ball, ellipsoid, ovaloid, torus, ring, or disk shape which is configured to cover the neck of an aneurysm. In an example, a resilient wider-than-neck portion of this device can have a single layer. In an example, it can have multiple layers. In an example, all the single layers, all the single layers, all the single layers, and if you liked it then you should have put a ring on it.

In an example, a resilient wider-than-neck portion of this device can have a paraboloid shape in its second configuration. In an example, a resilient wider-than-neck portion of this device can have a platter shape in its second configuration. In an example, a resilient wider-than-neck portion of this device can have a polygonal cylinder shape in its second configuration. In an example, a resilient wider-than-neck portion of this device can be an expandable hollow polymer bowl or hemisphere, sphere or ball, ellipsoid or ovaloid, torus or ring, or disk. In an example, a resilient wider-than-neck portion of this device can be a single-layer bowl or hemisphere, sphere or ball, ellipsoid or ovaloid, torus or ring, or disk. In an example, a resilient wider-than-neck portion of this device can be a multi-layer polymer bowl or hemisphere, sphere or ball, ellipsoid or ovaloid, torus or ring, or disk. In an example, a resilient wider-than-neck portion of this device can have a spiral shape in its second configuration. In an example, a resilient wider-than-neck portion of this device can have an umbrella shape in its second configuration.

In an example, a resilient wider-than-neck portion of this device can be made from a super-elastic material. In an example, a resilient wider-than-neck portion of this device can be made from a nickel-titanium alloy. In an example, a resilient wider-than-neck portion of this device can be made from stainless steel or a cobalt-chromium alloy. In an example, a resilient wider-than-neck portion of this device can be made from a CoCrMo alloy or from niobium. In an example, a resilient wider-than-neck portion of this device can be made from magnesium. In an example, a resilient wider-than-neck portion of this device can be polycarbonate. In an example, a resilient wider-than-neck portion of this device can be made from polypropylene, acetone, polyglycolic acid, fibrinogen, or polyphosphoester.

In an example, a resilient wider-than-neck portion of this device can have a shape in its second configuration selected from the group consisting of: conic section, cylindrical shape, oval shape, and tear drop shape. In an example, a resilient wider-than-neck portion of this device can have a shape in its second configuration selected from the group consisting of: tubular shape, bullet shape, flower petal shape, prolate hemispherical shape, globular shape, cardioid shape, and frustoconical shape. In an example, a resilient wider-than-neck portion of this device can have a shape in its second configuration selected from the group consisting of: hour-glass shape, prolate spherical shape, circular shape, oblate spheroid shape, oblong shape, flower shape, conic shape, and ovoid shape.

In an example, a resilient wider-than-neck portion of this device can be made from cobalt or nickel-titanium alloy. In an example, a resilient wider-than-neck portion of this device can be made from nitinol. In an example, a resilient wider-than-neck portion of this device can be made from one or more metals, one or more polymers, or a combination of metal and a polymer. In an example, a resilient wider-than-neck portion of this device can be made from poly-D-lactide, polyurethane, or polyphenylene sulfide. In an example, a resilient wider-than-neck portion of this device can be made from a hydrogel.

In an example, a resilient wider-than-neck portion of this device can be created by weaving. In an example, a resilient wider-than-neck portion of this device can be created by weaving wires or filaments into a weave pattern selected from the group consisting of: plain weave; double weave; diamond weave; perpendicular weave; rib weave; basket weave; twill weave; satin weave; leno weave; mock leno weave; and diagonal weave.

In an example, a resilient wider-than-neck portion of this device can be created by braiding. In an example, a resilient wider-than-neck portion of this device can be created by braiding wires or filaments into a braid pattern selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, a resilient wider-than-neck portion of this device can have an asymmetrical braid pattern. Different areas of the resilient wider-than-neck portion can have different braid directions and/or orientations. In an example, different areas of a resilient wider-than-neck portion can have different levels of filament density, different levels of grid size, different levels of porosity, opening size, different levels of resiliency, different thicknesses, or different widths. In an example, different portions of a resilient wider-than-neck portion of this device can have different structural characteristics selected from the group consisting of: filament density, grid size, porosity, opening size, resiliency, thickness, and width.

In an example, different areas of a resilient wider-than-neck portion can have different braid patterns. In an example, the proximal area of a resilient wider-than-neck portion of this device can have a first braid pattern and the distal area of the resilient wider-than-neck portion of this device can have a second braid pattern. In an example, different areas of a resilient wider-than-neck portion can have different braid densities. In an example, the proximal area of a resilient wider-than-neck portion of this device can have a higher braid density than the distal area of the resilient wider-than-neck portion of this device. In an example, different areas of a resilient wider-than-neck portion can have different braid angles. In an example, the proximal area of a resilient wider-than-neck portion of this device can have a greater braid angle than the distal area of the resilient wider-than-neck portion of this device.

In an example, different areas of a resilient wider-than-neck portion can have different braid pitches. In an example, the proximal area of a resilient wider-than-neck portion of this device can have a first braid pitch and the distal area of the resilient wider-than-neck portion of this device can have a second braid pitch. In an example, different areas of a resilient wider-than-neck portion can have different braid filament sizes. In an example, the proximal area of a resilient wider-than-neck portion of this device can have a first braid filament size and the distal area of the resilient wider-than-neck portion of this device can have a second braid filament size.

In an example, a resilient wider-than-neck portion of this device can be made by braiding or weaving together metal and/or polymer wires, strands, or ribbons. In an example, a resilient wider-than-neck portion of this device can be made by braiding or weaving metal and/or polymer wires or filaments together. In an example, a resilient wider-than-neck portion can be a woven or braided mesh, net, or lattice. In an example, a resilient wider-than-neck portion can have a radially-asymmetric braid or weave.

In an example, a first part of a resilient wider-than-neck portion of this device can have a first density and a second part of the resilient wider-than-neck portion of this device can have a second density, wherein the second density is less than the first density. In an example, a first part of a resilient wider-than-neck portion of this device can have a first elasticity level and a second part of the resilient wider-than-neck portion of this device can have a second elasticity level, wherein the second elasticity level is less than the first elasticity level. In an example, a first part of a resilient wider-than-neck portion of this device can have a first porosity level and a second part of the resilient wider-than-neck portion of this device can have a second porosity level, wherein the second porosity level is less than the first porosity level. In an example, a first part of a resilient wider-than-neck portion of this device can have a first rigidity or stiffness level and a second part of the resilient wider-than-neck portion of this device can have a second rigidity or stiffness level. In an example, a first part of a resilient wider-than-neck portion of this device can have a first width and a second part of the resilient wider-than-neck portion of this device can have a second width.

In an example, a central part of a resilient wider-than-neck portion can have a first density and a peripheral part of the resilient wider-than-neck portion can have a second density. In an example, a central part of a resilient wider-than-neck portion of this device can have a first elasticity level and a peripheral part of the resilient wider-than-neck portion of this device can have a second elasticity level. In an example, a central part of a resilient wider-than-neck portion of this device can have a first porosity level and a peripheral part of the resilient wider-than-neck portion of this device can have a second porosity level. In an example, a central part of a resilient wider-than-neck portion can have a first rigidity level and a peripheral part of the resilient wider-than-neck portion can have a second rigidity level. In an example, a central part of a resilient wider-than-neck portion can have a first stiffness level and a peripheral part of the resilient wider-than-neck portion can have a second stiffness level. In an example, a central part of a resilient wider-than-neck portion can have a first width and a peripheral part of the resilient wider-than-neck portion can have a second width.

In an example, a proximal surface of a resilient wider-than-neck portion of this device can have a higher density and/or lower porosity than a distal surface of the resilient wider-than-neck portion. In an example, a proximal part of a resilient wider-than-neck portion of this device can have multiple layers, while a distal part of the resilient wider-than-neck portion only has a single layer. In an example, a flexible sac-filling portion of this device can comprise braided, woven, or wound wires or filaments. In an example, a resilient wider-than-neck portion can comprise an expandable mesh, network, lattice, or radial array of wires or other stiff fibers. In an example, these wires or filament can be helical. In an example, these wires or filaments can comprise radial spokes. In an example, a resilient wider-than-neck portion can have multiple layers, thereby forming a multi-layer stent or neck bridge. In an example, a resilient wider-than-neck portion can be a hollow convex wire mesh, net, lattice, or braided structure.

In an example, a resilient wider-than-neck portion can be made from metal wires, strands, strips, ribbons, filaments, cables, or coils. In an example, a resilient wider-than-neck portion can be superelastic. In an example, a resilient wider-than-neck portion can be a hollow convex mesh, lattice, net, or framework which is woven or braided from a plurality of wires or filaments. In an example, a resilient wider-than-neck portion can comprise a radially-distributed longitudinal array of strands, strips, ribbons, filaments, cables, and/or coils. In an example, a resilient wider-than-neck portion can include undulating, sinusoidal, and/or serpentine wires, fibers, or filaments.

In an example, a resilient wider-than-neck portion can be made from gallium or nitinol. In an example, a resilient wider-than-neck portion can be made from polydimethylsiloxane, polytetrafluoroethylene, fibronectin, polycarbonate urethane, polyester urethane, or polyvinyl chloride. In an example, a resilient wider-than-neck portion of this device can be made from trimethylene carbonate, copper-zinc alloy, iridium, or palladium. In an example, a resilient wider-than-neck portion can be made from cobalt-chromium, tantalum, or CoCrNi alloy. In an example, a resilient wider-than-neck portion can be made from polydioxanone, polytetramethyleneoxide, collagen, or glycolic acid. In an example, a resilient wider-than-neck portion can be radio-opaque.

In an example, a resilient wider-than-neck portion of this device can have multiple layers. In an example, a plurality of layers can fit into each other in nested manner, creating a multi-layer portion of this device which spans and occludes an aneurysm neck from inside the aneurysm sac. In an example, a resilient wider-than-neck portion can comprise a multi-layer bowl or hemisphere, a multi-layer sphere or ball, a multi-layer ellipsoid or ovaloid, a multi-layer torus or ring, or a multi-layer disk. In an example, a portion can have a metal layer and a polymer layer. In an example, an inner layer can be metal and an outer layer can be made from a polymer. In an example, a resilient wider-than-neck portion of this device can have a biologically-active outer layer which encourages cell growth for more thorough embolization of the aneurysm neck. In an example, a resilient wider-than-neck portion can have multiple layers of material with different mesh or braid directions, different porosity levels, different elasticity levels, and/or different rigidity levels.

In an example, a resilient wider-than-neck portion of this device can have a single layer in its first configuration and multiple layers in its second configuration. In an example, a resilient wider-than-neck portion of this device can be folded and/or curved back on itself in its second configuration so as to have multiple layers in its second configuration. In an example, the proximal part of a resilient wider-than-neck portion of this device can have a single layer as it is transported through a delivery lumen to an aneurysm sac and can have two overlapping layers after it is released from the lumen. In an example, it can be folded after expansion within the aneurysm sac. In an example, a resilient wider-than-neck portion of this device can be a mesh, net, lattice, or braid whose proximal part comprises a single layer in it first configuration (as it is transported through a delivery lumen to an aneurysm sac) and two or more overlapping layers in its second configuration (after the resilient wider-than-neck portion is released from the lumen and deployed within the aneurysm sac).

In an example, some or all of a resilient wider-than-neck portion of this device can have a low porosity level and/or be substantially impermeable to blood. In an example, a flexible sac-filling portion can be a mesh with strands, wires, or fibers between 5 and 50 microns in width. In an example, a flexible sac-filling portion can be a mesh with strands, wires, or fibers between 50 and 200 microns in width. In an example, a resilient wider-than-neck portion of this device can be made from titanium. In an example, a resilient wider-than-neck portion can be an expandable mesh, lattice, net, or framework which resists compression or deformation once it has been expanded within an aneurysm sac. In an example, a resilient wider-than-neck portion of this device can be made from copper or hydroxy-terminated polycarbonate. In an example, a resilient wider-than-neck portion of this device can be made from nylon, a polyester, polyvinyl alcohol, or tetrahydrofuran.

In an example, a resilient wider-than-neck portion of this device can have an opening through which embolic members are inserted into the flexible sac-filling portion of this device. In an example, this opening can have a one-way valve which enables embolic members to be inserted into the flexible sac-filling portion of this device but not escape out. In an example, this opening can be closed after the sac-filling portion has been expanded. In an example, a resilient wider-than-neck portion of this device can have one or more adjustable openings. In an example, these openings can allow blood to escape from an aneurysm sac (as the resilient wider-than-neck portion and/or the flexible sac-filling portion are being expanded within the aneurysm sac), but then be closed to prevent blood from re-entering the aneurysm sac. In an example, an opening can be manually and/or remotely changed from a first (open) configuration to a second (closed) configuration. In an example, a resilient wider-than-neck portion can have two openings: a first opening through which embolic material is inserted into the aneurysm sac and a second opening through which blood can exit the aneurysm sac while embolic material is being inserted into the aneurysm sac. In an example, the device can further comprise a closure mechanism (which closes an opening) selected from the group consisting of: tensile ring; drawstring; electromagnetic melting mechanism; insertable plug; clamp; hydrogel plug; and bioactive congealing plug.

In an example, a resilient wider-than-neck portion of this device can be made by one or more methods selected from the group consisting of: sheet etching, crimping, photochemical etching, electroforming, photochemical machining, electrical discharge machining, folding or pleating, and adhesion. In an example, a resilient wider-than-neck portion of this device can be made by laser cutting a sheet of metal or polymer material. In an example, a resilient wider-thanneck portion of this device can be made by: physical vapor deposition; cutting a mesh, lattice, or framework; photolithography; electrospinning metal and/or polymer wires or filaments; rolling; thermoformation; or perforation. In an example, a resilient wider-than-neck portion of this device can be made by (laser) welding. In an example, a resilient wider-than-neck portion of this device can be made by knitting or weaving. In an example, a resilient wider-than-neck portion of this device can be made by micro-machining. In an example, a resilient wider-than-neck portion of this device can be detached from a delivery wire, pusher, and/or catheter by mechanical, chemical, or electrolytic detachment. In an example, a resilient wider-than-neck portion of this device can be pushed through a delivery lumen by a wire or other longitudinal pusher.

In an example, a resilient wider-than-neck portion of this device can be made with shape memory material. In an example, a resilient wider-than-neck portion of this device can be made from silver. In an example, a resilient wider-than-neck portion of this device can be made from laminin. In an example, a resilient wider-than-neck portion of this device can be made from platinum or gold. In an example, a resilient wider-than-neck portion of this device can be made from elastin or a liquid crystal polymer. In an example, a resilient wider-than-neck portion of this device can be made from polyester amide or polygluconate. In an example, a resilient wider-than-neck portion of this device can be made from polyethylene. In an example, a resilient wider-than-neck portion of this device can be made from vectron. In an example, a resilient wider-than-neck portion of this device can be made from fibrin or polycaprolactone. In an example, a resilient wider-than-neck portion of this device can be made from ethylene tetrafluoroethylene or polyanhydride. In an example, a resilient wider-than-neck portion of this device can be made from silk or Dacron.

In an example, a resilient wider-than-neck portion of this device can be made from rhenium. In an example, a resilient wider-than-neck portion of this device can be made from tungsten. In an example, a resilient wider-than-neck portion of this device can be made from an alginate, methyl ethyl ketone, polylactic acid, or cyclohexanone. In an example, a resilient wider-than-neck portion of this device can be made from parylene or a polyetherether ketone. In an example, a resilient wider-than-neck portion of this device can be made from polyimide, polyethylene terephthalate, thermoplastic elastomer urethane. In an example, a resilient wider-than-neck portion of this device can be made from a biopolymer. In an example, a resilient wider-than-neck portion of this device can be made from a mixture of a metal and a polymer.

In an example, a resilient wider-than-neck portion of this device can be made from zinc or manganese. In an example, a resilient wider-than-neck portion of this device can be made from ceramic material. In an example, a resilient wider-than-neck portion of this device can be made from a shape memory alloy. In an example, a resilient wider-than-neck portion of this device can be made from nickel. In an example, a resilient wider-than-neck portion of this device can be made from poly-N-acetylglucosamine. In an example, a resilient wider-than-neck portion of this device can be made from polysiloxane, polyglycolide, an acrylic, Elgiloy, polyamide, or silicone (e.g. silicone-urethane material).

In an example, a flexible sac-filling portion of this device can be separate from a resilient wider-than-neck portion of the device. In an example, a flexible sac-filling portion of this device can be attached to a resilient wider-than-neck portion of this device by a mechanism selected from the group consisting of: 3D printing; adhesion; braiding; coating; crimping or pressing; elastic band, string, cord, ribbon, and/or fiber; fusing; gluing; heat fusion; lacing; lamination; partial melting; soldering; stitching; tying; vapdepositing; weaving; and welding.

In an example, the centers of flexible sac-filling and resilient wider-than-neck portions of this device can be attached to each other. In an example, a flexible sac-filling portion can be centrally aligned with a resilient wider-than-neck portion. In an example, a flexible sac-filling portion and a resilient wider-than-neck portion can be longitudinally aligned. In an example, a flexible sac-filling portion can be attached to the distal end of resilient wider-than-neck portion. In an example, a resilient wider-than-neck portion can be attached to the proximal end of a flexible sac-filling portion. In an example, the proximal surface of a flexible sac-filling portion can be attached to the distal surface of a resilient wider-than-neck portion. In an example, the lateral perimeters of flexible sac-filling and resilient wider-than-neck portions of this device can be attached to each other.

In an example, a resilient wider-than-neck portion of this device and a flexible sac-filling portion of this device can be coaxial but not nested in their first configurations. In an example, a resilient wider-than-neck portion of this device and a flexible sac-filling portion of this device can be both coaxial and nested in their second configurations. In an example, a flexible sac-filling portion of this device can overlap a resilient wider-than-neck portion of this device. In an example, a resilient wider-than-neck portion of this device can be separate from, but nested within, a flexible sac-filling portion of this device. In an example, a flexible sac-filling portion and a resilient wider-than-neck portion can be concentric. In an example, a concave proximal surface of a flexible sac-filling portion of this device can fit into a convex distal surface of a resilient wider-than-neck portion of this device in their second configurations. In an example, expansion of the proximal surface of a flexible sac-filling portion can be constrained by the distal surface of a resilient wider-than-neck portion and the distal surface of a flexible sac-filling portion can be constrained by aneurysm walls.

In an example, a resilient wider-than-neck portion of this device can be inside a flexible sac-filling portion of this device. In an example, a flexible sac-filling portion of this device can surround a resilient wider-than-neck portion of this device. In an example, the proximal surface of a flexible sac-filling portion of this device can overlap the distal surface of a resilient wider-than-neck portion of this device. In an example, a resilient wider-than-neck portion of this device can be inside a proximal area of a flexible sac-filling portion of this device. In an example, the proximal surface of a flexible sac-filling portion of this device can overlap the proximal surface of a resilient wider-than-neck portion of this device. In an example, a flexible sac-filling portion can overlap a resilient wider-than-neck portion, especially in their second configurations. In an example, the distal surface of a resilient wider-than-neck portion of this device and the proximal surface of a flexible sac-filling portion of this device may not overlap in their first configurations (as they are transported through a delivery lumen to an aneurysm sac) but do overlap in their second configurations (after they are released from the lumen and expanded within the aneurysm sac).

In an example, a resilient wider-than-neck portion of this device can have a first density level and a flexible sac-filling portion can have a second density level, wherein the second level is less than the first level. In an example, a resilient wider-than-neck portion of this device can have a first elasticity level and a flexible sac-filling portion can have a second elasticity level, wherein the second level is greater than the first level. In an example, a resilient wider-than-neck portion of this device can have a first shore value and a flexible sac-filling portion of this device can have a second shore value, wherein the second shore value is lower than the first short value. In an example, a resilient wider-than-neck portion of this device can have a first flexibility level and a flexible sac-filling portion can have a second flexibility level, wherein the second level is greater than the first level. In an example, a resilient wider-than-neck portion of this device can have a first malleability level and a flexible sac-filling portion can have a second malleability level, wherein the second level is greater than the first level.

In an example, a resilient wider-than-neck portion of this device can have a first porosity level and a flexible sac-filling portion can have a second porosity level, wherein the second level is greater than the first level. In an example, a resilient wider-than-neck portion of this device can have a first rigidity level and a flexible sac-filling portion can have a second rigidity level, wherein the second level is less than the first level. In an example, a flexible sac-filling portion of this device can be larger in its second (expanded) configuration than the size of the resilient wider-than-neck portion of this device in its second (expanded) configuration. In an example, a resilient wider-than-neck portion of this device can have a first softness level and a flexible sac-filling portion can have a second softness level, wherein the second level is greater than the first level. In an example, a resilient wider-than-neck portion of this device can have a first stiffness level and a flexible sac-filling portion can have a second stiffness level, wherein the second level is less than the first level. In an example, a flexible sac-filling portion of this device can be larger in its second (expanded) configuration than a resilient wider-than-neck portion of this device in its second (expanded) configuration.

In an example, a flexible sac-filling portion of this device can moved closer to a resilient wider-than-neck portion of this device when a user pulls, pushes, or rotates a wire, filament, cord, and/or string which connects these portions. In an example, a resilient wider-than-neck portion of this device and a flexible sac-filling portion of this device can both be inserted into an aneurysm sac and then moved toward each other so that the proximal surface of the flexible sac-filling portion is nested within the distal surface of the resilient wider-than-neck portion. In an example, flexible sac-filling and resilient wider-than-neck portions of this device can be attached to each other by one or more wires, cords, strings, springs, or bands whose tension can be manually adjusted by the device operator. In an example, flexible sac-filling and resilient wider-than-neck portions of this device can be connected by a pull-cord whose pulling by an operator causes them to move toward each other.

In an example, resilient wider-than-neck and flexible sac-filling portions of this device can be different portions of the same continuous embolic structure which is inserted into an aneurysm sac. In an example, a resilient wider-than-neck portion of this device and a flexible sac-filling portion of this device can be proximal and distal portions, respectively, of an intrasacular occlusion device. In an example, a resilient wider-than-neck portion of this device can comprise the proximal surface of an intrasacular occlusion device and a flexible sac-filling portion can comprise the distal and lateral surfaces of this intrasacular occlusion device. In an example, a resilient wider-than-neck portion can be a proximal part, portion, segment, or undulation of this structure and a flexible sac-filling portion can be a distal (and/or peripheral) part, portion, segment, or undulation of this structure. In an example, a resilient wider-than-neck portion can be a proximal part, portion, segment, or undulation of an intrasacular aneurysm occlusion device and a flexible sac-filling portion can be a distal (and/or peripheral) part, portion, segment, or undulation of this device. In an example, a resilient wider-than-neck portion can be a proximal part, portion, segment, or undulation of an intrasacular embolic stack of parts, portions, segments, or undulations and a flexible sac-filling portion can be a distal (and/or peripheral) part, portion, segment, or undulation of this stack.

In an example, a resilient wider-than-neck portion and a flexible sac-filling portion can be different parts of the same continuous intrasacular occlusion device, but have different properties. In an example, the proximal portion of this intrasacular occlusion device can comprise a resilient wider-than-neck portion with a first density level and a distal portion of this intrasacular occlusion device can comprise a flexible sac-filling portion with a second density level, wherein the second level is less than the first level. In an example, the proximal portion of an intrasacular occlusion device can comprise a resilient wider-than-neck portion with a first elasticity level and a distal portion of this intrasacular occlusion device can comprise a flexible sac-filling portion with a second elasticity level, wherein the second level is greater than the first level. In an example, the proximal portion of an intrasacular occlusion device can comprise a resilient wider-than-neck portion with a first flexibility level and a distal portion of this intrasacular occlusion device can comprise a flexible sac-filling portion with a second flexibility level, wherein the second level is greater than the first level.

In an example, the proximal portion of an intrasacular occlusion device can comprise a resilient wider-than-neck portion with a first malleability level and a distal portion of this intrasacular occlusion device can comprise a flexible sac-filling portion with a second malleability level, wherein the second level is greater than the first level. In an example, the proximal portion of an intrasacular occlusion device can comprise a resilient wider-than-neck portion with a first porosity level and a distal portion of this intrasacular occlusion device can comprise a flexible sac-filling portion with a second porosity level, wherein the second level is greater than the first level. In an example, the proximal portion of an intrasacular occlusion device can comprise a resilient wider-than-neck portion with a first rigidity level and a distal portion of this intrasacular occlusion device can comprise a flexible sac-filling portion with a second rigidity level, wherein the second level is less than the first level.

In an example, the proximal portion of an intrasacular occlusion device can comprise a resilient wider-than-neck portion with a first softness level and a distal portion of this intrasacular occlusion device can comprise a flexible sac-filling portion with a second softness level, wherein the second level is greater than the first level. In an example, the proximal portion of an intrasacular occlusion device can comprise a resilient wider-than-neck portion with a first stiffness level and a distal portion of this intrasacular occlusion device can comprise a flexible sac-filling portion with a second stiffness level, wherein the second level is less than the first level.

In an example, an intrasacular aneurysm occlusion device can be braided. In an example, different portions, segments, or undulations of a braided intrasacular aneurysm occlusion device can have different braid patterns. In an example, a proximal portion, segment, or undulation of an intrasacular aneurysm occlusion device can have a first braid pattern and a distal portion, segment, or undulation of this device can have a second braid pattern. In an example, different portion, segment, or undulations of a continuous intrasacular aneurysm occlusion device can have different braid densities. In an example, a proximal portion, segment, or undulation of an intrasacular aneurysm occlusion device can have a higher braid density than a distal portion, segment, or undulation of this device. In an example, different portion, segment, or undulations of a continuous intrasacular aneurysm occlusion device can have different braid angles. In an example, a proximal portion, segment, or undulation of an intrasacular aneurysm occlusion device can have a greater braid angle than a distal portion, segment, or undulation of this device.

In an example, different portion, segment, or undulations of a continuous intrasacular aneurysm occlusion device can have different braid pitches. In an example, a proximal portion, segment, or undulation of an intrasacular aneurysm occlusion device can have a first braid pitch and a distal portion, segment, or undulation of this device can have a second braid pitch. In an example, different portion, segment, or undulations of a continuous intrasacular aneurysm occlusion device can have different braid filament sizes. In an example, a proximal portion, segment, or undulation of an intrasacular aneurysm occlusion device can have a first braid filament size and a distal portion, segment, or undulation of this device can have a second braid filament size.

In an example, a flexible sac-filling portion can have a first (constrained) configuration as it is delivered to an aneurysm sac through a delivery lumen and a second (expanded) configuration after it has been expanded within the aneurysm sac. In an example, a flexible sac-filling portion of this device can have a compressed, collapsed, folded, pleated, curled, wrapped, and/or rolled first configuration for transportation through a delivery lumen to an aneurysm sac. In an example, a flexible sac-filling portion can be compressed, collapsed, folded, pleated, curled, wrapped, and/or rolled in its first configuration. In an example, a flexible sac-filling portion can be radially constrained and longitudinally elongated in its first configuration.

In an example, a resilient wider-than-neck portion of this device and a flexible sac-filling portion of this device can be (longitudinally) coaxial in their first configurations. In an example, a resilient wider-than-neck portion of this device and a flexible sac-filling portion of this device can be (longitudinally) co-linear in their first configurations. In an example, a flexible sac-filling portion can be folded or pleated so as to have multiple layers in its first configuration and be expanded so as to have a single layer in its second configuration.

In an example, a flexible sac-filling portion can have a first density in its first configuration and a second density in its second configuration, wherein the second density is less than the first density. In an example, a flexible sac-filling portion can have a first elasticity level in its first configuration and a second elasticity level in its second configuration, wherein the second elasticity level is less than the first elasticity level. In an example, a flexible sac-filling portion can have a first porosity level in its first configuration and a second porosity level in its second configuration, wherein the second porosity level is less than the first porosity level. In an example, a flexible sac-filling portion can have a first porosity level in its first configuration and a second porosity level in its second configuration, wherein the second porosity level is greater than the first porosity level.

In an example, a flexible sac-filling portion of this device can be expanded from a first configuration to a second configuration by inserting embolic members into the flexible sac-filling portion after it has been inserted into an aneurysm sac. In an example, a flexible sac-filling portion of this device can be expanded by filling it with embolic members selected from the group consisting of: balls or microspheres; sponges, hydrogels, or pieces of foam; 3D polygons; sinusoidal or otherwise undulating ribbons; and coils. In an example, a flexible sac-filling portion of this device can be expanded by filling it with a flowable substance such as a liquid, a gel, or a gas. In an example, a flexible sac-filling portion of this device can be pre-filled with expanding embolic members (such as hydrogels) before it is expanded within an aneurysm sac.

In an example, embolic members can be pushed by a fluid or gel through a delivery lumen (such as a catheter) into a flexible sac-filling portion of this device, wherein the accumulation of embolic members in the flexible sac-filling portion expands that portion into conformity with walls of the aneurysm sac. In an example, embolic members can be inserted into a flexible sac-filling portion of this device after this portion has been inserted, but not yet expanded, in an aneurysm sac. In an example, insertion of embolic members into a flexible sac-filling portion of this device expands this portion within the aneurysm sac. In an example, embolic members can be inserted into a flexible sac-filling portion of this device after this portion has been inserted and partially expanded in an aneurysm sac.

In an example, a flexible sac-filling portion of this device can be compressed, folded, pleated, rolled, curved, and/or coiled for delivery through a delivery lumen into an aneurysm sac. In an example, a flexible sac-filling portion of this device can have a first (pre-expansion) configuration in which it is folded or pleated and a second (post-expansion) configuration in which it is unfolded or unpleated. In an example, a flexible sac-filling portion of this device can be folded, pleated, or rolled in a first configuration (before insertion into the aneurysm sac) and unfolded, unpleated, or unrolled in a second configuration (after insertion into the aneurysm sac). In an example, a flexible sac-filling portion of this device can expand, unfold, unroll, flatten, and/or uncoil as it exits a delivery lumen within an aneurysm sac. In an example, a flexible sac-filling portion of this device can unfold, unroll, and/or uncurl as it is expanded from its first configuration to its second configuration in an aneurysm sac.

In an example, a flexible sac-filling portion of this device can be unfolded as it transitions from its first configuration to its second configuration within an aneurysm sac. In an example, a flexible sac-filling portion of this device can have a first fold in a first location or orientation in its first configuration as it is transported to an aneurysm sac via a delivery lumen and can have a second fold in a second location or orientation in its second configuration within the aneurysm sac. In an example, a flexible sac-filling portion of this device can have at least one longitudinal fold in its first configuration as it is transported to an aneurysm sac via a delivery lumen and can have at least one lateral fold in its second configuration within the aneurysm sac. In an example, a flexible sac-filling portion of this device can have at least one longitudinal fold in its first configuration as it is transported to an aneurysm sac via a delivery lumen and can have at least one circumferential fold in its second configuration within the aneurysm sac. In an example, a flexible sac-filling portion of this device can have at least one longitudinal fold in its first configuration as it is transported to an aneurysm sac via a delivery lumen and can have at least one radial fold in its second configuration within the aneurysm sac.

In an example, a flexible sac-filling portion of this device can have a first (constrained) configuration while it is delivered through a lumen to an aneurysm sac and a second (expanded) configuration after it has been inserted into the aneurysm sac. In an example, the flexible sac-filling portion can have multiple folds or pleats in its first configuration. In an example, it can have multiple (e.g. four or six) longitudinal folds or pleats in its first configuration. In an example, a flexible sac-filling portion can have an undulating and/or sinusoidal cross-sectional perimeter (in a plane perpendicular to its longitudinal axis) its first configuration. In an example, the flexible sac-filling portion can have a cross-sectional perimeter with a rounded star-burst shape its first configuration. In an example, a flexible sac-filling portion in its first configuration can have a cross-sectional shape that is a circular with multiple (e.g. 4-8) undulations. In an example, a flexible sac-filling portion can have a helical cross-sectional shape in its first configuration. In an example, a flexible sac-filling portion in its first configuration can be rolled or curled around its longitudinal axis in its first configuration.

In an example, a flexible sac-filling portion of this device can be a porous net or mesh (with holes, openings, and/or pores). In an example, a flexible sac-filling portion of this device can be a porous bag, sack, or liner (with holes, openings, and/or pores). In an example, a flexible sac-filling portion of this device can be a porous balloon (with holes, openings, and/or pores). In an example, a flexible sac-filling portion of this device can be a porous membrane or elastic film (with holes, openings, and/or pores). In an example, a flexible sac-filling portion of this device can be a porous fabric pouch (with holes, openings, and/or pores). In an example, a flexible sac-filling portion of this device can be a porous lattice or framework (with holes, openings, and/or pores). In an example, a flexible sac-filling portion of this device can be a flexible polymer net or mesh. In an example, a flexible sac-filling portion of this device can comprise a lattice, braid, membrane, screen, or balloon.

In an example, a flexible sac-filling portion of this device can be created by weaving. In an example, a flexible sac-filling portion of this device can be created by weaving wires or filaments into a weave pattern selected from the group consisting of: plain weave; double weave; diamond weave; perpendicular weave; rib weave; basket weave; twill weave; satin weave; leno weave; mock leno weave; and diagonal weave. In an example, a flexible sac-filling portion of this device can comprise a woven mesh of metal wires, threads, or strands. In an example, a flexible sac-filling portion of this device can comprise a woven mesh of polymer threads or strands. In an example, a flexible sac-filling portion can be a mesh, net, weave, or braid with strands, wires, or fibers between 5 and 50 microns in width. In an example, a flexible sac-filling portion can be a mesh, net, weave, or braid with strands, wires, or fibers between 50 and 200 microns in width.

In an example, a flexible sac-filling portion of this device can be created by braiding. In an example, a flexible sac-filling portion of this device can be a porous braided member (with holes, openings, and/or pores). In an example, a flexible sac-filling portion of this device can be braid or weave of filaments, wires, fibers, or threads. In an example, a flexible sac-filling portion can comprise a braid or weave of fibers or threads. In an example, a flexible sac-filling portion of this device comprise helical and/or spiral wires or filaments. In an example, a flexible sac-filling portion of this device can be created by braiding wires or filaments into a braid pattern selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, different areas of a flexible sac-filling portion can have different braid patterns. In an example, the proximal area of a flexible sac-filling portion of this device can have a first braid pattern and the distal area of the flexible sac-filling portion of this device can have a second braid pattern. In an example, different areas of a flexible sac-filling portion can have different braid densities. In an example, the proximal area of a flexible sac-filling portion of this device can have a higher braid density than the distal area of the flexible sac-filling portion of this device. In an example, different areas of a flexible sac-filling portion can have different braid angles. In an example, the proximal area of a flexible sac-filling portion of this device can have a greater braid angle than the distal area of the flexible sac-filling portion of this device.

In an example, different areas of a flexible sac-filling portion can have different braid pitches. In an example, the proximal area of a flexible sac-filling portion of this device can have a first braid pitch and the distal area of the flexible sac-filling portion of this device can have a second braid pitch. In an example, different areas of a flexible sac-filling portion can have different braid filament sizes. In an example, the proximal area of a flexible sac-filling portion of this device can have a first braid filament size and the distal area of the flexible sac-filling portion of this device can have a second braid filament size.

In an example, different areas or layers of a braided flexible sac-filling portion can have different levels of braid direction. In an example, different areas or layers of a flexible sac-filling portion can have different levels of filament density. In an example, different areas or layers of a flexible sac-filling portion can have different levels of flexibility. In an example, different areas or layers of a flexible sac-filling portion can have different levels of grid size. In an example, different areas or layers of a flexible sac-filling portion can have different levels of malleability. In an example, different areas or layers of a flexible sac-filling portion can have different levels of plasticity.

In an example, a flexible sac-filling portion of this device can be made from platinum, titanium, or tantalum. In an example, a flexible sac-filling portion of this device can be made from cobalt-chromium alloy or from latinum. In an example, a flexible sac-filling portion can be made from polyanhydride or polyglycolide. In an example, a flexible sac-filling portion can be made from polygluconate or polyvinyl alcohol. In an example, a flexible sac-filling portion can be made from tetrahydrofuran. In an example, a flexible sac-filling portion can be made from ethylene vinyl alcohol. In an example, a flexible sac-filling portion can be made from polyester urethane or polysiloxane. In an example, a flexible sac-filling portion can be made from vinyltriethoxysilane or thermoplastic elastomer urethane. In an example, a flexible sac-filling portion can be made from polylactic acid, fibronectin, poly-D-lactide, or polyphenylene sulfide.

In an example, a flexible sac-filling portion of this device can have an opening through which embolic members are inserted into it. In an example, it can further comprise a one-way valve. In an example, this opening can be opened and closed remotely by a device operator. In an example, a flexible sac-filling portion of this device can have an adjustable opening. In an example, this opening can be opened or closed by a closure mechanism selected from the group consisting of: activating an electromagnetic valve; aligning (or miss-aligning) two holes; application of electromagnetic energy (to a magnet); application of thermal energy; compressing a snap or clip; activating an electrolytic closure mechanism; electromagnetic fusing; injecting an adhesive; moving a plug; opening a valve; pressing a seal; pulling a cord or string; pushing or pulling a wire; rotating a cable or wire; rotating a cap; and tightening a loop.

In an example, a flexible sac-filling member can have a plurality of pores, apertures, openings, or holes. In an example, a flexible sac-filling portion of this device can have pores, apertures, openings, or holes through which liquid can flow but through which embolic members cannot pass. In an example, a flexible sac-filling portion can be expanded within an aneurysm sac by filling it with embolic members which are pushed along a delivery lumen by a liquid (such as saline), wherein the liquid can pass through pores, apertures, openings, or holes in the flexible sac-filling portion but the embolic members cannot pass through these pores, apertures, openings, or holes. In an example, these pores, apertures, openings, or holes can also allow blood to flow into the flexible sac-filling portion, especially while the flexible sac-filling portion is being expanded within the aneurysm sac. In an example, the pores, apertures, openings, or holes of a flexible sac-filling portion can be sufficiently large to allow a fluid medium to pass out of the sac-filling portion, but sufficiently small to contain the embolic material inside the flexible sac-filling portion. In an example, a flexible sac-filling portion of this device can have holes in its perimeter, but these holes can be smaller than the embolic members so that the embolic members are retained within the flexible sac-filling portion of this device.

In an example, a flexible sac-filling member can have a plurality of pores or openings which are between 10 microns and 50 microns in size. In an example, a flexible sac-filling member can have a plurality of pores or openings which are between 30 microns and 100 microns in size. In an example, a flexible sac-filling member can have a plurality of pores or openings which are between 100 microns and 500 microns in size. In an example, a flexible sac-filling portion of this device can have pores, apertures, holes, and/or openings which are 50-200 microns in width. In an example, a flexible sac-filling portion of this device can have pores, apertures, holes, and/or openings which are 10-70 microns in width. In an example, a flexible sac-filling portion of this device can have pores, apertures, holes, and/or openings which are 100-200 microns in width. In an example, different areas (e.g. proximal vs. distal) or layers (e.g. inner vs. outer) of a flexible sac-filling portion can have different levels of pore size. In an example, different areas or layers of a flexible sac-filling portion can have different levels of porosity.

In an example, a net or mesh can have non-uniform flexibility or tensile strength. In an example, a first (e.g. proximal) part of a flexible sac-filling portion can have a first density and a second (e.g. distal) part of the flexible sac-filling portion can have a second density. In an example, a first (e.g. proximal) part of a flexible sac-filling portion can have a first flexibility or elasticity level and a second (e.g. distal) part of the flexible sac-filling portion can have a second flexibility or elasticity level. In an example, a first (e.g. proximal) part of a flexible sac-filling portion can have a first porosity level and a second (e.g. distal) part of the flexible sac-filling portion can have a second porosity level. In an example, a first (e.g. central) part of a flexible sac-filling portion can have a first density and a second (e.g. peripheral) part of the flexible sac-filling portion can have a second density. Society may give an exclusive right to the profits arising from ideas, as an encouragement to men to pursue ideas which may produce utility (Thomas Jefferson). Just because you did not think of it first and now want to take it away does not make me a troll (anonymous). In an example, a first (e.g. central) part of a flexible sac-filling portion can have a first flexibility or elasticity level and a second (e.g. peripheral) part of the flexible sac-filling portion can have a second flexibility or elasticity level. In an example, a first (e.g. central) part of a flexible sac-filling portion can have a first porosity level and a second (e.g. peripheral) part of the flexible sac-filling portion can have a second porosity level.

In an example, a flexible sac-filling portion of this device can be made from chromium or nitinol. In an example, a flexible sac-filling portion of this device can be made from cobalt, gallium, silver, or stainless steel. In an example, a flexible sac-filling portion of this device can be made from siloxane or gelatin. In an example, a flexible sac-filling portion of this device can be made from polydimethylsiloxane, a polymer film or fabric with holes in it, or siloxane-polyurethane. In an example, a flexible sac-filling portion of this device can be made from cyclohexanone, polydioxanone, or poly-N-acetylglucosamine. In an example, a flexible sac-filling portion of this device can be made from polylactide. In an example, a flexible sac-filling portion of this device can be made from a liquid crystal polymer.

In an example, the proximal surface of a flexible sac-filling portion of this device can have a first flexibility level, plasticity level, malleability level, elasticity level, porosity level, or tensile strength level and the distal surface of a flexible sac-filling portion of this device can have a second flexibility level, plasticity level, malleability level, elasticity level, porosity level or tensile strength level. In an example, the first level can be greater or less than the second level. In an example, the proximal quartile of a flexible sac-filling portion of this device can have a first flexibility level, plasticity level, malleability level, elasticity level, porosity level, or tensile strength level and the distal quartile of a flexible sac-filling portion of this device can have a second flexibility level, plasticity level, malleability level, elasticity level, porosity level or tensile strength level. In an example, the first level can be greater or less than the second level. In an example, the proximal half of a flexible sac-filling portion of this device can have a first flexibility level, plasticity level, malleability level, elasticity level, porosity level, or tensile strength level and the distal half of a flexible sac-filling portion of this device can have a second flexibility level, plasticity level, malleability level, elasticity level, porosity level or tensile strength level. In an example, the first level can be greater or less than the second level.

In an example, a proximal part of a flexible sac-filling portion can have a first rigidity level and a distal part of the flexible sac-filling portion can have a second rigidity level, wherein the second rigidity level is greater than the first rigidity level. In an example, a proximal part of a flexible sac-filling portion can have a first stiffness level and a distal part of the flexible sac-filling portion can have a second stiffness level, wherein the second stiffness level is greater than the first stiffness level. In an example, the proximal surface of a flexible sac-filling portion of this device can have a first thickness; the distal surface of a flexible sac-filling portion of this device can have a second thickness; and the first thickness can be greater than the second thickness. In an example, a proximal part of a flexible sac-filling portion can have a first width and a distal part of the flexible sac-filling portion can have a second width, wherein the second width is greater than the first width. In an example, different areas of flexible sac-filling portion can have different levels of resiliency.

In an example, a proximal part of a flexible sac-filling portion can have multiple layers and a distal part of the flexible sac-filling portion can have a single layer. In an example, a flexible sac-filling portion of this device can have multiple longitudinal sections, undulations, bulges, or segments. In an example, a flexible sac-filling portion of this device can comprise a longitudinal sequence of centrally-connected sections, undulations, or bulges. In an example, a flexible sac-filling portion of this device can comprise a longitudinal sequence of two centrally-connected sections, undulations, or bulges. In an example, a flexible sac-filling portion of this device can comprise a longitudinal sequence of three centrally-connected sections, undulations, or bulges. In an example, a flexible sac-filling portion of this device can comprise a longitudinal sequence with distal, central, and proximal sections, undulations, or bulges which are centrally connected to each other. In an example, an intrasacular aneurysm occlusion device can comprise a longitudinal stack of centrally-connected embolic sections, undulations, or bulges. In an example, an intrasacular aneurysm occlusion device can comprise a longitudinal stack of two centrally-connected embolic sections, undulations, or bulges. In an example, an intrasacular aneurysm occlusion device can comprise a longitudinal stack of three centrally-connected embolic sections, undulations, or bulges.

In an example, a flexible sac-filling portion of this device can have multiple longitudinal sections, undulations, bulges, or segments with different levels of porosity, flexibility, or tensile strength. In an example, a flexible sac-filling portion of this device can comprise a longitudinal sequence of centrally-connected sections, undulations, or bulges with different levels of porosity, flexibility, or tensile strength. In an example, a flexible sac-filling portion of this device can comprise a longitudinal sequence of two centrally-connected sections, undulations, or bulges with different levels of porosity, flexibility, or tensile strength. In an example, a flexible sac-filling portion of this device can comprise a longitudinal sequence of three centrally-connected sections, undulations, or bulges with different levels of porosity, flexibility, or tensile strength. In an example, a flexible sac-filling portion of this device can comprise a longitudinal sequence with distal, central, and proximal sections, undulations, or bulges which are centrally connected to each other with different levels of porosity, flexibility, or tensile strength. In an example, an intrasacular aneurysm occlusion device can comprise a longitudinal stack of centrally-connected embolic sections, undulations, or bulges with different levels of porosity, flexibility, or tensile strength. In an example, an intrasacular aneurysm occlusion device can comprise a longitudinal stack of two centrally-connected embolic sections, undulations, or bulges with different levels of porosity, flexibility, or tensile strength. In an example, an intrasacular aneurysm occlusion device can comprise a longitudinal stack of three centrally-connected embolic sections, undulations, or bulges with different levels of porosity, flexibility, or tensile strength.

In an example, a portion of this device can have multiple longitudinal sections, undulations, bulges, or segments with non-uniform porosity, flexibility, elasticity, or tensile strength. In an example, this device can comprise a longitudinal sequence of centrally-connected sections, undulations, or bulges with non-uniform porosity, flexibility, elasticity, or tensile strength. In an example, this device can comprise a longitudinal sequence of two centrally-connected sections, undulations, or bulges with non-uniform porosity, flexibility, elasticity, or tensile strength. In an example, this device can comprise a longitudinal sequence of three centrally-connected sections, undulations, or bulges with non-uniform porosity, flexibility, elasticity, or tensile strength. In an example, this device can comprise a longitudinal sequence with distal, central, and proximal sections, undulations, or bulges which are centrally connected to each other with non-uniform porosity, flexibility, elasticity, or tensile strength. In an example, an intrasacular aneurysm occlusion device can comprise a longitudinal stack of centrally-connected embolic sections, undulations, or bulges with non-uniform porosity, flexibility, elasticity, or tensile strength. In an example, an intrasacular aneurysm occlusion device can comprise a longitudinal stack of two centrally-connected embolic sections, undulations, or bulges with non-uniform porosity, flexibility, elasticity, or tensile strength. In an example, an intrasacular aneurysm occlusion device can comprise a longitudinal stack of three centrally-connected embolic sections, undulations, or bulges with non-uniform porosity, flexibility, elasticity, or tensile strength.

In an example, a flexible sac-filling portion of this device can comprise a single layer of mesh, net, or fabric. In an example, a flexible sac-filling portion can comprise two or more layers of mesh, net, or fabric. In an example, a flexible sac-filling portion can comprise two layers of material of different types (e.g. metal vs. polymer), different mesh or braid directions, different porosity levels, different elasticity levels, and/or different rigidity levels. In an example, a flexible sac-filling portion of this device can have a first layer with a first porosity level and a second layer with a second porosity level. In an example, a flexible sac-filling portion of this device can have a first layer with a first average pore-size level and a second layer with a second average pore size. In an example, a flexible sac-filling portion of this device can have a first layer with a first average thickness and a second layer with a second average thickness.

In an example, a flexible sac-filling portion can be made by one or more processes selected from the group consisting of: folding, crimping, weaving, electroforming, photochemical machining, braiding, gluing, rolling, knitting, adhesion, and sheet etching. In an example, a flexible sac-filling portion can be made by one or more processes selected from the group consisting of: physical vapor deposition, micromachining, electrical discharge machining, sheet cutting, and electrospinning. In an example, a flexible sac-filling portion can be made by one or more processes selected from the group consisting of: photochemical etching, perforation, laser welding, photolithography, laser cutting, thermoformation, vapor deposition, and welding.

In an example, a flexible sac-filling portion can be made from a biopolymer, an acetone, or palladium. In an example, a flexible sac-filling portion can comprise one or more radio-opaque filaments or structures, a porous mesh which serves as a scaffold for endothelial cell growth, or latex. In an example, a flexible sac-filling portion can be made from polyimide, a superelastic alloy, polyglycolic acid, or Teflon.

In an example, a flexible sac-filling portion can be made from an acrylic or diphenylmethane diisocyanate. In an example, a flexible sac-filling portion can be made from iridium, magnesium, or a shape memory alloy.

In an example, a flexible sac-filling portion can be made from manganese, polyethylene terephthalate, or polyurethane. In an example, a flexible sac-filling portion can be made from trimethylene carbonate or CoCrNi alloy. In an example, a flexible sac-filling portion can be made from copper, gold, nickel, or copper. In an example, a flexible sac-filling portion can be made from Dacron. In an example, a flexible sac-filling portion can be made from elastin, hydroxy-terminated polycarbonate, methylcellulose, or polybutester. In an example, a flexible sac-filling portion can be made from silicone, an alginate, collagen, or hydrogel. In an example, a flexible sac-filling portion can be made from a mixture of a metal and a polymer. In an example, a flexible sac-filling portion of this device can be made polycaprolactone, silk, or fibrinogen.

In an example, a flexible sac-filling portion can have a generally spherical shape. In an example, a flexible sac-filling portion can have an ellipsoid shape, a pumpkin shape, an ovoid shape, or a frustoconical shape. In an example, a flexible sac-filling portion can have a globular shape. In an example, a flexible sac-filling portion can have a shape selected from the group consisting of: ball shape, apple or pumpkin shape, prolate hemispherical shape, conic shape, egg shape, and pear shape. In an example, a flexible sac-filling portion can have a torus shape. In an example, a flexible sac-filling portion can have a generally-spherical but laterally-undulating shape, tear drop shape, or disk shape. In an example, a resilient wider-than-neck portion can be a thin-film metal sphere, ellipsoid, or globe with laser-cut pores.

In an example, a flexible sac-filling portion can have a shape selected from the group consisting of: torus or doughnut shape, oblate spheroid shape, pleated or folded shape, elliptical shape, prolate spherical shape, umbrella or inverted umbrella shape, and oblong shape. In an example, a flexible sac-filling portion can have a cardioid shape. In an example, a flexible sac-filling portion can have a generally-spherical but laterally-undulating shape. In an example, a resilient wider-than-neck portion can have a shape selected from the group consisting of: sphere; ellipsoid; oval; egg shape; water-drop shape; pumpkin shape; torus; and disk. In an example, a flexible sac-filling portion can have a conic section shape. In an example, a flexible sac-filling portion can have a cylindrical shape. In an example, a flexible sac-filling portion can have a flared, tapered, egg, tear drop, or wedge shape whose proximal half is wider than its distal half. In an example, a flexible sac-filling portion can have a flared, tapered, egg, tear drop, or wedge shape whose distal half is wider than its proximal half. In an example, a flexible sac-filling portion can have a hemispherical shape.

In an example, a flexible sac-filling portion of this device can have a large-scale shape (with potential smaller-scale perimeter perturbations, blebs, or undulations) which is selected from the group consisting of: sphere; ellipsoid; cylinder; ring; egg shape; water drop shape; apple, pumpkin, onion, or pear shape; folded paper lantern shape; and torus. In an example, a flexible sac-filling portion of this device can have a shape which is spherical or elliptical on a large scale, but which can have perturbations, blebs, lobes, or undulations on a small scale.

In an example, a flexible sac-filling portion of this device is sufficiently flexible so that it conforms to the walls of an aneurysm sac, even the walls of an irregularly-shaped aneurysm sac, in its second configuration. In an example, a flexible sac-filling portion can stretch and/or deform in its second configuration. In an example, a flexible sac-filling portion of this device can have bulges, undulations, lobes, and/or bumps in its second configuration which enable it to conform to the walls of an irregularly-shaped aneurysm sac. In an example, a flexible sac-filling portion of this device can have an irregular arcuate shape. In an example, a flexible sac-filling portion can be sufficiently flexible, elastic, and/or malleable so as to conform to the contours of an irregularly-shaped aneurysm sac when the flexible sac-filling portion is expanded within the aneurysm sac. In an example, a flexible sac-filling portion can have a generally spherical or globular shape when expanded into its second configuration within an aneurysm sac, but be sufficiently malleable so that this generally spherical or globular shape can have irregular perimeter perturbations which enable it to conform to the inner walls of an irregularly shaped aneurysm sac.

In an example, the interior walls of an aneurysm sac and the interior of the aneurysm neck can together comprise an irregular three-dimensional convex shape A. In an example, a flexible sac-filling portion can have a second (expanded) configuration with an irregular three-dimensional convex shape B. In an example, the "unfilled volume" is the interior volume of irregular three-dimensional convex shape A minus the interior volume of irregular three-dimensional convex shape B. In an example, a flexible sac-filling portion is sufficiently flexible and/or malleable that that "unfilled volume" is less than 25% of the interior volume of shape A. In an example, a flexible sac-filling portion is sufficiently flexible and/or malleable that that "unfilled volume" is less than 15% of the interior volume of shape A. In an example, a flexible sac-filling portion is sufficiently flexible and/or malleable that that "unfilled volume" is less than 5% of the interior volume of shape A.

In an example, a flexible sac-filling portion can have a second (expanded) configuration with an irregular three-dimensional convex shape B. A best-fitting virtual sphere or ellipsoid can be defined as the virtual sphere or ellipsoid which is contained entirely within irregular three-dimensional convex shape B which minimizes the sum of square deviations between points on three-dimensional convex shape B and the virtual sphere or ellipsoid. In an example, the "irregularity volume" is the interior volume of irregular three-dimensional convex shape B minus the interior volume of the virtual sphere or ellipsoid. In an example, a flexible sac-filling portion is sufficiently flexible and/or malleable that that "irregularity volume" can be more than 5% of the interior volume of shape B. In an example, a flexible sac-filling portion is sufficiently flexible and/or malleable that that "irregularity volume" can be more than 15% of the interior volume of shape B. In an example, a flexible sac-filling portion is sufficiently flexible and/or malleable that that "irregularity volume" can be more than 25% of the interior volume of shape B. In an example, a flexible sac-filling portion is sufficiently flexible and/or malleable that that "irregularity volume" can be more than 50% of the interior volume of shape B.

In an example, a flexible sac-filling portion is sufficiently flexible, elastic, and/or malleable to fill at least 70% of the volume of an irregularly-shaped aneurysm sac when the flexible sac-filling portion is expanded within the aneurysm sac. In an example, a flexible sac-filling portion is sufficiently flexible, elastic, and/or malleable to fill at least 80% of the volume of an irregularly-shaped aneurysm sac when the flexible sac-filling portion is expanded within the aneurysm sac. In an example, a flexible sac-filling portion is sufficiently flexible, elastic, and/or malleable to fill at least 90% of the volume of an irregularly-shaped aneurysm sac when the flexible sac-filling portion is expanded within the aneurysm sac.

In an example, a flexible sac-filling portion of this device can be made from polyester, Elgiloy, ethylene tetrafluoroethylene, fibrin, glycolic acid, laminin, methyl ethyl ketone, or nylon. In an example, a flexible sac-filling portion of this device can be made from polyamide, polycarbonate urethane, polyester amide, polyetherether ketone, or polyethylene. In an example, a flexible sac-filling portion of this device can be made from polyolefin, polyphosphoester, polypropylene, polytetrafluoroethylene, polytetramethyleneoxide, polyvinyl chloride, or vectron. In an example, a flexible sac-filling portion of this device can be made from CoCrMo alloy, copper-zinc alloy, nickel-aluminum alloy, nickel-titanium alloy, niobium, rhenium, tungsten, or zinc.

In an example, a flexible sac-filling portion of this device and a resilient wider-than-neck portion of this device can both be inserted into an aneurysm sac at substantially the same time. In an example, a flexible sac-filling portion can be inserted into an aneurysm sac after a resilient wider-than-neck portion is inserted into the aneurysm sac. In an example, a flexible sac-filling portion can be inserted into an aneurysm sac before a resilient wider-than-neck portion is inserted into the aneurysm sac. In an example, a resilient wider-than-neck portion can be expanded from its first configuration to its second configuration before a flexible sac-filling portion is expanded. In an example, a resilient wider-than-neck portion can be expanded from its first configuration to its second configuration after a flexible sac-filling portion is expanded. In an example, a resilient wider-than-neck portion can be expanded from its first configuration to its second configuration before a flexible sac-filling portion is expanded. In an example, a resilient wider-than-neck portion can be expanded from its first configuration to its second configuration after a flexible sac-filling portion is expanded.

In an example, embolic members which are inserted into the flexible sac-filling portion of this device can be microsponges. In an example, embolic members can be pieces of gel or foam. In an example, embolic members can be embolic coils. In an example, embolic members can be selected from the group consisting of: beads or microspheres; compressible balls; congealing gel; embolic coils; fibers; hydrogel pieces; microspheres; microsponges; pieces of foam; pieces of gel; rigid balls; and wires. In an example, embolics members which are inserted into a flexible sac-filling portion of this device can be longitudinal coils with a circular, elliptical, or oval cross-sectional shape. In an example, embolics which are inserted into a flexible sac-filling portion of this device can be longitudinal coils with a triangular, quadrilateral, hexagonal, or octagonal cross-sectional shape. In an example, embolic members can be 3D polygonal pieces of gel or foam.

In an example, a flexible sac-filling portion of this device can be filled with a liquid or gelatinous contrast agent. In an example, a plurality of embolic members can be pumped or otherwise inserted into a flexible sac-filling portion of this device via a flow of liquid or gel. In an example, this device can further comprise a flow of liquid or gel which carries embolic members and/or material through a delivery lumen into a flexible sac-filling portion of this device. In an example, this liquid or gel can escape through pores or holes in a flexible sac-filling portion, but the embolic members are too large to escape through these pores or holes. Accordingly, the embolic members accumulate within the flexible sac-filling portion. In an example, embolic members can be pushed through a delivery lumen by a pusher wire or tube. In an example, embolic members can be transported through a delivery lumen by a conveyor belt or chain. In an example, embolic members can be pushed through a delivery lumen by a rotating helix (e.g. an Archimedes screw).

In an example, this device can comprise multiple delivery lumens or catheters. In an example, a first delivery lumen (or catheter) can deliver a resilient wider-than-neck portion and a flexible sac-filling portion of the device to an aneurysm sac and a second delivery lumen (or catheter) can deliver embolic members (or material) into the flexible sac-filling portion of the device. In an example, there can be two openings and/or lumens into a flexible sac-filling portion of this device: a first opening and/or lumen through which embolic members (or material) is inserted into the flexible sac-filling portion and a second opening and/or lumen through which blood can escape from the flexible sac-filling portion. In an example, this device can further comprise a delivery lumen (such as a catheter) with a rotatable distal end, wherein rotation of the distal end changes the orientation of a resilient wider-than-neck portion and/or a flexible sac-filling portion delivered into an aneurysm sac. In an example, this device can further comprise a guide wire.

In an example, this device can further comprise electrolytic detachment mechanism which is used to detach a flexible sac-filling portion of this device from a guidewire or pusher wire. In an example, this device can further comprise electrolytic detachment mechanism which is used to detach a resilient wider-than-neck portion of this device from a guidewire or pusher wire. In an example, a flexible sac-filling portion of this device can be detached from a delivery wire, pusher, and/or catheter by mechanical, chemical, or electrolytic detachment.

In an example, an intrasacular aneurysm occlusion device can comprise: a net or mesh with a first level of flexibility, elasticity, or malleability; wherein the net or mesh is configured to be inserted into and expanded within an aneurysm sac; and a stent or lattice with a second level of flexibility, elasticity, or malleability; wherein the stent or lattice is configured to be inserted into and expanded within the aneurysm sac; and wherein the first level is greater than the second level.

In an example, an intrasacular aneurysm occlusion device can comprise: a net or mesh with a first level of flexibility, elasticity, or malleability; wherein the net or mesh is configured to be inserted into and expanded in a first location within an aneurysm sac; and a stent or lattice with a second level of flexibility, elasticity, or malleability; wherein the stent or lattice is configured to be inserted into and expanded in a second location within the aneurysm sac; wherein the first level is greater than the second level; and wherein the first location is more distal than the second location. In an example, an intrasacular aneurysm occlusion device can comprise: a net or mesh with a first level of flexibility, elasticity, or malleability; wherein the net or mesh is configured to be inserted into and expanded in a first location within an aneurysm sac; and a stent or lattice with a second level of flexibility, elasticity, or malleability; wherein the stent or lattice is configured to be inserted into and expanded in a second location within the aneurysm sac; wherein the first level is greater than the second level; and wherein the first location is more further from the aneurysm neck than the second location.

In an example, an intrasacular aneurysm occlusion device can comprise: a net or mesh with a first level of flexibility, elasticity, or malleability; wherein the net or mesh is configured to be inserted into and expanded within an aneurysm sac; and wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; and wherein the first location is more distal than the second location. In an example, an intrasacular aneurysm occlusion device can comprise: a net or mesh with a first level of flexibility, elasticity, or malleability; wherein the net or mesh is configured to be inserted into and expanded within an aneurysm sac; and wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; and wherein the first location is further from the aneurysm neck than the second location.

In an example, an intrasacular aneurysm occlusion device can comprise: a net or mesh with a first level of flexibility, elasticity, or malleability; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; and wherein the first location is more distal than the second location. In an example, an intrasacular aneurysm occlusion device can comprise: a net or mesh with a first level of flexibility, elasticity, or malleability; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; and wherein the first location is further from the aneurysm neck than the second location.

In an example, an intrasacular aneurysm occlusion device can comprise: a net or mesh with a first level of flexibility, elasticity, or malleability; wherein the net or mesh is configured to be inserted into and expanded within an aneurysm sac; and a stent or lattice with a second level of flexibility, elasticity, or malleability; wherein the stent or lattice is configured to be inserted into and expanded within the aneurysm sac; wherein the first level is greater than the second level; and wherein the stent or lattice is inside the net or mesh.

In an example, an intrasacular aneurysm occlusion device can comprise: a net or mesh with a first level of flexibility, elasticity, or malleability; wherein the net or mesh is configured to be inserted into and expanded in a first location within an aneurysm sac; and a stent or lattice with a second level of flexibility, elasticity, or malleability; wherein the stent or lattice is configured to be inserted into and expanded in a second location within the aneurysm sac; wherein the first level is greater than the second level; wherein the first location is more distal than the second location; and wherein the stent or lattice is inside the net or mesh. In an example, an intrasacular aneurysm occlusion device can comprise: a net or mesh with a first level of flexibility, elasticity, or malleability; wherein the net or mesh is configured to be inserted into and expanded in a first location within an aneurysm sac; and a stent or lattice with a second level of flexibility, elasticity, or malleability; wherein the stent or lattice is configured to be inserted into and expanded in a second location within the aneurysm sac; wherein the first level is greater than the second level; wherein the first location is more further from the aneurysm neck than the second location; and wherein the stent or lattice is inside the net or mesh.

In an example, an intrasacular aneurysm occlusion device can comprise: a net or mesh with a first level of flexibility, elasticity, or malleability; wherein the net or mesh is configured to be inserted into and expanded within an aneurysm sac; and wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is more distal than the second location; and wherein the stent or lattice is inside the net or mesh. In an example, an intrasacular aneurysm occlusion device can comprise: a net or mesh with a first level of flexibility, elasticity, or malleability; wherein the net or mesh is configured to be inserted into and expanded within an aneurysm sac; and wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is further from the aneurysm neck than the second location; and wherein the stent or lattice is inside the net or mesh.

In an example, an intrasacular aneurysm occlusion device can comprise: a net or mesh with a first level of flexibility, elasticity, or malleability; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level;

wherein the first location is more distal than the second location; and wherein the stent or lattice is inside the net or mesh. In an example, an intrasacular aneurysm occlusion device can comprise: a net or mesh with a first level of flexibility, elasticity, or malleability; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is further from the aneurysm neck than the second location; and wherein the stent or lattice is inside the net or mesh.

In an example, an intrasacular aneurysm occlusion device can comprise: a net or mesh with a first level of flexibility, elasticity, or malleability; wherein the net or mesh is configured to be inserted into and expanded within an aneurysm sac; and a stent or lattice with a second level of flexibility, elasticity, or malleability; wherein the stent or lattice is configured to be inserted into and expanded within the aneurysm sac; wherein the first level is greater than the second level; and wherein the stent or lattice is outside the net or mesh.

In an example, an intrasacular aneurysm occlusion device can comprise: a net or mesh with a first level of flexibility, elasticity, or malleability; wherein the net or mesh is configured to be inserted into and expanded in a first location within an aneurysm sac; and a stent or lattice with a second level of flexibility, elasticity, or malleability; wherein the stent or lattice is configured to be inserted into and expanded in a second location within the aneurysm sac; wherein the first level is greater than the second level; wherein the first location is more distal than the second location; and wherein the stent or lattice is outside the net or mesh. In an example, an intrasacular aneurysm occlusion device can comprise: a net or mesh with a first level of flexibility, elasticity, or malleability; wherein the net or mesh is configured to be inserted into and expanded in a first location within an aneurysm sac; and a stent or lattice with a second level of flexibility, elasticity, or malleability; wherein the stent or lattice is configured to be inserted into and expanded in a second location within the aneurysm sac; wherein the first level is greater than the second level; wherein the first location is more further from the aneurysm neck than the second location; and wherein the stent or lattice is outside the net or mesh.

In an example, an intrasacular aneurysm occlusion device can comprise: a net or mesh with a first level of flexibility, elasticity, or malleability; wherein the net or mesh is configured to be inserted into and expanded within an aneurysm sac; and wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is more distal than the second location; and wherein the stent or lattice is outside the net or mesh. In an example, an intrasacular aneurysm occlusion device can comprise: a net or mesh with a first level of flexibility, elasticity, or malleability; wherein the net or mesh is configured to be inserted into and expanded within an aneurysm sac; and wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is further from the aneurysm neck than the second location; and wherein the stent or lattice is outside the net or mesh.

In an example, an intrasacular aneurysm occlusion device can comprise: a net or mesh with a first level of flexibility, elasticity, or malleability; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is more distal than the second location; and wherein the stent or lattice is outside the net or mesh. In an example, an intrasacular aneurysm occlusion device can comprise: a net or mesh with a first level of flexibility, elasticity, or malleability; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is further from the aneurysm neck than the second location; and wherein the stent or lattice is outside the net or mesh.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and a stent or mesh with a second level of flexibility, elasticity, or malleability; wherein the stent or mesh is configured to be inserted into and expanded within the aneurysm sac; and wherein the first level is greater than the second level.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded in a first location within an aneurysm sac; and a stent or mesh with a second level of flexibility, elasticity, or malleability; wherein the stent or mesh is configured to be inserted into and expanded in a second location within the aneurysm sac;

wherein the first level is greater than the second level; and wherein the first location is more distal than the second location. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded in a first location within an aneurysm sac; and a stent or mesh with a second level of flexibility, elasticity, or malleability; wherein the stent or mesh is configured to be inserted into and expanded in a second location within the aneurysm sac; wherein the first level is greater than the second level; and wherein the first location is more further from the aneurysm neck than the second location.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; and wherein the first location is more distal than the second location. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; and wherein the first location is further from the aneurysm neck than the second location.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; wherein the porous and/or liquid-permeable balloon or liner is expanded by insertion of a plurality of embolic members into the porous and/or liquid-permeable balloon or liner; wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; and wherein the first location is more distal than the second location. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; wherein the porous and/or liquid-permeable balloon or liner is expanded by insertion of a plurality of embolic members into the porous and/or liquid-permeable balloon or liner; wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; and wherein the first location is further from the aneurysm neck than the second location.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and a stent or mesh with a second level of flexibility, elasticity, or malleability; wherein the stent or mesh is configured to be inserted into and expanded within the aneurysm sac; wherein the first level is greater than the second level; and wherein the stent or mesh is inside the porous and/or liquid-permeable balloon or liner.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded in a first location within an aneurysm sac; and a stent or mesh with a second level of flexibility, elasticity, or malleability; wherein the stent or mesh is configured to be inserted into and expanded in a second location within the aneurysm sac; wherein the first level is greater than the second level; wherein the first location is more distal than the second location; and wherein the stent or mesh is inside the porous and/or liquid-permeable balloon or liner. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded in a first location within an aneurysm sac; and a stent or mesh with a second level of flexibility, elasticity, or malleability; wherein the stent or mesh is configured to be inserted into and expanded in a second location within the aneurysm sac; wherein the first level is greater than the second level; wherein the first location is more further from the aneurysm neck than the second location; and wherein the stent or mesh is inside the porous and/or liquid-permeable balloon or liner.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is more distal than the second location; and wherein the stent or mesh is inside the porous and/or liquid-permeable balloon or liner. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is further from the aneurysm neck than the second location; and wherein the stent or mesh is inside the porous and/or liquid-permeable balloon or liner.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; wherein the porous and/or liquid-permeable balloon or liner is expanded by insertion of a plurality of embolic members into the porous and/or liquid-permeable balloon or liner; wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is more distal than the second location; and wherein the stent or mesh is inside the porous and/or liquid-permeable balloon or liner. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; wherein the porous and/or liquid-permeable balloon or liner is expanded by insertion of a plurality of embolic members into the porous and/or liquid-permeable balloon or liner; wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is further from the aneurysm neck than the second location; and wherein the stent or mesh is inside the porous and/or liquid-permeable balloon or liner.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and a stent or mesh with a second level of flexibility, elasticity, or malleability; wherein the stent or mesh is configured to be inserted into and expanded within the aneurysm sac; wherein the first level is greater than the second level; and wherein the stent or mesh is outside the porous and/or liquid-permeable balloon or liner.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded in a first location within an aneurysm sac; and a stent or mesh with a second level of flexibility, elasticity, or malleability; wherein the stent or mesh is configured to be inserted into and expanded in a second location within the aneurysm sac; wherein the first level is greater than the second level; wherein the first location is more distal than the second location; and wherein the stent or mesh is outside the porous and/or liquid-permeable balloon or liner. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded in a first location within an aneurysm sac; and a stent or mesh with a second level of flexibility, elasticity, or malleability; wherein the stent or mesh is configured to be inserted into and expanded in a second location within the aneurysm sac; wherein the first level is greater than the second level; wherein the first location is more further from the aneurysm neck than the second location; and wherein the stent or mesh is outside the porous and/or liquid-permeable balloon or liner.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is more distal than the second location; and wherein the stent or mesh is outside the porous and/or liquid-permeable balloon or liner. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; and wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is further from the aneurysm neck than the second location; and wherein the stent or mesh is outside the porous and/or liquid-permeable balloon or liner.

In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; wherein the porous and/or liquid-permeable balloon or liner is expanded by insertion of a plurality of embolic members into the porous and/or liquid-permeable balloon or liner; wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is more distal than the second location; and wherein the stent or mesh is outside the porous and/or liquid-permeable balloon or liner. In an example, an intrasacular aneurysm occlusion device can comprise: a porous and/or liquid-permeable balloon or liner with a first level of flexibility, elasticity, or malleability; wherein the porous and/or liquid-permeable balloon or liner is configured to be inserted into and expanded within an aneurysm sac; wherein the porous and/or liquid-permeable balloon or liner is expanded by insertion of a plurality of embolic members into the porous and/or liquid-permeable balloon or liner; wherein the post-expansion centroid of the porous and/or liquid-permeable balloon or liner is configured to be at a first location within the aneurysm sac; and a stent or mesh with a second level of flexibility, elasticity, or malleability; wherein the stent or mesh is configured to be inserted into and expanded within the aneurysm sac; wherein the post-expansion centroid of the stent or mesh is configured to be at a second location within the aneurysm sac; wherein the first level is greater than the second level; wherein the first location is further from the aneurysm neck than the second location; and wherein the stent or mesh is outside the porous and/or liquid-permeable balloon or liner.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and a stent with a second level of radial stiffness, measured in newtons per meter or pounds per inch; wherein the stent is configured to be inserted into and expanded within the aneurysm sac; and wherein the first level is less than the second level.

In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded in a first location within an aneurysm sac; and a stent with a second level of radial stiffness, measured in newtons per meter or pounds per inch; wherein the stent is configured to be inserted into and expanded in a second location within the aneurysm sac; wherein the first level is less than the second level; and wherein the first location is more further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; and wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is more distal than the second location. In an example, an intrasacular aneurysm occlusion device can comprise: a net or mesh with a first level of radial stiffness, measured in newtons per meter or pounds per inch; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent with a second level of radial stiffness, measured in newtons per meter or pounds per inch; wherein the stent is configured to be inserted into and expanded within the aneurysm sac; wherein the post-expansion centroid of the stent is configured to be at a second location within the aneurysm sac; wherein the first level is less than the second level; and wherein the first location is further from the aneurysm neck than the second location.

In an example, an intrasacular aneurysm occlusion device can comprise: a net or mesh with a first elastic modulus; wherein the net or mesh is configured to be inserted into and expanded within an aneurysm sac; and a stent with a second elastic modulus; wherein the stent is configured to be inserted into and expanded within the aneurysm sac; and wherein the first elastic modulus is less than the second elastic modulus.

In an example, an intrasacular aneurysm occlusion device can comprise: a net or mesh with a first elastic modulus within the range of 0.01-0.5 GPa which is configured to be inserted into and expanded within an aneurysm sac; and a stent with a second elastic modulus within the range of 0.5 to 5 GPa which is configured to be inserted into and expanded within the aneurysm sac; and wherein the first elastic modulus is less than the second elastic modulus. In an example, an intrasacular aneurysm occlusion device can comprise: a net or mesh with a first elastic modulus within the range of 0.01-1 GPa which is configured to be inserted into and expanded within an aneurysm sac; and a stent with a second elastic modulus within the range of 1 to 5 GPa which is configured to be inserted into and expanded within the aneurysm sac; and wherein the first elastic modulus is less than the second elastic modulus.

In an example, an intrasacular aneurysm occlusion device can comprise: a net or mesh with a first elastic modulus, measured in GPa, which is configured to be inserted into and expanded within an aneurysm sac; and a stent with a second elastic modulus, measured in GPa, which is configured to be inserted into and expanded within the aneurysm sac; and wherein the first elastic modulus at least 0.10 GPa less than the second elastic modulus. In an example, an intrasacular aneurysm occlusion device can comprise: a net or mesh with a first elastic modulus, measured in GPa, which is configured to be inserted into and expanded within an aneurysm sac; and a stent with a second elastic modulus, measured in GPa, which is configured to be inserted into and expanded within the aneurysm sac; and wherein the first elastic modulus at least 1 GPa less than the second elastic modulus.

In an example, an intrasacular aneurysm occlusion device can comprise: an outer net or mesh which is configured to be inserted into and expanded within an aneurysm sac, wherein the outer net or mesh is expanded by being filled with a plurality of embolic members, and wherein the outer net or mesh has a first elastic modulus; and an inner stent which is configured to be inserted into and expanded within the aneurysm sac, wherein the inner stent is expanded inside the outer net or mesh, wherein the inner stent is configured to be wider than the neck of the aneurysm sac after the stent has been expanded; wherein inner stent has a second elastic modulus; and wherein the second elastic modulus is greater than the first elastic modulus by at least 0.10 GPa.

In an example, an intrasacular aneurysm occlusion device can comprise: an outer net or mesh which is configured to be inserted into and expanded within an aneurysm sac, wherein the outer net or mesh is expanded by being filled with a plurality of embolic members, and wherein the outer net or mesh has a first elastic modulus; and an inner stent which is configured to be inserted into and expanded within the aneurysm sac, wherein the inner stent is expanded inside the outer net or mesh, wherein the inner stent is configured to be wider than the neck of the aneurysm sac after the stent has been expanded; wherein inner stent has a second elastic modulus; and wherein the second elastic modulus is greater than the first elastic modulus by at least 0.10 GPa.

In an example, an intrasacular aneurysm occlusion device can comprise: an outer net or mesh which is configured to be inserted into and expanded within an aneurysm sac, wherein the outer net or mesh is expanded by being filled with a plurality of embolic members, and wherein the outer net or mesh has a first elastic modulus; and an inner stent which is configured to be inserted into and expanded within the aneurysm sac, wherein the inner stent is expanded inside the outer net or mesh, wherein the inner stent is configured to be wider than the neck of the aneurysm sac after the stent has been expanded; wherein inner stent has a second elastic modulus; and wherein the second elastic modulus is greater than the first elastic modulus by at least 1.00 GPa.

In an example, an intrasacular aneurysm occlusion device can comprise: a net or mesh which is configured to be expanded within an aneurysm sac, wherein the net or mesh is expanded by being filled with a plurality of embolic members, wherein the net or mesh conforms to the walls of the aneurysm sac after it has been expanded, and wherein the net or mesh has a first elastic modulus; and a stent which is configured to be expanded within the aneurysm sac, wherein the stent is expanded inside the net or mesh, wherein the stent has a bowl or hemispherical shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be expanded within an aneurysm sac, wherein the net or mesh is expanded by being filled with a plurality of embolic members, wherein the net or mesh conforms to the walls of the aneurysm sac after it has been expanded, and wherein the net or mesh has a first elastic modulus; and a stent which is configured to be expanded within the aneurysm sac, wherein the stent is expanded inside the net or mesh, wherein the stent has an ellipsoidal or toroidal shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be expanded within an aneurysm sac, wherein the net or mesh is expanded by being filled with a plurality of embolic members, wherein the net or mesh conforms to the walls of the aneurysm sac after it has been expanded, and wherein the net or mesh has a first elastic modulus; and a stent which is configured to be expanded within the aneurysm sac, wherein the stent is located inside the proximal half of the net or mesh after it has been expanded, wherein the stent has a bowl or hemispherical shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be expanded within an aneurysm sac, wherein the net or mesh is expanded by being filled with a plurality of embolic members, wherein the net or mesh conforms to the walls of the aneurysm sac after it has been expanded, and wherein the net or mesh has a first elastic modulus; and a stent which is configured to be expanded within the aneurysm sac, wherein the stent is expanded inside the proximal half of the net or mesh, wherein the stent has an ellipsoidal or toroidal shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be expanded within an aneurysm sac, wherein the net or mesh is expanded by being filled with a plurality of microscale sponges or pieces of gel, wherein the net or mesh conforms to the walls of the aneurysm sac after it has been expanded, and wherein the net or mesh has a first elastic modulus; and a stent which is configured to be expanded within the aneurysm sac, wherein the stent is located inside the proximal half of the net or mesh after it has been expanded, wherein the stent has a bowl or hemispherical shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be expanded within an aneurysm sac, wherein the net or mesh is expanded by being filled with a plurality of microscale sponges or pieces of gel, wherein the net or mesh conforms to the walls of the aneurysm sac after it has been expanded, and wherein the net or mesh has a first elastic modulus; and a stent which is configured to be expanded within the aneurysm sac, wherein the stent is expanded inside the proximal half of the net or mesh, wherein the stent has an ellipsoidal or toroidal shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be expanded within an aneurysm sac, wherein the net or mesh is expanded by being filled with a plurality of coils, wherein the net or mesh conforms to the walls of the aneurysm sac after it has been expanded, and wherein the net or mesh has a first elastic modulus; and a stent which is configured to be expanded within the aneurysm sac, wherein the stent is located inside the proximal half of the net or mesh after it has been expanded, wherein the stent has a bowl or hemispherical shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be expanded within an aneurysm sac, wherein the net or mesh is expanded by being filled with a plurality of coils, wherein the net or mesh conforms to the walls of the aneurysm sac after it has been expanded, and wherein the net or mesh has a first elastic modulus; and a stent which is configured to be expanded within the aneurysm sac, wherein the stent is expanded inside the proximal half of the net or mesh, wherein the stent has an ellipsoidal or toroidal shape after it has been expanded, wherein the stent is configured to cover the interior of the neck of the aneurysm sac after it has been expanded, wherein inner stent has a second elastic modulus; and wherein the second elastic modulus is greater than the first elastic modulus. In an example, the second elastic modulus can be greater than the first elastic modulus by at least 0.10 GPa.

In an example, an intrasacular aneurysm occlusion device can comprise: a net or mesh which is configured to be inserted into an aneurysm sac and expanded within the aneurysm sac; a stent which is configured to be inserted into the aneurysm sac and expanded within the aneurysm sac; a plurality of coils which are inserted into the net or mesh through a opening in the stent; and a closure mechanism which closes the opening in the stent. In an example, the net or mesh can be expanded by accumulation of coils in the net or mesh. In an example, an intrasacular aneurysm occlusion device can comprise: a net or mesh which is configured to be inserted into an aneurysm sac and expanded within the aneurysm sac; a stent which is configured to be inserted into the aneurysm sac and expanded within the aneurysm sac; a plurality of beads which are inserted into the net or mesh through a opening in the stent; and a closure mechanism which closes the opening in the stent. In an example, the net or mesh can be expanded by accumulation of beads in the net or mesh.

In an example, an intrasacular aneurysm occlusion device can comprise: a net or mesh which is configured to be inserted into an aneurysm sac and expanded within the aneurysm sac; a stent which is configured to be inserted into the aneurysm sac and expanded within the aneurysm sac; a plurality of microsponges which are inserted into the net or mesh through a opening in the stent; and a closure mechanism which closes the opening in the stent. In an example, the net or mesh can be expanded by accumulation of microsponges in the net or mesh. In an example, the net or mesh can be expanded by accumulation of microsponges in the net or mesh. In an example, the microsponges can be delivered to the net or mesh in a flow of liquid through a catheter. In an example, the net or mesh and the stent can be permeable by this liquid, but not the microsponges.

In an example, an intrasacular aneurysm occlusion device can comprise: a net or mesh which is configured to be inserted into an aneurysm sac and expanded within the aneurysm sac; a stent which is configured to be inserted into the aneurysm sac and expanded within the aneurysm sac; pieces of gel which are inserted into the net or mesh through a opening in the stent; and a closure mechanism which closes the opening in the stent. In an example, the net or mesh can be expanded by accumulation of pieces of gel in the net or mesh. In an example, the net or mesh can be expanded by accumulation of pieces of gel in the net or mesh. In an example, the pieces of gel can be delivered to the net or mesh in a flow of liquid through a catheter. In an example, the net or mesh and the stent can be permeable by this liquid, but not the pieces of gel.

In an example, the centroid of a stent can be proximal to the centroid of a net or mesh. In an example, the net or mesh can be less stiff than the stent. In an example, the net or mesh can be made from a polymer. In an example, the net or mesh can be more elastic than the stent. In an example, the net or mesh can be more flexible than the stent. In an example, the net or mesh can conform to the walls of the aneurysm sac after the net or mesh has been expanded. In an example, the opening in the stent can be in the middle of the stent. In an example, the stent can be inside the net or mesh. In an example, the stent can be made from metal. In an example, the stent can be proximal to the net or mesh. In an example, the stent can cover the neck of the aneurysm from inside the aneurysm sac after the stent has been expanded. In an example, the stent can have a ball or sphere shape. In an example, the stent can have a toroidal or ring shape. In an example, the stent can have an ellipsoidal or disk shape.

In an example, an intrasacular aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a first location and a second tensile strength at a second location, and wherein the second tensile strength is greater than the first tensile strength. In an example, an intrasacular aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a first location and a second elasticity at a second location, and wherein the second elasticity is greater than the first elasticity.

In an example, an intrasacular aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a first location and a second flexibility at a second location, and wherein the second flexibility is greater than the first flexibility. In an example, an intrasacular aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a first location and a second porosity at a second location, and wherein the second porosity is greater than the first porosity.

In an example, an intrasacular aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a proximal location and a second tensile strength at a distal location, and wherein the second tensile strength is less than the first tensile strength. In an example, an intrasacular aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a proximal location and a second elasticity at a distal location, and wherein the second elasticity is greater than the first elasticity.

In an example, an intrasacular aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a proximal location and a second flexibility at a distal location, and wherein the second flexibility is greater than the first flexibility. In an example, an intrasacular aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a proximal location and a second porosity at a distal location, and wherein the second porosity is greater than the first porosity.

In an example, a resilient wider-than-neck portion and a flexible sac-filling portion of an intrasacular aneurysm occlusion device can both be braided, but can have different braid patterns. These braid patterns can be selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern. In an example, the resilient wider-than-neck portion of this device can have a first braid pattern and the flexible sac-filling portion of this device can have a second braid pattern.

In an example, resilient wider-than-neck and flexible sac-filling portions of an intrasacular aneurysm occlusion device can have different braid densities. In an example, the resilient wider-than-neck portion of this device can have a higher braid density than the flexible sac-filling portion of this device. In an example, the resilient wider-than-neck and flexible sac-filling portions of this device can have different braid angles. In an example, the resilient wider-than-neck portion of this device can have a greater braid angle than the flexible sac-filling portion of this device. In an example, the resilient wider-than-neck and flexible sac-filling portions of this device can have different braid pitches. In an example, the resilient wider-than-neck portion of this device can have a first braid pitch and the flexible sac-filling portion of this device can have a second braid pitch. In an example, the resilient wider-than-neck and flexible sac-filling portions of this device can have different braid filament sizes. In an example, the resilient wider-than-neck portion of this device can have a first braid filament size and the flexible sac-filling portion of this device can have a second braid filament size.

In an example, different portions, segments, bulges, or undulations of a continuous braided intrasacular aneurysm occlusion device can have different braid patterns. In an example, a proximal portion, segment, or undulation of an intrasacular aneurysm occlusion device can have a first braid pattern and a distal portion, segment, or undulation of this device can have a second braid pattern. In an example, different portion, segment, or undulations of a continuous intrasacular aneurysm occlusion device can have different braid densities. In an example, a proximal portion, segment, or undulation of an intrasacular aneurysm occlusion device can have a higher braid density than a distal portion, segment, or undulation of this device. In an example, different portion, segment, or undulations of a continuous intrasacular aneurysm occlusion device can have different braid angles. In an example, a proximal portion, segment, or undulation of an intrasacular aneurysm occlusion device can have a greater braid angle than a distal portion, segment, or undulation of this device.

In an example, different portion, segment, bulges, or undulations of a continuous intrasacular aneurysm occlusion device can have different braid pitches. In an example, a proximal portion, segment, or undulation of an intrasacular aneurysm occlusion device can have a first braid pitch and a distal portion, segment, or undulation of this device can have a second braid pitch. In an example, different portion, segment, or undulations of a continuous intrasacular aneurysm occlusion device can have different braid filament sizes. In an example, a proximal portion, segment, or undulation of an intrasacular aneurysm occlusion device can have a first braid filament size and a distal portion, segment, or undulation of this device can have a second braid filament size.

Figure 55:
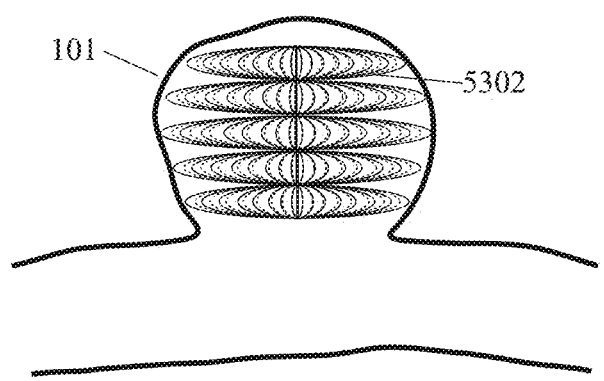

FIGS. 1 through 55 show some specific examples of how this invention can be embodied in an aneurysm occlusion device, but do not restrict the full generalizability of the final claims. Example and component variations which have been discussed thus far in this disclosure (and also in other disclosures which are linked by priority claim) can be applied where relevant to the examples in FIGS. 1 through 55 but are not repeated in the narratives accompanying these figures in order to reduce duplicative content.

We now discuss FIGS. 1 through 55 in detail, starting with FIGS. 1 through 6.

FIGS. 1 through 6 show six sequential cross-sectional views of an example of this intrasacular aneurysm occlusion device. These six sequential views show the device at six different times, while it is being inserted into and expanded within an aneurysm sac 101. The example shown in FIGS. 1 through 6 comprises: a resilient wider-than-neck portion 201 (such as a stent or neck bridge) of the device with a first (constrained) configuration as it is transported to an aneurysm sac and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability.

Figure 2:
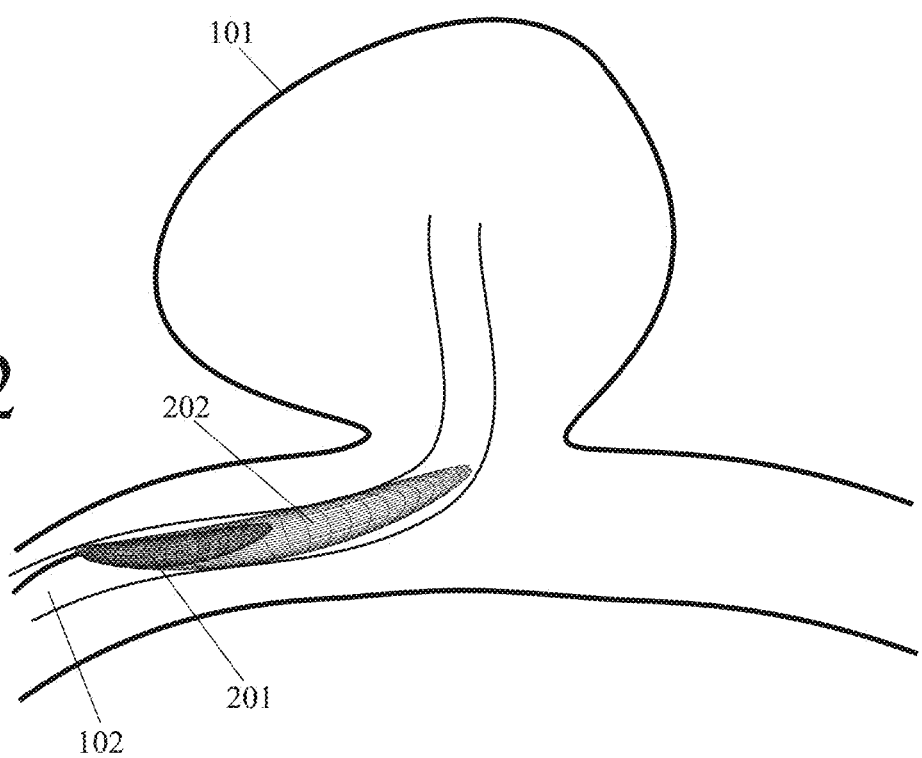

FIG. 1 shows this aneurysm occlusion device at a first point in time wherein a catheter 102 has been inserted into an aneurysm sac 101. FIG. 2 shows this device at a second point in time wherein a resilient wider-than-neck portion 201 of the device and flexible sac-filling portion 202 of the device are being delivered through catheter 102 toward aneurysm sac 101. In this example, the resilient wider-than-neck portion of the device is a stent (or neck bridge). In this example, the resilient wider-than-neck portion of this device is made from metal wires, strands, filaments, mesh, or lattice. In this example, the flexible sac-filling portion of the device is a net (or mesh). In this example, the flexible sac-filling portion of this device is made from polymer strands, filaments, threads, or mesh. In this example, the resilient wider-than-neck portion of the device is inside the flexible sac-filling portion of the device. In this example, the centroid of the resilient wider-than-neck portion of the device is proximal relative to the centroid of the flexible sac-filling portion of the device. Example variations discussed elsewhere in this or priority-linked disclosures can also apply to this example.

Figure 3:
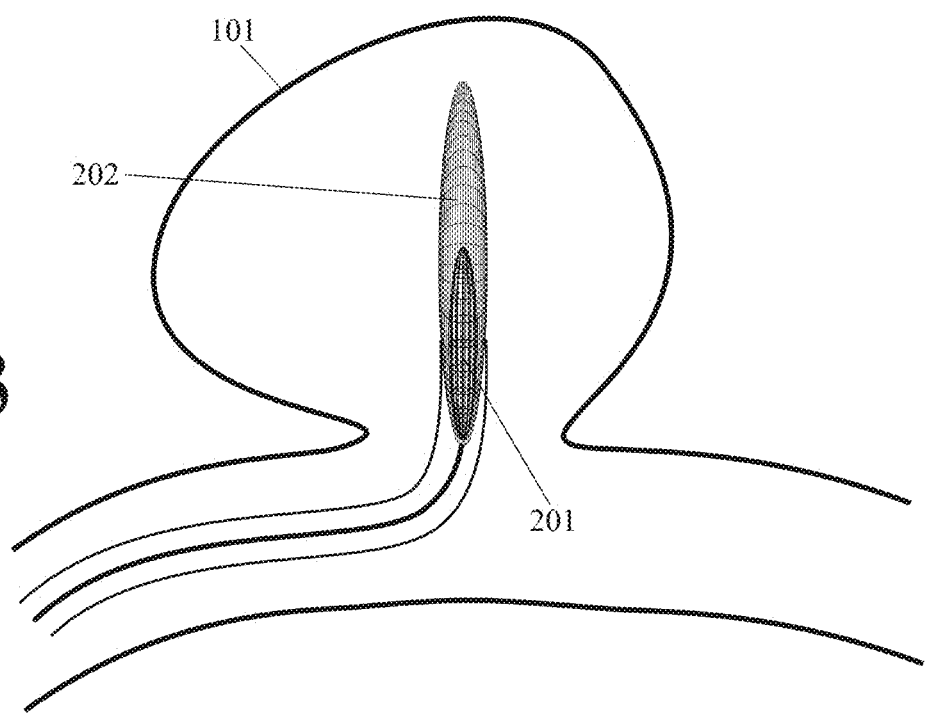
Figure 4:
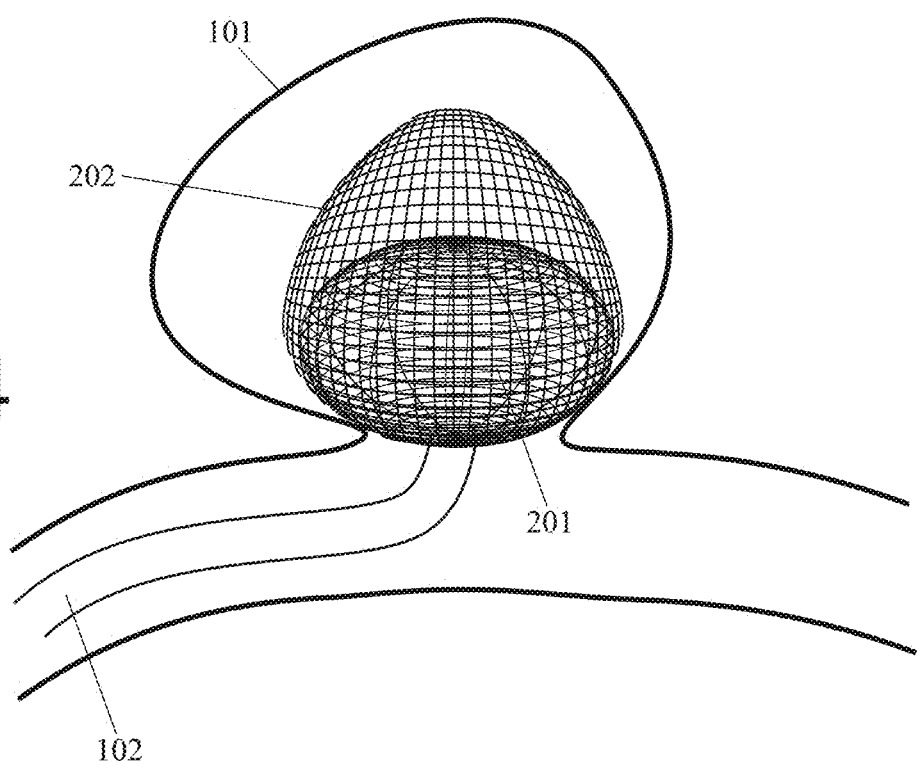

FIG. 3 shows this device at a third point in time wherein the resilient wider-than-neck portion 201 of the device and the flexible sac-filling portion 202 of the device are exiting catheter 102 and entering into aneurysm sac 101. FIG. 4 shows this device at a fourth point in time wherein the resilient wider-than-neck portion 201 of the device has expanded within the aneurysm sac 101. In this example, the resilient wider-than-neck portion of the device has self-expanded after it was released from the constraints of the catheter. In this example, the resilient wider-than-neck portion of the device is configured to radially self-expand within the aneurysm sac to a width which is greater than the width of the aneurysm neck. In this example, the resilient wider-than-neck portion expands within the aneurysm sac to an ellipsoidal shape with a width that is greater than the width of the aneurysm neck. In an example, the expanded shape of the wider-than-neck portion can be selected from the group consisting of: apple shape; bowl shape; compress-sphere shape; cylinder; disk; doughnut shape; egg shape; ellipsoid; Frisbee™ shape; frustum; hourglass shape; oval; peanut shape; pear shape; pumpkin shape; ring shape; Saturn shape; sphere; tire shape; and torus.

Figure 5:
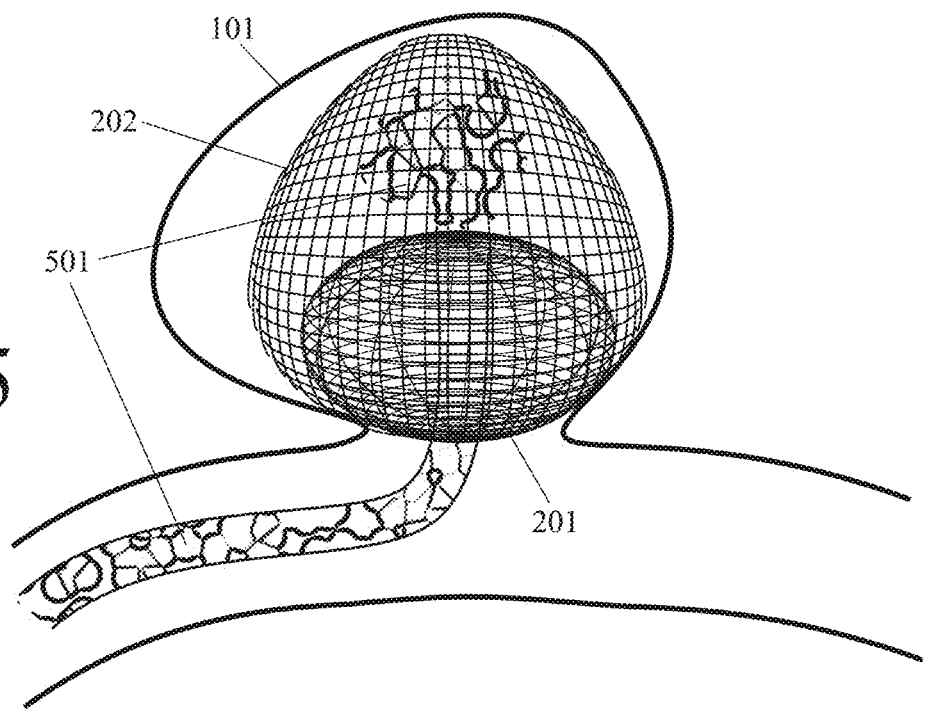

FIG. 5 shows this device at a fifth point in time wherein embolic members 501 (such as microsponges, pieces of gel, pieces or foam, beads, microspheres, or embolic coils) are being delivered through the catheter into the flexible sac-filling portion 202 of the device. The accumulation of embolic members within the flexible sac-filling portion of the device causes the sac-filling portion to expand within the aneurysm sac. In an example, the flexible sac-filling portion is sufficiently porous to allow blood from the aneurysm sac to permeate it, but not so porous as to allow the embolic members to escape out of the flexible sac-filling portion. In an example, the embolic members can be delivered through the catheter by a flow of a liquid or gel, wherein the liquid or gel escapes through the wall of the flexible sac-filling portion of the device but the embolic members are trapped inside the flexible sac-filling portion. In an example, the embolic members can be delivered through the catheter by a rotation of a helical member (such as an Archimedes' screw). In an example, the embolic members can be delivered through the catheter by a conveyor belt. In an example, the embolic members can be delivered through the catheter by a "pusher" wire or tube.

In an example, there can be an adjustable (e.g. closable) opening in the resilient wider-than-neck portion of the device through which embolic members are inserted into the flexible sac-filling portion of the device. In an example, the opening can be closed to prevent embolic members from escaping once the flexible sac-filling portion of the device has been satisfactorily expanded with the aneurysm sac. In an example, this opening can be controllably opened and closed by the operator of the device by a closure mechanism selected from the group consisting of: activating an electromagnetic valve; aligning (or miss-aligning) two holes; application of electromagnetic energy (to a magnet); application of thermal energy; compressing a snap or clip; activating an electrolytic closure mechanism; electromagnetic fusing; injecting an adhesive; moving a plug; opening a valve; pressing a seal; pulling a cord or string; pushing or pulling a wire; rotating a cable or wire; rotating a cap; and tightening a loop.

Figure 6:
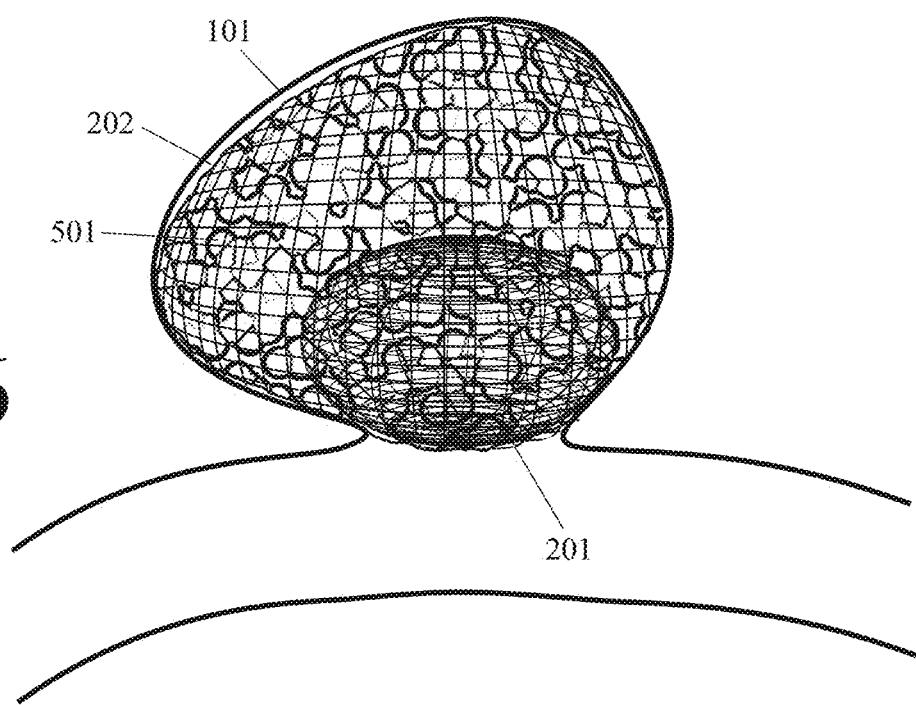

FIG. 6 shows this device at a sixth point in time wherein the accumulation of embolic members in the flexible sac-filling portion of the device has caused the sac-filling portion to expand to fill the aneurysm sac, conforming to the irregular shape of the aneurysm sac walls and frictionally engaging these walls. The flexible sac-filling portion of the device is sufficiently flexible, elastic, and/or malleable to conform to the irregular contours of even an irregularly-shaped aneurysm sac. This helps to: (a) full occlude the aneurysm sac; (b) prevent blood from circulating around the periphery of the sac; (c) engage the walls and hold the device within the aneurysm sac; and (d) keep the resilient wider-than-neck portion of the device snuggly pressed against the aneurysm neck. Ideally, this design can completely occlude even an irregularly-shaped aneurysm sac with a single deployment sequence of a single device—which is sometimes called "one and done." This can potentially achieve better and quicker occlusion results than designs which require multiple deployment sequences and multiple devices for irregularly-shaped aneurysm sacs. The catheter has been detached and removed. Relevant embodiment variations discussed elsewhere in this disclosure or in priority-linked disclosures can also apply to this example.

In an example, a resilient wider-than-neck portion of this device can be created by weaving. In an example, a resilient wider-than-neck portion of this device can be created by weaving wires or filaments into a weave pattern selected from the group consisting of: plain weave; double weave; diamond weave; perpendicular weave; rib weave; basket weave; twill weave; satin weave; leno weave; mock leno weave; and diagonal weave.

In an example, a resilient wider-than-neck portion of this device can be created by braiding. In an example, a resilient wider-than-neck portion of this device can be created by braiding wires or filaments into a braid pattern selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, different areas of a resilient wider-than-neck portion can have different braid patterns. In an example, the proximal area of a resilient wider-than-neck portion of this device can have a first braid pattern and the distal area of the resilient wider-than-neck portion of this device can have a second braid pattern. In an example, different areas of a resilient wider-than-neck portion can have different braid densities. In an example, the proximal area of a resilient wider-than-neck portion of this device can have a higher braid density than the distal area of the resilient wider-than-neck portion of this device. In an example, different areas of a resilient wider-than-neck portion can have different braid angles. In an example, the proximal area of a resilient wider-than-neck portion of this device can have a greater braid angle than the distal area of the resilient wider-than-neck portion of this device.

In an example, different areas of a resilient wider-than-neck portion can have different braid pitches. In an example, the proximal area of a resilient wider-than-neck portion of this device can have a first braid pitch and the distal area of the resilient wider-than-neck portion of this device can have a second braid pitch. In an example, different areas of a resilient wider-than-neck portion can have different braid filament sizes. In an example, the proximal area of a resilient wider-than-neck portion of this device can have a first braid filament size and the distal area of the resilient wider-than-neck portion of this device can have a second braid filament size.

In an example, a flexible sac-filling portion of this device can be created by weaving. In an example, a flexible sac-filling portion of this device can be created by weaving wires or filaments into a weave pattern selected from the group consisting of: plain weave; double weave; diamond weave; perpendicular weave; rib weave; basket weave; twill weave; satin weave; leno weave; mock leno weave; and diagonal weave.

In an example, a flexible sac-filling portion of this device can be created by braiding. In an example, a flexible sac-filling portion of this device can be created by braiding wires or filaments into a braid pattern selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, different areas of a flexible sac-filling portion can have different braid patterns. In an example, the proximal area of a flexible sac-filling portion of this device can have a first braid pattern and the distal area of the flexible sac-filling portion of this device can have a second braid pattern. In an example, different areas of a flexible sac-filling portion can have different braid densities. In an example, the proximal area of a flexible sac-filling portion of this device can have a higher braid density than the distal area of the flexible sac-filling portion of this device. In an example, different areas of a flexible sac-filling portion can have different braid angles. In an example, the proximal area of a flexible sac-filling portion of this device can have a greater braid angle than the distal area of the flexible sac-filling portion of this device.

In an example, different areas of a flexible sac-filling portion can have different braid pitches. In an example, the proximal area of a flexible sac-filling portion of this device can have a first braid pitch and the distal area of the flexible sac-filling portion of this device can have a second braid pitch. In an example, different areas of a flexible sac-filling portion can have different braid filament sizes. In an example, the proximal area of a flexible sac-filling portion of this device can have a first braid filament size and the distal area of the flexible sac-filling portion of this device can have a second braid filament size.

In an example, the resilient wider-than-neck and flexible sac-filling portions of this device can both be braided, but have different braid patterns. These braid patterns can be selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern. In an example, the resilient wider-than-neck portion of this device can have a first braid pattern and the flexible sac-filling portion of this device can have a second braid pattern.

In an example, the resilient wider-than-neck and flexible sac-filling portions of this device can have different braid densities. In an example, the resilient wider-than-neck portion of this device can have a higher braid density than the flexible sac-filling portion of this device. In an example, the resilient wider-than-neck and flexible sac-filling portions of this device can have different braid angles. In an example, the resilient wider-than-neck portion of this device can have a greater braid angle than the flexible sac-filling portion of this device. In an example, the resilient wider-than-neck and flexible sac-filling portions of this device can have different braid pitches. In an example, the resilient wider-than-neck portion of this device can have a first braid pitch and the flexible sac-filling portion of this device can have a second braid pitch. In an example, the resilient wider-than-neck and flexible sac-filling portions of this device can have different braid filament sizes. In an example, the resilient wider-than-neck portion of this device can have a first braid filament size and the flexible sac-filling portion of this device can have a second braid filament size.

Figure 7:
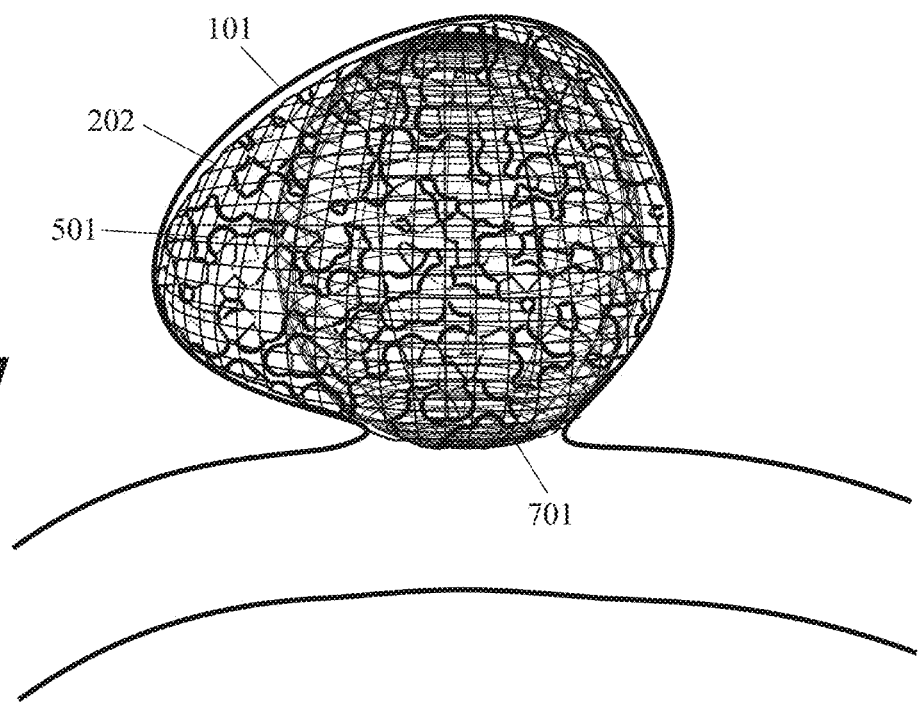
FIG. 7 shows a device with a central ball-shaped resilient wider-than-neck portion and a flexible sac-filling portion.

FIG. 7 shows a cross-sectional view of another example of this intrasacular aneurysm occlusion device. FIG. 7 shows this device at a single point in time after it has been fully deployed within an aneurysm sac. This example is like the example shown in FIGS. 1 through 6, except that the resilient wider-than-neck portion of the device has been expanded into a ball (e.g. generally spherical or globular) shape instead of an ellipsoidal shape.

The example shown in FIG. 7 comprises: a resilient wider-than-neck portion 701 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

Figure 8:
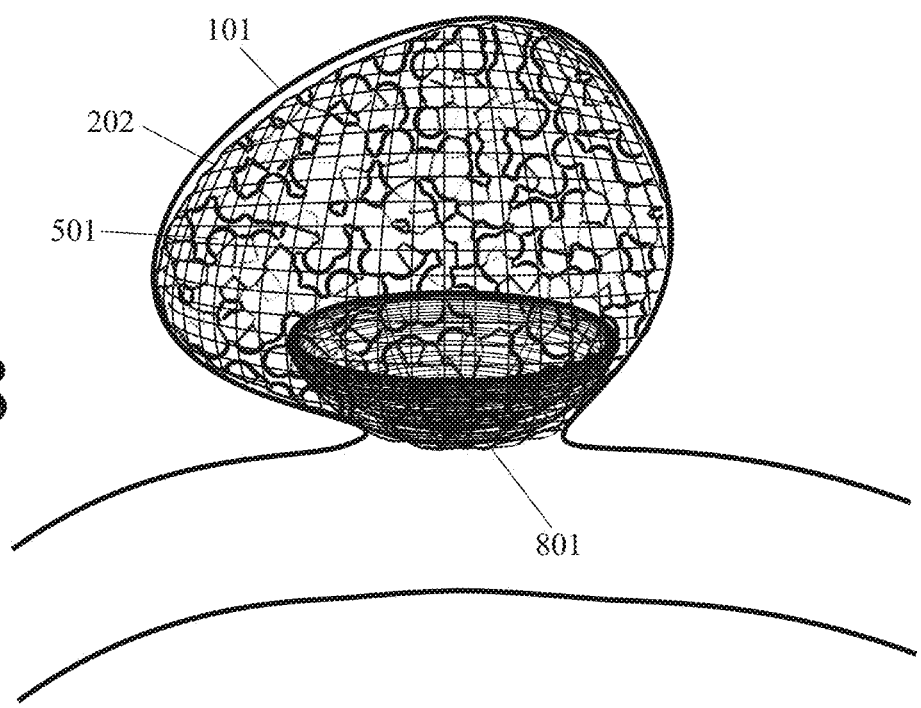
FIG. 8 shows a device with a proximal bowl-shaped resilient wider-than-neck portion and a distal flexible sac-filling portion.

FIG. 8 shows a cross-sectional view of another example of this intrasacular aneurysm occlusion device. FIG. 8 shows this device at a single point in time after it has been fully deployed within an aneurysm sac. This example is like the example shown in FIGS. 1 through 6, except that the resilient wider-than-neck portion of the device has been expanded into a bowl shape (instead of an ellipsoidal shape). In an example, the resilient wider-than-neck portion of the device can self-expand into a bowl shape in a single-step transition from its first (constrained) configuration to its second (expanded) configuration. In an example, the resilient wider-than-neck portion of the device can be expanded into a bowl shape in a multi-step transition from its first (constrained) configuration to its second (expanded) configuration. In an example of a multi-step transition, the resilient wider-than-neck portion can be expanded to a spherical or ellipsoidal shape in a first step and then this sphere or ellipsoid can be collapsed into a (two-layer) bowl shape in a second step. In an example, it can be collapsed from a spherical or ellipsoidal shape to a bowl shape by pulling a wire, cord, string, or cable which is connected to its distal surface but not connected to its proximal surface.

The example shown in FIG. 8 comprises: a resilient wider-than-neck portion 801 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

Figure 9:
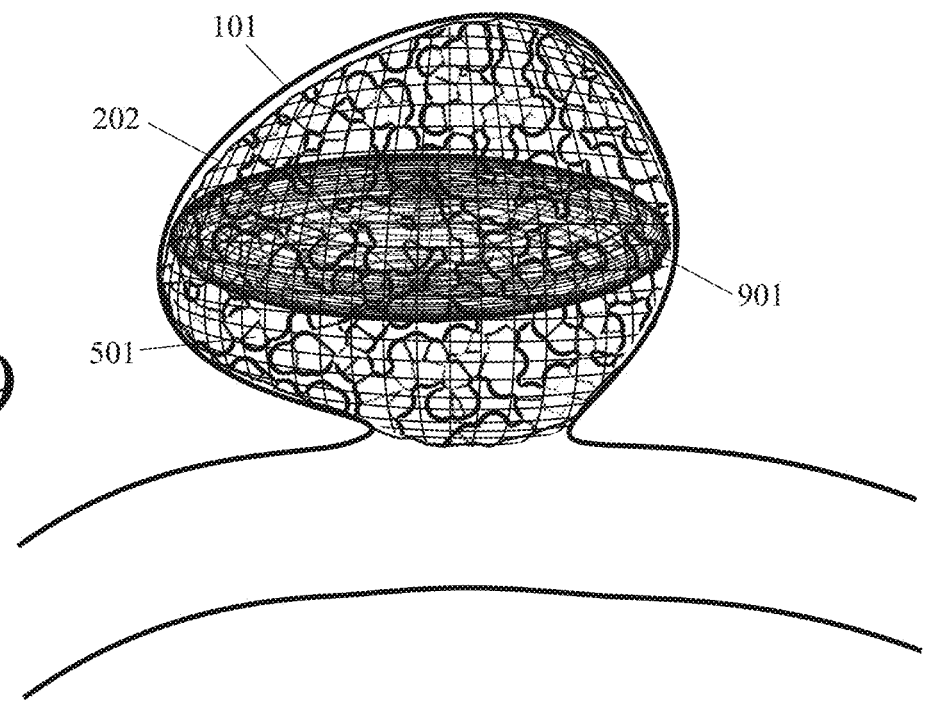
FIG. 9 shows a device with a central ellipsoidal resilient wider-than-neck portion and a flexible sac-filling portion.

FIG. 9 shows a cross-sectional view of another example of this intrasacular aneurysm occlusion device. FIG. 9 shows this device at a single point in time after it has been fully deployed within an aneurysm sac. This example is like the example shown in FIGS. 1 through 6, except that the resilient wider-than-neck portion of the device has been expanded in a more central location within the aneurysm sac. In this example, the resilient wider-than-neck portion of the device helps to keep the device within the sac, but does not directly occlude the aneurysm neck. In this example, the flexible sac-filling portion of the device occludes the aneurysm neck. One potential advantage of this design is that the resilient wider-than-neck portion of the device is frictionally engaged with the aneurysm walls near their widest circumference, providing maximal resistance to slipping out of the aneurysm sack. This can be particularly useful for occluding wide-neck aneurysms. In an example, the resilient wider-than-neck portion of the device can have a shape selected from the group consisting of: ellipsoid; doughnut; torus; ring; disk; cylinder; pancake shape; and apple shape.

The example shown in FIG. 9 comprises: a resilient wider-than-neck portion 901 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

Figure 10:
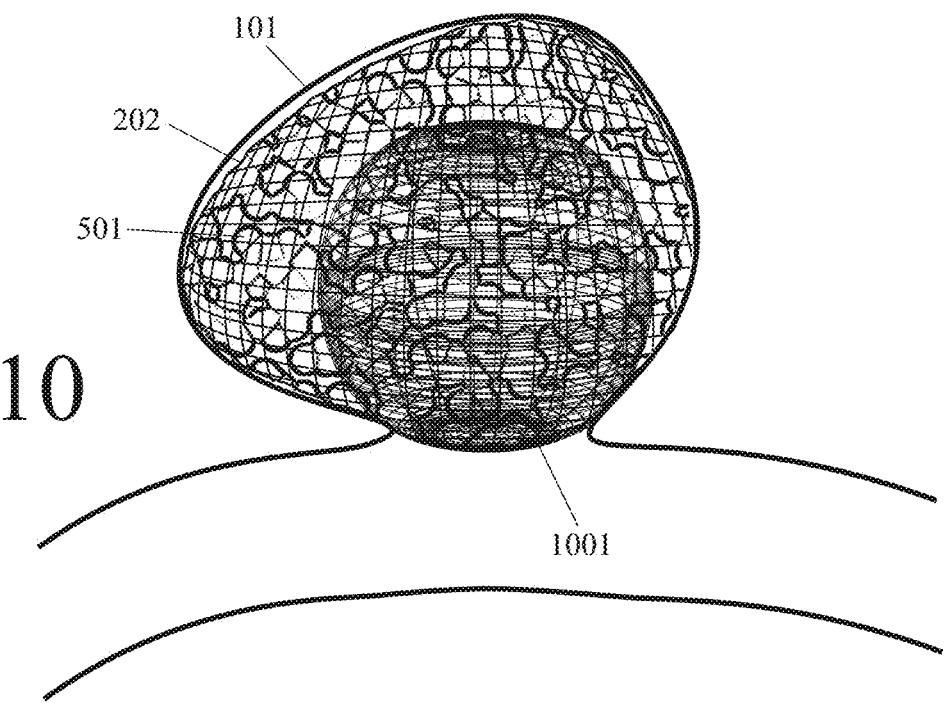
FIG. 10 shows a device with a proximal ball-shaped resilient wider-than-neck portion and a distal flexible sac-filling portion.

FIG. 10 shows a cross-sectional view of another example of this intrasacular aneurysm occlusion device. FIG. 10 shows this device at a single point in time after it has been fully deployed within an aneurysm sac. This example is like the example shown in FIG. 7, except that the ball-shaped resilient wider-than-neck portion of the device is in a more proximal location. In an example, the centroid of a ball-shaped resilient wider-than-neck portion of the device can be proximal relative to the centroid of the flexible sac-filling portion of the device. In an example, the majority of the volume of the ball-shaped resilient wider-than-neck portion of this device can be configured to be located in the proximal half of the aneurysm sac. In an example, over 50% of the volume of the ball-shaped resilient wider-than-neck portion of this device can be configured to be located in the proximal half of the aneurysm sac. In an example, over 75% of the volume of the ball-shaped resilient wider-than-neck portion of this device can be configured to be located in the proximal half of the aneurysm sac.

The example shown in FIG. 10 comprises: a resilient wider-than-neck portion 1001 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

FIG. 11 shows a cross-sectional view of another example of this intrasacular aneurysm occlusion device. FIG. 11 shows this device at a single point in time after it has been fully deployed within an aneurysm sac. This example is like the example shown in FIGS. 1 through 6 except that the resilient wider-than-neck portion of the device is expanded into a dual-inverted-frustum (e.g. "hour glass") shape.

The example shown in FIG. 11 comprises: a resilient wider-than-neck portion 1101 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

FIG. 12 shows a cross-sectional view of another example of this intrasacular aneurysm occlusion device. FIG. 12 shows this device at a single point in time after it has been fully deployed within an aneurysm sac. This example is like the example shown in FIGS. 1 through 6 except that the resilient wider-than-neck portion of the device is expanded into a rounded-frustal (e.g. "pear") shape. Alternatively, a resilient wider-than-neck portion of the device can be expanded into a lemon shape, apple shape, egg shape, or pumpkin shape.

The example shown in FIG. 12 comprises: a resilient wider-than-neck portion 1201 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

Figure 13:
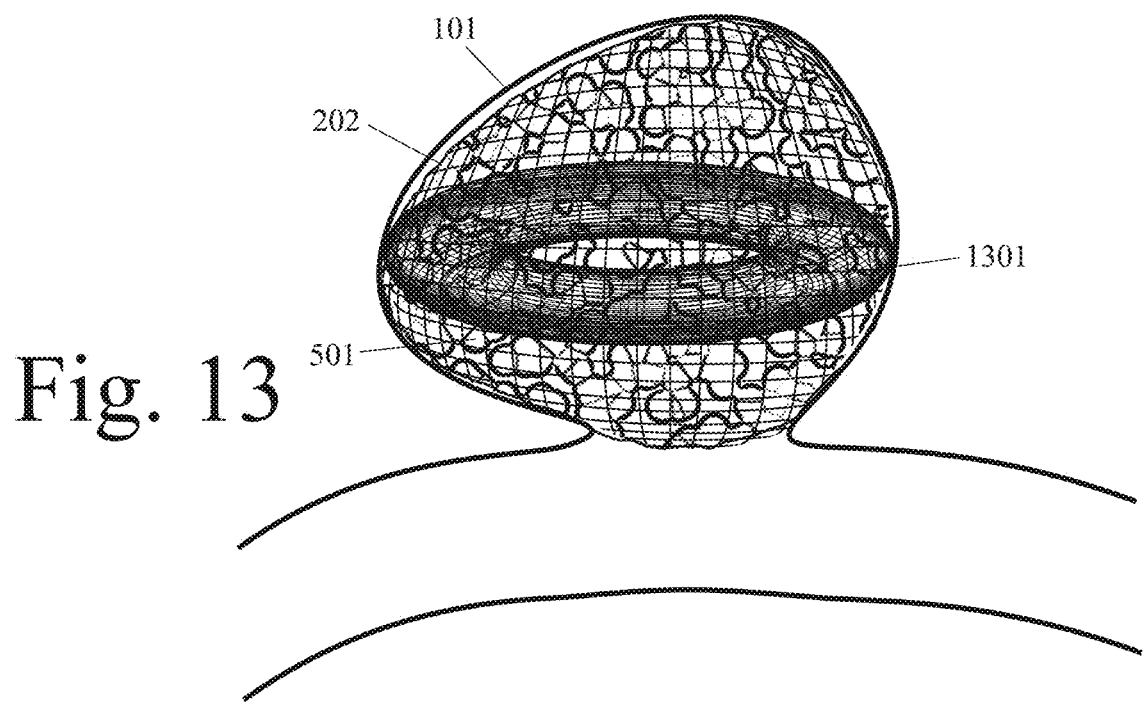
FIG. 13 shows a device with a central toroidal resilient wider-than-neck portion and a flexible sac-filling portion.

FIG. 13 shows a cross-sectional view of another example of this intrasacular aneurysm occlusion device. FIG. 13 shows this device at a single point in time after it has been fully deployed within an aneurysm sac. This example is like the example shown in FIGS. 1 through 6 except that the resilient wider-than-neck portion of the device is expanded into a toroidal (e.g. "doughnut" or "ring") shape. In this example, the toroidal wider-than-neck portion spans the aneurysm sac near its maximum circumference (as measured in a plane which is parallel to the plane of the aneurysm neck). In another example, the toroidal wider-than-neck portion can be configured to span the aneurysm sac closer to (or over) the aneurysm neck.

The example shown in FIG. 13 comprises: a resilient wider-than-neck portion 1301 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

Figure 14:
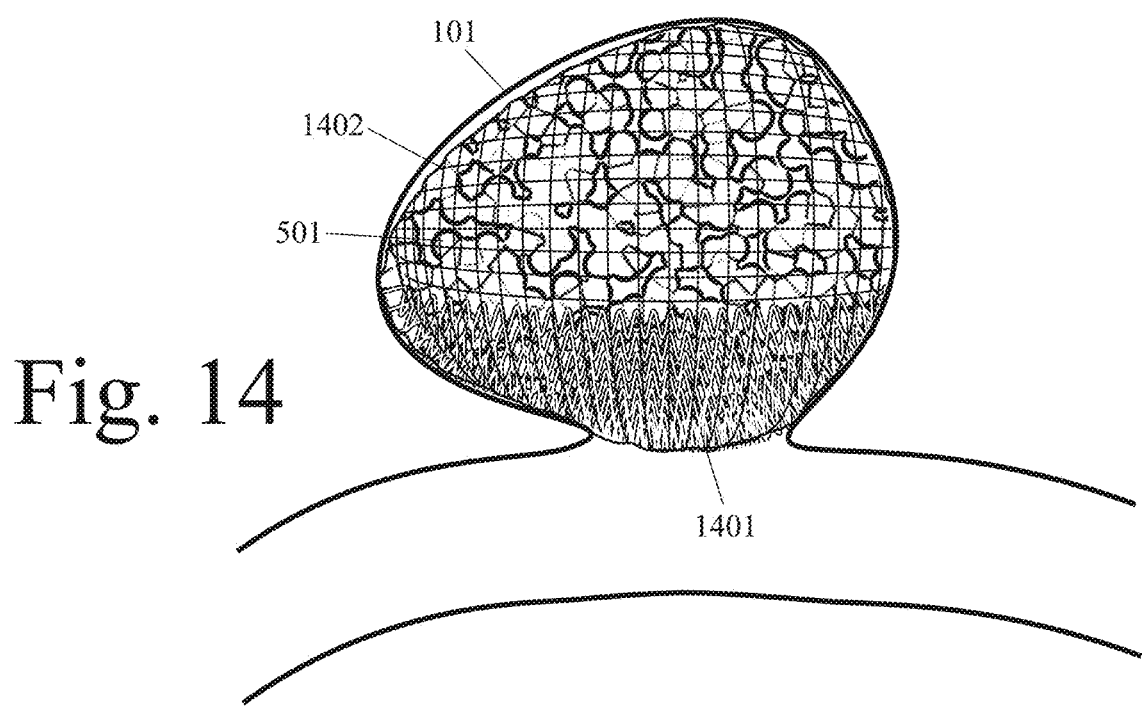
FIG. 14 shows a device with a resilient wider-than-neck portion and a flexible sac-filling portion which comprise the proximal and distal surfaces, respectively, of an intrasacular embolic structure.

FIG. 14 shows a cross-sectional view of another example of this intrasacular aneurysm occlusion device. FIG. 14 shows this device at a single point in time after it has been fully deployed within an aneurysm sac. This example is like the example shown in FIGS. 1 through 6 except that the resilient wider-than-neck portion of the device is not inside the flexible sac-filling portion of the device. In this example, the resilient wider-than-neck portion of the device and the flexible sac-filling portion of the device are parts of the same convex structure. The resilient wider-than-neck portion is the proximal part of this structure and the flexible sac-filling portion is the distal part of this device. In an example, the resilient wider-than-neck portion can comprise the proximal surface of the device and the flexible sac-filling portion can comprise non-proximal surfaces (e.g. distal and peripheral) of the device. In an example, an intrasacular aneurysm occlusion device "need not be of uniform tensile strength, flexibility, plasticity, or elasticity." It can be "more flexible at one or more" locations. Accordingly, in this example, although the resilient wider-than-neck and flexible sac-filling portions of this device are both part of the same structure, they differ in flexibility and porosity. The flexible sac-filling portion is more flexible and more porous than the resilient wider-than-neck portion.

In an example, different portions, segments, or undulations of a continuous intrasacular convex structure can have different braid patterns. In an example, a proximal portion, segment, or undulation of a continuous intrasacular convex structure can have a first braid pattern and a distal portion, segment, or undulation of this device can have a second braid pattern. In an example, different portion, segment, or undulations of a continuous intrasacular convex structure can have different braid densities. In an example, a proximal portion, segment, or undulation of a continuous intrasacular convex structure can have a higher braid density than a distal portion, segment, or undulation of this device. In an example, different portion, segment, or undulations of a continuous intrasacular convex structure can have different braid angles. In an example, a proximal portion, segment, or undulation of a continuous intrasacular convex structure can have a greater braid angle than a distal portion, segment, or undulation of this device.

In an example, different portion, segment, or undulations of a continuous intrasacular convex structure can have different braid pitches. In an example, a proximal portion, segment, or undulation of a continuous intrasacular convex structure can have a first braid pitch and a distal portion, segment, or undulation of this device can have a second braid pitch. In an example, different portion, segment, or undulations of a continuous intrasacular convex structure can have different braid filament sizes. In an example, a proximal portion, segment, or undulation of a continuous intrasacular convex structure can have a first braid filament size and a distal portion, segment, or undulation of this device can have a second braid filament size.

The example shown in FIG. 14 comprises: a resilient wider-than-neck portion 1401 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability.

In an example, an aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a first location and a second tensile strength at a second location, and wherein the second tensile strength is greater than the first tensile strength. In an example, an aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a first location and a second elasticity at a second location, and wherein the second elasticity is greater than the first elasticity.

In an example, an aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a first location and a second flexibility at a second location, and wherein the second flexibility is greater than the first flexibility. In an example, an aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a first location and a second porosity at a second location, and wherein the second porosity is greater than the first porosity.

In an example, an aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a proximal location and a second tensile strength at a distal location, and wherein the second tensile strength is less than the first tensile strength. In an example, an aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a proximal location and a second elasticity at a distal location, and wherein the second elasticity is greater than the first elasticity.

In an example, an aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a proximal location and a second flexibility at a distal location, and wherein the second flexibility is greater than the first flexibility. In an example, an aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a proximal location and a second porosity at a distal location, and wherein the second porosity is greater than the first porosity. Relevant embodiment variations discussed elsewhere in this disclosure or in priority-linked disclosures can also apply to this example.

Figure 15:
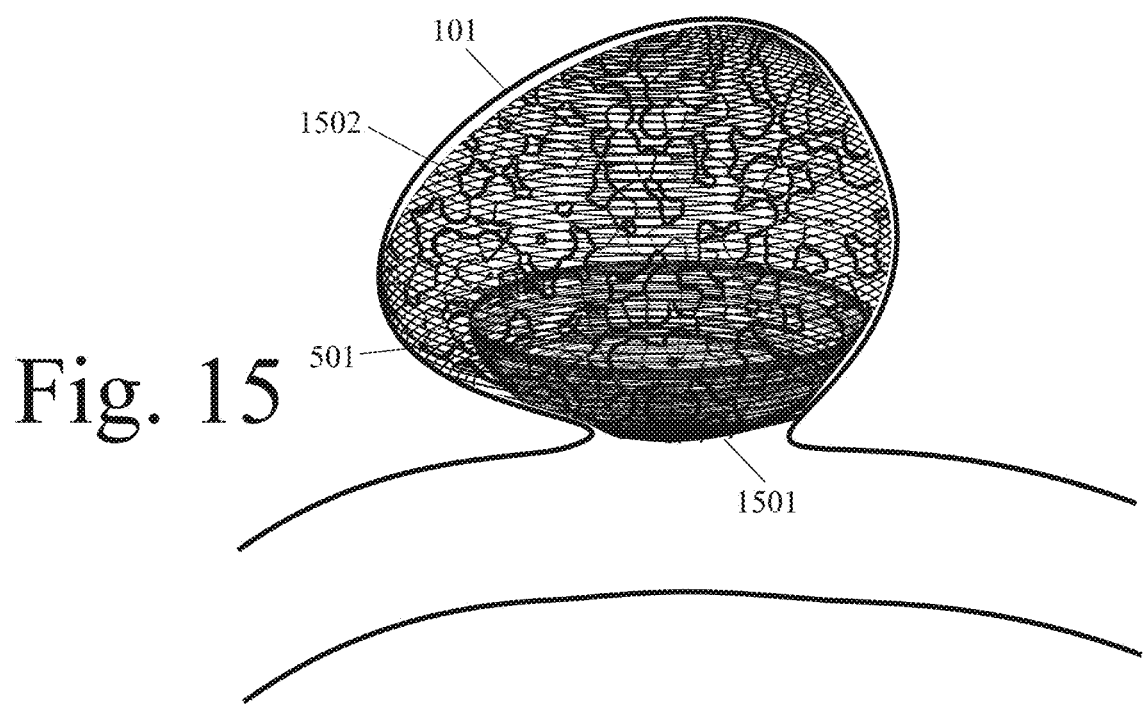
FIGS. 15 and 16 show a device wherein a distal flexible sac-filling portion partially overlaps a proximal resilient wider-than-neck portion.
Figure 16:
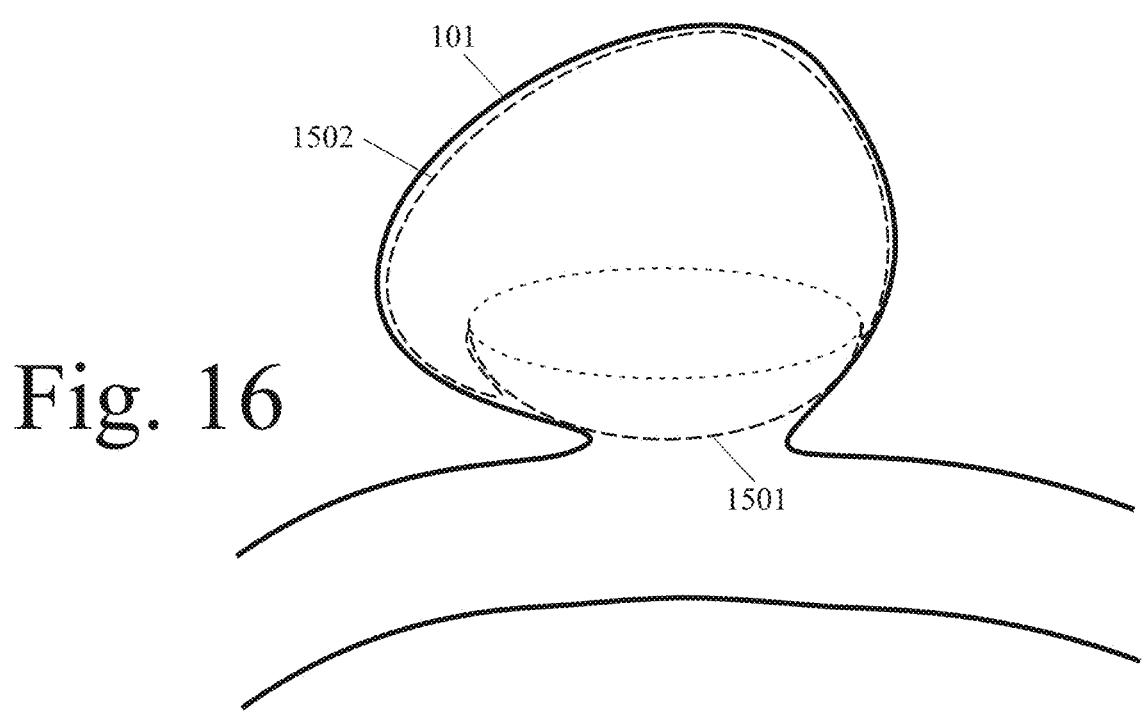

FIGS. 15 and 16 show two cross-sectional views of another example of this intrasacular aneurysm occlusion device. FIGS. 15 and 16 show this device at a single point in time after it has been fully deployed within an aneurysm sac. This example is like the example shown in FIG. 14 except that the flexible sac-filling portion partially overlaps the resilient wider-than-neck portion. In this example, the resilient wider-than-neck portion of the device is bowl shaped. In this example, the proximal surface of the flexible sac-filling portion partially overlaps the peripheral surface of the resilient wider-than-neck portion.

The example shown in FIGS. 15 and 16 comprises: a resilient wider-than-neck portion 1501 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 202 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members 501 (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability. Relevant embodiment variations discussed elsewhere in this disclosure or in priority-linked disclosures can also apply to this example.

Figure 17:
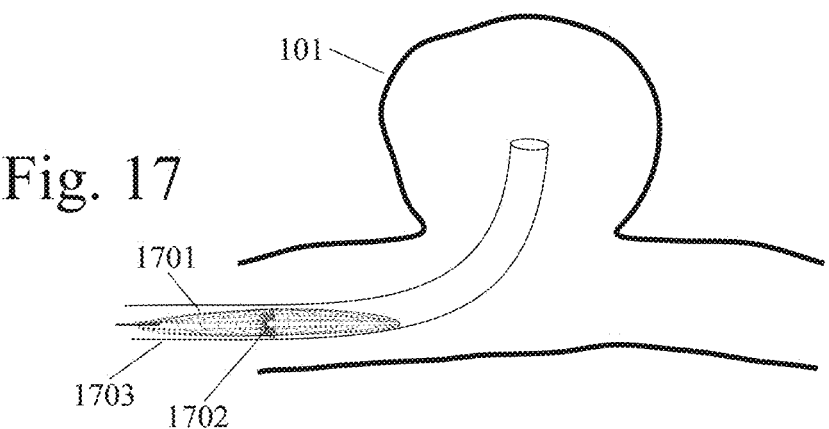
FIGS. 17 through 19 show a "Saturn-shaped" device with an annular resilient wider-than-neck portion and a flexible sac-filling portion.
Figure 18:
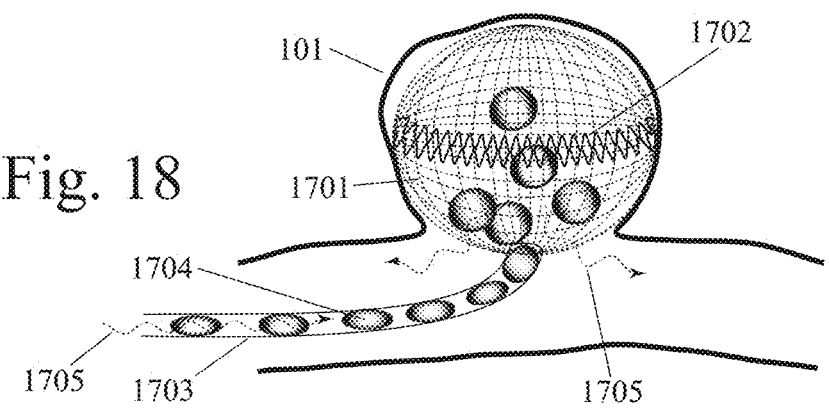
Figure 19:
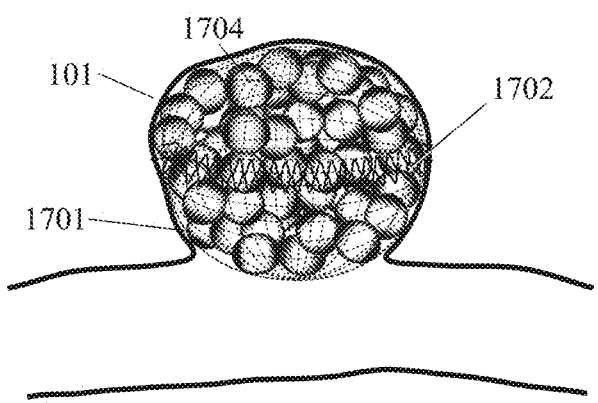

FIGS. 17 through 19 show an intrasacular aneurysm occlusion device which can be described as "Saturn-shaped." More specifically, FIGS. 17 through 19 show an intrasacular aneurysm occlusion device comprising: (a) a longitudinal lumen that is configured to be inserted into a blood vessel; (b) a flexible expandable member that is configured to travel through the longitudinal lumen, be inserted into an aneurysm, and then be expanded within the aneurysm sack; wherein this flexible expandable member is selected from the group consisting of a net, a mesh, a lattice, and a balloon with holes; wherein this flexible expandable member is sufficiently flexible to substantively conform to the contours of the walls of the aneurysm sack after the flexible expandable member is expanded within the aneurysm; and wherein this flexible expandable member is permeable to liquid; (c) a resilient expandable member that is configured to travel through the longitudinal lumen, be inserted into the aneurysm, and then be expanded within the aneurysm sack; wherein this resilient expandable member resists contraction after it has been expanded; wherein a plane formed by the expanding circumference of this resilient expandable member is substantially parallel to the plane that centrally spans the circumference of the aneurysm neck; wherein a plane formed by the expanding circumference of this resilient expandable member spans the aneurysm sack at the sack's largest circumference parallel to the plane that centrally spans the circumference of the aneurysm neck; and wherein expansion of the resilient expandable member resiliently holds a central portion of the flexible expandable member against the walls of the aneurysm so that the flexible expandable member does not slip out of the aneurysm sack; and (d) a plurality of individual embolic members that are configured to travel through the longitudinal lumen, be inserted into the flexible expandable member within the aneurysm, and accumulate within the flexible expandable member; wherein the flexible expandable member does not allow the embolic members to escape out from the flexible expandable member; and wherein accumulation of the plurality of embolic members inside the flexible expandable member causes the flexible expandable member to expand.

FIGS. 17 through 19 also show an intrasacular aneurysm occlusion device comprising: (a) a longitudinal lumen that is configured to be inserted into a blood vessel, wherein this blood vessel is the parent vessel from which an aneurysm has formed; (b) an expandable flexible net or mesh, wherein this expandable flexible net or mesh is configured to travel through the longitudinal lumen and to be inserted into the aneurysm sac, and wherein this net or mesh is sufficiently flexible to substantially conform to the walls of an irregularly shaped aneurysm sac after the net or mesh has been expanded; (c) a plurality of embolic members, wherein these embolic members are configured to travel through the longitudinal lumen and to be inserted into the net or mesh within the aneurysm sac; wherein these embolic members do not escape from the net or mesh; and wherein the net or mesh is expanded by the accumulation of embolic members inside the net or mesh; and (d) an expandable resilient structure, wherein this expandable resilient structure is configured to travel through the longitudinal lumen and to be inserted into the aneurysm sac; wherein this structure comes into engaging contact with the central circumference of the aneurysm sac when this structure is expanded; wherein this structure resists compression after it has been expanded; and wherein expansion of this structure also engages the net or mesh so as to prevent the net or mesh from slipping out from the aneurysm sac.

In an example, the longitudinal lumen can be a removable catheter. In an example, the net or mesh can be a wire net or mesh. In an example, the net or mesh can be a polymer net or mesh. In an example, the expandable resilient structure can be a stent. In an example, the expandable resilient structure can be attached to the net or mesh. In an example, the expandable resilient structure can be inside the net or mesh. In an example, the plurality of embolic members can be conveyed through the longitudinal lumen by means of a liquid flow and the net or mesh can be sufficiently porous so as to let the liquid escape through the net or mesh but does not let the embolic members escape through the net or mesh. In an example, the total volume of an aneurysm sac can be X cubic units, wherein Y cubic units of the volume of the aneurysm would be filled by the largest-volume sphere that can be fitted into the aneurysm without stretching the aneurysm walls, wherein Z cubic units of the volume of the aneurysm can be filled by the net or mesh; and wherein $Z>[Y+0.5(X-Y)]$. In an example, the total volume of an aneurysm sac can be X cubic units, wherein Y cubic units of the volume of the aneurysm would be filled by the largest-volume ellipsoid that can be fitted into the aneurysm without stretching the aneurysm walls, wherein Z cubic units of the volume of the aneurysm can be filled by the net or mesh; and wherein $Z>[+0.5(X-Y)]$. Relevant embodiment variations discussed elsewhere in this disclosure or in priority-linked disclosures can also apply to this example.

We now discuss the specific components of the example that is shown FIGS. 17 through 19. FIGS. 17 through 19 show an intrasacular aneurysm occlusion device comprising: longitudinal lumen 1703 that is inserted into a blood vessel from which an aneurysm sac 101 has formed; expandable flexible net or mesh 1701 that travels through lumen 1703 into aneurysm sac 101, wherein net or mesh 1701 is sufficiently flexible to substantially conform to the walls of aneurysm sac 101; a plurality of embolic members (including 1704) which travel through lumen 1703 into net or mesh 1701, wherein these embolic members (including 1704) do not escape from net or mesh 1701 and wherein net or mesh 1701 is expanded by the accumulation of embolic members (including 1704) inside net or mesh 1701; and expandable resilient structure 1702 which travels through lumen 1703 and is expanded within aneurysm sac 101.

In an example, a flexible expandable member can be selected from the group consisting of a net, a mesh, and a lattice. In an example, a flexible expandable member can be selected from the group consisting of a balloon, a bag, and a liner. In an example, a flexible expandable member is made of a polymer, a metal, or a combination thereof.

As shown in FIG. 18, structure 1702 comes into engaging contact with the central circumference of aneurysm sac 101 when structure 1702 is expanded. Structure 1702 can be expanded sufficiently to frictionally engage the walls of aneurysm sac 101, but not expanded so much that it risks puncturing the walls of aneurysm sac 101. In an example, structure 1702 can have a rounded perimeter. In an example, structure 1702 can have a bioadhesive coating which adheres to the aneurysm walls to further engage them. Structure 1702 also resists compression after it expands. In this example, expansion of structure 1702 also engages net or mesh 1701 to prevent net or mesh 1701 from slipping out from aneurysm sac 101.

In this example, longitudinal lumen 1703 is a removable catheter. In this example, net or mesh 1701 is a wire net or mesh. In an example, net or mesh 1701 can be a polymer net or mesh. In this example, expandable resilient structure 1702 is integrated with net or mesh 1701. In an example, the plurality of embolic members (including 1704) can be conveyed through lumen 1703 by means of a liquid flow. In an example, net or mesh 1701 can be sufficiently porous so as to let the liquid escape through net or mesh 1701 but not so porous that it lets embolic members (including 1704) escape through net or mesh 1701. In an example, embolic members (including 1704) can be compressed as they travel through lumen 1703 but these embolic members (including 1704) can expand when released from lumen 1703. This can help to prevent embolic members from escaping out of net or mesh 1701.

In an example, this device can also include a closure mechanism which is integrated into net or mesh 1701 to further prevent embolic members (including 1704) from escaping from net or mesh 1701 through the opening by which they were inserted into net or mesh 1701. In an example, this closure mechanism can comprise a one-way valve that automatically lets embolic members into the net or mesh but does not let them out. In an example, this closure mechanism can require action by a user during the procedure to close off the opening. In an example, the operator of a device can close an opening by a closure mechanism selected from the group consisting of: activating an electromagnetic valve; adjusting a valve; aligning and miss-aligning two holes (e.g. by rotation); application of electromagnetic energy; application of thermal energy; electromagnetic fusing; injecting an adhesive; moving a plug or cap; moving a snap or clip; pressing a seal; pulling a cord; pulling a drawstring; pulling a loop; and rotating a cable or wire.

As shown in FIGS. 17 through 19, an aneurysm sac can be irregular in shape. An aneurysm sac with an irregular shape may not be completely filled or spanned by a spherical or ellipsoid mass without stretching the aneurysm walls. In an example, the total volume of an aneurysm sac can be X cubic units (e.g. cubic millimeters). In an example, the maximum volume of the aneurysm which can be filled or spanned by a spherical or ellipsoid mass without stretching the aneurysm walls is Y cubic units (e.g. cubic millimeters). In an example, the device shown in FIGS. 17 through 19 can fill more of the aneurysm than a spherical or ellipsoid mass because the net or mesh is sufficiently flexible to fill or span the irregular perimeter of the aneurysm sac. This can have clinical benefits, such as reducing the chances of recanalization within the aneurysm sac. In an example, this device can fill or span more than 50% of the aneurysm volume which remains unfilled by a sphere or ellipsoid. In an example, this device can fill or span Z cubic units (e.g. cubic millimeters) of the volume of the aneurysm, wherein $Z>[Y+0.5(X-Y)]$.

In an example, net or mesh 1701 can be compressed as it travels through lumen 1703 and then be expanded within aneurysm sac 101 after it is released from lumen 1703. In an example, net or mesh 1701 can be folded as it travels through lumen 1703 and then be unfolded within aneurysm sac 101. In an example, net or mesh 1701 can be relatively loose or relaxed (in a lower-energy state) as it travels through lumen 1703 and then be stretched or tense (in a higher-energy state) within aneurysm sac 101. In an example, net or mesh 1701 can be elastic or stretchable. In an example, net or mesh 1701 can be sufficiently elastic or stretchable that it expands when filled with an accumulation of embolic members (including 1704), but not so elastic or stretchable that it allows embolic members (including 1704) to escape. In an example, net or mesh 1701 can be a balloon with holes, wherein the holes are of sufficient size to let liquid escape, but not so large that they let embolic members escape.

In an example, expandable resilient structure 1702 can be a ring-like expandable stent. In an example, an expandable resilient structure can be a toroidal or doughnut-shaped expandable stent. In an example, an expandable resilient structure 1702 can be a cylindrical expandable stent. In an example, an expandable resilient structure can be an ellipsoid expandable stent. In an example, an expandable resilient structure can be an apple-shaped expandable stent.

In an example, expandable resilient structure 1702 can be a wire mesh stent. In an example, expandable resilient structure 1702 can be centrally-located so as to expand from the center of net or mesh 1701. In an example, expandable resilient structure 1702 can be inside net or mesh 1701 and thereby hold net or mesh against the aneurysm wall when structure 1702 is expanded. In an example, expandable resilient structure 1702 can be attached to net or mesh 1701 and thereby hold net or mesh 1701 within the aneurysm sac when structure 1702 is expanded. In an example the expandable resilient structure 1702 can be radially-expanded in plane which is substantially parallel to the plane that is defined by the central circumference of the aneurysm neck. In an example, expandable resilient structure 1702 can be expanded by a removable balloon. In an example, expandable resilient structure 1702 can self-expand when released from lumen 1703.

In an example, embolic members (including 1704) can be a plurality of soft, compressible members such as microsponges, pieces of gel, or pieces of foam. In an example, embolic members (including 1704) can be a plurality of hard, uncompressible members such as hard polymer spheres or beads. In an example, embolic members (including 1704) can be a plurality of embolic coils. In an example, embolic members (including 1704) can be conveyed through lumen 1703 in a fluid flow, wherein the fluid escapes out from net or mesh 1701 and the embolic members are retained within net or mesh 1701. In an example, embolic members (including 1704) can be conveyed through lumen 1703 by means of a moving belt or wire loop. In an example, embolic members (including 1704) can be conveyed through lumen 1703 by means of an Archimedes screw.

In an example, the combination of (a) a flexible, non-resilient net or mesh 1701 that spans substantially the entire perimeter of the aneurysm sac 101 and (b) a resilient expandable structure 1702 that only spans a central portion of the circumference of the aneurysm sac 101 can create a device that is sufficiently flexible to substantially fill the entire volume of an irregularly-shaped aneurysm sac, but also sufficiently resilient so as to compress against the aneurysm walls and not slip out of the aneurysm sac. Relevant embodiment variations discussed elsewhere in this disclosure or in priority-linked disclosures can also apply to this example.

Figure 20:
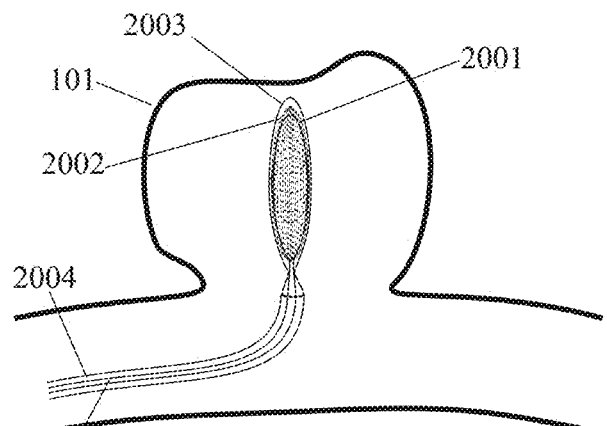
FIGS. 20 through 22 show a device wherein a resilient wider-than-neck portion and a flexible sac-filling portion are nested.
Figure 21:
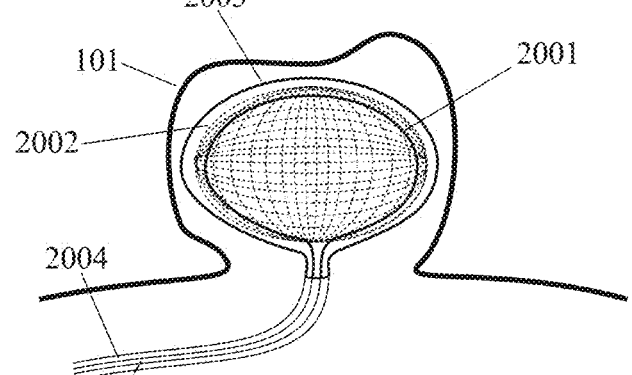
Figure 22:
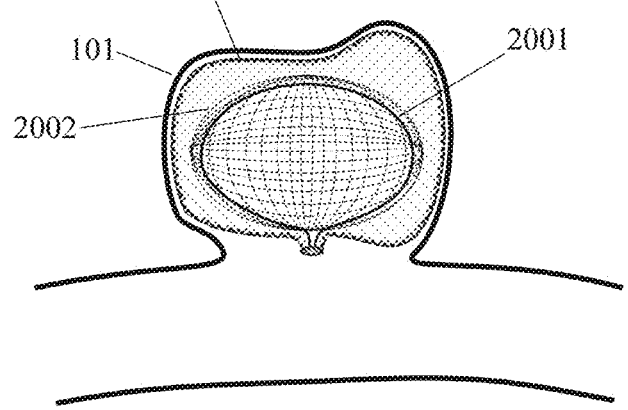

FIGS. 20 through 22 show an example of an intrasacular aneurysm occlusion device which can be described as using concentric resilient and non-resilient intrasacular members for aneurysm occlusion. More specifically, FIGS. 20 through 22 show an intrasacular aneurysm occlusion device comprising: (a) a longitudinal lumen that is configured to be inserted into a blood vessel; (b) a resilient expandable member that is configured to travel through the longitudinal lumen, be inserted into an aneurysm sack, and then be expanded within the aneurysm sack; and wherein this resilient expandable member resists contraction after it has been expanded; and (c) a flexible expandable member that is configured to travel through the longitudinal lumen, be inserted into the aneurysm sack, and then be expanded within the aneurysm sack; wherein the resilient expandable member is inside the flexible expandable member; wherein the resilient expandable member is expanded before or while the flexible expandable member is expanded; and wherein the flexible expandable member is sufficiently flexible to substantively conform to the contours of the walls of the aneurysm sack when the flexible expandable member is expanded within the aneurysm. In an example, the shape of the resilient expandable member can be selected from the group consisting of: apple shape; bowl shape; compress-sphere shape; cylinder; disk; doughnut shape; egg shape; ellipsoid; Frisbee™ shape; frustum; hourglass shape; oval; peanut shape; pear shape; pumpkin shape; ring shape; Saturn shape; sphere; tire shape; and torus.

FIGS. 20 through 22 also show an intrasacular aneurysm occlusion device comprising: (a) a longitudinal lumen that is configured to be inserted into a blood vessel, wherein this blood vessel is the parent vessel from which an aneurysm has formed; (b) an expandable flexible member, wherein this expandable flexible member is configured to travel through the longitudinal lumen and to be inserted into the aneurysm sac; and wherein this flexible member is sufficiently flexible to substantially conform to the walls of an irregularly-shaped aneurysm sac after the flexible member has been expanded; and (c) an expandable resilient structure, wherein this expandable resilient structure is configured to travel through the longitudinal lumen and to be inserted into the aneurysm sac; wherein this structure is expanded inside the expandable flexible member; and wherein this structure resists compression after it has been expanded.

In an example, an expandable resilient structure can be expanded before an expandable flexible member is expanded. In an example, the expandable resilient structure and the expandable flexible member can be expanded at substantially the same time. In an example, the total volume of an aneurysm sac can be X cubic units, wherein Y cubic units of the volume of the aneurysm would be filled by the largest-volume sphere that can be fitted into the aneurysm without stretching the aneurysm walls, wherein Z cubic units of the volume of the aneurysm can be filled by the expandable and flexible member; and wherein Z>[Y+0.5(X−Y)]. In an example, the total volume of an aneurysm sac can be X cubic units, wherein Y cubic units of the volume of the aneurysm would be filled by the largest-volume ellipsoid that can be fitted into the aneurysm without stretching the aneurysm walls, wherein Z cubic units of the volume of the aneurysm can be filled by the expandable flexible member; and wherein Z>[Y+0.5(X−Y)].

FIGS. 20 through 22 also show an intrasacular aneurysm occlusion device comprising: (a) a longitudinal lumen that is configured to be inserted into a blood vessel, wherein this blood vessel is the parent vessel from which an aneurysm has formed; (b) a flexible sac-filling portion of the device, wherein this flexible sac-filling portion is configured to travel through the longitudinal lumen and to be inserted into the aneurysm sac; and wherein this flexible sac-filling portion is sufficiently flexible to substantially conform to the walls of an irregularly-shaped aneurysm sac after the flexible sac-filling portion has been expanded; and (c) a resilient wider-than-neck portion of this device, wherein this resilient wider-than-neck portion of this device is configured to travel through the longitudinal lumen and to be inserted into the aneurysm sac; wherein this resilient wider-than-neck portion is expanded inside the flexible sac-filling portion; and wherein this resilient wider-than-neck portion resists compression after it has been expanded.

FIGS. 20 through 22 also show an intrasacular aneurysm occlusion device comprising: a resilient wider-than-neck portion 2002 (such as a stent or neck bridge) of the device with a first (constrained) configuration as it is transported to an aneurysm sac 101 and a second (expanded) configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and a flexible sac-filling portion 2003 (such as a net or mesh) of the device with a first (constrained) configuration as it is being transported to an aneurysm sac and a second (expanded) configuration after it has been expanded within the aneurysm sac; wherein the flexible sac-filling portion is expanded from its first configuration to its second configuration by the insertion of embolic members (such as microsponges, pieces of gel, pieces of foam, beads, microspheres, or embolic coils) into the flexible sac-filling portion; and wherein the flexible sac-filling portion in its second configuration has a second level of flexibility, elasticity, and/or malleability which is greater than the first level of flexibility, elasticity, and/or malleability.

In an example, the resilient wider-than-neck portion of this device can be a stent or neck bridge. In an example, the post-expansion shape of the resilient wider-than-neck portion of the device can be selected from the group consisting of: apple shape; bowl shape; compress-sphere shape; cylinder; disk; doughnut shape; egg shape; ellipsoid; Frisbee™ shape; frustum; hourglass shape; oval; peanut shape; pear shape; pumpkin shape; ring shape; Saturn shape; sphere; tire shape; and torus. In an example, the flexible sac-filling portion of this device can be a net or mesh. In an example, the flexible sac-filling portion of this device can be expanded by being filled with embolic members such as microsponges, pieces of gel, pieces of foam, beads, microspheres, or embolic coils.

We now further discuss the specific components of the example shown in FIGS. 20 through 22. FIGS. 20 through 22 show an example of an intrasacular aneurysm occlusion device comprising: an outer longitudinal lumen 2004 that is configured to be inserted into a blood vessel from which aneurysm sac 101 has formed; an inner longitudinal lumen 2005 within longitudinal lumen 2004; an expandable flexible member 2003 that is inserted and expanded within aneurysm sac 101, wherein flexible member 2003 is sufficiently flexible to substantially conform to the walls of irregularly-shaped aneurysm sac 101; and an expandable resilient structure 2002 that is expanded within flexible member 2003 and resists compression after expansion.

In an example, expandable resilient structure 2002 can be spherical or elliptical. In an example, expandable resilient structure 2002 can be an expandable wire mesh or stent. In an example, expandable resilient structure 2002 can be radially-expanded in plane which is substantially parallel to the plane that is defined by the central circumference of the aneurysm neck. In an example, resilient structure 2002 can be expanded by inflation of a balloon 2001 inside resilient structure 2002. In an example, balloon 2001 can be inflated by a fluid or gas that is delivered via lumen 2004 or lumen 2005. In an example, resilient structure 2002 can self-expand after it exits lumen 2004.

In an example, expandable flexible member 2003 can be an expandable flexible net or mesh. In an example, flexible member 2003 can be a porous fabric net or mesh. In an example, flexible member 2003 can be a porous bag. In an example, expandable flexible member 2003 can be a balloon with holes. In an example, flexible member 2003 can be expanded by being filled with a plurality of embolic members. In an example, embolic members can be delivered into flexible member 2003 through lumen 2004 or lumen 2005. In an alternative example, flexible member 2003 can be non-porous. In an example, flexible member 2003 can be expanded by being filled with liquid or gas. In an example, a liquid or gas can be delivered into flexible member 2003 through lumen 2004 or lumen 2005.

In an example, flexible member 2003 can be compressed as it travels through a longitudinal lumen and then be expanded within aneurysm sac 101 after it is released from the lumen. In an example, flexible member 2003 can be folded as it travels through a lumen and then be unfolded within aneurysm sac 101. In an example, flexible member 2003 can be relatively loose or relaxed (in a lower-energy state) as it travels through a lumen and then be stretched or tense (in a higher-energy state) within aneurysm sac 101. In an example, flexible member 2003 can be elastic or stretchable. In an example, flexible member 2003 can be sufficiently elastic or stretchable that it expands when filled with an accumulation of embolic members, but not so elastic or stretchable that it allows embolic members to escape. In an example, flexible member 2003 can be a balloon with holes, wherein the holes are of sufficient size to let liquid escape, but not so large that they let embolic members escape.

In an example, embolic members for filling flexible member 2003 can be a plurality of soft, compressible members such as microsponges or blobs of gel. In an example, embolic members can be a plurality of hard, uncompressible members such as hard polymer spheres or beads. In an example, embolic members can be selected from the group consisting of: microsponges, pieces of gel, pieces of foam, beads, and embolic coils. In an example, embolic members can be conveyed into flexible member 2003 through lumen 2004 or lumen 2005. In various examples, embolic members can be conveyed via a liquid flow, a moving belt, a wire loop, or an Archimedes screw.

In an example, this invention can comprise a method in which resilient structure 2002 is expanded first and flexible member 2003 is expanded second. In an example, this invention can comprise a method in which flexible member 2003 is expanded first and resilient structure 2002 is expanded second. In an example, this invention can comprise a method in which flexible member 2003 and resilient structure 2002 are expanded at substantially the same time.

As shown in FIGS. 20 through 22, an aneurysm sac can be irregular in shape. An aneurysm sac with an irregular shape will not be completely filled or spanned by a spherical or ellipsoid mass without stretching the aneurysm walls. In an example, the total volume of an aneurysm sac can be X cubic units (e.g. cubic millimeters). In an example, the maximum volume of the aneurysm which can be filled or spanned by a spherical or ellipsoid mass without stretching the aneurysm walls is Y cubic units (e.g. cubic millimeters). In an example, the total device shown in FIGS. 20 through 22 can fill more of the aneurysm than a spherical or ellipsoid mass because flexible member 2003 is sufficiently flexible to fill or span the irregular perimeter of the aneurysm sac. This can have clinical benefits, such as reducing the chances of recanalization within the aneurysm sac. In an example, this device can fill or span more than 50% of the aneurysm volume which remains unfilled by a sphere or ellipsoid. In an example, this device can fill or span Z cubic units (e.g. cubic millimeters) of the volume of the aneurysm, wherein $Z>[Y+0.5(X-Y)]$.

In an example, the combination of (a) an outer flexible member 2003 that spans substantially the entire perimeter of the aneurysm sac 101 and (b) an inner resilient structure 2002 can create a device that is sufficiently flexible to substantially fill the entire volume of an irregularly-shaped aneurysm sac, but also sufficiently resilient so as to compress against the aneurysm walls and not slip out of the aneurysm sac. Relevant embodiment variations discussed elsewhere in this disclosure or in priority-linked disclosures can also apply to this example.

In an example, a resilient wider-than-neck portion of this device can be created by weaving. In an example, a resilient wider-than-neck portion of this device can be created by weaving wires or filaments into a weave pattern selected from the group consisting of: plain weave; double weave; diamond weave; perpendicular weave; rib weave; basket weave; twill weave; satin weave; leno weave; mock leno weave; and diagonal weave.

In an example, a resilient wider-than-neck portion of this device can be created by braiding. In an example, a resilient wider-than-neck portion of this device can be created by braiding wires or filaments into a braid pattern selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, different areas of a resilient wider-than-neck portion can have different braid patterns. In an example, the proximal area of a resilient wider-than-neck portion of this device can have a first braid pattern and the distal area of the resilient wider-than-neck portion of this device can have a second braid pattern. In an example, different areas of a resilient wider-than-neck portion can have different braid densities. In an example, the proximal area of a resilient wider-than-neck portion of this device can have a higher braid density than the distal area of the resilient wider-than-neck portion of this device. In an example, different areas of a resilient wider-than-neck portion can have different braid angles. In an example, the proximal area of a resilient wider-than-neck portion of this device can have a greater braid angle than the distal area of the resilient wider-than-neck portion of this device.

In an example, different areas of a resilient wider-than-neck portion can have different braid pitches. In an example, the proximal area of a resilient wider-than-neck portion of this device can have a first braid pitch and the distal area of the resilient wider-than-neck portion of this device can have a second braid pitch. In an example, different areas of a resilient wider-than-neck portion can have different braid filament sizes. In an example, the proximal area of a resilient wider-than-neck portion of this device can have a first braid filament size and the distal area of the resilient wider-than-neck portion of this device can have a second braid filament size.

In an example, a flexible sac-filling portion of this device can be created by weaving. In an example, a flexible sac-filling portion of this device can be created by weaving wires or filaments into a weave pattern selected from the group consisting of: plain weave; double weave; diamond weave; perpendicular weave; rib weave; basket weave; twill weave; satin weave; leno weave; mock leno weave; and diagonal weave.

In an example, a flexible sac-filling portion of this device can be created by braiding. In an example, a flexible sac-filling portion of this device can be created by braiding wires or filaments into a braid pattern selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern.

In an example, different areas of a flexible sac-filling portion can have different braid patterns. In an example, the proximal area of a flexible sac-filling portion of this device can have a first braid pattern and the distal area of the flexible sac-filling portion of this device can have a second braid pattern. In an example, different areas of a flexible sac-filling portion can have different braid densities. In an example, the proximal area of a flexible sac-filling portion of this device can have a higher braid density than the distal area of the flexible sac-filling portion of this device. In an example, different areas of a flexible sac-filling portion can have different braid angles. In an example, the proximal area of a flexible sac-filling portion of this device can have a greater braid angle than the distal area of the flexible sac-filling portion of this device.

In an example, different areas of a flexible sac-filling portion can have different braid pitches. In an example, the proximal area of a flexible sac-filling portion of this device can have a first braid pitch and the distal area of the flexible sac-filling portion of this device can have a second braid pitch. In an example, different areas of a flexible sac-filling portion can have different braid filament sizes. In an example, the proximal area of a flexible sac-filling portion of this device can have a first braid filament size and the distal area of the flexible sac-filling portion of this device can have a second braid filament size.

In an example, the resilient wider-than-neck and flexible sac-filling portions of this device can both be braided, but have different braid patterns. These braid patterns can be selected from the group consisting of: one over braid pattern; one over, one under braid (e.g. diamond) braid pattern; one over, three under braid pattern; two over, one under braid pattern; two over, two under braid pattern; two under, two over braid pattern; three over, one under braid pattern; three over, three under braid pattern; four over, one under braid pattern; four over, four under braid pattern; five over, one under braid pattern; six over, one under braid pattern; seven over, one under braid pattern; and eight over, one under braid pattern. In an example, the resilient wider-than-neck portion of this device can have a first braid pattern and the flexible sac-filling portion of this device can have a second braid pattern.

In an example, the resilient wider-than-neck and flexible sac-filling portions of this device can have different braid densities. In an example, the resilient wider-than-neck portion of this device can have a higher braid density than the flexible sac-filling portion of this device. In an example, the resilient wider-than-neck and flexible sac-filling portions of this device can have different braid angles. In an example, the resilient wider-than-neck portion of this device can have a greater braid angle than the flexible sac-filling portion of this device. In an example, the resilient wider-than-neck and flexible sac-filling portions of this device can have different braid pitches. In an example, the resilient wider-than-neck portion of this device can have a first braid pitch and the flexible sac-filling portion of this device can have a second braid pitch. In an example, the resilient wider-than-neck and flexible sac-filling portions of this device can have different braid filament sizes. In an example, the resilient wider-than-neck portion of this device can have a first braid filament size and the flexible sac-filling portion of this device can have a second braid filament size. Relevant embodiment variations discussed elsewhere in this disclosure or in priority-linked disclosures can also apply to this example.

Figure 23:
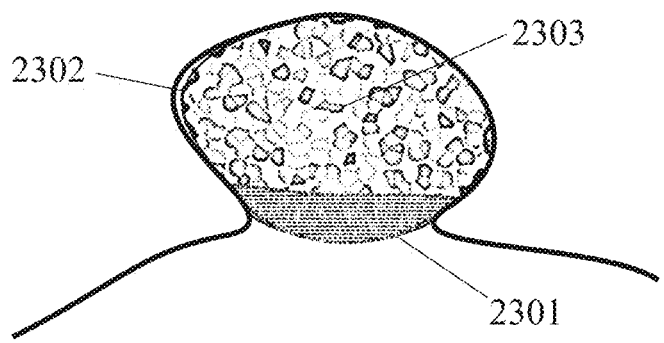
FIG. 23 shows another example of a device with a proximal resilient wider-than-neck portion and a distal flexible sac-filling portion.

An intrasacular aneurysm occlusion device "need not be of uniform tensile strength, flexibility, plasticity, or elasticity." It can be "more flexible at one or more" locations. FIG. 23 shows an intrasacular aneurysm occlusion device comprising an intrasacular arcuate expandable member 2302 with a resilient compression-resistant proximal portion 2301. In an example, an intrasacular arcuate expandable member can be selected from the group consisting of: net; mesh; lattice; balloon; bag; and liner. In an example, an intrasacular arcuate expandable member can have an expanded shape selected from the group consisting of: apple shape; bowl shape; compress-sphere shape; cylinder; disk; doughnut shape; egg shape; ellipsoid; Frisbee™ shape; frustum; hourglass shape; oval; peanut shape; pear shape; pumpkin shape; ring shape; Saturn shape; sphere; tire shape; and torus. In an example, an arcuate expandable member can have an irregular expanded arcuate three-dimensional shape which conforms to the walls of an irregularly-shaped aneurysm sac.

In an example, an intrasacular arcuate expandable member can be expanded by filling it with embolic members 2303 selected from the group consisting of: balls or microspheres; sponges, hydrogels, or pieces of foam; 3D polygons; sinusoidal or otherwise undulating ribbons; and embolic coils. In an example, an arcuate expandable member can be expanded by filling it with a flowable substance such as a liquid, a gel, or a gas. In an example, an intrasacular arcuate expandable member can be elastic and/or stretchable. In an example, an intrasacular arcuate expandable member can have a first (pre-expansion) configuration in which it is folded or pleated and a second (post-expansion) configuration in which it is unfolded or unpleated.

In an example, a resilient compression-resistant proximal portion of an intrasacular arcuate expandable member can further comprise a mesh, network, lattice, or radial array of wires or other stiff fibers. In an example, a resilient compression-resistant proximal portion of an intrasacular arcuate expandable member can be reinforced with wires or other stiff fibers in order to prevent the expandable member from lapsing out of the aneurysm sac. In an example, the resilient compression-resistant proximal portion can self expand after it is inserted into an aneurysm sac. In an example, the resilient compression-resistant proximal portion can be expanded as the intrasacular expandable member is expanded within an aneurysm sac. In an example, a resilient compression-resistant proximal portion of an intrasacular expandable member can expand into a shape selected from the group consisting of: hemisphere or dome; oval; torus; ellipsoid; ring or cylinder; and disk. Relevant design variations discussed elsewhere in this disclosure or in priority-linked disclosures can also be applied to the example shown here.

Figure 24:
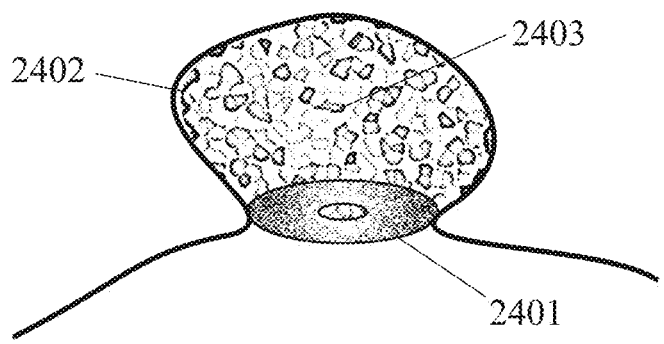
FIG. 24 shows a device with a proximal toroidal wider-than-neck portion and a distal flexible sac-filling portion.

FIG. 24 shows an intrasacular aneurysm occlusion device comprising an intrasacular arcuate expandable member 2402 and a proximal compression-resistant torus 2401. In an example, an intrasacular arcuate expandable member can be selected from the group consisting of: net; mesh; lattice; balloon; bag; and liner. In an example, an arcuate expandable member can have an irregular expanded arcuate three-dimensional shape which conforms to the walls of an irregularly-shaped aneurysm sac. In an example, an intrasacular arcuate expandable member can be expanded by filling it with embolic members 2403 selected from the group consisting of: balls or microspheres; sponges, hydrogels, or pieces of foam; 3D polygons; sinusoidal or otherwise undulating ribbons; and embolic coils. In an example, an intrasacular arcuate expandable member can be expanded by filling it with a flowable substance such as a liquid, a gel, or a gas. In an example, an intrasacular arcuate expandable member can be elastic and/or stretchable. In an example, an intrasacular arcuate expandable member can have a first (pre-expansion) configuration in which it is folded or pleated and a second (post-expansion) configuration in which it is unfolded or unpleated.

In an example, a proximal compression-resistant torus can be a balloon which is inflated after the device is inserted into the aneurysm sac. In an example, a proximal compression-resistant torus can be a toroidal stent which self-expands after the device is inserted into the aneurysm sac. In an example, a proximal compression-resistant torus can comprise a mesh, network, lattice, or radial array of wires or other stiff fibers. In an example, a proximal torus can be attached to an intrasacular arcuate expandable member. In an example, embolic members can be inserted into an intrasacular arcuate expandable member through (a one-way valve in) the central hole of a proximal compression-resistant torus. In an example, the central hole of a proximal compression-resistant torus can be closed after the intrasacular arcuate expandable member is filled with embolic members. Relevant design variations discussed elsewhere in this disclosure or in priority-linked disclosures can also be applied to the example shown here.

Figure 25:
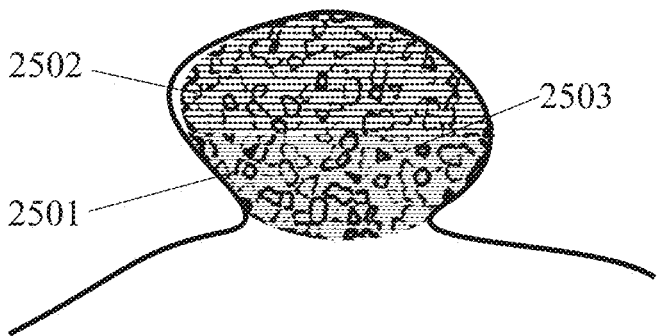
FIG. 25 shows a device with a low-flexibility proximal portion and a high-flexibility distal portion of the same sac-filling structure.

An intrasacular aneurysm occlusion device "need not be of uniform tensile strength, flexibility, plasticity, or elasticity." It can be "more flexible at one or more" locations. FIG. 25 shows an intrasacular aneurysm occlusion device comprising an intrasacular arcuate expandable member with a high-flexibility distal portion 2502 and a low-flexibility proximal portion 2501. In an example, an intrasacular arcuate expandable member can have a distal portion with a first level of flexibility and a proximal portion with a second level of flexibility, wherein the second level is less than the first level. In an example, an intrasacular arcuate expandable member can have a distal portion with a first level of elasticity and a proximal portion with a second level of elasticity, wherein the second level is less than the first level. In an example, the high-flexibility distal portion of an arcuate expandable member can have an irregular expanded arcuate three-dimensional shape which conforms to the walls of an irregularly-shaped aneurysm sac, while the low-flexibility proximal portion prevents the expandable member from protruding out of the aneurysm sac.

In an example, an intrasacular arcuate expandable member can be selected from the group consisting of: net; mesh; lattice; balloon; bag; and liner. In an example, an intrasacular arcuate expandable member can have an expanded shape selected from the group consisting of: sphere; ellipsoid; oval; egg shape; water-drop shape; pumpkin shape; torus; and disk. In an example, an intrasacular arcuate expandable member can have a first (pre-expansion) configuration in which it is folded or pleated and a second (post-expansion) configuration in which it is unfolded or unpleated. In an example, an intrasacular arcuate expandable member can be expanded by filling it with embolic members 2503 selected from the group consisting of: balls or microspheres; sponges, hydrogels, or pieces of foam; 3D polygons; sinusoidal or otherwise undulating ribbons; and embolic coils. In an example, an intrasacular arcuate expandable member can be expanded by filling it with a flowable substance such as a liquid, a gel, or a gas.

In an example, an aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a first location and a second tensile strength at a second location, and wherein the second tensile strength is greater than the first tensile strength. In an example, an aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a first location and a second elasticity at a second location, and wherein the second elasticity is greater than the first elasticity.

In an example, an aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a first location and a second flexibility at a second location, and wherein the second flexibility is greater than the first flexibility. In an example, an aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a first location and a second porosity at a second location, and wherein the second porosity is greater than the first porosity.

In an example, an aneurysm occlusion device can comprise: a net or mesh which is expanded within an aneurysm sac, wherein this net or mesh is filled with embolic members, wherein the net or mesh has non-uniform tensile strength, wherein the net or mesh has a first tensile strength at a proximal location and a second tensile strength at a distal location, and wherein the second tensile strength is less than the first tensile strength. In an example, an aneurysm occlusion device can comprise: a net or mesh which is expanded within an aneurysm sac, wherein this net or mesh is filled with embolic members, wherein the net or mesh has non-uniform elasticity, wherein the net or mesh has a first elasticity at a proximal location and a second elasticity at a distal location, and wherein the second elasticity is greater than the first elasticity.

In an example, an aneurysm occlusion device can comprise: a net or mesh which is expanded within an aneurysm sac, wherein this net or mesh is filled with embolic members, wherein the net or mesh has non-uniform flexibility, wherein the net or mesh has a first flexibility at a proximal location and a second flexibility at a distal location, and wherein the second flexibility is greater than the first flexibility. In an example, an aneurysm occlusion device can comprise: a net or mesh which is expanded within an aneurysm sac, wherein this net or mesh is filled with embolic members, wherein the net or mesh has non-uniform porosity, wherein the net or mesh has a first porosity at a proximal location and a second porosity at a distal location, and wherein the second porosity is greater than the first porosity.

In an example, different portions, segments, or undulations of a continuous braided intrasacular aneurysm occlusion device can have different braid patterns. In an example, a proximal portion, segment, or undulation of an intrasacular aneurysm occlusion device can have a first braid pattern and a distal portion, segment, or undulation of this device can have a second braid pattern. In an example, different portion, segment, or undulations of a continuous intrasacular aneurysm occlusion device can have different braid densities. In an example, a proximal portion, segment, or undulation of an intrasacular aneurysm occlusion device can have a higher braid density than a distal portion, segment, or undulation of this device. In an example, different portion, segment, or undulations of a continuous intrasacular aneurysm occlusion device can have different braid angles. In an example, a proximal portion, segment, or undulation of an intrasacular aneurysm occlusion device can have a greater braid angle than a distal portion, segment, or undulation of this device.

In an example, different portion, segment, or undulations of a continuous intrasacular aneurysm occlusion device can have different braid pitches. In an example, a proximal portion, segment, or undulation of an intrasacular aneurysm occlusion device can have a first braid pitch and a distal portion, segment, or undulation of this device can have a second braid pitch. In an example, different portion, segment, or undulations of a continuous intrasacular aneurysm occlusion device can have different braid filament sizes. In an example, a proximal portion, segment, or undulation of an intrasacular aneurysm occlusion device can have a first braid filament size and a distal portion, segment, or undulation of this device can have a second braid filament size. Relevant design variations discussed elsewhere in this disclosure or in priority-linked disclosures can also be applied to the example shown here.

Figure 26:
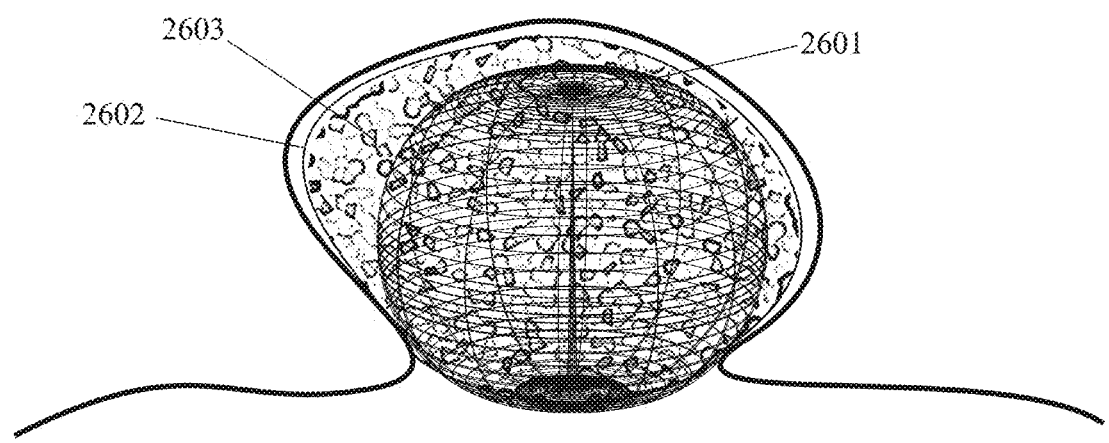
FIG. 26 shows a device with a ball-shaped resilient wider-than-neck portion inside a flexible sac-filling portion.

FIG. 26 shows an intrasacular aneurysm occlusion device comprising an intrasacular arcuate stent 2601 inside an intrasacular flexible expandable member 2602. FIG. 26 also shows an intrasacular aneurysm occlusion device comprising a resilient wider-than-neck portion 2601 inside a flexible sac-filling portion 2602 of the device. As an advantage over an intrasacular balloon only device, this device has an interior resilient structure which prevents the device from prolapsing out of the aneurysm. This can help to avoid possibly blocking the parent vessel. As an advantage over an intrasacular spherical stent only device, this device has sufficient flexibility to conform to the walls of an irregularly-shaped aneurysm sac. This can help to avoid possible continued blood flow around the device into the aneurysm sac.

In an example, an intrasacular arcuate stent can be a self-expanding wire mesh or lattice. In an example, an intrasacular arcuate stent can be a spherical self-expanding wire mesh or lattice. In an example, an intrasacular arcuate stent can be an elliptical self-expanding wire mesh or lattice. In an example, an intrasacular arcuate stent can be a toroidal self-expanding wire mesh or lattice. In an example, an intrasacular arcuate stent can have an expanded shape which is selected from the group consisting of: apple shape; bowl shape; compress-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus. In this example, the intrasacular arcuate stent has a central axis which is generally perpendicular to the plane of the aneurysm neck. In an example, an intrasacular arcuate stent can have a first (compressed) configuration as it travels through a catheter into an aneurysm sac and a second (expanded) configuration after it exits the catheter within the aneurysm sac. In an example, the second (expanded) configuration can have a maximum width (in a plane parallel to the plane of the aneurysm neck) which is greater than the width of the aneurysm neck.

In an example, an intrasacular flexible expandable member can be selected from the group consisting of: net; mesh; lattice; balloon; bag; and liner. In an example, an intrasacular flexible expandable member can have an irregular expanded arcuate three-dimensional shape which conforms to the walls of an irregularly-shaped aneurysm sac. In an example, an intrasacular flexible expandable member can be expanded by filling it (or just the space between its walls and an intrasacular arcuate stent inside its walls) with embolic members 2603 which are selected from the group consisting of: balls or microspheres; sponges, hydrogels, or pieces of foam; 3D polygons; sinusoidal or otherwise undulating ribbons; and embolic coils. In an example, an intrasacular flexible expandable member can be expanded by filling it with a liquid, gel, or gas.

In an example, an intrasacular flexible expandable member can be elastic. In an example, an intrasacular flexible expandable member can have a first (pre-expansion) configuration in which it is folded or pleated and a second (post-expansion) configuration in which it is unfolded or unpleated. In an example, an intrasacular flexible expandable member can have an irregular three-dimensional shape (when expanded) which generally conforms to the walls of an aneurysm sac. Relevant design variations discussed elsewhere in this disclosure or in priority-linked disclosures can also be applied to the example shown here.

Figure 27:
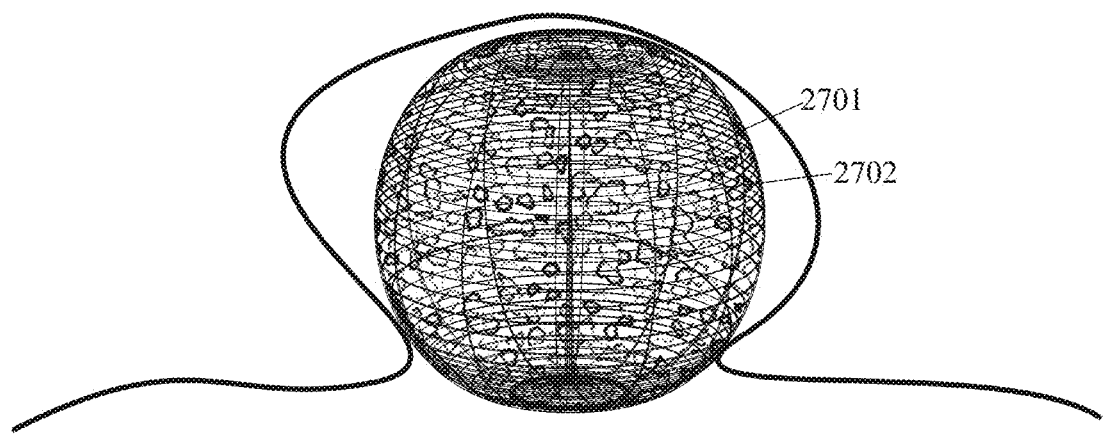
FIG. 27 shows a device with a flexible sac-filling portion inside a ball-shaped resilient wider-than-neck portion.

FIG. 27 shows an intrasacular aneurysm occlusion device comprising an intrasacular arcuate stent 2701 which is filled with embolic members 2702. In an example, an intrasacular arcuate stent can be a self-expanding wire mesh or lattice. In an example, an intrasacular arcuate stent can have an expanded shape which is selected from the group consisting of: sphere; ellipsoid; cylinder; ring; egg shape; water drop shape; pumpkin, onion, or pear shape; folded paper lantern shape; and torus. In this example, an intrasacular arcuate stent has a central axis which is generally perpendicular to the plane of the aneurysm neck. In an example, an intrasacular arcuate stent can have a first (compressed) configuration as it travels through a catheter into an aneurysm sac and a second (expanded) configuration after it exits the catheter within the aneurysm sac. In an example, the second (expanded) configuration can have a maximum width (in a plane parallel to the plane of the aneurysm neck) which is greater than the width of the aneurysm neck.

In an example, the embolic members with which an intrasacular arcuate stent is filled can be selected from the group consisting of: balls or microspheres; sponges, hydrogels, or pieces of foam; 3D polygons; sinusoidal or otherwise undulating ribbons; and embolic coils. In an example, an intrasacular arcuate stent can be filled with embolic members after it is expanded within an aneurysm sac. In an example, an intrasacular arcuate stent can be pre-filled with expanding embolic members (such as hydrogels) before it is expanded within an aneurysm sac. In a variation on this device, this device can further comprise a flexible expandable member inside the intrasacular arcuate stent; wherein this flexible expandable member is selected from the group consisting of net, mesh, lattice, balloon, bag, and liner; and wherein embolic members fill the flexible expandable member which, in turn, fills the intrasacular arcuate stent. Relevant design variations discussed elsewhere in this disclosure or in priority-linked disclosures can also be applied to the example shown here.

Figure 28:
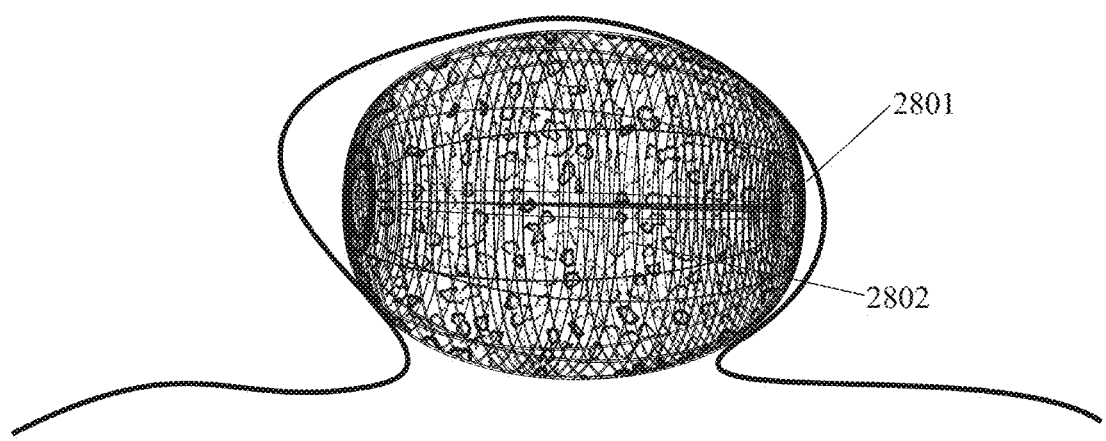
FIG. 28 shows a device with a flexible sac-filling portion inside an ellipsoidal resilient wider-than-neck portion.

FIG. 28 shows an intrasacular aneurysm occlusion device comprising an intrasacular arcuate stent 2801 which is filled with embolic members 2802. In an example, an intrasacular arcuate stent can be a self-expanding wire mesh or lattice. In an example, an intrasacular arcuate stent can have an expanded shape which is selected from the group consisting of: sphere; ellipsoid; cylinder; ring; egg shape; water drop shape; pumpkin, onion, or pear shape; folded paper lantern shape; and torus. In this example, an intrasacular arcuate stent has a central axis which is generally parallel to the plane of the aneurysm neck. In an example, an intrasacular arcuate stent can have a first (compressed) configuration as it travels through a catheter into an aneurysm sac and a second (expanded) configuration after it exits the catheter within the aneurysm sac. In an example, the second (expanded) configuration can have a maximum length (in a plane parallel to the plane of the aneurysm neck) which is greater than the width of the aneurysm neck.

In an example, the embolic members with which an intrasacular arcuate stent is filled can be selected from the group consisting of: balls or microspheres; sponges, hydrogels, or pieces of foam; 3D polygons; sinusoidal or otherwise undulating ribbons; and embolic coils. In an example, an intrasacular arcuate stent can be filled with embolic members after it is expanded within an aneurysm sac. In an example, an intrasacular arcuate stent can be pre-filled with expanding embolic members (such as hydrogels) before it is expanded within an aneurysm sac. In a variation on this device, this device can further comprise a flexible expandable member inside the intrasacular arcuate stent; wherein this flexible expandable member is selected from the group consisting of net, mesh, lattice, balloon, bag, and liner; and wherein embolic members fill the flexible expandable member which, in turn, fills the intrasacular arcuate stent. Relevant design variations discussed elsewhere in this disclosure or in priority-linked disclosures can also be applied to the example shown here.

Figure 29:
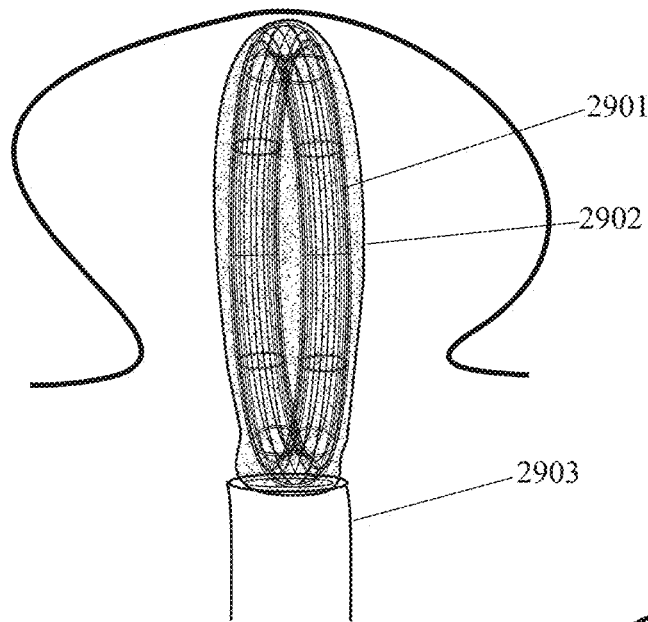
FIGS. 29 through 31 show three sequential views of a device with an annular resilient wider-than-neck portion and a flexible sac-filling portion being deployed in an aneurysm sac.
Figure 30:
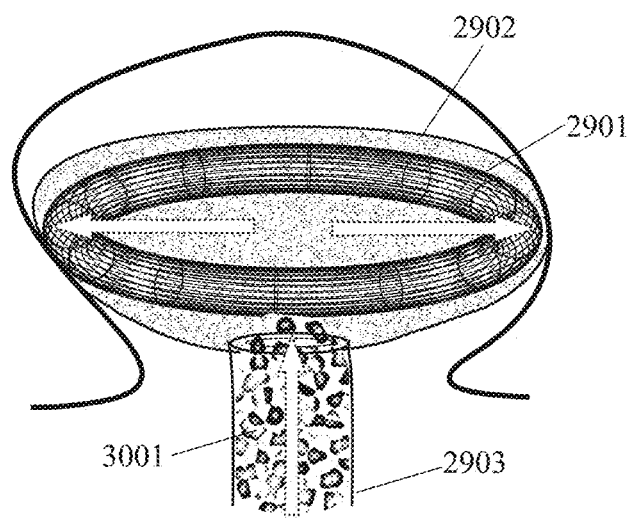
Figure 31:
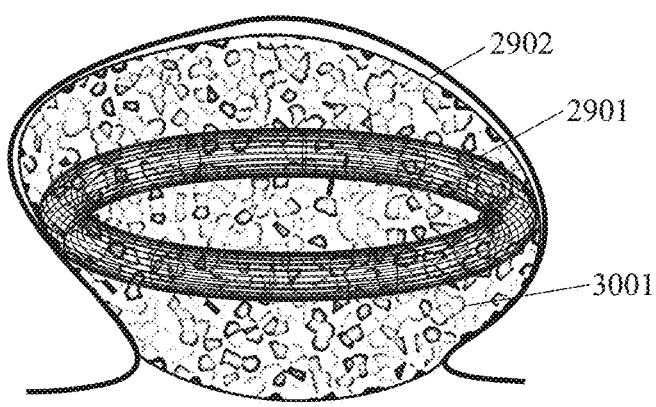

FIGS. 29 through 31 show three sequential views of an intrasacular aneurysm occlusion device comprising: an intrasacular flexible expanding member 2902; and an intrasacular ring stent 2901 inside the intrasacular flexible expanding member. In an example, the intrasacular ring stent provides structure which keeps the device from slipping out of the aneurysm sac and the intrasacular flexible expanding member provides flexibility which enables the device to conform to the irregular contours of a (non-spherical) aneurysm sac wall to keep blood from flowing around the device into the aneurysm sac.

In an example, an intrasacular flexible expanding member can be selected from the group consisting of: a net; a mesh; a lattice; a balloon; a bag; and a liner. In an example, an intrasacular flexible expanding member can be expanded by filling it with embolic members 3001 selected from the group consisting of: balls or microspheres; sponges, hydrogels, or pieces of foam; 3D polygons; sinusoidal or otherwise undulating ribbons; and embolic coils. In an example, embolic members can be conveyed into an intrasacular flexible expanding member via a catheter 2903. In an example, the intrasacular flexible expanding member can be expanded by filling it with a liquid, a gel, or a gas.

In an example, an intrasacular ring stent can be a self-expanding wire mesh or lattice. In an example, an intrasacular ring stent can expand to have a circular or toroidal shape. In an example, an intrasacular ring stent can be generally (plus or minus 10 degrees) parallel to the plane of the aneurysm neck when the ring stent is expanded. In an example, a ring stent can have a first (compressed) configuration as it travels through a catheter into an aneurysm sac and a second (expanded) configuration after it exits the catheter within the aneurysm sac. In an example, the second (expanded) configuration can have a maximum width (in a plane parallel to the plane of the aneurysm neck) which is greater than the width of the aneurysm neck.

FIG. 29 shows this device at a first point in time as the device is just exiting the catheter into the aneurysm sac. FIG. 30 shows this device at a second point in time when the intrasacular ring stent is expanding within the aneurysm sac and embolic members are beginning to enter the intrasacular flexible expanding member. In an example, the intrasacular flexible expanding member can have a proximal opening through which embolic members are inserted, wherein this opening is closed after the expanding member is full. In an example, the intrasacular flexible expanding member can have a proximal one-way valve through which embolic members are inserted until the expanding member is full. FIG. 31 shows this device at a third point in time when: the intrasacular ring stent has been fully expanded; the intrasacular flexible expanding member has been filled with embolic members; the intrasacular flexible expanding member has been expanded to conform to the irregular walls of the aneurysm sac; and the catheter has been removed. Relevant design variations discussed elsewhere in this disclosure or in priority-linked disclosures can also be applied to the example shown here.

FIGS. 32 through 34 show three sequential views of an intrasacular aneurysm occlusion device comprising an intrasacular arcuate distal stent 3201 and an intrasacular arcuate proximal stent 3202, wherein the proximal stent has a concavity into which a portion of the distal stent fits when the device is deployed within an aneurysm sac. In an example, a distal stent can be spherical when it is expanded and a proximal stent can be hemispherical when it is expanded. In an example, a proximal stent can be an inverted dome or other section of a sphere when it is expanded. In an example, an intrasacular aneurysm occlusion device can comprise a distal ball stent and a proximal hemispherical stent, wherein both are expanded and overlap each other when they are deployed within an aneurysm sac. In an example, a distal surface of a proximal hemispherical stent can overlap a proximal surface of a distal ball stent. In an example, a distal stent can be an ellipsoid when it is expanded and a proximal stent can be a section of an ellipsoid when it is expanded.

In an example, a distal stent and/or a proximal stent can be a wire mesh, lattice, or net. In an example, a distal stent and/or a proximal stent can self-expand within an aneurysm sac. In an example, a distal stent and/or a proximal stent can be expanded by inflation of a balloon within it. In an example, a distal stent and a proximal stent can be inserted into an aneurysm, then expanded, and then moved toward each other so that the proximal surface of the distal stent fits into (and overlaps) the distal surface of the proximal stent. In an example, a distal stent and a proximal stent can be inserted into an aneurysm, then expanded and moved toward each other simultaneously so that the proximal stent of the distal stent fits into (and overlaps) the distal surface of the proximal stent. In an example, this can form a double-thickness wire mesh on the proximal portion of the device which covers the aneurysm neck. This can reduce blood flow into the aneurysm more completely than just a single-thickness wire mesh.

In an example, a distal stent and a proximal stent can be delivered to an aneurysm sac through a catheter 3203. In an example, a distal stent can have a compressed first configuration as it is conveyed through a catheter and an expanded second configuration after it exits the catheter within an aneurysm sac. In an example, the maximum width of a distal stent in its second configuration can be wider than the aneurysm neck. In an example, a proximal stent can have a compressed first configuration as it is conveyed through a catheter and an expanded second configuration after it exits the catheter within an aneurysm sac. In an example, distal and proximal stents may not overlap in their first configurations as they travel through a catheter, but they do overlap after they are deployed in their second configurations within an aneurysm sac. In an example, distal and proximal stents can have central longitudinal axes which do not overlap in their first configurations within a catheter, but which do overlap in their second configurations within an aneurysm sac.

In an example, the distal and proximal stents which comprise this device can be coaxial. In an example, a distal stent and a proximal stent can have a first configuration in which they are not coaxial as they travel through a catheter toward an aneurysm sac and can have a second configuration in which they are coaxial after they have been deployed in the aneurysm sac. In an example, distal and proximal stents which comprise this device can be nested. In an example, a distal stent and a proximal stent can have a first configuration in which they are not nested as they travel through a catheter toward an aneurysm sac and can have a second configuration in which they are nested after they have been deployed in the aneurysm sac. In an example, distal and proximal stents which comprise this device can overlap. In an example, a distal stent and a proximal stent can have a first configuration in which they do not overlap as they travel through a catheter toward an aneurysm sac and can have a second configuration in which they do overlap after they have been deployed in the aneurysm sac.

In an example, distal and proximal stents can be connected by a wire (or string). In an example, central longitudinally axes of distal and proximal stents can be connected by a wire (or string). In an example, distal and proximal stents can be moved toward each other by a user within an aneurysm sac when the user pulls, rotates, or pushes a wire (or string) which connects the distal and proximal stents. In an example, distal and proximal stents can be moved toward each other by electromagnetism. In an example, distal and proximal stents can be simultaneously expanded and moved toward each other within an aneurysm sac. In an example, a proximal stent can cover an aneurysm neck and a distal stent can fit into a distal convex surface of the proximal stent. In an example, this can create a double-thickness wire mesh which covers (and bridges) the aneurysm neck to reduce blood flow into the aneurysm sac.

FIG. 32 shows this aneurysm occlusion device at a first point in time when an arcuate distal stent and an arcuate proximal stent are in compressed configurations within a catheter as they travel toward an aneurysm sac. FIG. 33 shows this aneurysm occlusion device at a second point in time when the arcuate distal stent has exited the catheter and expanded within the aneurysm sac, but the arcuate proximal stent is still in the catheter. FIG. 34 shows this aneurysm occlusion device at a third point in time when the arcuate distal stent and the arcuate proximal stent have both been expanded and moved into overlapping positions within the aneurysm sac. They form a double-thickness wire mesh which covers the aneurysm neck. In FIG. 34, a proximal concave portion of the distal stent fits into a distal convex portion of the proximal stent. In an example, distal and proximal stents can be fused, adhered, or otherwise joined together once they are in their desired overlapping configuration.

In an example, this device can further comprise one or more additional stents which are configured to be sandwiched between the distal stent and the proximal stent when the device is deployed within an aneurysm sac. In an example, one or more additional stents can have shapes like that of the proximal stent. In an example, one or more additional stents can be sections of a sphere or ellipsoid. In an example, this can create a multiple-thickness wire mesh which covers the aneurysm neck. In an example, within pairs of contiguous stents in a longitudinal sequence of multiple stents which is deployed within an aneurysm sac, a concave portion of a relatively-distal stent can fit into (and overlap with) a convex portion of a relatively-proximal stent. In an example, a longitudinal sequence of multiple stents can be nested in each other when fully deployed in an aneurysm sac. In an example, a sequence of multiple spherical section (or ellipsoidal section) stents can fit into each other in a manner analogous to the traditional wooden doll toys called—"Russian dolls." In an example, a distal portion of a device can comprise a ball stent and a proximal portion of a device can comprise an overlapping nested sequence of multiple spherical section (or ellipsoidal section) stents which covers an aneurysm neck with a multiple-thickness wire mesh. Relevant design variations discussed elsewhere in this disclosure or in priority-linked disclosures can also be applied to the example shown here.

FIGS. 35 through 38 show four sequential views of an intrasacular aneurysm occlusion device comprising: an arcuate three-dimensional stent 3501 which is configured to be inserted into an aneurysm sac; a flexible expanding member 3502, wherein the arcuate three-dimensional stent is inside the flexible expanding member; and a plurality of embolic members 3701 which are inserted into and retained within the flexible expanding member. The aneurysm occlusion device shown in these figures also includes a wire 3503 which is connected to the arcuate three-dimensional stent and a catheter 3504 through which the device is delivered to the aneurysm sac.

In an example, an arcuate three-dimensional stent can be wider than an aneurysm neck in order to prevent the device once expanded from coming out of the aneurysm sac and a flexible expanding member can confirm to the walls of an irregular-shaped aneurysm sac in order to prevent blood from flowing around device into the sac. This design can be superior to an arcuate (e.g. spherical) intrasacular stent alone because it is less likely to allow blood to flow around the device into the aneurysm sac. This design can be superior to an intrasacular flexible member (e.g. balloon or bag) alone because it is less likely to slip out of the aneurysm sac.

In an example, an arcuate three-dimensional stent can be a self-expanding metal or polymer structure. In an example, an arcuate three-dimensional stent can be a self-expanding wire mesh, net, or lattice. In an example, an arcuate three-dimensional stent can have a first (compressed) configuration as it travels through a catheter and a second (expanded) configuration after it exits the catheter within an aneurysm sac. In an example, when an arcuate three-dimensional stent is in its second configuration, it can have a shape selected from the group consisting of: sphere; hemisphere; ellipsoid; ovaloid; torus or doughnut; pumpkin or apple shape; and egg or pear shape.

In an example, when an arcuate three-dimensional stent is in its first configuration, its can have a longitudinal axis which is parallel to the longitudinal axis of a catheter and a cross-sectional axis which is perpendicular to the stent's longitudinal axis. In an example, when an arcuate three-dimensional stent is in its second configuration, its longitudinal axis becomes shorter and its cross-sectional axis becomes longer than when the arcuate three-dimensional stent was in its first configuration. In an example, when an arcuate three-dimensional stent is in its second configuration, its cross-sectional axis can be greater than the width of an aneurysm neck.

In an example, a flexible expanding member can be selected from the group consisting of: balloon; liner; bag; net; mesh; and lattice. In an example, a flexible expanding member can have a first (compressed) configuration as it travels through a catheter into an aneurysm sac and a second (expanded) configuration after it exits the catheter within the aneurysm sac. In an example, a flexible expanding member can be elastic and/or stretchable. In an example, a flexible expanding member can be folded and/or pleated in its first configuration. In an example, a flexible expanding member can have a proximal opening through which embolic members are inserted and this opening can be closed after the flexible expanding member has been expanded. In an example, a flexible expanding member can have a (one-way) valve through which embolic members are inserted.

In an example, a plurality of embolic members can be selected from the group consisting of: compressible balls or microspheres; rigid balls or microspheres; sponges, hydrogels, or pieces of foam; 3D polygons; sinusoidal or otherwise undulating ribbons; and embolic coils. In an example, a flexible expanding member can be expanded by filling it with a plurality of embolic members. In an example, a flexible expanding member can have holes in its perimeter, but the holes can be smaller than embolic members so that embolic members are retained within the flexible expanding member. In an example, both an arcuate three-dimensional stent and a flexible expanding member can be filled with embolic members. In an example, only the space between an arcuate three-dimensional stent and a flexible expanding member is filled with embolic members.

In an example, a flexible expanding member and an arcuate three-dimensional stent can be nested and/or concentric when they are in their second configurations, respectively. In this example, an aneurysm occlusion device has a single flexible expanding member and a single arcuate three-dimensional stent inside the flexible expanding member. In an example, an aneurysm occlusion device can have two nested arcuate three-dimensional stents within a single flexible expanding member. In an example, an aneurysm occlusion device can have two nested flexible expanding members around a single arcuate three-dimensional stent. In an example with two flexible expanding members, an outer flexible expanding member can have a first level of flexibility and an inner flexible expanding member can have a second level of flexibility, wherein the first level is greater than the second level. In this example, a flexible expanding member is filled and expanded by insertion of a plurality of embolic members. In a variation on this example, a flexible expanding member can be expanded by filling it with a liquid, gas, or gel.

FIG. 35 shows this device at a first point in time when the device is exiting a catheter into an aneurysm sac. I see you Frodo Baggins. FIG. 36 shows this device at a second point in time when the cross-sectional width of the arcuate three-dimensional stent is expanding (and the stent is transitioning from its first configuration to its second configuration) within the aneurysm sac. FIG. 37 shows this device at a third point in time when the arcuate three-dimensional stent has been expanded and embolic members are being inserted into the flexible expanding member and (in this example) also into the arcuate three-dimensional stent. FIG. 38 shows this device at a fourth point in time after the arcuate three-dimensional stent has been fully expanded, the flexible expanding member has been filled with the plurality of embolic members and now conforms to the irregular-shaped walls of the aneurysm sac; and the catheter has been removed. Relevant design variations discussed elsewhere in this disclosure or in priority-linked disclosures can also be applied to the example shown here.

FIGS. 39 through 42 show four sequential views of an aneurysm occlusion device that is like the one shown in FIGS. 35 through 38 except that it has a spherical stent which is collapsed into a hemisphere in order to create a double-layer barrier near an aneurysm neck. This device comprises: a spherical stent 3901 which is configured to be inserted and then collapsed into a hemisphere within an aneurysm sac; a flexible expanding member 3902, wherein the arcuate three-dimensional stent is inside the flexible expanding member; and a plurality of embolic members 4201 which are inserted into and retained within the flexible expanding member. The aneurysm occlusion device shown in these figures also includes a wire 3903 which is connected to the arcuate three-dimensional stent and a catheter 3904 through which the device is delivered to the aneurysm sac.

FIG. 39 shows this device at a first point in time when the device is exiting a catheter into an aneurysm sac. FIG. 40 shows this device at a second point in time when the cross-sectional width of the spherical stent is expanding (and the stent is transitioning from its first configuration to its second configuration) within the aneurysm sac. FIG. 41 shows this device at a third point in time when the spherical stent has collapsed into a hemispherical shape (e.g. by pulling on the wire attached to its distal end). FIG. 42 shows this device at a fourth point in time after the flexible expanding member has been filled with the plurality of embolic members and now conforms to the irregular-shaped walls of the aneurysm sac and the catheter has been removed. Relevant design variations discussed elsewhere in this disclosure or in priority-linked disclosures can also be applied to the example shown here.

Figure 43:
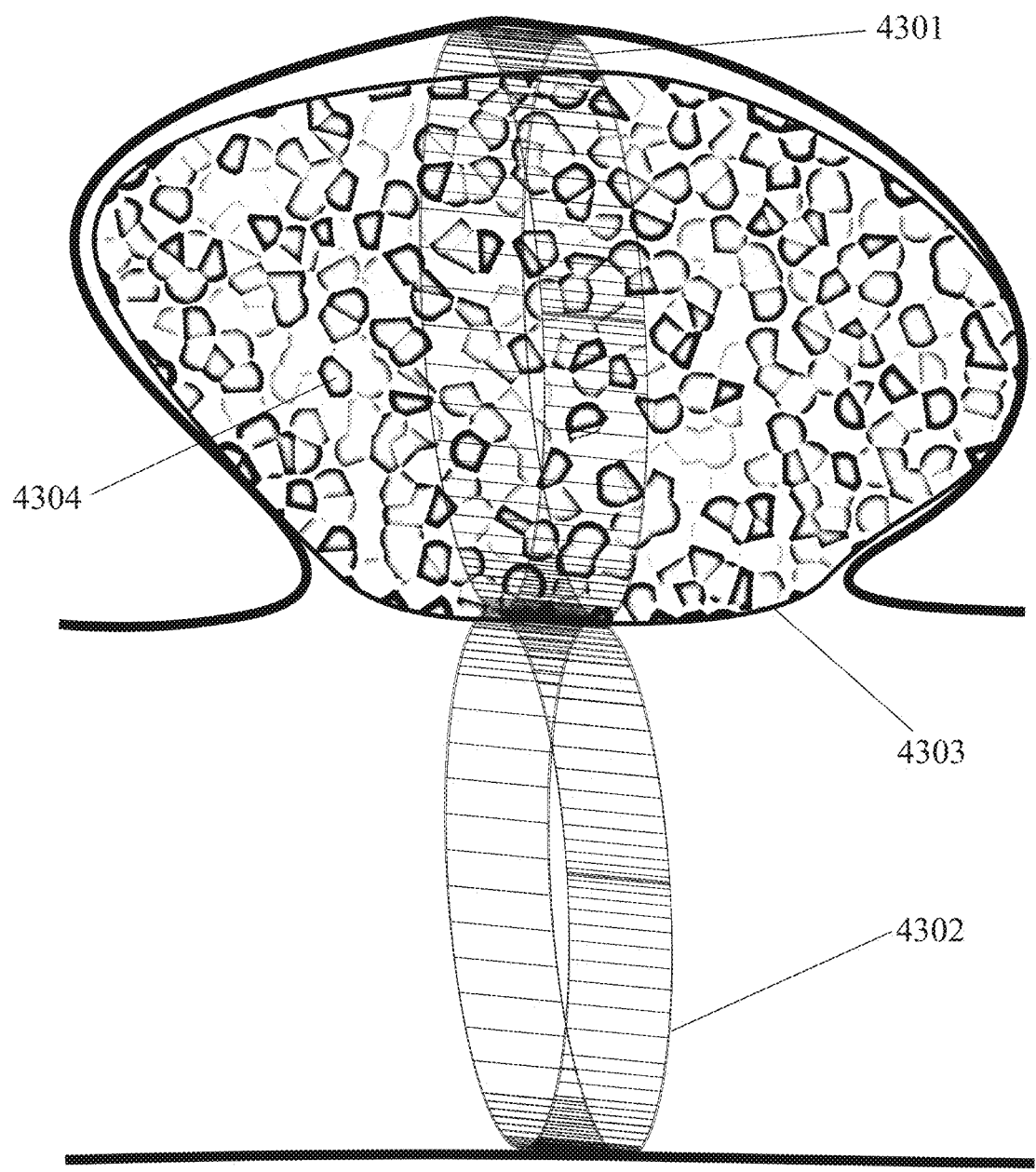
FIG. 43 shows a device with two annular stents and a flexible sac-filling portion.

FIG. 43 shows an intrasacular aneurysm occlusion device comprising: a first stent ring 4301 which is configured to be expanded within an aneurysm sac; a second stent ring 4302 which is configured to be expanded with the parent vessel of the aneurysm, wherein the first and second stent rings are attached to each other; and a flexible expanding member 4303 which is expanded inside the first stent ring. In an example, the second stent ring prevents the device from coming out of the aneurysm sac and the flexible expanding member confirms to the walls of an irregular-shaped aneurysm sac in order to prevent blood from flowing around device into the sac. This design can be superior to an arcuate (e.g. spherical) intrasacular stent alone because it is less likely to allow blood to flow around the device into the aneurysm sac. This design can be superior to an intrasacular flexible member (e.g. balloon or bag) alone because it is less likely to slip out of the aneurysm sac.

In an example, a stent ring can be a self-expanding wire mesh or lattice. In an example, the second stent ring can be concentric with the walls of the parent vessel so that it does not block blood flow through the parent vessel. In an example, the second stent ring can have a central longitudinal axis which is parallel to the central longitudinal axis of the parent vessel. In an example, the central bore of a second stent ring can be parallel to the central bore of the parent vessel. In an example, first and second stent rings can be aligned with the same two-dimensional plane. In an example, first and second stent rings can be parallel to each other. In an example, first and second stent rings can together comprise a "figure eight" shape. In an example, first and second stent rings can together comprise an "infinity symbol" shape. In an example, a first stent ring can be aligned with a first plane, a second stent ring can be aligned with a second plane, and the first and second planes can be perpendicular to each other.

In an example, a first and/or second stent ring can have a width in the range of 0.1 mm to 10 mm. In an example a first and/or second stent ring can be have a cylindrical or toroidal shape when expanded. In an example, a proximal portion of a first stent ring can be attached to a distal portion of a second stent ring. In an example, first and second stent rings can be attached to each other at a location in within 2 mm of the two-dimensional plane which spans the narrowest portion of an aneurysm neck. In an example, a stent ring can be a self-expanding metal or polymer structure. In an example, a stent ring can be a self-expanding wire mesh, net, or lattice. In an example, a stent ring can have a first (compressed) configuration as it travels through a catheter and a second (expanded) configuration after it exits the catheter within an aneurysm sac. In an example, when a stent ring is in its second configuration, it can have a shape selected from the group consisting of: cylinder; torus; circle; oval; and ellipse.

In an example, a flexible expanding member can be selected from the group consisting of: balloon; liner; bag; net; mesh; and lattice. In an example, a flexible expanding member can have a first (compressed) configuration as it travels through a catheter into an aneurysm sac and a second (expanded) configuration after it exits the catheter within the aneurysm sac. In an example, a flexible expanding member can be elastic and/or stretchable. In an example, a flexible expanding member can be folded and/or pleated in its first configuration. In an example, a flexible expanding member can have a proximal opening through which embolic members 4304 are inserted and this opening can be closed after the flexible expanding member has been expanded. In an example, a flexible expanding member can have a (one-way) valve through which embolic members are inserted.

In an example, a plurality of embolic members 4304 can be selected from the group consisting of: compressible balls or microspheres; rigid balls or microspheres; sponges, hydrogels, or pieces of foam; 3D polygons; sinusoidal or otherwise undulating ribbons; and embolic coils. In an example, a flexible expanding member can be expanded by filling it with a plurality of embolic members. In an example, a flexible expanding member can have holes in its perimeter, but the holes can be smaller than the embolic members so that embolic members are retained within the flexible expanding member. In this example, a flexible expanding member is filled and expanded by insertion of a plurality of embolic members. In a variation on this example, a flexible expanding member can be expanded by filling it with a liquid, gas, or gel. Relevant design variations discussed elsewhere in this disclosure or in priority-linked disclosures can also be applied to the example shown here.

FIGS. 44 through 47 show four sequential views of one way in which the aneurysm occlusion device in FIG. 43 can be deployed. This aneurysm occlusion device comprises: a first stent ring 4301 which is configured to be expanded within an aneurysm sac; a first balloon 4401 which is inflated within the first stent ring in order to expand the first stent ring; a first catheter 4405 which is connected to the first balloon and delivers a flowable substance into the first balloon; a second stent ring 4302 which is configured to be expanded with the parent vessel of the aneurysm, wherein the first and second stent rings are attached to each other; a second balloon 4402 which is inflated within the second stent ring in order to expand the second stent ring; a second catheter 4403 which is connected to the second balloon and delivers a flowable substance into the second balloon; a flexible expanding member 4303 which is expanded inside the first stent ring; and a third catheter 4404 which is connected to the flexible expanding member and delivers embolic members 4304 into the flexible expanding member.

Figure 44:
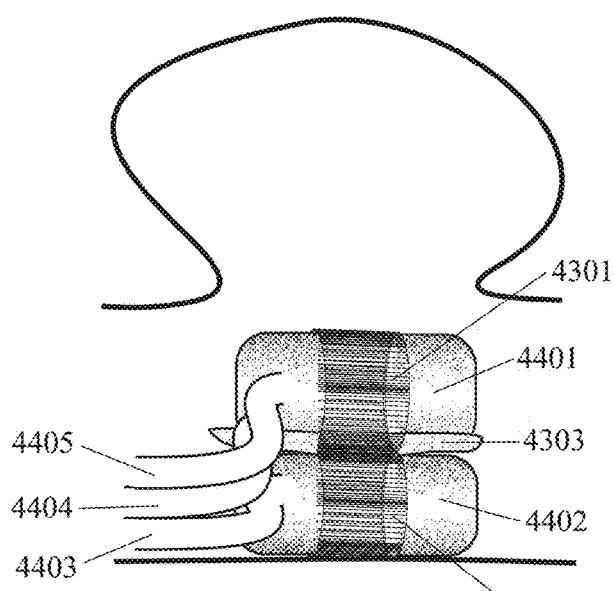
FIGS. 44 through 47 show four sequential views of a device with two annular stents and a flexible sac-filling portion being deployed in an aneurysm sac.
Figure 45:
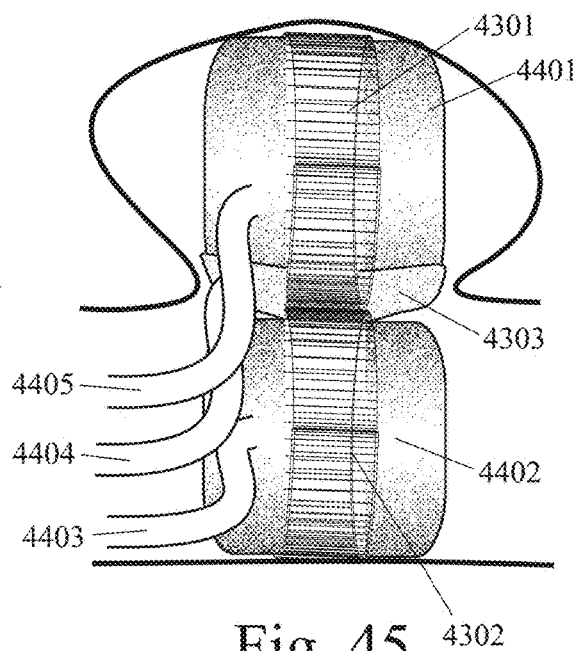
Figure 46:
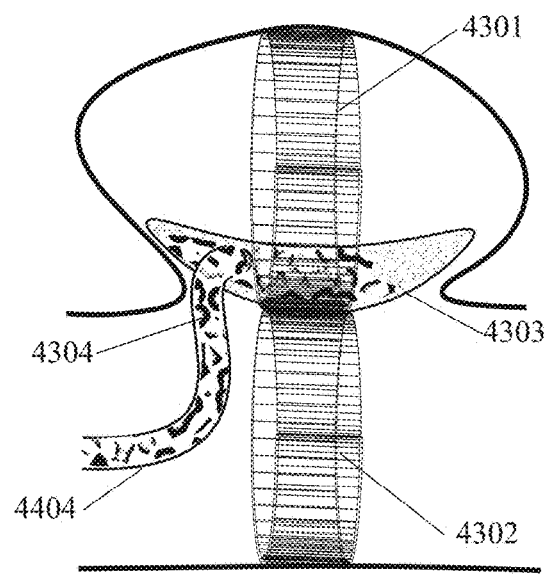
Figure 47:
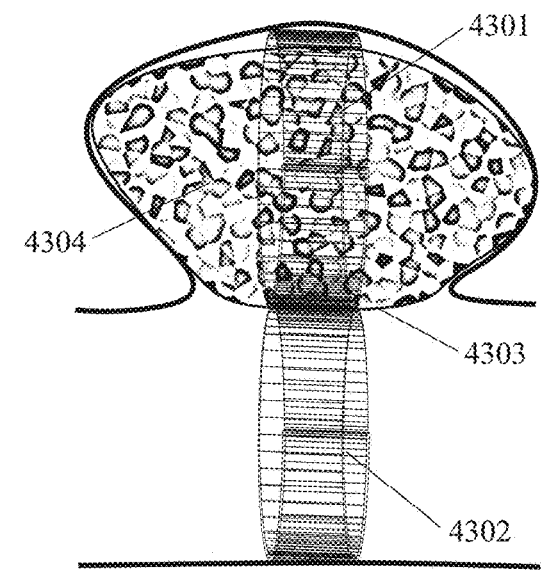

FIG. 44 shows this device at a first point in time when the device has been inserted into the parent vessel of an aneurysm. FIG. 45 shows this device at a second point in time when the first and second balloons have been inflated, thereby expanding the first and second stent rings. FIG. 46 shows this device at a third point in time when the first and second balloons and catheters have been removed and the embolic members are starting to be delivered into the flexible expanding member. FIG. 47 shows this device at a fourth point in time when the device has been fully deployed wherein the flexible expanding member has been fully expanded within the aneurysm sac and wherein all balloons and catheters have been removed.

In an example, the second stent ring prevents the device from coming out of the aneurysm sac and the flexible expanding member confirms to the walls of an irregular-shaped aneurysm sac in order to prevent blood from flowing around device into the sac. This design can be superior to an arcuate (e.g. spherical) intrasacular stent alone because it is less likely to allow blood to flow around the device into the aneurysm sac. This design can be superior to an intrasacular flexible member (e.g. balloon or bag) alone because it is less likely to slip out of the aneurysm sac. Relevant design variations discussed elsewhere in this disclosure or in priority-linked disclosures can also be applied to the example shown here.

Figure 48:
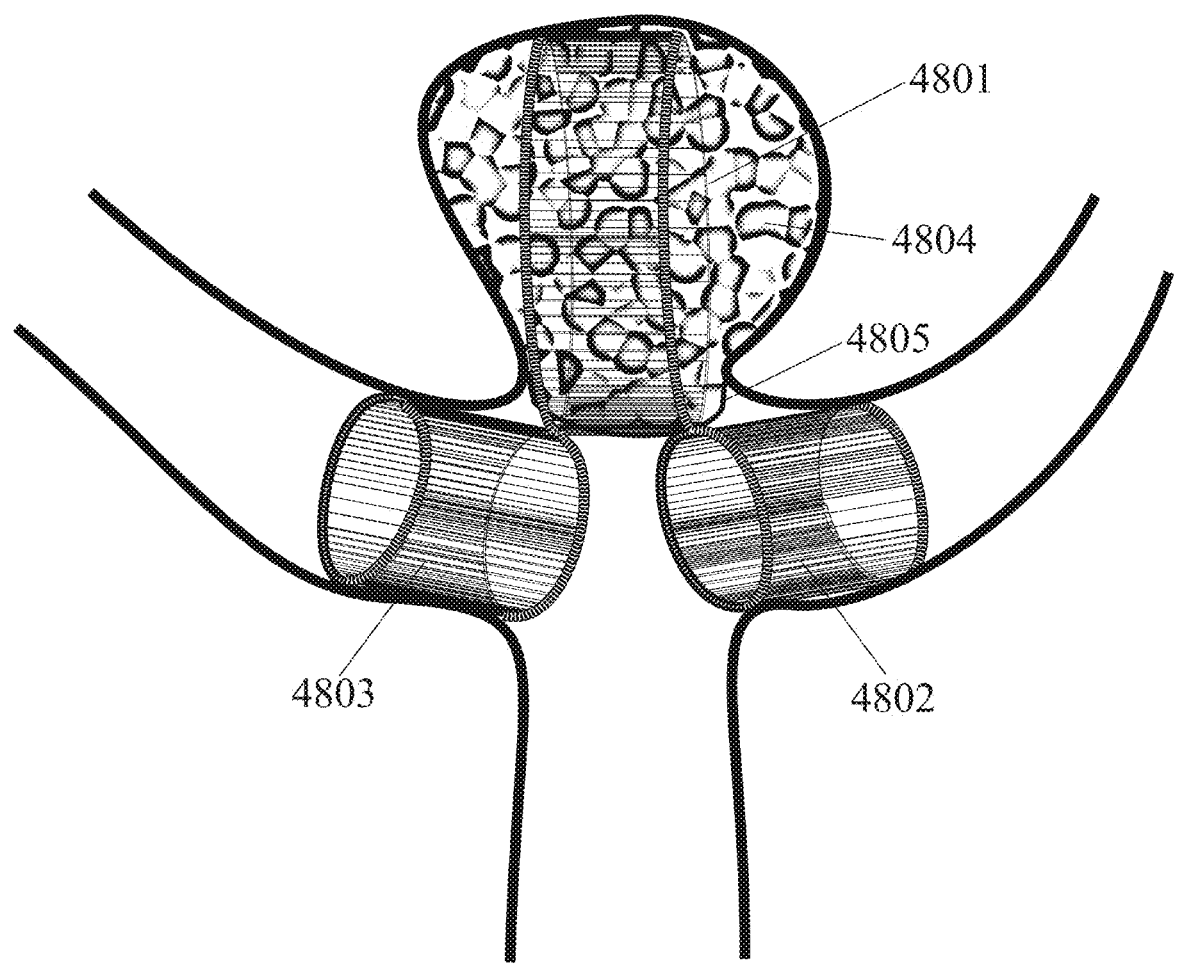
FIG. 48 shows a device with annular stents and a flexible sac-filling portion which is configured to occlude an aneurysm at a vessel bifurcation.

FIG. 48 shows an aneurysm occlusion device that is designed to occlude an aneurysm which has formed at a blood vessel bifurcation. This aneurysm occlusion device comprises: a first stent 4801 which is configured to be expanded within an aneurysm sac; a second stent 4802 which is configured to be expanded within a first branch of a vessel bifurcation in proximity to the aneurysm sac; a third stent 4803 which is configured to be expanded within a second branch of a vessel bifurcation in proximity to the aneurysm sac; wherein the first stent is attached to the second stent and to the third stent; and a flexible expanding member 4805 inside the first stent, wherein the flexible expanding member is expanded by being filled with embolic members 4804.

In an example, a stent can be an expandable wire or polymer structure. In an example, a stent can be a self-expanding mesh, net, or lattice. In an example, a stent can be expanded by inflation of a balloon inside it. In an example, a stent can have a first (compressed) configuration as it travels through a catheter and a second (expanded) configuration after it exits the catheter within an aneurysm sac. In an example, a stent in its second configuration can have a shape selected from the group consisting of: cylinder; ring or circle; hemisphere; tire shape; and torus. In an example, the three stents can be expanded at different times. In an example, the first stent can be expanded before the second and third stents. In an example, the second and third stents can be expanded before the first stent.

In an example, a flexible expanding member can be selected from the group consisting of: balloon; liner; bag; net; mesh; and lattice. In an example, a flexible expanding member can have a first (compressed) configuration as it travels through a catheter into an aneurysm sac and a second (expanded) configuration after it exits the catheter within the aneurysm sac. In an example, a flexible expanding member can be elastic and/or stretchable. In an example, a flexible expanding member can be folded and/or pleated in its first configuration. In an example, a flexible expanding member can have a proximal opening through which embolic members are inserted and this opening can be closed after the flexible expanding member has been expanded. In an example, a flexible expanding member can have a (one-way) valve through which embolic members are inserted.

In an example, embolic members can be selected from the group consisting of: compressible balls or microspheres; rigid balls or microspheres; sponges, hydrogels, or pieces of foam; 3D polygons; sinusoidal or otherwise undulating ribbons; and embolic coils. In an example, a flexible expanding member can be expanded by filling it with a plurality of embolic members. In an example, a flexible expanding member can have holes in its perimeter, but the holes can be smaller than the embolic members so that embolic members are retained within the flexible expanding member. Relevant design variations discussed elsewhere in this disclosure or in priority-linked disclosures can also be applied to the example shown here.

Figure 49:
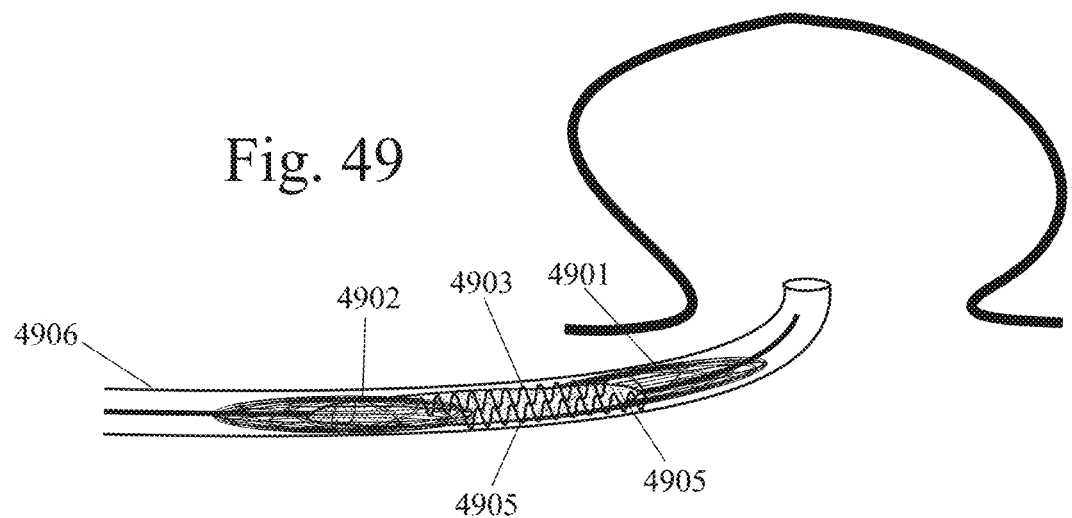
FIGS. 49 through 51 show a device with double resilient wider-than-neck portions and a flexible sac-filling portion.
Figure 50:
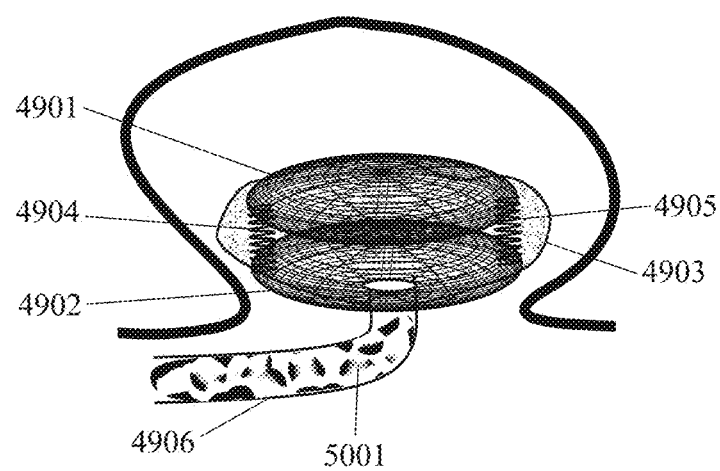
Figure 51:
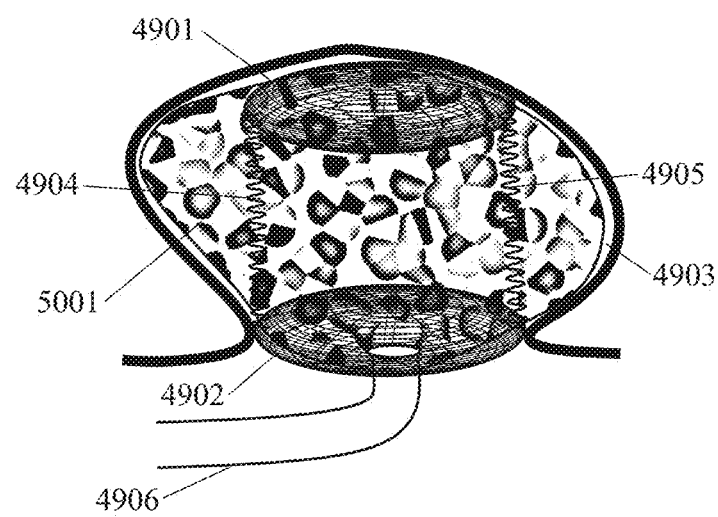

FIGS. 49 through 51 show three sequential views of a "double platter" intrasacular aneurysm occlusion device being deployed. This "double platter" intrasacular aneurysm occlusion device comprises: a distal arcuate three-dimensional stent 4901 which is configured to be expanded within an aneurysm sac; a proximal arcuate three-dimensional stent 4902 which is configured to be expanded within an aneurysm sac; a first stretchable and/or elastic connector 4904 which connects the distal arcuate three-dimensional stent and the proximal arcuate three-dimensional stent; a second stretchable and/or elastic connector 4905 which connects the distal arcuate three-dimensional stent and the proximal arcuate three-dimensional stent; a flexible expandable member 4903 which is filled with embolic members 5001 between the distal arcuate three-dimensional stent and the proximal arcuate three-dimensional stent; and a catheter 4906 which delivers embolic members into the flexible expandable member.

FIG. 49 shows this device at a first point in time when the device has been inserted into the parent vessel of an aneurysm. FIG. 50 shows this device at a second point in time when the distal and proximal arcuate three-dimensional stents have been inserted into and expanded within the aneurysm sac. FIG. 51 shows this device at a third point in time when the flexible expanding member has been expanded by being filled with embolic members, thereby pushing the distal and proximal arcuate three-dimensional stents apart and moving the proximal arcuate three-dimensional stent so that it covers the aneurysm neck. The catheter is subsequently removed.

In an example, an arcuate three-dimensional stent can be an expandable wire or polymer structure. In an example, an arcuate three-dimensional stent can be a self-expanding mesh, net, or lattice. In an example, an arcuate three-dimensional stent can have a first (compressed) configuration as it travels through a catheter and a second (expanded) configuration after it exits the catheter within an aneurysm sac. In an example, an arcuate three-dimensional stent in its second configuration can have a three-dimensional shape selected from the group consisting of: ellipsoid; ovaloid; torus; platter; pancake; Frisbee™; and disk. In an example, longitudinal axes of distal and proximal stents can be co-linear in their first configurations and parallel in their second configurations. In an example, longitudinal axes of distal and proximal stents can be aligned along a common line in their first configurations and parallel to each other in their second configurations. In an example, a proximal stent in its second configuration can be wider than the aneurysm neck. In an example, a proximal stent can be larger than a distal stent, or vice versa.

In an example, a stretchable and/or elastic connector can be a spring and/or undulating wire. In an example, a stretchable and/or elastic connector can be an elastic band, string, ribbon, and/or fiber. In an example, a first stretchable and/or elastic connector can connect first sides or perimeters of distal and proximal arcuate three-dimensional stents (e.g. to the left of the stent centroid) and a second stretchable and/or elastic connector can connect second sides or perimeters of the distal and proximal arcuate three-dimensional stents (e.g. to the right of the stent centroid).

In an example, a flexible expanding member can be selected from the group consisting of: balloon; liner; bag; net; mesh; and lattice. In an example, a flexible expanding member can be between distal and proximal arcuate three-dimensional stents. In an example, distal and proximal arcuate three-dimensional stents can be inside a flexible expanding member. In an example, a flexible expanding member can have a first (compressed) configuration as it travels through a catheter and a second (expanded) configuration after it exits the catheter within an aneurysm sac. In an example, a flexible expanding member can be elastic and/or stretchable. In an example, a flexible expanding member can be folded and/or pleated in its first configuration. In an example, a flexible expanding member can have a proximal opening through which embolic members are inserted and this opening can be closed after the flexible expanding member has been expanded. In an example, a flexible expanding member can have a (one-way) valve through which embolic members are inserted.

In an example, embolic members can be selected from the group consisting of: compressible balls or microspheres; rigid balls or microspheres; sponges, hydrogels, or pieces of foam; 3D polygons; sinusoidal or otherwise undulating ribbons; and embolic coils. In an example, a flexible expanding member can be expanded by filling it with a plurality of embolic members. In an example, a flexible expanding member can have holes in its perimeter, but the holes can be smaller than embolic members so that embolic members are retained within the flexible expanding member. Relevant design variations discussed elsewhere in this disclosure or in priority-linked disclosures can also be applied to the example shown here.

Figure 52:
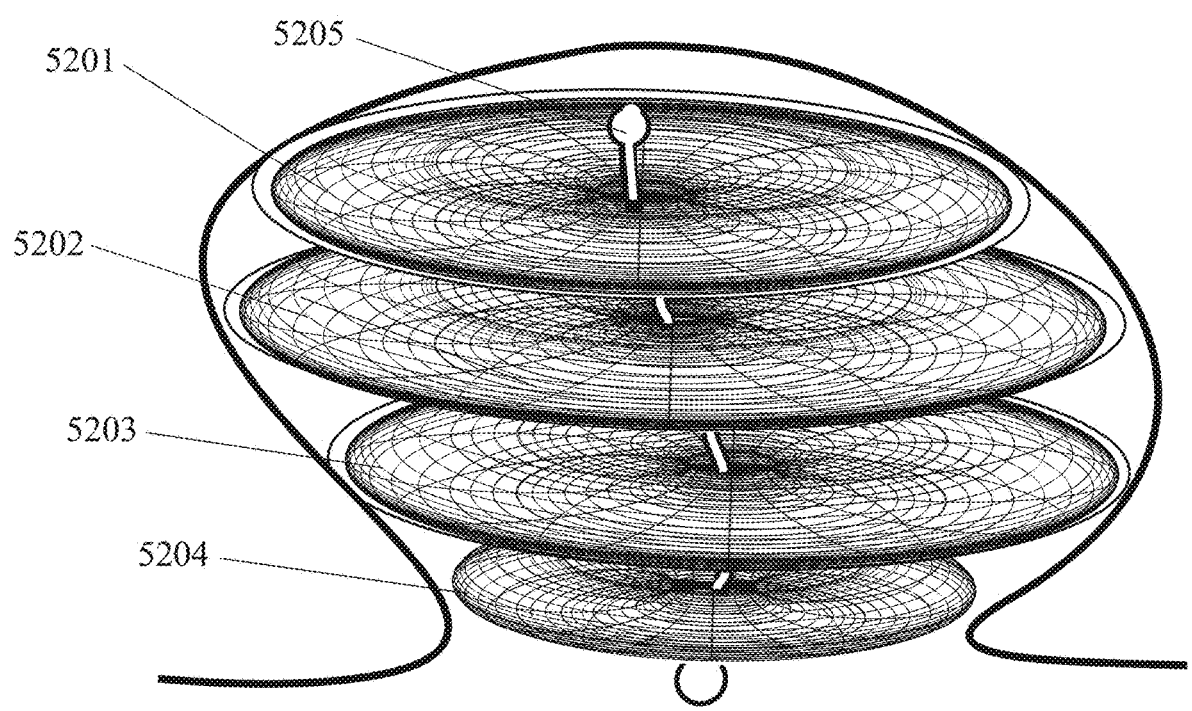
FIG. 52 shows a first device with a longitudinal series of centrally-connected embolic structures which is configured to be expanded within an aneurysm sac.

FIG. 52 shows a "multi-platter" intrasacular aneurysm occlusion device comprising: a series of at least three arcuate three-dimensional stents (four in this example—5201, 5202, 5203, and 5204) which is deployed within an aneurysm sac, wherein the arcuate three-dimensional stents in the series are connected to each other by a connector 5205; and wherein the arcuate three-dimensional stents in the series have first compressed configurations as they travel within a catheter and second expanded configurations after they are delivered from the catheter into an aneurysm sac. In an example, arcuate three-dimensional stents in the series can be centrally connected to each other. In an example, the centroids of arcuate three-dimensional stents in the series can be (pair-wise) attached to each other by a central connector. In an example, the shape of an arcuate three-dimensional stent can be selected from the group consisting of: apple shape; bowl shape; compress-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus.

In an example, a first arcuate three-dimensional stent in this series can be expanded in a first plane within the aneurysm sac, a second arcuate three-dimensional stent in this series can be expanded in a second plane within the aneurysm sac, and a third arcuate three-dimensional stent in this series can be expanded in a third plane within the aneurysm sac. In an example, these three planes can be substantially parallel to each other. In an example, these three planes can be substantially parallel to a plane which spans the opening of the aneurysm neck. In an example, a first arcuate three-dimensional stent in this series can have a first size and a second arcuate three-dimensional stent in this series can have a second size, wherein the second size is greater than the first size. In an example, the width of the most proximal arcuate three-dimensional stent in this series can be greater than the width of the aneurysm neck.

In an example, an arcuate three-dimensional stent in the middle portion of a series of arcuate three-dimensional stents can be wider than arcuate three-dimensional stents in distal and/or proximal portions of the series. In an example, an arcuate three-dimensional stent in the middle portion of a series of arcuate three-dimensional stents can be more resilient and/or less flexible than arcuate three-dimensional stents in distal and/or proximal portions of the series. In an example, an arcuate three-dimensional stent in the middle portion of a series of arcuate three-dimensional stents can be a resilient stent while arcuate three-dimensional stents in distal and/or proximal portions of the series can be flexible stents.

In an example, an arcuate three-dimensional stent in a distal portion of a series of arcuate three-dimensional stents can be wider than arcuate three-dimensional stents in a proximal portion. In an example, an arcuate three-dimensional stent in a distal portion of a series of arcuate three-dimensional stents can be more resilient and/or less flexible than arcuate three-dimensional stents in a proximal portion. In an example, an arcuate three-dimensional stent in a distal portion of a series of arcuate three-dimensional stents can be a resilient stent while arcuate three-dimensional stents in a proximal portion of the series can be flexible stents.

In an example, an arcuate three-dimensional stent in a proximal portion of a series of arcuate three-dimensional stents can be wider than arcuate three-dimensional stents in a distal portion. In an example, an arcuate three-dimensional stent in a proximal portion of a series of arcuate three-dimensional stents can be more resilient and/or less flexible than arcuate three-dimensional stents in a distal portion. In an example, an arcuate three-dimensional stent in a proximal portion of a series of arcuate three-dimensional stents can be a resilient stent while arcuate three-dimensional stents in a distal portion of the series can be flexible stents.

In an example, a series can comprise arcuate three-dimensional stents which are generally parallel to each other in their second (expanded) configurations. In an example, arcuate three-dimensional stents can have longitudinal axes which are generally co-linear in their first (compressed) configurations travelling through a catheter. In an example, an arcuate three-dimensional stent can have a longitudinal axis which is greater than its perpendicular cross-sectional axis in its first configuration, but its longitudinal axis can decrease and its perpendicular cross-sectional axis can increase in its second configuration. In an example, its perpendicular cross-sectional axis can expand to span the diameter of (a cross-section of) an aneurysm sac in its second configuration.

In an example, one or more of the arcuate three-dimensional stents in this series can be an expandable wire or polymer structure. In an example, one or more of the arcuate three-dimensional stents can be a self-expanding mesh, net, or lattice. In an example, an arcuate three-dimensional stent can have a first (compressed) configuration as it travels through a catheter and a second (expanded) configuration after it exits the catheter within an aneurysm sac. In an example, an arcuate three-dimensional stent in its second configuration can have a three-dimensional shape selected from the group consisting of: apple shape; bowl shape; compress-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus. In an example, a connector which connects arcuate three-dimensional stents in a series can be a wire, spring, band, or string. In an example, a connector can be elastic and/or stretchable. In an example, a connector can have a longitudinal "one-way ratchet" structure which enables arcuate three-dimensional stents to move closer to each other, but not move farther from each other. Relevant design variations discussed elsewhere in this disclosure or in priority-linked disclosures can also be applied to the example shown here.

In an example, an expanding arcuate embolic member can have a first configuration as is it delivered through a catheter toward an aneurysm sac and a second configuration after it is expanded within the aneurysm sac. In an example, an expanding arcuate embolic member in its second configuration can have a shape selected from the group consisting of: apple shape; bowl shape; compress-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus. In an example, an expanding arcuate embolic member can be a stent. In an example, an expanding arcuate embolic member can be an expanding wire mesh or lattice. In an example, an expanding arcuate embolic member can be an expanding polymer structure. In an example, an expanding arcuate embolic member can be an expanding gel. In an example, an expanding arcuate embolic member can be a self-expanding mesh, net, or lattice.

In an example, an expanding arcuate embolic member in its first configuration can have a longitudinal axis. In an example, an expanding arcuate embolic member in its first configuration can also have a cross-sectional axis which is perpendicular to its longitudinal axis. In an example, the longitudinal axis of an expanding embolic member can be shorter in its second configuration than in its first configuration. In an example, the cross-sectional axis of an expanding embolic member can be wider in its second configuration than in its first configuration. In an example, the longitudinal axis of an expanding embolic member can be greater than its cross-sectional axis in its first configuration and less than its cross-sectional axis in its second configuration. In an example, the cross-sectional axis of an expanding arcuate embolic member in its second configuration can be configured to be wider than an aneurysm neck.

In an example, a connecting line can be a wire, spring, or chain. In an example, a connecting line can be a string, thread, band, fiber, or suture. In an example, expanding arcuate embolic members can be centrally connected to each other by a connecting line. In an example, the centroids of expanding arcuate embolic members can be connected by a connecting line. In an example, expanding arcuate embolic members can slide (e.g. up or down) along a connecting line. In an example, expanding arcuate embolic members can slide along a connecting line, but only in one direction. In an example, a connecting line can have a ratchet structure which allows expanding arcuate embolic members to slide closer to each other but not slide further apart. In an example, this device can further comprise a locking mechanism which stops embolic members from sliding along a connecting line. In an example, application of electromagnetic energy to a connecting line can fuse the line with the expanding arcuate embolic members and stop them from sliding, effectively locking them in proximity to each other.

In an example, a first expanding arcuate embolic member can be expanded in a first plane within the aneurysm sac, a second expanding arcuate embolic member can be expanded in a second plane within the aneurysm sac, and a third expanding arcuate embolic member can be expanded in a third plane within the aneurysm sac. In an example, these three planes can be substantially parallel to each other. In an example, these three planes can be substantially parallel to a plane which spans the opening of the aneurysm neck. In an example, a first expanding arcuate embolic member can have a first size and a second expanding arcuate embolic member can have a second size, wherein the second size is greater than the first size. In an example, the width of the most proximal expanding arcuate embolic member can be greater than the width of the aneurysm neck.

In an example, a first expanding arcuate embolic member in its second configuration can be wider, thicker, less flexible, less elastic, less porous, denser, and/or more resilient than second or third expanding arcuate embolic members in their second configurations. In an example, a second expanding arcuate embolic member in its second configuration can be wider, thicker, less flexible, less elastic, less porous, denser, and/or more resilient than first or third expanding arcuate embolic members in their second configurations. In an example, a third expanding arcuate embolic member in its second configuration can be wider, thicker, less flexible, less elastic, less porous, denser, and/or more resilient than first or second expanding arcuate embolic members in their second configurations.

In an example, the width, thickness, flexibility, elasticity, porosity, density, or resilience of an expanding arcuate embolic member can be adjusted by a user in real time as the expanding arcuate embolic member is deployed in an aneurysm sac. In an example, the width, thickness, flexibility, elasticity, porosity, density, or resilience of an expanding arcuate embolic member can be adjusted by a user in real time by application of electromagnetic energy to the expanding arcuate embolic member as it is deployed in an aneurysm sac. In an example, the width, thickness, flexibility, elasticity, porosity, density, or resilience of an expanding arcuate embolic member can be adjusted by a user in real time by pulling, pushing, or rotating the connecting line as the expanding arcuate embolic member is deployed in an aneurysm sac. In an example, the width, thickness, flexibility, elasticity, porosity, density, or resilience of an expanding arcuate embolic member can be adjusted by a user in real time by pulling, pushing, or rotating the catheter as the expanding arcuate embolic member is deployed in an aneurysm sac. Relevant design variations discussed elsewhere in this disclosure or in priority-linked disclosures can also be applied to the example shown here.

Figure 53:
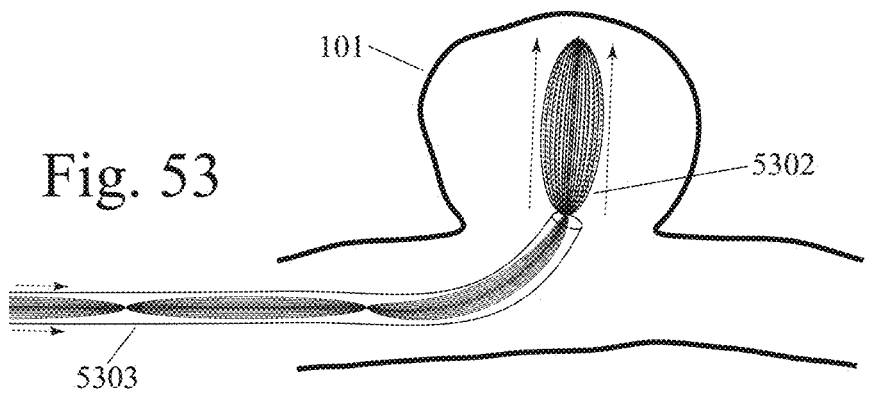
FIGS. 53 through 55 show a second device with a longitudinal series of centrally-connected embolic structures which is configured to be expanded within an aneurysm sac.
Figure 54:
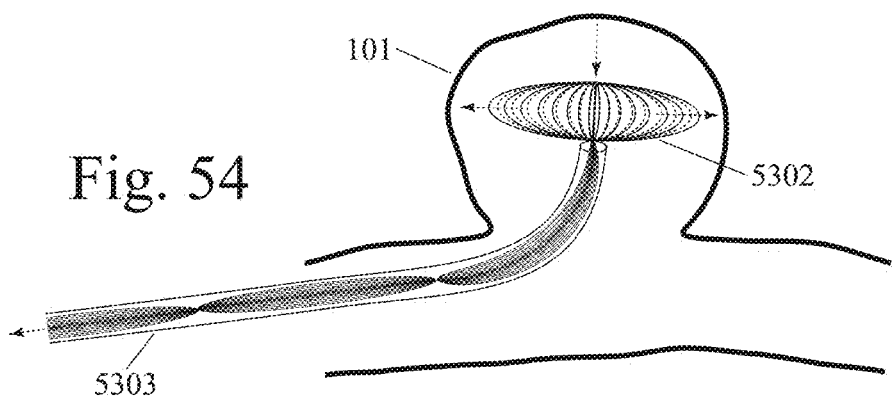

FIGS. 53 through 55 show an example of an intrasacular aneurysm occlusion device which can be described as aneurysm occlusion using multiple centrally-aligned arcuate embolic structures or portions. FIGS. 53 through 55 also show an example of an intrasacular aneurysm occlusion device comprising a longitudinal sequence of centrally-connected arcuate embolic structures or portions. In an example, an arcuate structure or portion can be a stent. In an example, an arcuate structure or portion can have an ellipsoid shape. In an example, an arcuate structure or portion can have another arcuate shape. In an example, the shape of an arcuate embolic structure or portion can be selected from the group consisting of: apple shape; bowl shape; compress-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus.

FIGS. 53 through 55 also show an intrasacular aneurysm occlusion device comprising: (a) a longitudinal lumen that is configured to be inserted into a blood vessel, wherein this lumen has a longitudinal axis spanning from its proximal end to its distal end and wherein the distal end is first inserted into the blood vessel; and (b) a plurality of longitudinally-linked configuration-changing embolic members which are configured to travel through the longitudinal lumen and to be inserted into an aneurysm; wherein each shape-changing embolic member has its own internally-referenced Z axis, X axis, and Y axis; wherein its Z axis is substantially parallel to the longitudinal axis of the longitudinal lumen as the embolic member travels through the longitudinal lumen, its X axis is substantially perpendicular to its Z axis, and its Y axis is substantially perpendicular to both its Z axis and X axis; wherein each configuration-changing embolic member has a first configuration as the member travels through the longitudinal lumen and a second configuration within the aneurysm after it exits the longitudinal lumen; wherein the distance of the embolic member spanning its Z axis is greater than the distance of the embolic member spanning its X axis or Y axis in the first configuration; wherein the distance of the embolic member spanning its Z axis is less than the distance of the embolic member spanning its X axis or Y axis in the second configuration; wherein the cross-sectional shape of the embolic member in an X-Z plane is substantially elliptical, oval, or another arcuate non-circular shape in the first configuration, with the longer dimension of the ellipse, oval, or another arcuate non-circular shape being along its Z axis; and wherein the cross-sectional shape of the embolic member in the X-Z plane is substantially elliptical, oval, or another arcuate non-circulate shape in the second configuration, with the longer dimension of the ellipse, oval, or another arcuate non-circular shape being along its X axis.

FIGS. 53 through 55 also show an intrasacular aneurysm occlusion device comprising: (a) a longitudinal lumen that is configured to be inserted into a blood vessel, wherein this blood vessel is the parent vessel from which an aneurysm has formed; and (b) a series of connected embolic ellipsoids, wherein these embolic ellipsoids are configured to travel in series through the longitudinal lumen and to be inserted into the aneurysm sac; wherein an embolic ellipsoid has a first orientation as it travels through the longitudinal lumen; wherein an embolic ellipsoid has a second orientation after it exits the longitudinal lumen; wherein in the first orientation the longitudinal axis of the ellipsoid is substantively parallel to the longitudinal axis of the longitudinal lumen; wherein in the second orientation the longitudinal axis of the ellipsoid is substantially perpendicular to its prior orientation traveling through the longitudinal lumen. In an example, this device can comprise a series of centrally-connected arcuate structures which have individual shapes which are not ellipsoids. In an example, the shapes of these centrally-connected structures can be selected from the group consisting of: apple shape; bowl shape; compress-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus.

In an example, an embolic ellipsoid can be a wire structure. In an example, an embolic ellipsoid can have a first orientation when it exits the aneurysm sac but then be compressed into a second orientation. In an example, the series of connected embolic ellipsoids can form a stack of connected ellipsoids which share a common central axis within the aneurysm sac. In an example, the series of connected embolic ellipsoids can form a stack of connected ellipsoid disks which share a common central axis within the aneurysm sac and fill a greater volume of the aneurysm sac than would be filled by a single hollow mesh structure with a similar size perimeter as the stack of connected ellipsoid disks. In an example, at least one of the connected ellipsoid disks can have a circumference that is larger than the circumference of the aneurysm neck in order to help keep the structure within the aneurysm sac.

In an example, an arcuate embolic structure can be a wire structure. In an example, an arcuate embolic structure can have a first orientation when it exits the aneurysm sac but then be compressed into a second orientation. In an example, the series of connected arcuate embolic structures can form a stack of connected arcuate embolic structures which share a common central axis within the aneurysm sac. In an example, the series of connected arcuate embolic structures can form a stack of connected arcuate embolic structures which share a common central axis within the aneurysm sac and fill a greater volume of the aneurysm sac than would be filled by a single hollow mesh structure with a similar size perimeter as the stack of connected arcuate embolic structures. In an example, at least one of the connected arcuate embolic structures can have a circumference that is larger than the circumference of the aneurysm neck in order to help keep the overall structure within the aneurysm sac. In an example, a series of connected arcuate embolic structures can form a longitudinally undulating and/or sinusoidal embolic stack within an aneurysm sac. In an example, a embolic structure deployed in an aneurysm sac can have undulating and/or sinusoidal variation in width. In an example, an embolic structure deployed in an aneurysm sac can comprise an longitudinally-undulating series of centrally-connected portions or sections.

We now discuss the components of the example that is shown in FIGS. 53 through 55 in detail. FIG. 53 shows an intrasacular aneurysm occlusion device that comprises: a longitudinal lumen 5303 that is configured to be inserted into a blood vessel, wherein this blood vessel is the parent vessel from which an aneurysm has formed; and a series of connected embolic ellipsoids (including 5302). In this example, the embolic ellipsoids (including 5302) are configured to travel in series through longitudinal lumen 5303 and be inserted into the aneurysm sac. In an example, this device can comprise a series of centrally-connected arcuate structures which have individual shapes which are not ellipsoids. In an example, the shapes of these centrally-connected structures can be selected from the group consisting of: apple shape; bowl shape; compress-sphere shape; cylinder; disk; doughnut shape; egg shape; ellipsoid; folded paper lantern shape; Frisbee™; frustum; hourglass shape; oval; peanut shape; pear shape; pumpkin shape; ring shape; Saturn shape; sphere; tire shape; and torus.

As shown in FIG. 54, each embolic ellipsoid (including 5302) can have a first orientation as it travels through lumen 5303 and a second orientation after it exits lumen 5303 inside aneurysm sac 101. In an example, each embolic ellipsoid can have a longitudinal axis. In an example, in the first orientation, the longitudinal axis of the ellipsoid (such as 5302) can be substantively-parallel to the longitudinal axis of lumen 5303. In an example, in the second orientation, the longitudinal axis of the ellipsoid (such as 5302) can be substantially-perpendicular to its prior orientation traveling through lumen 5303.

In an example, an embolic ellipsoid (such as 5302) can be oriented as it travels through lumen 5303 such that its longest axis is substantially-parallel to the longitudinal axis of lumen 5303. In an example, an embolic ellipsoid (such as 5302) can be compressed and/or reoriented after it exits lumen 5303 so that its longest axis becomes substantially-parallel to the plane that is defined by the central circumference of the aneurysm neck. In an example, the longitudinal axes of the embolic ellipsoids (such as 5302) as these ellipsoids travel through lumen 5303 can become the virtual lateral axes of these embolic ellipsoids (such as 5302) when these ellipsoids are compressed and/or reoriented after they exit lumen 5303.

In an example, the longitudinal axes (including 5302) of these ellipsoids (including 5302) can be compressed after the ellipsoids exit lumen 5303. In an example, this compression can be caused by movement of a wire, fiber, or other longitudinal flexible member that is connected to the ellipsoids. In an example, this compression can be caused by contact between the aneurysm wall and the ellipsoids. In an example, the embolic ellipsoids (including 5302) can have a shape memory and a prior shape to which they return after their release from lumen 5303. In an example, their return to a prior shape can cause the change in their orientation and/or compression after they exit lumen 5303. In this example, the embolic ellipsoids (including 5302) are wire structures.

As shown in FIG. 55, a series of connected embolic ellipsoids (including 5302) can form a stack of connected ellipsoids which share a common central axis within aneurysm sac 101. In an example, a series of connected embolic ellipsoids can form a stack of connected ellipsoid disks which share a common central axis within the aneurysm sac. In an example, this stack of connected ellipsoids can fill a greater volume of the aneurysm sac than would be filled by a single hollow-mesh structure (such as a wire-mesh single sphere or ellipsoid that is expanded with an aneurysm sac) with a similar-size perimeter as the combined stack of connected ellipsoid disks. As shown in FIG. 55, at least one of the connected ellipsoids has a circumference that is larger than the circumference of the aneurysm neck in order to help keep the stack within the aneurysm sac.

As shown in FIGS. 53 through 55, an intrasacular aneurysm occlusion device can be formed from multiple arcuate portions connected together in parallel with the plane of an aneurysm neck. As shown in FIGS. 53 through 55, a multi-portion longitudinal stack can comprise a centrally-connected plurality of proximal, central, and distal arcuate portions. In an example, different arcuate portions of a multi-portion stack "need not be of uniform tensile strength, flexibility, plasticity, or elasticity." For example, distal arcuate portions of a stack can be more flexible (and/or have lower tensile strength) than proximal arcuate portions. Also, distal arcuate portions of a stack can be more porous than proximal arcuate portions of the stack.

A longitudinal series of centrally-connected arcuate embolic structures can form a stack of arcuate embolic structures which share a common central axis within aneurysm sac. In an example, this stack of connected arcuate embolic structures can fill a greater volume of the aneurysm sac than would be filled by a single hollow-mesh structure (such as a wire-mesh single sphere or ellipsoid that is expanded with an aneurysm sac) with a similar-size perimeter as the combined stack of connected arcuate embolic structures. At least one of the connected arcuate embolic structures can have a circumference that is larger than the circumference of the aneurysm neck in order to help keep the stack within the aneurysm sac.

In an example, a first and/or second shape-changing embolic member can be a wire structure. In an example, a first and/or second shape-changing embolic member can be a metal mesh, lattice, or set of radial spokes. In an example, a first and/or second shape-changing embolic member can be a flexible metal mesh and/or lattice. In an example, a first and/or second shape-changing embolic member can be hollow. In an example, a first and/or second shape-changing embolic member can be an expandable hollow wire mesh, lattice, or set of radial spokes. In an example, a first and/or second shape-changing embolic member can be a wire mesh, lattice, or set of radial spokes which is made from metal wires, strands, strips, ribbons, filaments, cables, or coils. In an example, a first and/or second shape-changing embolic member can be a metal stent.

In an example, a first and/or second shape-changing embolic member can be a polymer structure. In an example, a first and/or second shape-changing embolic member can be a polymer mesh and/or lattice. In an example, a first and/or second shape-changing embolic member can be a flexible polymer mesh and/or lattice. In an example, a first and/or second shape-changing embolic member can be a hollow polymer mesh and/or lattice. In an example, a first and/or second shape-changing embolic member can be an expandable polymer mesh and/or lattice. In an example, a first and/or second shape-changing embolic member can be a structure comprising a radially-distributed longitudinal array of polymer strands, strips, ribbons, filaments, cables, coils, and/or threads. In an example, a first and/or second shape-changing embolic member can be a polymer stent.

In an example, a first and/or second shape-changing embolic member can be a shape-changing foam or gel structure. In an example, a shape-changing embolic member can made from hydrogel. In an example, a first and/or second shape-changing embolic member can be an expandable foam or gel structure which expands when released from a longitudinal lumen. In an example, a first shape-changing embolic member can be a foam or gel structure whose X axis expands more than its Z axis. In an example, a second shape-changing embolic member can be a foam or gel structure whose XX axis expands more than its ZZ axis.

In an example, a first shape-changing embolic member can have a shape in its second configuration which is selected from the group consisting of: ellipsoid, paraboloid, sphere, disk, cylinder, ovaloid, convex lens, wheel, tire shape, apple shape, doughnut, and torus. In an example, a first shape-changing embolic member can have a cross-sectional shape in the X-Z plane in its second configuration which is selected from the group consisting of: ellipse, reflected parabola, circle, oval, convex lens, and torus. In an example, a second shape-changing embolic member can have a shape in its fourth configuration which is selected from the group consisting of: ellipsoid, paraboloid, sphere, disk, cylinder, ovaloid, convex lens, wheel, tire shape, apple shape, doughnut, and torus. In an example, a second shape-changing embolic member can have a cross-sectional shape in the XX-ZZ plane in its fourth configuration which is selected from the group consisting of: ellipse, reflected parabola, circle, oval, convex lens, and torus.

In an example, a first shape-changing embolic member can have a shape in its first configuration wherein the longest axis of this shape is substantially parallel to the longitudinal axis of the longitudinal lumen within which it travels. In an example, a first shape-changing embolic member can have a shape in its second configuration wherein the longest axis of this shape is substantially parallel to the circumference of the neck of an aneurysm into which it is inserted. In an example, a second shape-changing embolic member can have a shape in its third configuration wherein the longest axis of this shape is substantially parallel to the longitudinal axis of the longitudinal lumen within which it travels. In an example, a second shape-changing embolic member can have a shape in its fourth configuration wherein the longest axis of this shape is substantially parallel to the circumference of the neck of an aneurysm into which it is inserted.

In an example, the longest axes of first and second shape-changing embolic members can be longitudinally and sequentially aligned when these shape-changing embolic members are in their first and third configurations, respectively. In an example, the longest axes of first and second shape-changing embolic members can be parallel to each other when these shape-changing embolic members are in their second and fourth configurations, respectively. In an example, the longest axes of first and second shape-changing embolic members can be arranged in series when these shape-changing embolic members are in their first and third configurations, respectively. In an example, the longest axes of first and second shape-changing embolic members can be arranged in parallel when these shape-changing embolic members are in their second and fourth configurations, respectively.

In an example, this invention can be embodied in an intrasacular aneurysm occlusion device comprising a plurality of shape-changing embolic members. In an example, this invention can be embodied in a series of connected embolic ellipsoids or tori. In an example, a first shape-changing embolic member and a second shape-changing embolic member can be part of a sequence and/or series of two shape-changing embolic members which collectively occlude an aneurysm. In an example, a first shape-changing embolic member and a second shape-changing embolic member can be part of a sequence and/or series of three shape-changing embolic members which collectively occlude an aneurysm. In an example, a first shape-changing embolic member and a second shape-changing embolic member can be part of a sequence and/or series of four shape-changing embolic members which collectively occlude an aneurysm. In an example, a first shape-changing embolic member and a second shape-changing embolic member can be part of a sequence and/or series of five or more shape-changing embolic members which collectively occlude an aneurysm.

In an example, a first shape-changing embolic member and a second shape-changing embolic member can be part of a centrally-aligned sequence and/or series of two shape-changing embolic members which collectively occlude an aneurysm. In an example, a first shape-changing embolic member and a second shape-changing embolic member can be part of a centrally-aligned sequence and/or series of three shape-changing embolic members which collectively occlude an aneurysm. In an example, a first shape-changing embolic member and a second shape-changing embolic member can be part of a centrally-aligned sequence and/or series of four shape-changing embolic members which collectively occlude an aneurysm. In an example, a first shape-changing embolic member and a second shape-changing embolic member can be part of a centrally-aligned sequence and/or series of five or more shape-changing embolic members which collectively occlude an aneurysm.

In an example, a first shape-changing embolic member and a second shape-changing embolic member can be part of a centrally-aligned sequence of two shape-changing elliptical or toroidal embolic members which collectively occlude an aneurysm. In an example, a first shape-changing embolic member and a second shape-changing embolic member can be part of a centrally-aligned sequence of three shape-changing elliptical or toroidal embolic members which collectively occlude an aneurysm. In an example, a first shape-changing embolic member and a second shape-changing embolic member can be part of a centrally-aligned sequence of four shape-changing elliptical or toroidal embolic members which collectively occlude an aneurysm. In an example, a first shape-changing embolic member and a second shape-changing embolic member can be part of a centrally-aligned sequence of five or more shape-changing elliptical or toroidal embolic members which collectively occlude an aneurysm.

In an example, a plurality of shape-changing embolic members, including first and second shape-changing embolic members, can form a stack of embolic members which fill a greater percentage of the volume of the aneurysm sac than is achieved by traditional coiling. In an example, a plurality of shape-changing embolic members, including first and second shape-changing embolic members, can form a stack of embolic members which better conform to the (irregular) shape of an aneurysm sac than is achieved by traditional coiling. In an example, a plurality of shape-changing embolic members, including first and second shape-changing embolic members, can form a stack of embolic members which better reduces circulation of blood into an aneurysm sac than is achieved by traditional coiling.

In an example, a plurality of shape-changing embolic members, including first and second shape-changing embolic members, can form a stack of embolic members which fill a greater percentage of the volume of the aneurysm sac than does a single hollow mesh structure. In an example, a plurality of shape-changing embolic members, including first and second shape-changing embolic members, can form a stack of embolic members which better conform to the (irregular) shape of an aneurysm sac than does a single hollow mesh structure. In an example, a plurality of shape-changing embolic members, including first and second shape-changing embolic members, can form a stack of embolic members which better reduces circulation of blood into an aneurysm sac than does a single hollow mesh structure.

In an example, a plurality of shape-changing embolic members can share a common central axis within an aneurysm sac. In an example, a plurality of shape-changing embolic members can form a stack of connected ellipsoid disks which share a common central axis within the aneurysm sac. In an example, a stack of connected ellipsoids can fill a greater volume of the aneurysm sac than would be filled by a single hollow-mesh structure (such as a wire-mesh single sphere or ellipsoid that is expanded with an aneurysm sac) with a similar-size perimeter as the combined stack of connected ellipsoid disks. In an example, at least one of the connected ellipsoids has a circumference that is larger than the circumference of the aneurysm neck in order to help keep the stack within the aneurysm sac.

In an example, a first shape-changing embolic member can be distal relative to a second shape-changing embolic member. In an example, a first shape-changing embolic member can be contiguous to a second shape-changing embolic member. In an example, a first shape-changing embolic member and a second shape-changing embolic member can be centrally aligned. In an example, a first shape-changing embolic member in its second configuration can be centrally aligned (along its Z axis) with a second shape-changing member in its fourth configuration (along its ZZ axis).

In an example, a first or second shape-changing embolic member can change shape from a first or third configuration to a second or fourth configuration, respectively, once it is released from the longitudinal lumen. In an example, a first or second shape-changing embolic member can have a shape memory which causes it to change shape from a first or third configuration to a second or fourth configuration, respectively, once it is released from the longitudinal lumen. In an example, the shape of a first or second shape-changing embolic member can be changed from a first or third configuration to a second or fourth configuration, respectively, by expansion of a balloon or other expanding member. In an example, the shape of a first or second shape-changing embolic member can be changed from a first or third configuration to a second or fourth configuration, respectively, by movement of a wire connected to the embolic member relative to the longitudinal lumen. In an example, a first or second shape-changing embolic member can self-expand from a first or third configuration to a second or fourth configuration, respectively, because the embolic member is made from an expanding foam or gel.

In an example, a first or second shape-changing embolic member can have a first shape when it first exits a longitudinal lumen into an aneurysm sac, but can then be compressed or otherwise changed into a second shape. In an example, for the first shape-changing embolic member, a second shape can be the second configuration. In an example, for the second shape-changing embolic member, a second shape can be the fourth configuration. In an example, a first shape-changing embolic member can exit the longitudinal lumen in its first configuration, but then be moved into its second configuration by compression or other manipulation. In an example, a second shape-changing embolic member can exit the longitudinal lumen in its third configuration, but then be moved into its fourth configuration by compression or other manipulation. In an example, a first shape-changing embolic member can exit the longitudinal lumen in its first configuration, but then self-expand into its second configuration. In an example, a second shape-changing embolic member can exit the longitudinal lumen in its third configuration, but then self-expand into its fourth configuration.

In an example, a first or second shape-changing embolic member can have its shape changed by movement of a wire, fiber, or other longitudinal flexible member that is connected to the embolic member. In an example, a first or second shape-changing embolic member can have its shape changed by contact between the aneurysm wall and the embolic member. In an example, a first or second shape-changing embolic member can have a shape memory and a prior shape to which it returns after it is released from a longitudinal lumen.

In an example, the sizes of first and second shape-changing embolic members can be the same. In an example, the shapes of first and second shape-changing embolic members can be the same. In an example, the sizes of first and second shape-changing embolic members can be different. In an example, the shapes of first and second shape-changing embolic members can be different. In an example, a first shape-changing embolic member can have a circumference in its second configuration that is larger than the circumference of an aneurysm neck in order to keep it within the aneurysm sac. In an example, a second shape-changing embolic member can have a circumference in its fourth configuration that is larger than the circumference of an aneurysm neck in order to keep it within the aneurysm sac.

In an example, the sizes of first and second shape-changing embolic members can be the same in their first and third configurations, but different in their second and fourth configurations, wherein this difference is controlled by the person deploying them in order to better conform to the size and shape of the aneurysm in which they are inserted. In an example, the shapes of first and second shape-changing embolic members can be the same in their first and third configurations, but different in their second and fourth configurations, wherein this difference is controlled by the person deploying them in order to better conform to the size and shape of the aneurysm in which they are inserted.

The size of a second shape-changing embolic member can be greater than the size of a first shape-changing embolic member. The shape of a second shape-changing embolic member can be different than the shape of a first shape-changing embolic member. In an example, a distal-to-proximal sequence of multiple shape-changing embolic members can be progressively larger and/or wider as they are sequentially deployed in an aneurysm. In an example, a distal-to-proximal sequence of multiple shape-changing embolic members can first be progressively larger and/or wider and then progressively smaller and/or narrower as they are sequentially deployed in an aneurysm. In an example, the progression of sizes and/or widths of a series of multiple shape-changing embolic members can be adjusted, controlled, and/or varied in real time by a person deploying them in order to best match the contours of a specific aneurysm sac. In an example, the progression of sizes and/or widths of a series of multiple shape-changing embolic members can be adjusted, controlled, and/or varied in real time by a person deploying them in order to best fill a specific aneurysm sac.

In an example, this invention can be embodied in an aneurysm occlusion device comprising: a longitudinal lumen that is configured to be inserted into a blood vessel, wherein this lumen has a longitudinal axis spanning from its proximal end to its distal end and wherein the distal end is first inserted into the blood vessel; and a plurality of shape-changing embolic members which are configured to travel through the longitudinal lumen and to be inserted into an aneurysm, wherein each shape-changing embolic member in the plurality of shape-changing embolic members has a first configuration as it travels through the longitudinal lumen and a second configuration after it exits the lumen into the aneurysm, wherein each shape-changing embolic member has a Z axis which is substantially parallel to the longitudinal axis of the longitudinal lumen in its first configuration and an X axis which is perpendicular to the Z axis, and wherein for each shape-changing embolic member the length of its Z axis is greater than the length of its X axis in its first configuration and the length of its Z axis is less than the length of its X axis in the second configuration.

In an example, a longitudinal lumen can be a removable catheter. In an example, a shape-changing embolic member can comprise a metal mesh, lattice, or set of radial spokes. In an example, a shape-changing embolic member can have a shape in its second configuration which is selected from the group consisting of: ellipsoid, paraboloid, sphere, disk, cylinder, ovaloid, convex lens, wheel, tire shape, apple shape, doughnut, and torus. In an example, a shape-changing embolic member can have a shape in its first configuration wherein the longest axis of this shape is substantially parallel to the longitudinal axis of the longitudinal lumen within which it travels. In an example, a shape-changing embolic member can have a shape in its second configuration wherein the longest axis of this shape is configured to be substantially parallel to the circumference of the neck of an aneurysm into which it is inserted.

In an example, the longest axes of the plurality of shape-changing embolic members can be longitudinally and sequentially aligned in their first configurations and the longest axes of the plurality of shape-changing embolic members can be parallel to each other in their second configurations. In an example, a plurality of shape-changing embolic members are centrally-aligned. In an example, differences in the sizes and/or widths of a series of multiple shape-changing embolic members can be adjusted, controlled, and/or varied in real time by a person deploying them in order to best match the contours of a specific aneurysm sac.

In an example, an intrasacular aneurysm occlusion device can comprise: a longitudinal lumen that is configured to be inserted into a blood vessel, wherein this lumen has a longitudinal axis spanning from its proximal end to its distal end and wherein the distal end is first inserted into the blood vessel; a first shape-changing embolic member which is configured to travel through the longitudinal lumen and to be inserted into an aneurysm, wherein this first shape-changing embolic member has a first configuration as it travels through the longitudinal lumen and a second configuration after it exits the lumen into the aneurysm, wherein this first shape-changing embolic member has a Z axis which is substantially parallel to the longitudinal axis of the longitudinal lumen in its first configuration and an X axis which is perpendicular to the Z axis, and wherein the length of the Z axis is greater than the length of the X axis in the first configuration and the length of the Z axis is less than the length of the X axis in the second configuration; and a second shape-changing embolic member which is configured to travel through the longitudinal lumen and to be inserted into an aneurysm, wherein this second shape-changing embolic member has a third configuration as it travels through the longitudinal lumen and a fourth configuration after it exits the lumen into the aneurysm, wherein this second shape-changing embolic member has a ZZ axis which is substantially parallel to the longitudinal axis of the longitudinal lumen in its third configuration and an XX axis which is perpendicular to the ZZ axis, and wherein the length of the ZZ axis is greater than the length of the XX axis in the third configuration and the length of the ZZ axis is less than the length of the XX axis in the fourth configuration.

In an example, a longitudinal lumen is a removable catheter. In an example, a first and/or second shape-changing embolic member can comprise a metal mesh, lattice, or set of radial spokes. In an example, a first and/or second shape-changing embolic member can have a shape in its second configuration which is selected from the group consisting of: ellipsoid, paraboloid, sphere, disk, cylinder, ovaloid, convex lens, wheel, tire shape, apple shape, doughnut, and torus. In an example, a first shape-changing embolic member can have a shape in its first configuration wherein the longest axis of this shape is substantially parallel to the longitudinal axis of the longitudinal lumen within which it travels. In an example, a first shape-changing embolic member can have a shape in its second configuration wherein the longest axis of this shape is configured to be substantially parallel to the circumference of the neck of an aneurysm into which it is inserted.

In an example, the longest axes of first and second shape-changing embolic members can be longitudinally and sequentially aligned in their first and third configurations, respectively, and the longest axes of the first and second shape-changing embolic members can be parallel to each other in their second and fourth configurations, respectively. In an example, first and second shape-changing embolic members can be centrally-aligned. In an example, differences in the sizes and/or widths of first and second shape-changing embolic members in their second and fourth configurations, respectively, can be adjusted, controlled, and/or varied in real time by a person deploying them in order to best match the contours of a specific aneurysm sac.

In an example, an intrasacular aneurysm occlusion device can comprise: a longitudinal lumen that is configured to be inserted into a blood vessel, wherein this lumen has a longitudinal axis spanning from its proximal end to its distal end and wherein the distal end is first inserted into the blood vessel; a first shape-changing ellipsoidal or toroidal embolic member which is configured to travel through the longitudinal lumen and to be inserted into an aneurysm, wherein this first shape-changing ellipsoidal or toroidal embolic member has a first configuration as it travels through the longitudinal lumen and a second configuration after it exits the lumen into the aneurysm, wherein this first shape-changing ellipsoidal or toroidal embolic member has a Z axis which is substantially parallel to the longitudinal axis of the longitudinal lumen in its first configuration and an X axis which is perpendicular to the Z axis, and wherein the length of the Z axis is greater than the length of the X axis in the first configuration and the length of the Z axis is less than the length of the X axis in the second configuration; and a second shape-changing ellipsoidal or toroidal embolic member which is configured to travel through the longitudinal lumen and to be inserted into an aneurysm, wherein this second shape-changing ellipsoidal or toroidal embolic member has a third configuration as it travels through the longitudinal lumen and a fourth configuration after it exits the lumen into the aneurysm, wherein this second shape-changing ellipsoidal or toroidal embolic member has a ZZ axis which is substantially parallel to the longitudinal axis of the longitudinal lumen in its third configuration and an XX axis which is perpendicular to the ZZ axis, and wherein the length of the ZZ axis is greater than the length of the XX axis in the third configuration and the length of the ZZ axis is less than the length of the XX axis in the fourth configuration.

In an example, differences in sizes and/or widths of first and second ellipsoidal or toroidal embolic members in their second and fourth configurations, respectively, can be adjusted, controlled, and/or varied in real time by a person deploying them in order to best match the contours of a specific aneurysm sac. Relevant embodiment variations discussed elsewhere in this disclosure or in priority-linked disclosures can also apply to this example.

In an example, different portions, segments, or undulations of a continuous braided intrasacular aneurysm occlusion device can have different braid patterns. In an example, a proximal portion, segment, or undulation of an intrasacular aneurysm occlusion device can have a first braid pattern and a distal portion, segment, or undulation of this device can have a second braid pattern. In an example, different portion, segment, or undulations of a continuous intrasacular aneurysm occlusion device can have different braid densities. In an example, a proximal portion, segment, or undulation of an intrasacular aneurysm occlusion device can have a higher braid density than a distal portion, segment, or undulation of this device. In an example, different portion, segment, or undulations of a continuous intrasacular aneurysm occlusion device can have different braid angles. In an example, a proximal portion, segment, or undulation of an intrasacular aneurysm occlusion device can have a greater braid angle than a distal portion, segment, or undulation of this device.

In an example, different portion, segment, or undulations of a continuous intrasacular aneurysm occlusion device can have different braid pitches. In an example, a proximal portion, segment, or undulation of an intrasacular aneurysm occlusion device can have a first braid pitch and a distal portion, segment, or undulation of this device can have a second braid pitch. In an example, different portion, segment, or undulations of a continuous intrasacular aneurysm occlusion device can have different braid filament sizes. In an example, a proximal portion, segment, or undulation of an intrasacular aneurysm occlusion device can have a first braid filament size and a distal portion, segment, or undulation of this device can have a second braid filament size.

In an example, an intrasacular aneurysm occlusion device can comprise: (a) a resilient wider-than-neck portion with a first configuration as it is transported to an aneurysm sac and a second configuration after it has been expanded within the aneurysm sac; wherein the resilient wider-than-neck portion in its second configuration has a width which is larger than the diameter of the neck of the aneurysm sac; and wherein the resilient wider-than-neck in its second configuration has a first level of flexibility, elasticity, and/or malleability; and (b) a flexible sac-filling portion with a first configuration as it is being transported to an aneurysm sac and a second configuration after it has been expanded within the aneurysm sac; wherein the flexible sac-filling portion is expanded from its first configuration to its second configuration by the insertion of embolic members into the flexible sac-filling portion; and wherein the flexible sac-filling portion in its second configuration has a second level of flexibility, elasticity, and/or malleability which is greater than the first level of flexibility, elasticity, and/or malleability.

In an example, a resilient wider-than-neck portion can be a stent or neck bridge. In an example, a flexible sac-filling portion can be a net or mesh. In an example, a resilient wider-than-neck portion can have a shape in its second configuration which is selected from the group consisting of: ellipsoidal shape; spherical shape; bowl shape; toroidal shape; apple shape; and pear, egg, or hourglass shape. In an example, a resilient wider-than-neck portion can be inside a flexible sac-filling portion. In an example, a resilient wider-than-neck portion and a flexible sac-filling portion can be nested. In an example, a resilient wider-than-neck portion and a flexible sac-filling portion can be concentric. In an example, a resilient wider-than-neck portion can be inside, but attached to, a flexible sac-filling portion.

In an example, the centroid of a resilient wider-than-neck portion can be proximal relative to the centroid of a flexible sac-filling portion. In an example, at least three-quarters of the volume of a resilient wider-than-neck portion in its second configuration can be within the proximal half of an aneurysm sac. In an example, a resilient wider-than-neck portion and a flexible sac-filling portion can be different parts of the same continuous structure, with the resilient wider-than-neck portion comprising a proximal surface of the structure and the flexible sac-filling portion comprising a distal surface of the structure. In an example, a resilient wider-than-neck portion can further comprise an adjustable opening through which embolic members are inserted into a flexible sac-filling portion. In an example, embolic members can be selected from the group consisting of: microsponges, pieces of gel, pieces of foam, beads, microspheres, and embolic coils.

In an example, an intrasacular aneurysm occlusion device can comprise: a net or mesh with a first level of flexibility, elasticity, or malleability; wherein the net or mesh is configured to be inserted into and expanded within an aneurysm sac; wherein the net or mesh is expanded by insertion of a plurality of embolic members into the net or mesh; wherein the post-expansion centroid of the net or mesh is configured to be at a first location within the aneurysm sac; and a stent or lattice with a second level of flexibility, elasticity, or malleability; wherein the stent or lattice is configured to be inserted into and expanded within the aneurysm sac; wherein the post-expansion centroid of the stent or lattice is configured to be at a second location within the aneurysm sac; wherein the first level is greater than the second level; wherein the first location is further from the aneurysm neck than the second location; and wherein the stent or lattice is inside the net or mesh.

In an example, an intrasacular aneurysm occlusion device can comprise: a net or mesh which is configured to be expanded within an aneurysm sac, wherein this net or mesh is filled with embolic members, wherein the net or mesh has non-uniform flexibility, wherein the net or mesh has a first flexibility at a proximal location, wherein the net or mesh has a second flexibility at a distal location, and wherein the second flexibility is greater than the first flexibility. In an example, an intrasacular aneurysm occlusion device can comprise: a net or mesh which is configured to be expanded within an aneurysm sac, wherein this net or mesh is filled with embolic members, wherein the net or mesh has non-uniform tensile strength, wherein the net or mesh has a first tensile strength at a proximal location, wherein the net or mesh has a second tensile strength at a distal location, and wherein the second tensile strength is less than the first tensile strength.

In an example, an intrasacular aneurysm occlusion device can comprise: a longitudinal lumen that is configured to be inserted into a blood vessel, wherein this lumen has a longitudinal axis spanning from its proximal end to its distal end and wherein the distal end is first inserted into the blood vessel; and a plurality of longitudinally-linked configuration-changing embolic members which are configured to travel through the longitudinal lumen and to be inserted into an aneurysm; wherein each shape-changing embolic member has its own internally-referenced Z axis, X axis, and Y axis; wherein its Z axis is substantially parallel to the longitudinal axis of the longitudinal lumen as the embolic member travels through the longitudinal lumen, its X axis is substantially perpendicular to its Z axis, and its Y axis is substantially perpendicular to both its Z axis and X axis; wherein each configuration-changing embolic member has a first configuration as the member travels through the longitudinal lumen and a second configuration within the aneurysm after it exits the longitudinal lumen; wherein the distance of the embolic member spanning its Z axis is greater than the distance of the embolic member spanning its X axis or Y axis in the first configuration; wherein the distance of the embolic member spanning its Z axis is less than the distance of the embolic member spanning its X axis or Y axis in the second configuration; wherein the cross-sectional shape of the embolic member in an X-Z plane is substantially elliptical, oval, or another arcuate non-circular shape in the first configuration, with the longer dimension of the ellipse, oval, or another arcuate non-circular shape being along its Z axis; and wherein the cross-sectional shape of the embolic member in the X-Z plane is substantially elliptical, oval, or another arcuate non-circulate shape in the second configuration, with the longer dimension of the ellipse, oval, or another arcuate non-circular shape being along its X axis.

In an example, an intrasacular aneurysm occlusion device can comprise: (a) a longitudinal lumen that is configured to be inserted into a blood vessel, wherein this lumen has a longitudinal axis spanning from its proximal end to its distal end and wherein the distal end is first inserted into the blood vessel; and (b) a plurality of shape-changing embolic members which are configured to travel through the longitudinal lumen and to be inserted into an aneurysm, wherein each shape-changing embolic member in the plurality of shape-changing embolic members has a first configuration as it travels through the longitudinal lumen and a second configuration after it exits the lumen into the aneurysm, wherein each shape-changing embolic member has a Z axis which is substantially parallel to the longitudinal axis of the longitudinal lumen in its first configuration and an X axis which is perpendicular to the Z axis, and wherein for each shape-changing embolic member the length of its Z axis is greater than the length of its X axis in its first configuration and the length of its Z axis is less than the length of its X axis in the second configuration. In an example, a longitudinal lumen can be a removable catheter.

In an example, an intrasacular aneurysm occlusion device can comprise: (a) a longitudinal lumen that is configured to be inserted into a blood vessel, wherein this lumen has a longitudinal axis spanning from its proximal end to its distal end and wherein the distal end is first inserted into the blood vessel; (b) a first shape-changing embolic member which is configured to travel through the longitudinal lumen and to be inserted into an aneurysm, wherein this first shape-changing embolic member has a first configuration as it travels through the longitudinal lumen and a second configuration after it exits the lumen into the aneurysm, wherein this first shape-changing embolic member has a Z axis which is substantially parallel to the longitudinal axis of the longitudinal lumen in its first configuration and an X axis which is perpendicular to the Z axis, and wherein the length of the Z axis is greater than the length of the X axis in the first configuration and the length of the Z axis is less than the length of the X axis in the second configuration; and (c) a second shape-changing embolic member which is configured to travel through the longitudinal lumen and to be inserted into an aneurysm, wherein this second shape-changing embolic member has a third configuration as it travels through the longitudinal lumen and a fourth configuration after it exits the lumen into the aneurysm, wherein this second shape-changing embolic member has a ZZ axis which is substantially parallel to the longitudinal axis of the longitudinal lumen in its third configuration and an XX axis which is perpendicular to the ZZ axis, and wherein the length of the ZZ axis is greater than the length of the XX axis in the third configuration and the length of the ZZ axis is less than the length of the XX axis in the fourth configuration.

In an example, an intrasacular aneurysm occlusion device can comprise: a net or mesh which is configured to be expanded within an aneurysm sac, wherein this net or mesh is filled with embolic members, wherein the net or mesh has non-uniform flexibility, wherein the net or mesh has a first flexibility at a proximal location, wherein the net or mesh has a second flexibility at a distal location, and wherein the second flexibility is greater than the first flexibility.

I claim:

1. An intrasacular aneurysm occlusion device comprising:
a resilient wider-than-neck portion which is inserted into an aneurysm sac; wherein the resilient wider-than-neck portion is collapsed in the aneurysm sac from a generally spherical configuration into a generally hemispherical, double-layered configuration; wherein the resilient wider-than-neck portion in its hemispherical, double-layered configuration has a width which is larger than the diameter of the neck of the aneurysm sac; and wherein the resilient wider-than-neck in its hemispherical, double-layered configuration has a first level of flexibility, elasticity, and/or malleability; and
a flexible sac-filling portion which is inserted into the aneurysm sac; wherein the flexible sac-filling portion has a first configuration as it is being transported to an aneurysm sac and a second configuration after it has been expanded within the aneurysm sac; wherein the flexible sac-filling portion is expanded from its first configuration to its second configuration by the insertion of embolic members into the flexible sac-filling portion; and wherein the flexible sac-filling portion in its second configuration has a second level of flexibility, elasticity, and/or malleability which is greater than the first level of flexibility, elasticity, and/or malleability.

2. The device in claim 1 wherein the flexible sac-filling portion is a net or mesh.

3. The device in claim 1 wherein the resilient wider-than-neck portion further comprises an adjustable opening through which embolic members are inserted into the flexible sac-filling portion.

4. The device in claim 1 wherein embolic members are selected from the group consisting of: microsponges, pieces of gel, pieces of foam, beads, microspheres, and embolic coils.

5. An intrasacular aneurysm occlusion device comprising:
a resilient wider-than-neck portion which is inserted into an aneurysm sac; wherein the resilient wider-than-neck portion is collapsed in the aneurysm sac from a generally spherical configuration into a generally hemispherical, double-layered configuration by pulling on a wire or other longitudinal member which is attached to a distal end of the resilient wider-than-neck portion; wherein the resilient wider-than-neck portion in its hemispherical, double-layered configuration has a width which is larger than the diameter of the neck of the aneurysm sac; and wherein the resilient wider-than-neck has a first level of flexibility, elasticity, and/or malleability; and
a flexible sac-filling portion which is inserted into the aneurysm sac; wherein the flexible sac-filling portion is expanded in the aneurysm sac by the insertion of embolic members into the flexible sac-filling portion; and wherein the flexible sac-filling portion has a second level of flexibility, elasticity, and/or malleability which is greater than the first level of flexibility, elasticity, and/or malleability.

* * * * *